United States Patent
Bourotte et al.

(10) Patent No.: US 9,586,963 B2
(45) Date of Patent: Mar. 7, 2017

(54) DERIVATIVES OF 6-SUBSTITUTED TRIAZOLOPYRIDAZINES AS REV-ERB AGONISTS

(71) Applicant: GENFIT, Loos (FR)

(72) Inventors: Maryline Bourotte, Perenchies (FR); Jean-Francois Delhomel, Arras (FR); Mathieu Dubernet, Santes (FR); Marie-Helene Gouy, Paris (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 14/344,255

(22) PCT Filed: Sep. 27, 2012

(86) PCT No.: PCT/EP2012/069014
§ 371 (c)(1),
(2) Date: Mar. 11, 2014

(87) PCT Pub. No.: WO2013/045519
PCT Pub. Date: Apr. 4, 2013

(65) Prior Publication Data
US 2015/0038503 A1     Feb. 5, 2015

(30) Foreign Application Priority Data

Sep. 27, 2011 (EP) .................................. 11306234
Apr. 11, 2012 (EP) .................................. 12163795

(51) Int. Cl.
C07D 487/04 (2006.01)
(52) U.S. Cl.
CPC .................. C07D 487/04 (2013.01)
(58) Field of Classification Search
None
See application file for complete search history.

(56) References Cited

FOREIGN PATENT DOCUMENTS

| WO | WO-2004/058769 | 7/2004 |
| WO | WO-2010/089507 | 8/2010 |
| WO | WO-2011/022619 | 2/2011 |

OTHER PUBLICATIONS

Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*

(Continued)

*Primary Examiner* — San-Ming Hui
*Assistant Examiner* — Andrew Lee
(74) *Attorney, Agent, or Firm* — Cesari and McKenna LLP

(57) ABSTRACT

The present invention provides novel 6-substituted [1,2,4]triazolo[4,3-b]pyridazines that are agonists of Rev-Erb. These compounds, and pharmaceutical compositions comprising the same, are suitable means for treating any disease wherein the activation of Rev-Erb has therapeutic effects, for instance in inflammatory and circadian rhythm-related disorders or cardiometabolic diseases.

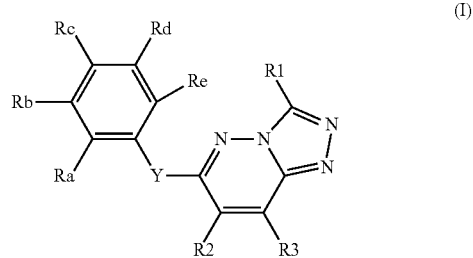

24 Claims, 18 Drawing Sheets

(56) References Cited

OTHER PUBLICATIONS

Guan, et al., "Synthesis and anticonvulsant activity of a new 6-alkoxy-[1,2,4] triazolo [4,3-*b*] pyridazine", European Journal of Medicinal Chemistry, 45 (2010).
Goldfarb, "Method of using lifespan-altering compounds for altering the lifespan of eukaryotic organisms, and screening for such compounds", Chemical Abtracts Service, Columbus, OH, 2009.
Sun et al "Synthesis and Anti-Inflammatory Activity Evaluation of Some Novel 6-Alkoxy (Phenoxy)-[1,2,4]Triazolo[3,4-α]Phthalazine-3-Amine Derivatives" European Journal of Medicinal Chemistry vol. 45, pp. 4807-4812. 2010.

* cited by examiner

Protocol SA

Protocol SB

Protocol SC with Ra or Rb or Rc
or Rf or Rg or Rh: OMe with Ra or Rb or Rc
or Rf or Rg or Rh: OH Protocol SD Ra or Rb is not H
Y is O or S Rb is W or W-Z-
R2 and R3 are hydrogen
Ra and Rc-Rj are H
(see Table 1-1)

Rb is W or W-Z-
R2 and R3 are hydrogen
at least one of Rf, Rg, or Rh is other than hydrogen atom H
(see Table 1-2)

Ra is W or W-Z-
R2 and R3 are hydrogen
Rb-Rj are H
(see Table 2-1)

Ra is W
R2 and R3 are hydrogen
Rb-Re are hydrogen
at least one of Rf-Rj is other than hydrogen atom
(see Table 2-2)

Ra is W or W-Z-
R2 and R3 are hydrogen
Rf-Rj are hydrogen
at least one of Rb-Re is other than hydrogen atom
(see Table 2-3)

Ra is W or W-Z-
R2 and R3 are hydrogen
Rf-Rj are hydrogen
at least one of Rb-Re is other than hydrogen atom
(see Table 2-3)

Ra is W or W-Z-
R2 and R3 are hydrogen
Rf-Rj are hydrogen
at least one of Rb-Re is other than hydrogen atom
(see Table 2-3)

Ra is W or W-Z-
R2 and R3 are hydrogen
At least one of Rb-Re is other than hydrogen
At least one of Rf-Rj is other than hydrogen
(see Table 2-4)

Ra is W or W-Z-
R2 and R3 are hydrogen
At least one of Rb-Re is other than hydrogen
At least one of Rf-Rj is other than hydrogen
(see Table 2-4)

Ra is W
At least one R2 and R3 is not hydrogen
Rf-Rj are hydrogen
At least one Rb-Re is other than hydrogen atom
(see Table 3-1)

Ra is W
At least one R2 and R3 is not hydrogen
At least one Rf-Rj is other than hydrogen atom
At least one Rb-Re is other than hydrogen atom
(see Table 3-2)

A)

B)

A)

B)

C)

12a

12b

12c

13a

13b

13c

14a

14b

15a

15b

DERIVATIVES OF 6-SUBSTITUTED TRIAZOLOPYRIDAZINES AS REV-ERB AGONISTS

CROSS-REFERENCE TO RELATED APPLICATIONS

This application is the National Stage of International Application No. PCT/EP2012/069014 filed on Sep. 27, 2012, which claims the benefit of European Application Nos. 11306234.3 filed on Sep. 27, 2011, and 12163795.3 filed on Apr. 11, 2012. The contents of these applications are hereby incorporated by reference in their entirety.

TECHNICAL FIELD

The present invention relates to novel 6-substituted 1,2,4-triazolo-[4,3-b]-pyridazines that are agonists of Rev-Erb and the pharmaceutical use of such compounds.

BACKGROUND

Nuclear receptors (NRs) are a class of transcription factors that are activated, or repressed, by natural or pharmaceutical ligands that, one once bound to a NR, induce a receptor conformation that modulates the interaction with transcriptional cofactors and/or gene promoters (McKenna and O'Malley, 2002). Among NRs, Rev-Erb alpha (also named NR1D1; nuclear receptors subfamily 1, group D, member 1) regulates the transcription of a large number of genes via recruitment of cofactors and ligands to promoter sequences within the chromatin (Harding and Lazar, 1995; Raghuram S et al., 2007; Yin L et al., 2007). Heme is a physiological ligand of Rev-Erb alpha, having a Kd of 2-3 µM, and inducing a conformational change in Rev-Erb alpha which results in the suppression of the expression of specific target genes (Moore J T et al., 2006).

Rev-Erb alpha is widely expressed, but expression levels are higher in liver, adipose tissue, skeletal muscle, and brain. Rev-Erb alpha is part of the core clock machinery located in mammals in the suprachiasmatic nucleus (SCN) of the hypothalamus that influences peripheral clocks in synergy with other cues including nutrient status (Green C B et al., 2008). The circadian cycle is regulated by several autoregulatory feedback loops in gene expression. Per2, Arnt and Single-minded (PAS) domain basic helix-loop-helix transcription factor circadian locomotor output cycles kaput (CLOCK) and brain and muscle aryl hydrocarbon receptor nuclear translocator (ARNT)-like protein 1 (BMAL1) modulate Rev-Erb alpha expression which, in turn, modulates BMAL1 and CLOCK transcription by binding response elements in the BMAL1 promoter, leading to the circadian pattern of BMAL1 expression (Sato T K et al., 2004; Kojetin D et al., 2011). Mice deficient in Rev-Erb alpha expression display loss of the diurnal pattern of BMAL1 expression and exhibit alterations in their circadian behavior patterns (Preitner N et al., 2002).

Rev-Erb alpha is also reported to repress the transcription of genes such as Elovl3 (a very long-chain fatty acid elongase; Anzulovich A et al., 2006) and PAI-1 (Plasminogen activator inhibitor 1, a regulator of the fibrinolytic system and modulator of inflammation, atherothrombosis and atherosclerosis; Raspe E et al., 2001). Other reported Rev-Erb alpha target genes are involved in fatty acid/lipid absorption such as Cd36, and Fabp-3 and -4 (Ramakrishnan S et al., 2005) and in inflammatory bone disorders such as osteoarthritis (Chaturvedi P et al., 2006).

Rev-Erb alpha expression is also expressed in vascular smooth and skeletal muscle cells, suggesting that it can modulate inflammation by regulating IkappaBalpha/NFkappaB dependent gene expression (Ramakrishnan S et al., 2005; Migita H et al., 2004). In human macrophages, Rev-Erb alpha expression diminishes the production of cytokines in response to lipopolysaccharide. These data demonstrate the anti-inflammatory role of Rev-Erb alpha (Barish G D et al., 2005; Fontaine C et al., 2008). Recently, it has been reported an important role of Rev-Erb alpha in inflammatory response (WO 2011/022619) and in the hepatic gluconeogenesis (Grant D et al., 2010).

Rev-Erb alpha is also highly induced during adipogenesis (Chawla A and Lazar M, 1993), possibly due to the interaction with heme (Kumar N et al., 2010), and displays biphasic expression profiles during fat cell development both in vivo and in 3T3-L1 preadipocytes, suggesting its involvement in adipocyte differentiation (WO 2003/060106; Fontaine C et al., 2003). Overexpression of Rev-Erb alpha in these cells increases expression of adipogenesis markers, including aP2, PPARgamma and C/EBPalpha, and a small increase in lipid accumulation. Rev-Erb alpha overexpression synergizes with the PPARgamma ligand Rosiglitazone to increase these markers of adipogenesis. In fact, organs with high metabolic activity, including liver and adipose tissue, display circadian rhythm in the expression of genes involved in key metabolic pathways (Ando H et al., 2005). Mice deficient in Rev-Erb alpha display elevated very low-density lipoprotein triglyceride levels, which correlates with elevated serum and liver levels of ApoCIII, a key player in serum triglyceride metabolism (Raspe E et al., 2002).

People with altered sleep-wake pattern and chronic desynchronization, for example night shift workers, have much higher propensity for cardiovascular diseases and metabolic disorders (Suwazono Y et al., 2008; Lund J et al., 2001). In fact, circadian misalignment leads to decreased leptin throughout the entire cycle, increased glucose, despite increased insulin, suggesting decreased insulin sensitivity and increased blood pressure. Rev-Erb alpha has been proposed as a core clock component that coordinates the circadian metabolic response, suggesting a great potential for Rev-Erb alpha ligands for the medical management of diseases that are associated by circadian rhythm-related disorders (Duez H et al., 2009).

Compounds that modulate Rev-Erb alpha activity thus have the potential to contribute to or even to control the crosstalk between circadian and many other physiological processes, as listed above and in particular for lipid homeostasis (Solt L et al., 2011). In fact, Rev-Erb alpha deficient mice display a dyslipidemic phenotype with elevated very low-density lipoprotein triglyceride levels along with increased liver and serum ApoCIII expression (Raspe E et al., 2001; Raspe E et al., 2002).

The first two synthetic, structurally similar Rev-Erb alpha ligands have been identified: recently. The antagonist SR8278 (Kojetin D et al., 2010) and the agonist GSK4112 (Grant D et al., 2010). GSK4112 was identified in a FRET assay as able to dose-dependently increasing the interaction of a peptide derived from NCoR (Nuclear receptor Co-Repressor) with Rev-Erb alpha (Meng Q J et al., 2008). The treatment with GSK4112 decreases Bmal1 expression in cell culture in a dose-dependent manner and induces adipogenesis in 3T3-L1 cells as demonstrated by lipid accumulation and increased expression of key adipogenic genes (Kumar N et al., 2010; Kojetin D et al., 2011). GSK4112 is therefore a Rev-Erb alpha agonist, regulating the expression of Rev-Erb alpha responsive target genes in a manner similar to Rev-Erb alpha physiological ligand, heme (Raghuram S et al., 2007).

Even if no human diseases or disorders have been exclusively attributed to Rev-Erb alpha dysfunctions, more and more studies associate Rev-Erb alpha with the pathological conditions, in particular those associated to the CNS activity but also to lipid homeostasis and metabolism. Very recently, the role of Rev-Erb beta has been highlightended in mice carrying the deletion of the two isoforms. Indeed since the phenotypic characterization of the Rev-Erba deficient mice, the Rev-Erb beta dependant compensation mechanism was raised. As a consequence of the total absence of Rev-Erbs, the authors reported that the circadian rhythms of Rev-Erb alpha and Rev-Er beta deficient mice were severely perturbed. In addition to the major circadian "arrhythmias", metabolic perturbations have also been measured. Lipid homeostasis and glucose levels were impaired in Rev-Erbs deficient mice.

GSK4112 and SR8278 have been described as Rev-Erb ligand but displayed poor pharmacokinetic properties because of high clearance and rapid metabolism that decrease their bioavailability, limiting their use in in vitro and biochemical studies. Since SR9009 and SR9011 compounds, which are GSK4122 derivatives, have been tested in different mouse models. As published by Solt et al, those two compounds were suitable for in vivo studies. Solt et al., reported that those two compounds, in addition to have an influence on the circadian clock, were also able to improve the metabolic parameters of diet induced obese mice. The changes measured on biochemical parameters were also associated to a modified gene expression profile in metabolic tissues such as liver, skeletal muscle and adipose tissue.

Thus, those recent results have provided important clues about the nodal role of both Rev-Erbs in the control of the circadian clock and the energetic metabolism. The possibility to pharmacologically modulate the activity of Rev-Erbs represent an interesting option to take pathologies related to metabolic disorders, such as T2 Diabetes but also other circadian associated disorders. (Kumar N et al., 2010; Burns T P, 2008; Solt L et al., 2011). Rev-Erb function is essential for a proper control of pathogen induced inflammation. Loss-of function for Rev-Erb may result in exaggerated host mortality upon exposure to pathogenic organisms, such as certain bacteria, viruses or parasites. Treatment with Rev-Erb ligands may prevent the increased mortality and/or morbidity in patients that suffer from infections with life-threatening pathogens.

Methods for identifying synthetic or natural Rev-Erb alpha and/or dual alpha/beta Rev-Erb modulators in association to specific biological mechanisms and/or disorders have been described in the literature (WO 99/67637; WO 2003/060106; WO 2004/053124; WO 2005/076004). However, none of them allowed identifying 6-substituted [1,2,4]triazolo[4,3-b]pyridazines as a chemical scaffold of interest for generating Rev-Erb agonists. In fact, compounds of this chemotype are described in the literature for having distinct properties such as ion channel modulators (US 2011/021521), $GABA_A$ receptor agonists (WO 99/67245; US 2009/143385), Benzodiazepine receptors modulators (Guan L P et al., 2010), Kinase modulators (WO 2004/058769; WO 2008/051805) or biocides (JP 54128595; DE 3222342).

SUMMARY OF INVENTION

The present invention provides 6-substituted [1,2,4]triazolo[4,3-b]pyridazines of formula (I) as defined below and that are agonists of Rev-Erb:

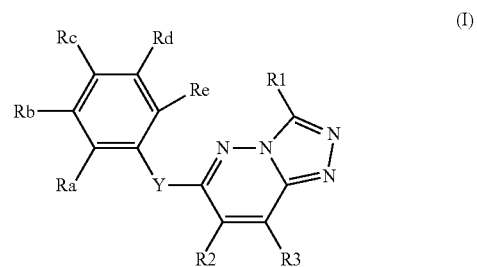

The present invention also provides pharmaceutical compositions comprising the compounds of General Formula (I) since they meet the criteria stated in the literature for compounds that activate Rev-Erb in vitro and in cellular models, indicating that these compounds can have properties of pharmaceutical interest, for instance anti-inflammatory properties. Accordingly, further objects of the invention include methods of treatment comprising the administration of said pharmaceutical composition for the treatment of an inflammatory or a circadian rhythm-related disorder.

Further objects of the present invention, including preferred compounds of General Formula (I), methods of preparing 6-substituted [1,2,4]triazolo[4,3-b]pyridazines of General Formula (I) and preferred medical uses or methods, in combination or not with other compounds, are provided in the Detailed Description.

DESCRIPTION OF THE FIGURES

Abbreviations used in the figures and in the text:
Cpd: Compound
DMEM: Dulbecco's Modified Eagle's Medium
DMSO: Dimethyl Sulfoxide
$EC_{50}$: Half maximal effective concentration
Eq: Equivalent
FBS: Fetal Bovine Serum
Gal4-RE: Gal4 Response Element
His: Histidine
o/n: overnight
MP: Melting point
P/S: Penicillin/Streptomycin
PBS: Phosphate Buffered Saline
pBS-SK+: Plasmid pBluescript SK+
RT: Room Temperature
TR-FRET: Time Resolved-Fluorescence Resonance Energy Transfer FIG. 1—Intermediate compounds for the synthesis of the Compounds of General Formula (I)

Intermediates are independently generated for the synthesis of compounds of General Formula (I): for example 3,6-disubstituted-[1,2,4]triazolo[4,3-b]pyridazine (6-chloro-3-trifluoromethyl-[1,2,4]triazolo[4,3-b]pyridazine, Intermediate B; 3,6-dichloro-[1,2,4]triazolo[4,3-b]pyridazine, Intermediate D.

In a same manner were synthesized 3,6-disubstituted-[1,2,4]triazolo[4,3-b]pyridazines and 3,6-disubstituted-[1,2,4]triazolo[4,3-a]phtalazines substituted in position 7 and/or 8.

FIG. 2—General synthesis scheme of Compounds of General Formula (I)

Figure 2A:
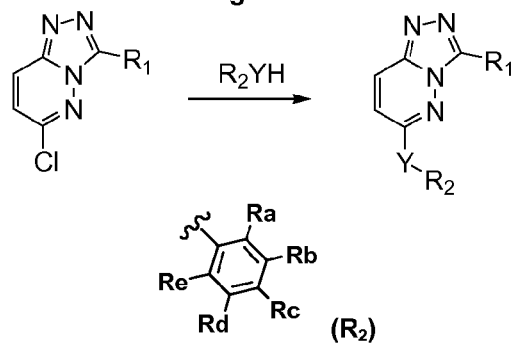
Figure 2B:
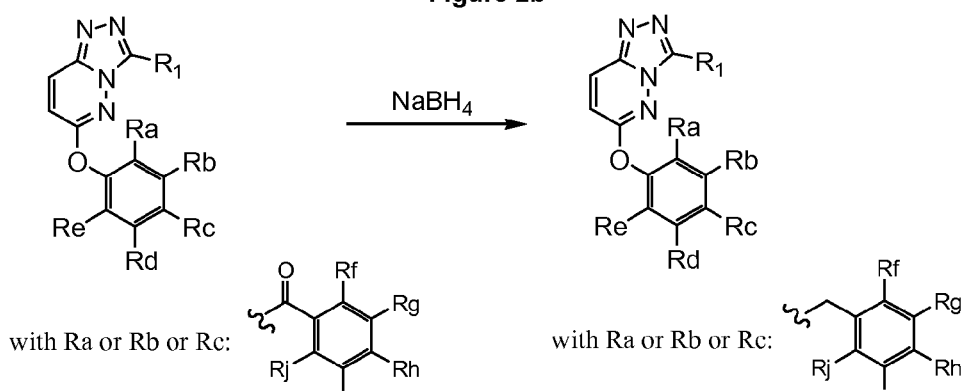
Figure 2C:
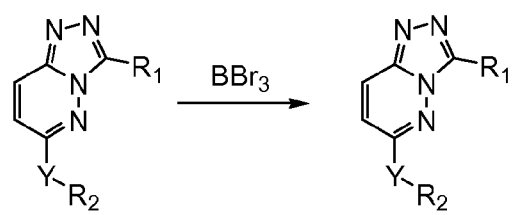

A large panel of Compounds of General Formula (I) that contains biphenyl and phenyl-heterocycle groups in the 6-substituted position of [1,2,4]triazolo[4,3-b]pyridazine are generated using the Protocol SB summarized in FIG. 2a. Further specific Compounds of General Formula (I) that were generated and tested in the Examples were obtained by modifying the 6-substituted position of [1,2,4]triazolo[4,3-b]pyridazine (FIG. 2c) using additional protocols (for example Protocols SC and SD; FIGS. 2b and 2c, respectively).

Figure 3:
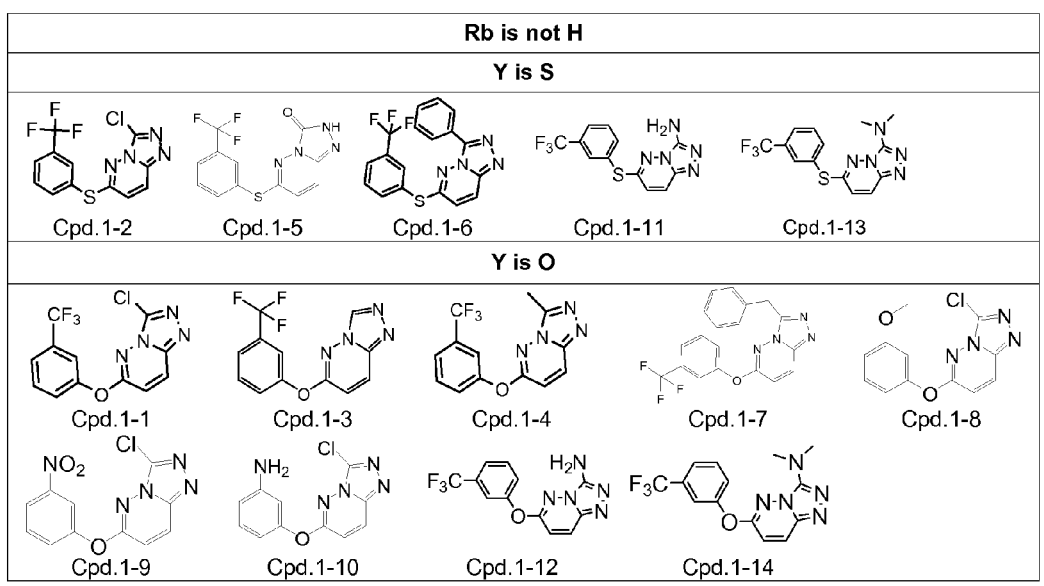
Figure 3:
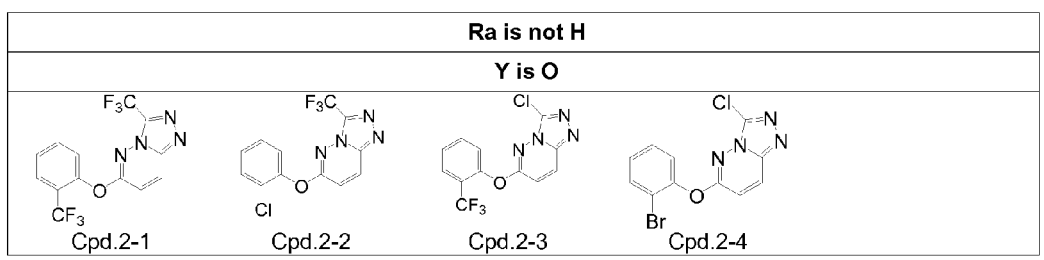

FIG. 3—Compounds of General Formula (I) in which Rb and Ra are not W or W—Z—

Examples of such compounds are represented in distinct groups that are defined on the basis of the type of Y group and the presence of a group other than hydrogen, W or W—Z— in either Ra or Rb (see Protocol SA and SB in Example 1 for details on their synthesis).

Figure 4:
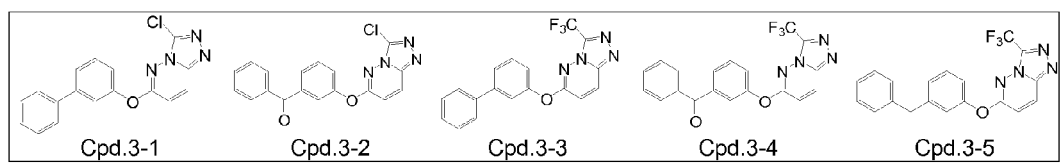
Figure 4:
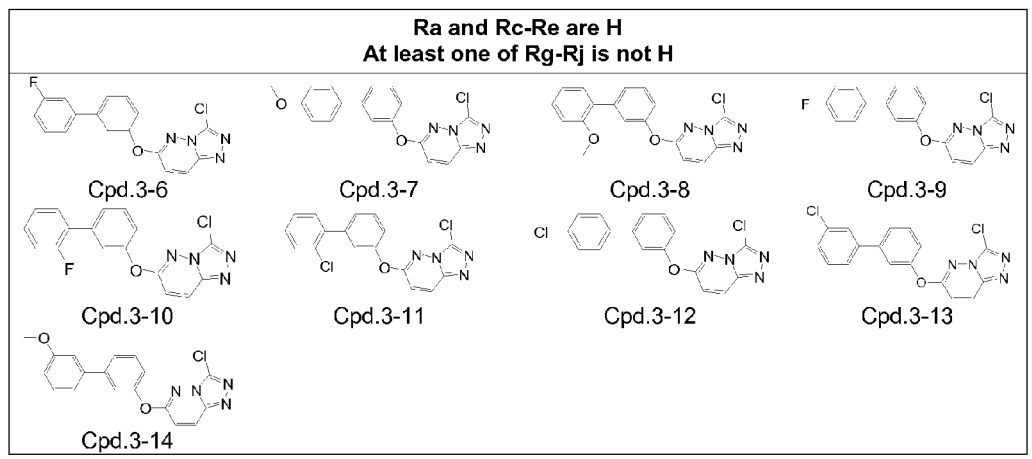

FIG. 4—Compounds of General Formula (I) in which Rb is W or W—Z— Examples of such compounds are represented in distinct groups that are defined on the basis of the type of W or W—Z—, and the absence or presence of Rf, Rg, or Rh groups other than hydrogen (see Tables 1-1 and 1-2 in Example 2 for details on their synthesis).

Figure 5:
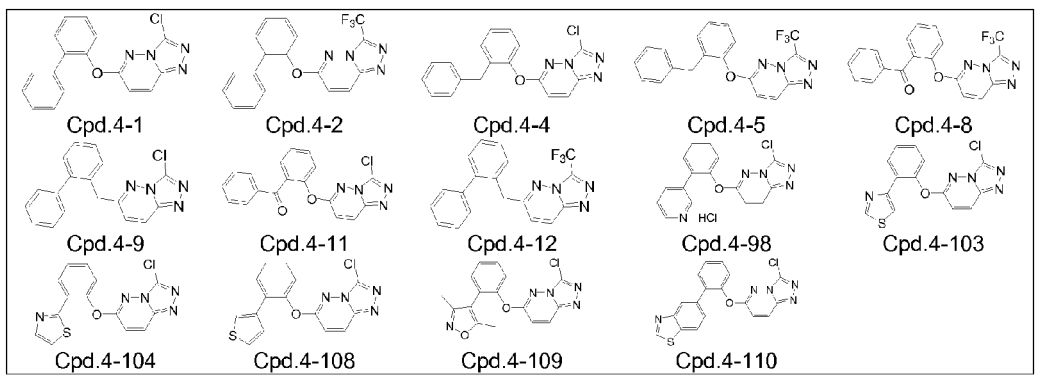
Figure 5:
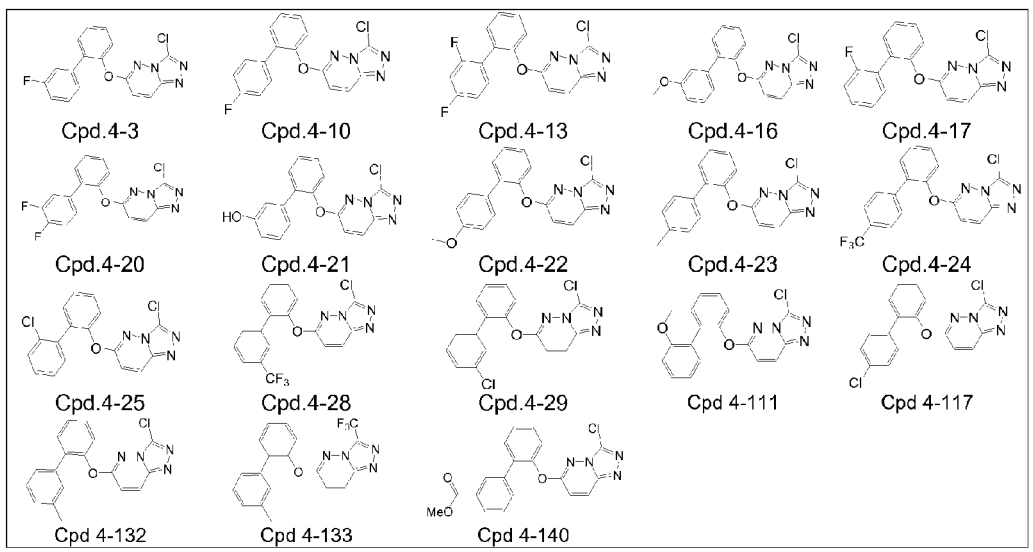

FIG. 5—Compounds of General Formula (I) in which Ra is W or W—Z—, R2 and R3 are hydrogen, and Rb-Re are hydrogen Examples of such compounds are represented in distinct groups that are defined on the basis of the absence or presence of Rf, Rg, Rh, Ri or Rj groups other than hydrogen (see Tables 2-1 and 2-2 in Example 2 for details on their synthesis).

Figure 6A:
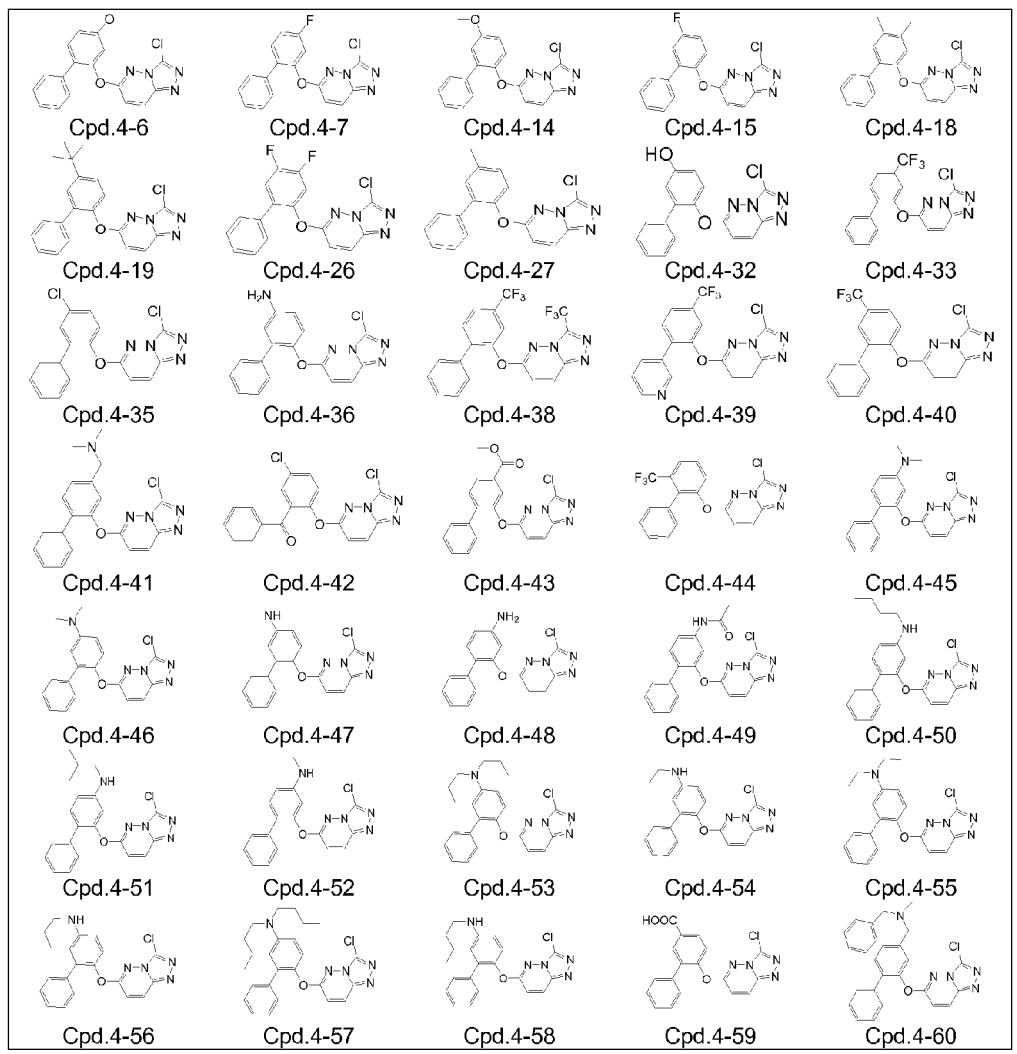
Figure 6B:
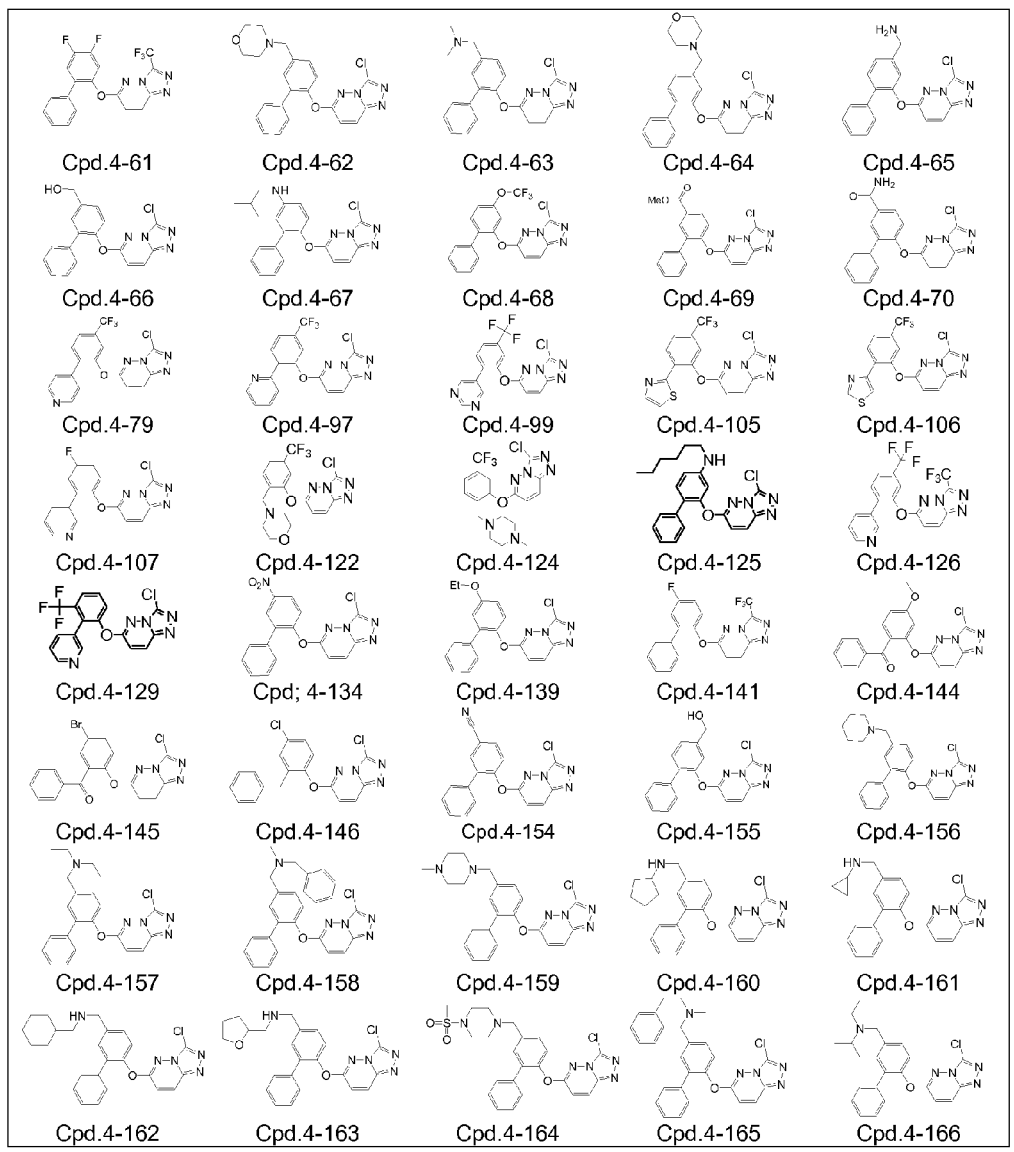
Figure 6C:
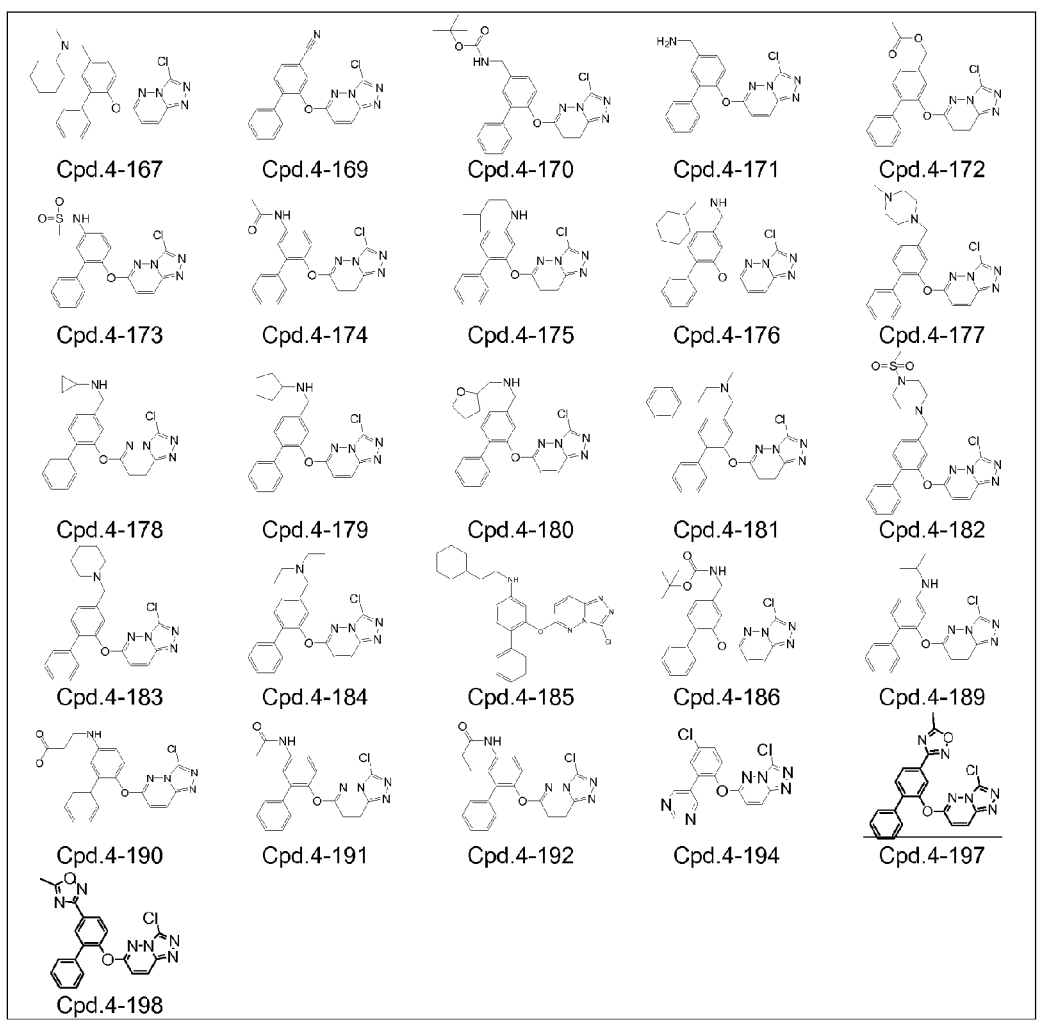

FIGS. 6a to 6c—Compounds of General Formula (I) in which Ra is W or W—Z—, R2 and R3 are hydrogen, and Rf-Rj are hydrogen Examples of such compounds are given. At least one Rb-Re is other than hydrogen (see Tables 2-3 in Example 2 for details on their synthesis).

Figure 7A:
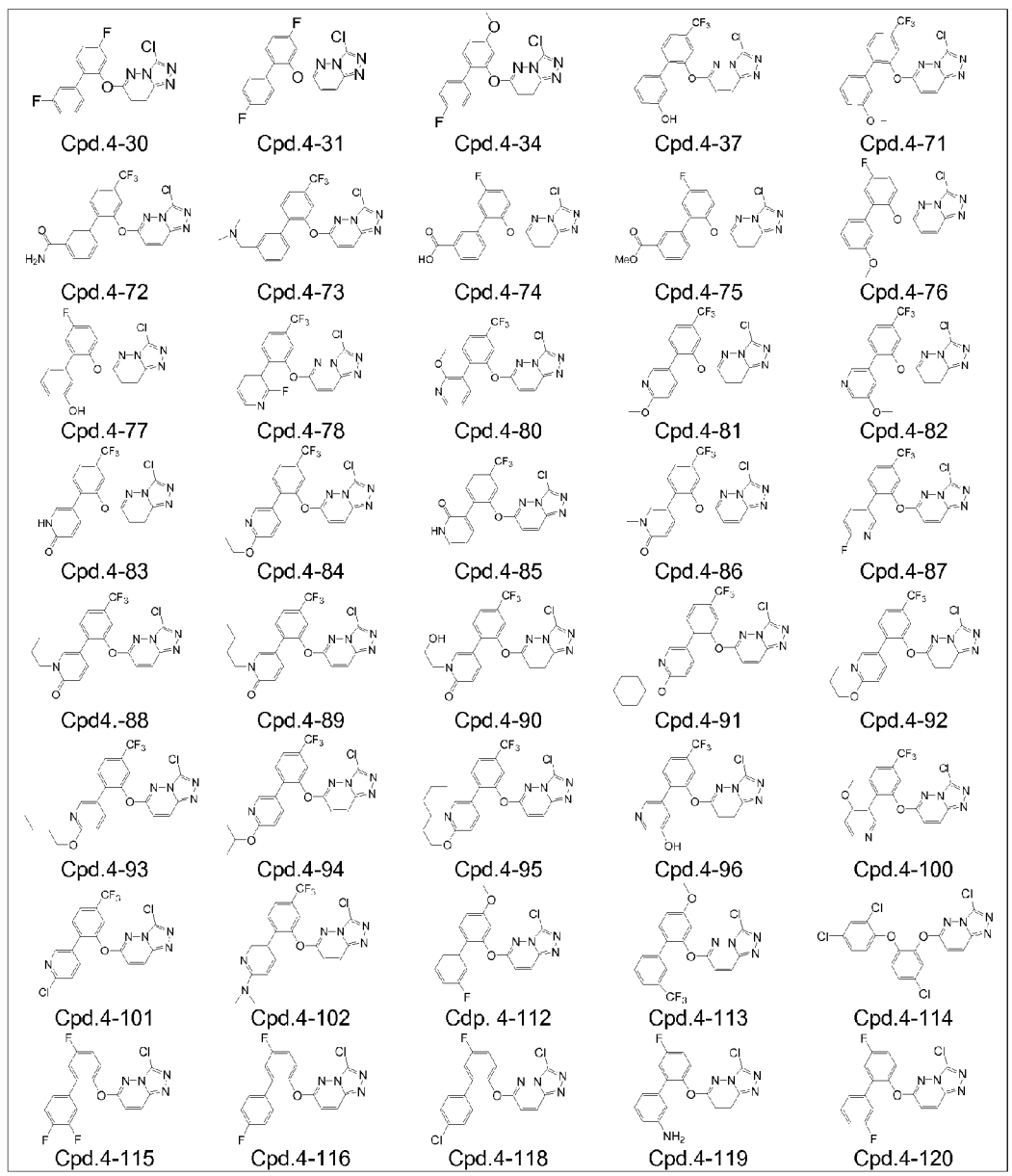
Figure 7B:
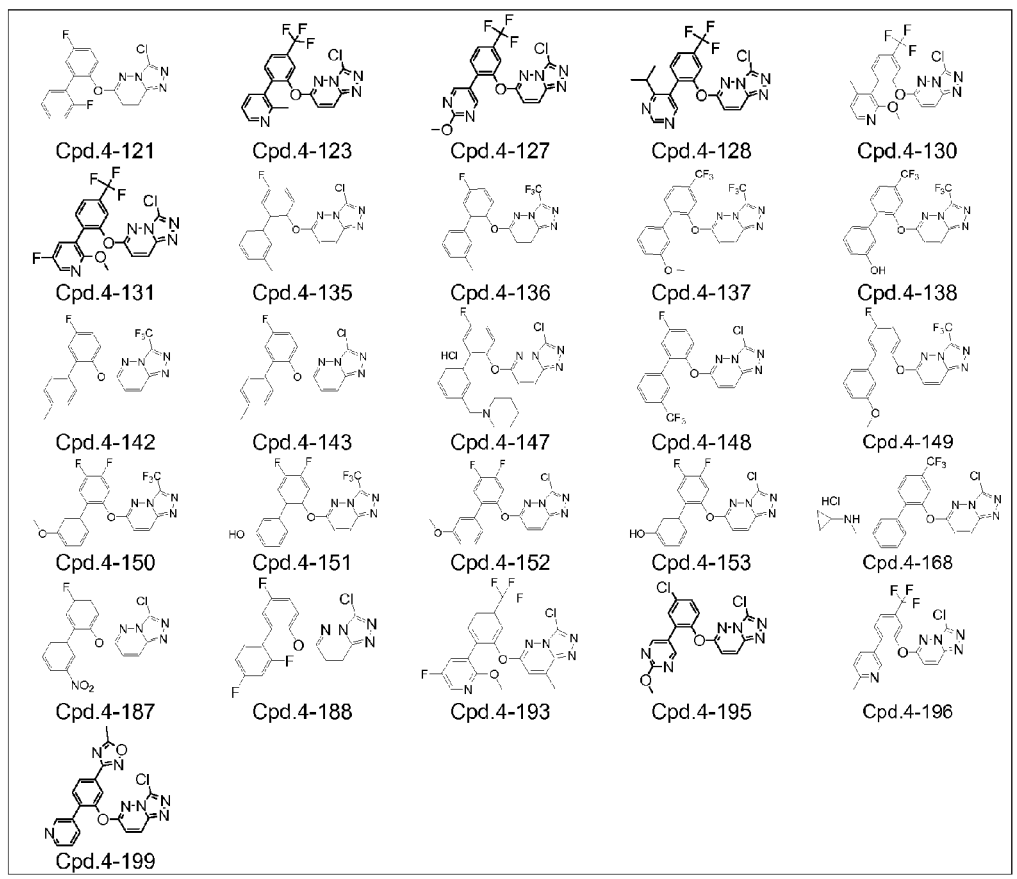

FIGS. 7a and 7b—Compounds of General Formula (I) in which Ra is W or W—Z—, R2 and R3 are hydrogen, with at least one Rb-Re and Rf-Rj are other than hydrogen Examples of such compounds are given. These compounds show at least one substituent other than hydrogen in Rb-Re position and at least one substituent other than hydrogen in Rf-Rj position (see Tables 2-4 in Example 2 for details on their synthesis).

Figure 8:
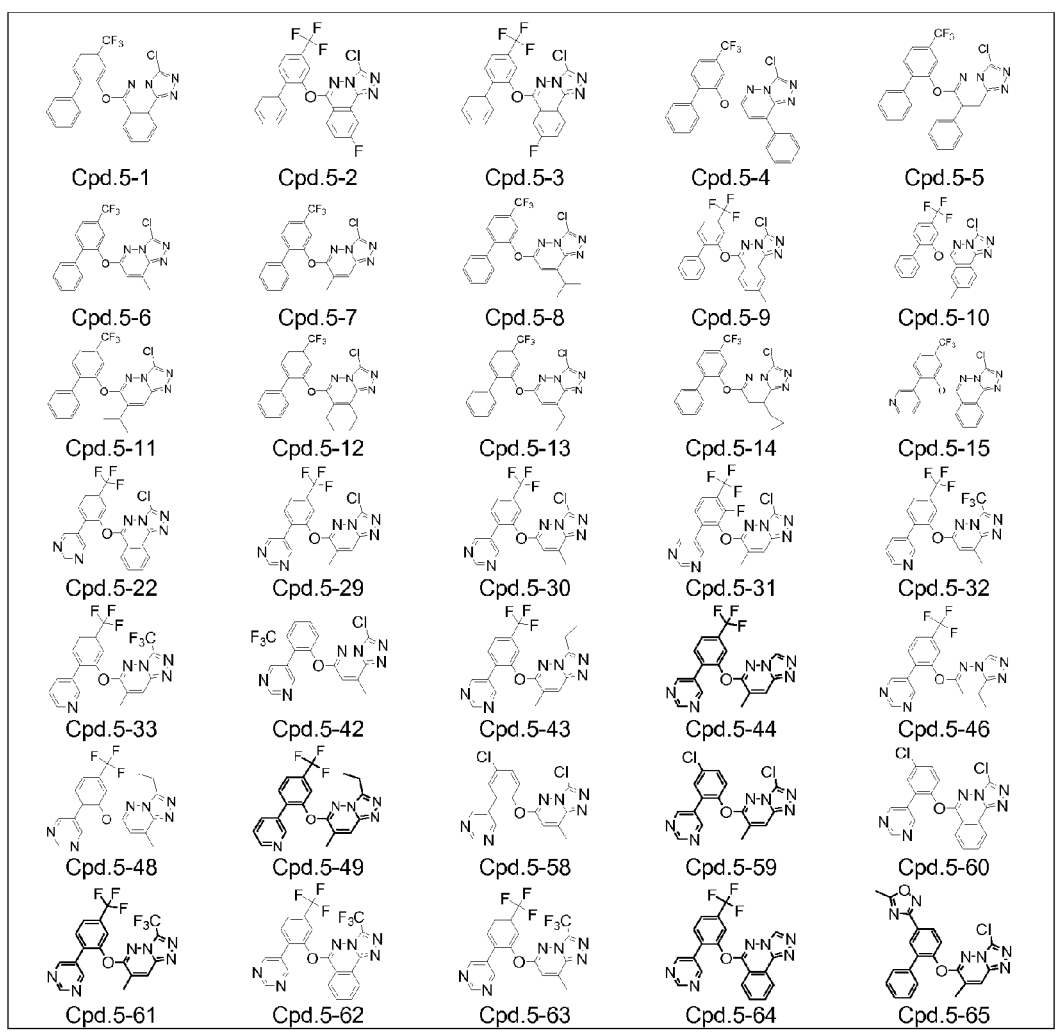
Figure 9:
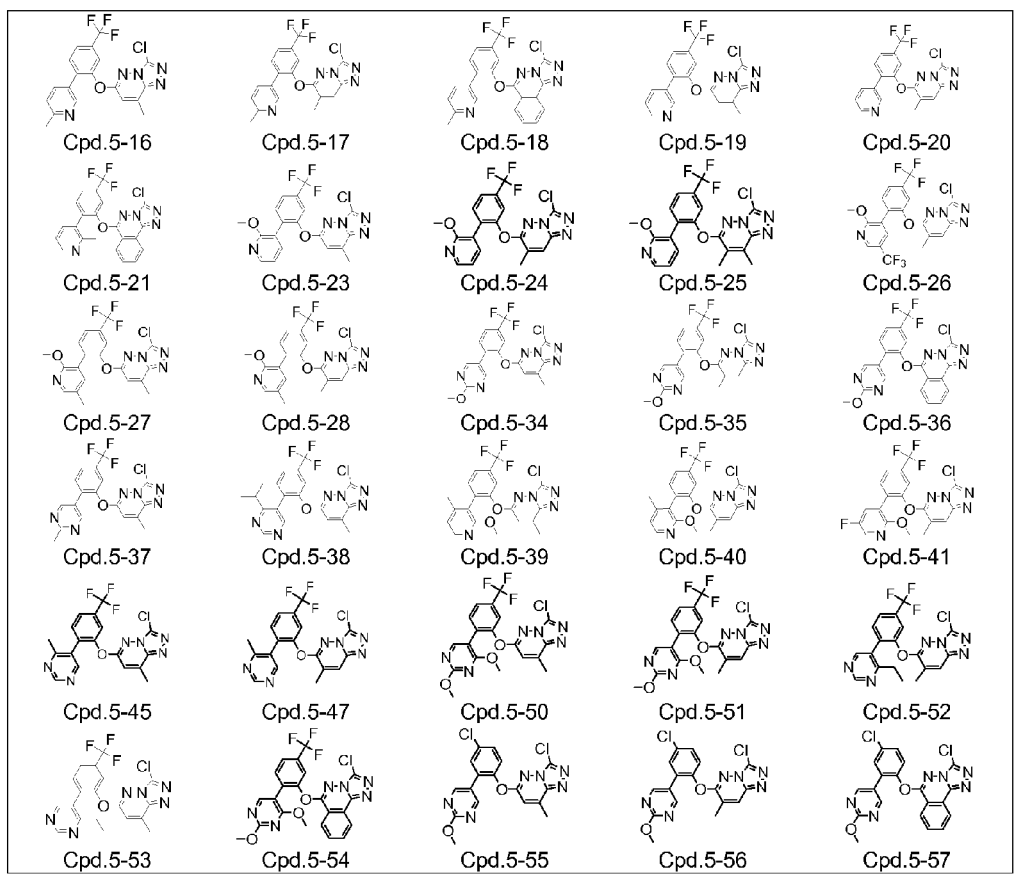

FIGS. 8 and 9—Compounds of general formula (I) in which Ra is W and R2 or R3 is other than hydrogen Examples of such compounds are represented in distinct groups that are defined on the basis of the absence or presence of Rf, Rg, Rh, Ri or Rj groups other than hydrogen (see Tables 3-1 and 3-2 in Example 2 for details on their synthesis).

Figure 10:
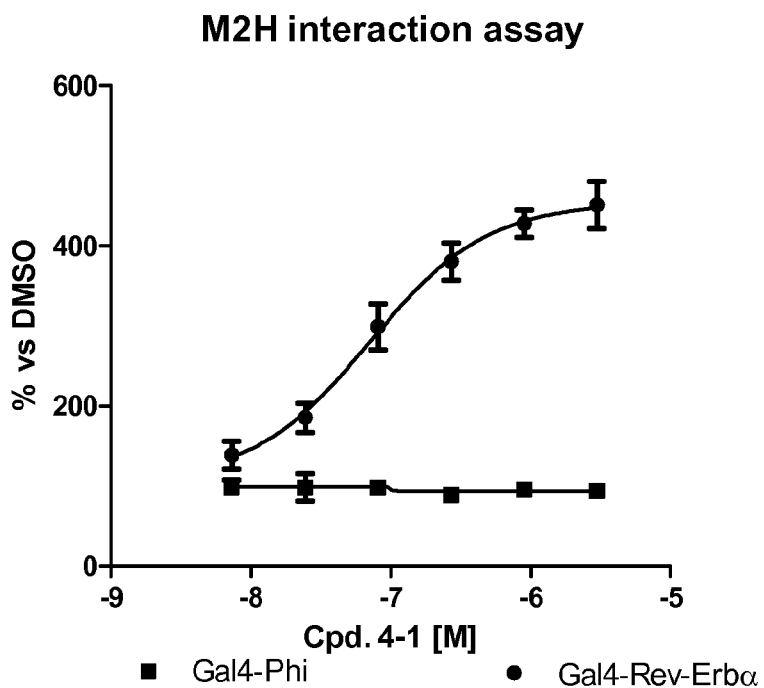
Figure 10:
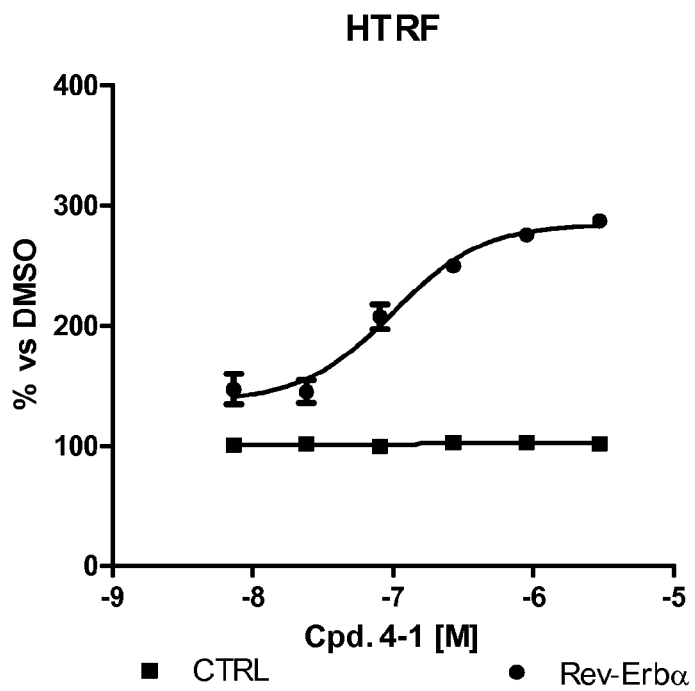

FIG. 10—In vitro activity of compounds of General Formula (I) on Rev-Erb alpha

The dose-response effect of Compound 4-1 are compared in test and control conditions using the M2H interaction assay (Gal4-Rev-Erb alpha and Gal4-Phi; A) and in TR-FRET assay (HTRF; Rev-Erb alpha and CTRL; B).

Figure 11:
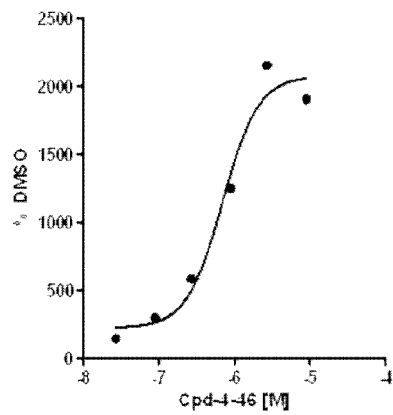
Figure 11:
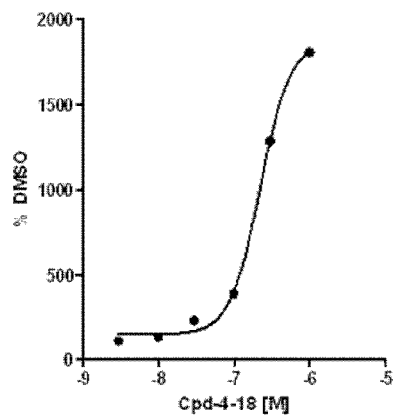
Figure 11:
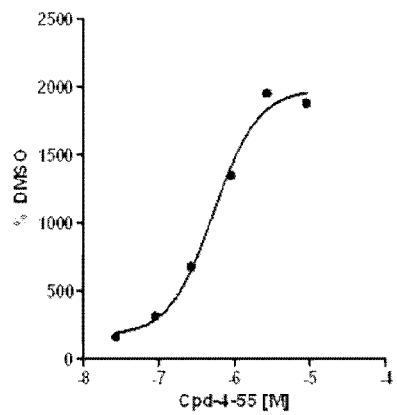

FIG. 11—In vitro activity of compounds of General Formula (I) on Rev-Erb beta

The dose-response effects of Cpd.4-18, Cpd.4-46 and Cpd.4-55 are presented using the M2H interaction assay using the Gal4-Rev-Erb betachimera).

Figure 12:
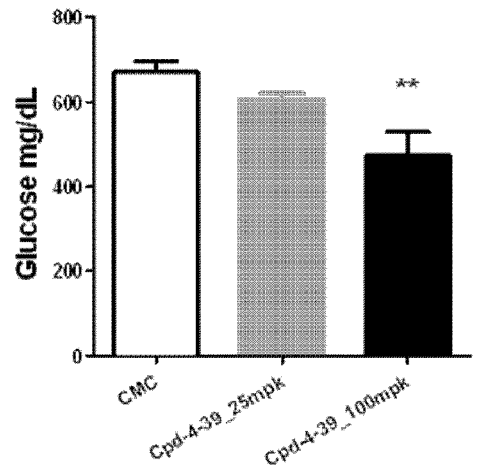
Figure 12:
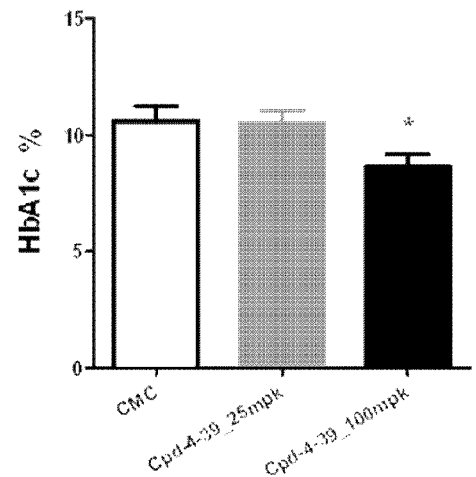
Figure 12:
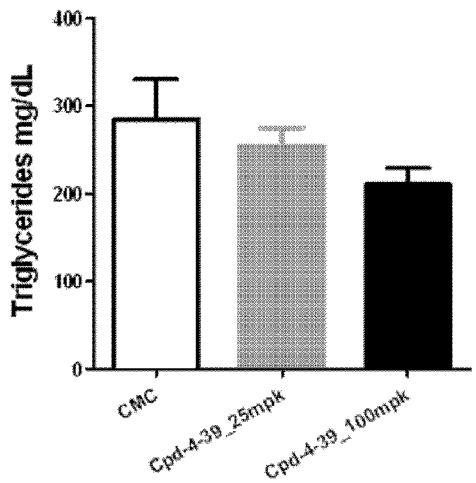

FIGS. 12a to 12c—In vivo activity of compounds of General Formula (I)

The effects on glycemia (FIG. 12a), on Hb1Ac (FIG. 12b) and on circulating triglycerides from plasmatic samples of db/db mice treated with compound Cpd.4-39 at 25 and 100 mpk were presented.

Figure 13:
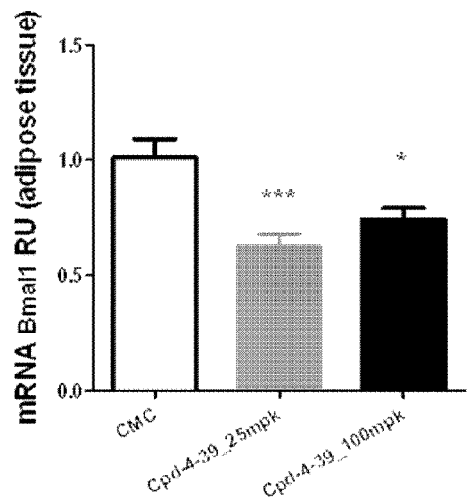
Figure 13:
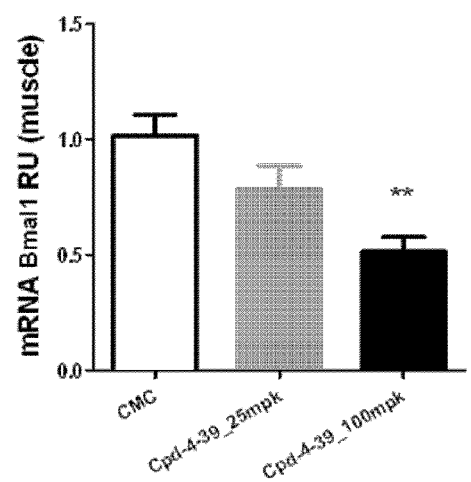
Figure 13:
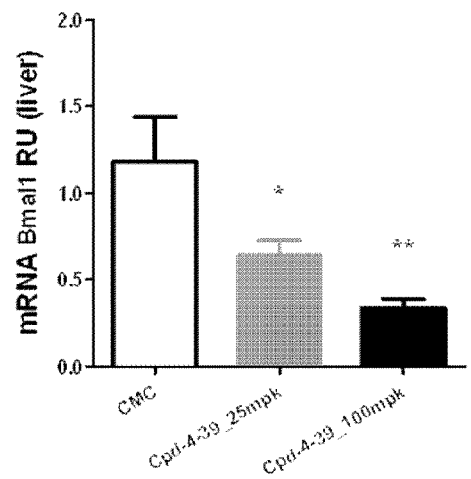

FIGS. 13a to 13c—Gene expression studies of compounds of General Formula (I) Cpd.4-39 at 25 and 100 mpk on a Rev-Erb alpha target gene Bmal1 gene expression in the studied organs (adipose tissue (FIG. 13a), muscle (FIG. 13b) and liver (FIG. 13c) of the treated db/db mice.

Figure 14:
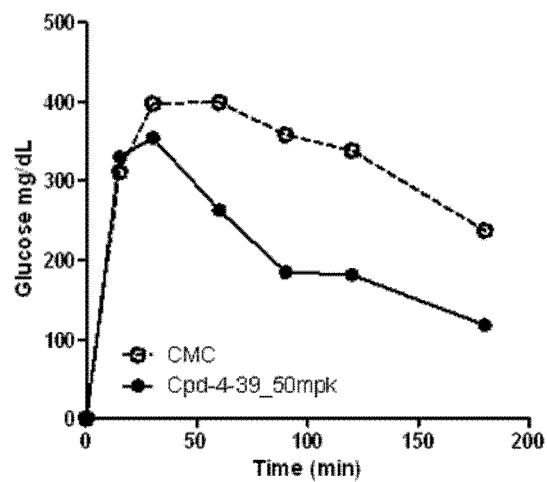
Figure 14:
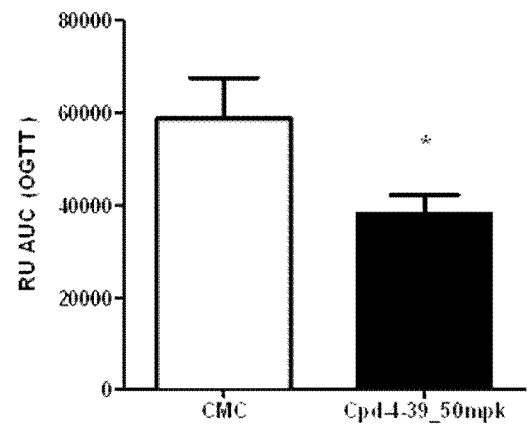

FIGS. 14a and 14b—In vivo activity of Cpd.4-39

Figure 15:
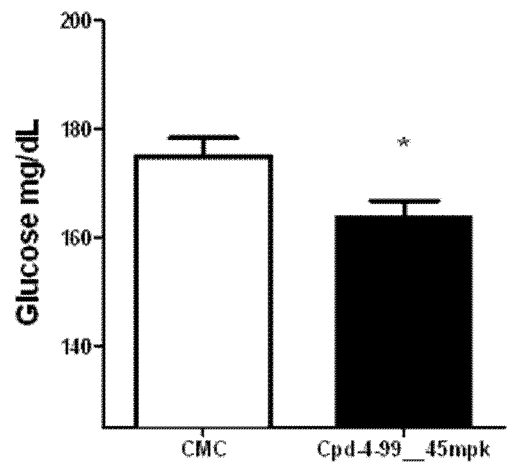
Figure 15:
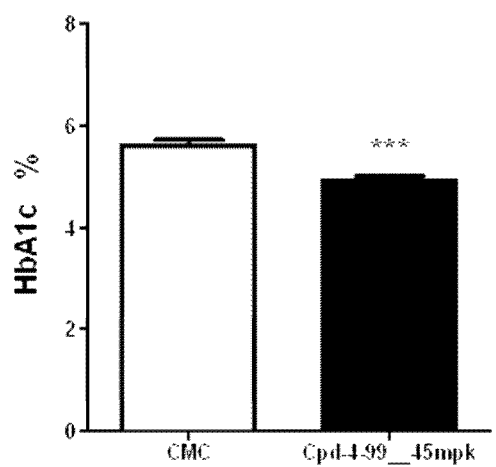

Effect of Compound Cpd.4-39 at 50 mpk on the glucose tolerance of treated db/db mice FIGS. 15a and 15b—In vivo activity of Cpd.4-99

Effect of Compound Cpd.4-99 at 45 mpk on the glycemia and Hb1Ac levels of diet induce obese mice.

DETAILED DESCRIPTION OF THE INVENTION

The present invention provides novel 6-substituted [1,2,4]triazolo[4,3-b]pyridazines that are agonists of Rev-Erb. These compounds, and pharmaceutical compositions comprising the same, are suitable means for treating any disease wherein the activation of Rev-Erb has positive effects, for instance in inflammatory disorders or circadian rhythm-related disorders.

The compounds of the present invention have the general formula (I):

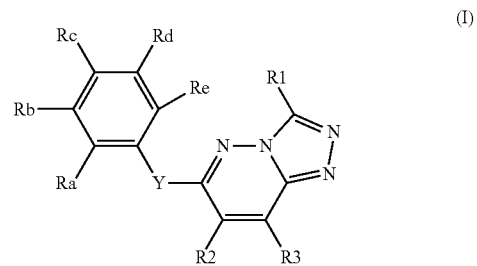

wherein

R1 represents a hydrogen atom, a halogen atom, an amino group, a hydroxyl group, a COOH group, a CO-alkyl group, a COO-alkyl group, a $CONH_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a $CONH_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, or cycloalkylamino group, with a alkylcarbamate group, or with an heterocyclic group substituted or not with an alkyl group, or with an alkylsulfonyl group, wherein either Ra represents a W or W—Z— group, and Rb represents a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group; and wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

each of Y and Z represents independently an oxygen atom, a sulphuratom, a CH$_2$, or a carbonyl group;

with the proviso that when Rb is a W—Z group and Z is a CH$_2$ group, W is not a morpholino or a 2-oxa-5-azabicyclo[2.2.1]heptyl group; with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group.

According to a particular embodiment, the invention relates to a compound of formula (I) wherein:

R1 represents a hydrogen atom, a halogen atom, a hydroxyl group, a COOH group, a CO-alkyl group, a COO-alkyl group, a CONH$_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a CONH$_2$ group, an amino group, an alkyl group, an alkoxy group, an alkylthio group or an alkylamino group;

W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, an alkyl group, an alkoxy group, a cycloalkyloxy group, an alkylthio group, or an alkylamino group;

each of Y and Z represents independently an oxygen atom, a sulphur atom, a CH2, or a carbonyl group;

wherein either
Ra represents a W or W—Z— group, and Rb represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group; and wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

with the proviso that when Rb is a W—Z group and Z is a CH$_2$ group, W is not a morpholino or a 2-oxa-5-azabicyclo[2.2.1]heptyl group; and with the proviso that when Rb is a W group, R1 is a methyl group, Y is an oxygen atom and Ra, Rc, Rd, Re, R2 and R3 are hydrogen atoms, W is not a pyrrolidinone group.

According to a specific variant of this embodiment, the compound is as defined with the further proviso that when Rb is a W group, R1 is a trifluoromethyl group, Y is an oxygen atom and Ra, Rc, Rd, Re, R2 and R3 are hydrogen atoms, W is not a triazole group.

According to a further particular embodiment, the invention relates to a compound of formula (I) wherein:

R1 represents a hydrogen atom, a halogen atom, a hydroxyl group, a COOH group, a CO-alkyl group, a COO-alkyl group, a CONH$_2$ group, an alkyl group, an alkoxy group, an alkylthio group, or an alkylamino group;

Ra, Rb, Rc, Rd, and Re represent independently a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group, a W group, or a W—Z— group;

W represents a cyclic group selected from a cycloalkyl, aryl and heterocyclic group, W being further substituted or not with one or more substituent groups chosen from a halogen atom, an hydroxyl group, a COOH group, a CO-alkyl group, a COO-alkyl group, a CONH$_2$ group, an amino group, an alkyl group, an alkoxy group, an alkylthio group, or an alkylamino group;

any of the alkyl, alkoxy, alkylthio, or alkylamino groups in R1, Ra, Rb, Rc, Rd, Re, or within W is substituted or not with one or more halogen atoms, an aryl group, an heterocyclic group, an alkylamino group, or an amino group; and each of Y and Z represents independently an oxygen atom, a sulphur atom, a CH$_2$, or a carbonyl group.

According to a specific particular variant of this embodiment, the compound of the invention is of formula (I) with the proviso that when Rb is a W—Z group and Z is a CH$_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group.

In a particular embodiment, Ra is a W or W—Z group. According to this embodiment and to the definition of the compound of formula (I) provided above, Rb is not a W or W—Z group.

In a particular embodiment, either R2 is a hydrogen atom and R3 is an alkyl (in particular a C1-C3 alkyl) or cyclic group or R3 is a hydrogen atom and R2 is an alkyl or cyclic group (in particular a phenyl or cyclopropyl group).

In a particular embodiment, R3 is a hydrogen atom and R2 is an alkyl (in particular a C1-C3 alkyl) or cyclic group.

In a further embodiment, R2 and R3, together with the carbon atoms to which they are attached form a phenyl group.

In a further particular embodiment, the compounds according to the invention are of formula (I) wherein R2 and R3 are hydrogen atoms.

In a particular embodiment, W is a monocyclic or polycyclic (in particular a bicyclic) group. In a particular embodiment, W is a substituted cyclic group.

In a particular embodiment, W is a cycloalkyl, aryl or heterocyclic group (in particular a heteroaryl group) comprising a five- or a six-atom ring. Preferably, W is a cyclopentyl, a cyclohexyl, phenyl, pyridine, pyrrolidine, tetrahydropyrane, thiazole, benzothiazole, thiophene, isoxazole, oxazole, pyrazine, morpholine, tetrahydropyran, piperazine, piperidine, pyrimidine, or pyridazine group. More preferably, W is a phenyl, pyrimidine or pyridine group, in particular a phenyl group or pyridine group, having one of the following structures that may represent either Ra or Rb:

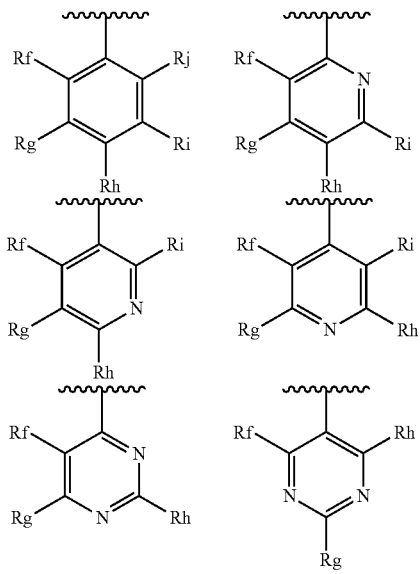

wherein Rf, Rg, Rh, Ri, and Rj independently represent an hydrogen atom, an halogen atom, a hydroxyl group, an amino group, a nitro group, a alkylsulfonamide group, a NH—CO-alkyl group, an alkyl group, an alkoxy group, a cycloalkyloxy group, an alkylamino group, an alkylthio group, a COOH group, a CO-alkyl group, a COO-alkyl group or a $CONH_2$ group.

wherein any of the alkyl, alkoxy, alkylamino, and alkylthio group in Rf, Rg, Rh, Ri, and Rj is substituted or not with one or more halogen atoms, an aryl group, an heterocyclic group, an alkylamino group, a cycloalkylamino group, an amino group or a hydroxy group.

In a particular embodiment, Rf, Rg, Rh, Ri, and Rj independently represent an hydrogen atom, an halogen atom, a hydroxyl group, an amino group, an alkyl group, an alkoxy group, an alkylamino group, an alkylthio group, a COOH group, a CO-alkyl group, a COO-alkyl group or a $CONH_2$ group and any of the alkyl, alkoxy, alkylamino, and alkylthio group in Rf, Rg, Rh, Ri, and Rj is substituted or not with one or more halogen atoms, an aryl group, an heterocyclic group, an alkylamino group, an amino group or a hydroxy group.

Representative cyclic groups that can correspond to W include substituted or unsubstituted phenyl, pyridinyl (e.g. pyridin-2-yl, pyridin-3-yl, pyridin-4-yl), pyrimidinyl (e.g. pyrimidin-2-yl, pyrimidin-4-yl, pyrimidin-5-yl), pyridinonyl (e.g. pyridin-2(1H)-one-3-yl, -4-yl, -5-yl or 6-yl), 3,5-diméthylisoxasol-4-yl, thiazolyl (e.g. thiazol-2-yl or -4-yl), benzo[d]thiazolyl (e.g. benzo[d]thiazol-5-yl) and thiophenyl (e.g. thiophen-3-yl).

More preferably, W is a substituted or unsubstituted phenyl, pyridine or pyrimidine group as defined above.

In a particular embodiment, at least one group among Ra, Rb, Rc, Rd and Re, in particular among Ra, Rb, Rc and Rd, is a halogen atom, a hydroxyl group, a COOH group, a CO-alkyl group, a COO-alkyl group, a $CONH_2$ group, an amino group, an alkyl group, an alkoxy group, an alkylthio group, or an alkylamino group. Preferably Ra represents a W or W—Z— group and at least one of Rb, Rc, and Rd (and more preferably Rc and/or Rd) is a halogen atom, an hydroxyl group, a COOH group, a CO-alkyl group, a COO-alkyl group, a $CONH_2$ group, an amino group, an alkyl group, an alkoxy group, an alkylthio group, or an alkylamino group.

In a particular embodiment, Re represents a hydrogen or halogen atom, in particular a hydrogen atom.

In another embodiment, Ra is a W or W—Z group, and Rb is a hydrogen atom or an unsubstituted or substituted alkyl group, in particular a $CF_3$ group. In a further embodiment, Rb is a W or W—Z group and Ra is a hydrogen atom.

In a particular embodiment, R1 is a hydrogen atom; a halogen atom, an alkyl group substituted or not with a cyclic group, in particular an aryl group more particularly a phenyl group, an alkoxy group, an alkylthio group, or an alkylamino group. In a further particular embodiment, R1 is a halogen atom, in particular a chlorine atom, or a $CF_3$ group.

In a particular embodiment, R1 is a substituted or unsubstituted alkyl group, in particular a CF3 group, or a halogen atom, in particular a chlorine atom, and Rd is a substituted or unsubstituted alkyl group, in particular a CF3 group. In a specific variant of this embodiment, R2 and R3 independently represent a hydrogen atom or an alkyl group, in particular a methyl group.

A particular embodiment is, when any of the substituent groups (that is, R1, R2, R3, Ra, Rb, Rc, Rd, Re, Rf, Rg, Rh, Ri, and/or Rj) is an alkyl group, an alkoxy group, an alkylthio group, or an alkylamino group, said group have 1 to 4 carbon atoms (i.e., 1, 2, 3 or 4 carbon atoms) and preferably is substituted with one or more halogen atoms, for example 1, 2, 3 or 4 halogen atoms. In a particular variant, Rd is a $CF_3$ group.

In a further particular embodiment, Rc or Rd is an oxadiazole group.

In a particular embodiment, Y is an oxygen atom or a $CH_2$ group and/or Z, if present, is a CO or $CH_2$ group that links W to a phenyl group within General Formula (I).

In a particular embodiment, Ra represents a W or W—Z— group, and R1 and at least one of Rb, Rc, and Rd (and more preferably Rc and/or Rd) represent independently a halogen atom, an alkyl, an alkoxy, an alkylthio, or an alkylamino group. In particular, the alkyl group of Rb, Rc, and/or Rd can be substituted with one or more halogen atoms, an aryl group, an heterocyclic group, an amino group, or an alkylamino group.

In a particular embodiment, Ra represents a W group and R1 and at least one group among Rb, Rc and Rd, in particular among Rc and Rd, are a halogen atom or an alkyl group having 1 to 4 carbon atoms that is substituted with one or more halogen atoms. More preferably, R1 and at least one group among Rb, Rc and Rd, in particular among Rc and Rd, are a chlorine atom or a $CF_3$ group.

In a particular embodiment, three out of R1, Ra, Rb, Rc, Rd, and Re in the compounds of General Formula (I) are hydrogen atoms. More preferably, such hydrogen atoms correspond to Re, one group between Ra and Rb, and one group between Rc and Rd.

In a particular embodiment, at least one of the Rf, Rg, Rh, Ri, and Rj groups present in the W group is a substituent group chosen from a halogen atom, a hydroxyl group, a COOH group, a CO-alkyl group, a COO-alkyl group, a $CONH_2$ group, an amino group, an alkyl group, an alkoxy group, an alkylthio group, or an alkylamino group. Preferably, at least one of the Rf, Rg, Rh, Ri and Rj (and more preferably Rf and/or Rg) is a substituent group chosen from an halogen atom, an alkyl group, an alkoxy group, an alkylthio group, or an alkylamino group.

In a further embodiment, Ra or Rb is a —$CH_2$-phenyl group.

In a particular embodiment, Ra is a W group and Rb, Rc, Rd and Re are independently selected in the group consisting of a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group.

In another embodiment, Z is an oxygen atom, a sulphur atom or a carbonyl group.

In a preferred embodiment of the invention, Ra is a W group selected in the group consisting of a pyrimidine and pyridine group and R2 and R3, together with the carbon atoms to which they are attached, form a phenyl group.

In a particular embodiment, Rb represents a W or W—Z group and R2, R3, Ra, Rc, Rd, Re, Rf, Rg, Rh, Ri and Rj are hydrogen atoms. In a specific variant of this embodiment, W is a phenyl group.

In a particular embodiment, Rb represents a W or W—Z group, R2 and R3 represent hydrogen atoms and at least one of Rf, Rg, Rh, Ri and Rj is different from a hydrogen atom. In a specific variant of this embodiment, W is a phenyl group.

In another particular embodiment of the invention, Ra represents a W or W—Z group and R2, R3, Rb, Rc, Rd, Re, Rf, Rg, Rh, Ri and Rj are hydrogen atoms.

In another embodiment of the invention, Ra represent a W group, Rb, Rc, Rd, Re are hydrogen atoms and at least one of Rf, Rg, Rh, Ri and Rj is different from a hydrogen atom.

In a further embodiment of the invention, Ra represent a W or W—Z group, R2, R3, Rf, Rg, Rh, Ri, and Rj represent hydrogen atoms, and at least one of Rb, Rc, Rd and Re is different from a hydrogen atom.

In another embodiment of the invention, Ra represent a W or W—Z group, R2 and R3 represent hydrogen atoms, at least one of Rb, Rc, Rd and Re is different from a hydrogen atom and at least one of Rf, Rg, Rh, Ri and Rj is different from a hydrogen atom.

In a further embodiment of the invention, Ra is a W group, at least one of R2 and R3 is not a hydrogen atom, Rf, Rg, Rh, Ri and Rj represent hydrogen atoms and at least one of Rb, Rc, Rd and Re is different from a hydrogen atom.

In another embodiment of the invention, Ra is a W group, at least one of R2 and R3 is not a hydrogen atom, at least one of Rf, Rg, Rh, Ri, Rj is not a hydrogen atom and at least one of Rb, Rc, Rd and Re is not a hydrogen atom.

Specific embodiments of the invention also relates to a compound of formula (I) comprising at least one of the following features, preferably all of these features. It should be understood that the present invention discloses any possible combination of these features:

when Rb is a hydrogen atom or a CF3 group, Ra is a substituted or unsubstituted phenyl, pyridinyl, thiophenyl, benzo[d]thiazolyl, or pyrimidinyl;

when Ra is a hydrogen atom, Rb is a substituted or unsubstituted alkyl group, for example a CF3 group, or is a substituted or unsubstituted phenyl group;

Z is an oxygen atom, a CO group or a $CH_2$ group;

Rc is a hydrogen or halogen atom, a COO-alkyl group, an alkylamino group, an alkylcarbamate group, a substituted or unsubstituted heterocyclic group such as an oxadiazolyl group (for example a 1,2,4-oxadiazol-3-yl or a 5-methyl-1,2,4-oxadiazol-3-yl group) or an alkyl group substituted or not with one or more halogen atoms, for example a CF3 group;

Rd is a hydrogen or halogen atom, an alkoxy group substituted or not with one or more halogen atoms (for example an OCF3 group), a COO-alkyl group, a cyano group, a substituted or unsubstituted heterocyclic group such as an oxadiazolyl group (for example a 1,2,4-oxadiazol-3-yl or a 5-methyl-1,2,4-oxadiazol-3-yl group) or an alkyl group substituted or not with one or more halogen atoms (e.g. a CF3 group), an alkylcarbonyloxy group, or a cycloalkylamino group;

Re is a hydrogen atom;

Y is an oxygen or sulphur atom; and/or

R1 is a halogen atom such as a chlorine atom, or an alkyl group substituted with one or more halogen atoms such as a CF3 group.

In a first preferred series of compounds of General Formula (I), Rb is a phenyl or a phenyl-Z group. Examples of such compounds having further substituent groups that are defined according to the embodiments of the invention are shown in FIG. 4 and include:

Cpd.3-1: 6-(biphenyl-3-yloxy)-3-chloro-[1,2,4]triazolo[4,3-b]pyridazine;

Cpd.3-2: (3-(3-chloro-[1,2,4]triazolo[4,3-b]pyridazin-6-yloxy)phenyl)(phenyl)methanone;

Cpd.3-3: 6-(biphenyl-3-yloxy)-3-(trifluoromethyl)-[1,2,4]triazolo[4,3-b]pyridazine;

Cpd.3-4: (3-(3-(trifluoromethyl)-[1,2,4]triazolo[4,3-b]pyridazin-6-yloxy)phenyl)(phenyl)methanone;

Cpd.3-5: 6-(3-benzylphenoxy)-3-(trifluoromethyl)-[1,2,4]triazolo[4,3-b]pyridazine;

Cpd.3-6: 6-(3'-fluoro-biphenyl-3-yloxy)-3-chloro-[1,2,4]triazolo[4,3-b]pyridazine;

Cpd.3-7: 6-(4'-methoxy-biphenyl-3-yloxy)-3-chloro-[1,2,4]triazolo[4,3-b]pyridazine;

Cpd.3-8: 6-(2'-methoxy-biphenyl-3-yloxy)-3-chloro-[1,2,4]triazolo[4,3-b]pyridazine;

Cpd.3-9: 6-(4'-fluoro-biphenyl-3-yloxy)-3-chloro-[1,2,4]triazolo[4,3-b]pyridazine;

Cpd.3-10: 6-(2'-fluoro-biphenyl-3-yloxy)-3-chloro-[1,2,4]triazolo[4,3-b]pyridazine;

Cpd.3-11: 6-(2'-chloro-biphenyl-3-yloxy)-3-chloro-[1,2,4]triazolo[4,3-b]pyridazine;

Cpd.3-12: 6-(4'-chloro-biphenyl-3-yloxy)-3-chloro-[1,2,4]triazolo[4,3-b]pyridazine;

Cpd.3-13: 3-chloro-6-(3'-chlorobiphenyl-3-yloxy)-[1,2,4]triazolo[4,3-b]pyridazine;

Cpd.3-14: 3-chloro-6-(3'-methoxybiphenyl-3-yloxy)-[1,2,4]triazolo[4,3-b]pyridazine.

In a second preferred series of compounds of General Formula (I), Ra is a phenyl, pyridine, or phenyl-Z group. Examples of such compounds having further substituent groups that are defined according to the embodiments of the invention are shown in FIGS. 5 to 9 and include:

Cpd.4-1: 6-(biphenyl-2-yloxy)-3-chloro-[1,2,4]triazolo[4,3-b]pyridazine;
Cpd 4-2: 6-(biphenyl-2-yloxy)-3-(trifluoromethyl)-[1,2,4]triazolo[4,3-b]pyridazine;
Cpd.4-3: 6-(3'-fluoro-biphenyl-2-yloxy)-3-chloro-[1,2,4]triazolo[4,3-b]pyridazine;
Cpd.4-4: 6-(2-benzylphenoxy)-3-chloro-[1,2,4]triazolo[4,3-b]pyridazine;
Cpd.4-5: 6-(2-benzylphenoxy)-3-(trifluoromethyl)-[1,2,4]triazolo[4,3-b]pyridazine;
Cpd.4-6: 6-(4-methoxy-biphenyl-2-yloxy)-3-chloro-[1,2,4]triazolo[4,3-b]pyridazine;
Cpd.4-7: 6-(4-fluoro-biphenyl-2-yloxy)-3-chloro-[1,2,4]triazolo[4,3-b]pyridazine;
Cpd.4-8: (2-(3-(trifluoromethyl)-[1,2,4]triazolo[4,3-b]pyridazin-6-yloxy)phenyl)(phenyl)methanone;
Cpd.4-9: 6-(biphenyl-2-ylmethyl)-3-chloro-[1,2,4]triazolo[4,3-b]pyridazine;
Cpd.4-10: 6-(4'-fluoro-biphenyl-2-yloxy)-3-chloro-[1,2,4]triazolo[4,3-b]pyridazine;
Cpd.4-11: (2-(3-chloro-[1,2,4]triazolo[4,3-b]pyridazin-6-yloxy)phenyl)(phenyl)methanone;
Cpd.4-12: 6-(biphenyl-2-ylmethyl)-3-(trifluoromethyl)-[1,2,4]triazolo[4,3-b]pyridazine;
Cpd.4-13: 6-(2',4'-difluoro-biphenyl-2-yloxy)-3-chloro-[1,2,4]triazolo[4,3-b]pyridazine;
Cpd.4-14: 6-(5-methoxybiphenyl-2-yloxy)-3-chloro-[1,2,4]triazolo[4,3-b]pyridazine;
Cpd.4-15: 6-(5-fluoro-biphenyl-2-yloxy)-3-chloro-[1,2,4]triazolo[4,3-b]pyridazine;
Cpd.4-16: 6-(3'-methoxy-biphenyl-2-yloxy)-3-chloro-[1,2,4]triazolo[4,3-b]pyridazine;
Cpd.4-17: 6-(2'-fluoro-biphenyl-2-yloxy)-3-chloro-[1,2,4]triazolo[4,3-b]pyridazine;
Cpd.4-18: 6-(4,5-dimethyl-biphenyl-2-yloxy)-3-chloro-[1,2,4]triazolo[4,3-b]pyridazine;
Cpd.4-19: 6-(5-tert-butyl-biphenyl-2-yloxy)-3-chloro-[1,2,4]triazolo[4,3-b]pyridazine;
Cpd.4-20: 6-(3',4'-difluoro-biphenyl-2-yloxy)-3-chloro-[1,2,4]triazolo[4,3-b]pyridazine;
Cpd.4-21: 6-(3'-hydroxy-biphenyl-2-yloxy)-3-chloro-[1,2,4]triazolo[4,3-b]pyridazine;
Cpd.4-22: 6-(4'-methoxy-biphenyl-2-yloxy)-3-chloro-[1,2,4]triazolo[4,3-b]pyridazine;
Cpd.4-23: 6-(4'-methyl-biphenyl-2-yloxy)-3-chloro-[1,2,4]triazolo[4,3-b]pyridazine;
Cpd.4-24: 6-(4'-trifluoromethyl-biphenyl-2-yloxy)-3-chloro-[1,2,4]triazolo[4,3-b]pyridazine;
Cpd.4-25: 6-(2'-chloro-biphenyl-2-yloxy)-3-chloro-[1,2,4]triazolo[4,3-b]pyridazine;
Cpd.4-26: 6-(4,5-difluoro-biphenyl-2-yloxy)-3-chloro-[1,2,4]triazolo[4,3-b]pyridazine;
Cpd.4-27: 6-(5-methyl-biphenyl-2-yloxy)-3-chloro-[1,2,4]triazolo[4,3-b]pyridazine;
Cpd.4-28: 6-(3'-trifluoromethyl-biphenyl-2-yloxy)-3-chloro-[1,2,4]triazolo[4,3-b]pyridazine;
Cpd.4-29: 6-(3'-chloro-biphenyl-2-yloxy)-3-chloro-[1,2,4]triazolo[4,3-b]pyridazine;
Cpd.4-30: 6-(3'-fluoro-4-fluoro-biphenyl-2-yloxy)-3-chloro-[1,2,4]triazolo[4,3-b]pyridazine;
Cpd.4-31: 6-(4'-fluoro-4-fluoro-biphenyl-2-yloxy)-3-chloro-[1,2,4]triazolo[4,3-b]pyridazine;
Cpd.4-32: 6-(5-hydroxy-biphenyl-2-yloxy)-3-chloro-[1,2,4]triazolo[4,3-b]pyridazine;
Cpd.4-33: 6-(4-trifluoromethyl-biphenyl-2-yloxy)-3-chloro-[1,2,4]triazolo[4,3-b]pyridazine;
Cpd.4-34: 6-(4'-fluoro-4-methoxy-biphenyl-2-yloxy)-3-chloro-[1,2,4]triazolo[4,3-b]pyridazine;
Cpd.4-35: 6-(5-chloro-biphenyl-2-yloxy)-3-chloro-[1,2,4]triazolo[4,3-b]pyridazine;
Cpd.4-36: 6-(5-amino-biphenyl-2-yloxy)-3-chloro-[1,2,4]triazolo[4,3-b]pyridazine;
Cpd.4-37: 6-(3'-hydroxy-4-trifluoromethyl-biphenyl-2-yloxy)-3-chloro-[1,2,4]triazolo[4,3-b]pyridazine;
Cpd.4-38 6-(4-trifluoromethyl-biphenyl-2-yloxy)-3-(trifluoromethyl)-[1,2,4]triazolo[4,3-b]pyridazine;
Cpd.4-39: 6-[2-(pyridin-3-yl)-4-(trifluoromethyl)phenyloxy]-3-chloro-[1,2,4]triazolo[4,3-b]pyridazine;
Cpd.4-40: 6-(5-trifluoromethyl-biphenyl-2-yloxy)-3-chloro-[1,2,4]triazolo[4,3-b]pyridazine.
Cpd.4-41: 3-chloro-6-(4-N,N-dimethylaminomethyl-biphenyl-2-yloxy)-[1,2,4]triazolo[4,3-b]pyridazine;
Cpd.4-42: (5-chloro-2-(3-chloro-[1,2,4]triazolo[4,3-b]pyridazin-6-yloxy)phenyl)(phenyl)methanone;
Cpd.4-43: 3-chloro-6-(4-methyloxycarbonyl-biphenyl-2-yloxy)-[1,2,4]triazolo[4,3-b]pyridazine;
Cpd.4-44: 3-chloro-6-(4-trifluoromethyl-biphenyl-2-yloxy)-[1,2,4]triazolo[4,3-b]pyridazine;
Cpd.4-45: 3-chloro-6-(4-N,N-dimethylamino-biphenyl-2-yloxy)-[1,2,4]triazolo[4,3-b]pyridazine;
Cpd.4-46: 3-chloro-6-(5-dimethylamino-biphenyl-2-yloxy)-[1,2,4]triazolo[4,3-b]pyridazine;
Cpd.4-47: 3-chloro-6-(5-methylamino-biphenyl-2-yloxy)-[1,2,4]triazolo[4,3-b]pyridazine;
Cpd.4-48: 3-chloro-6-(4-amino-biphenyl-2-yloxy)-[1,2,4]triazolo[4,3-b]pyridazine;
Cpd.4-49: 3-chloro-6-(4-acetamido-biphenyl-2-yloxy)-[1,2,4]triazolo[4,3-b]pyridazine;
Cpd.4-50: 3-chloro-6-(4-N-butylamino-biphenyl-2-yloxy)-[1,2,4]triazolo[4,3-b]pyridazine;
Cpd.4-51: 3-chloro-6-(4-N-2-methylpropylamino-biphenyl-2-yloxy)-[1,2,4]triazolo[4,3-b]pyridazine;
Cpd.4-52: 3-chloro-6-(4-N-methylamino-biphenyl-2-yloxy)-[1,2,4]triazolo[4,3-b]pyridazine;
Cpd.4-53: 3-chloro-6-(5-dipropylamino-biphenyl-2-yloxy)-[1,2,4]triazolo[4,3-b]pyridazine;
Cpd.4-54: 3-chloro-6-(5-ethylamino-biphenyl-2-yloxy)-[1,2,4]triazolo[4,3-b]pyridazine;
Cpd.4-55: 3-chloro-6-(5-diethylamino-biphenyl-2-yloxy)-[1,2,4]triazolo[4,3-b]pyridazine;
Cpd.4-56: 3-chloro-6-(5-propylamino-biphenyl-2-yloxy)-[1,2,4]triazolo[4,3-b]pyridazine;
Cpd.4-57: 3-chloro-6-(5-dibutylamino-biphenyl-2-yloxy)-[1,2,4]triazolo[4,3-b]pyridazine;
Cpd.4-58: 3-chloro-6-(5-butylamino-biphenyl-2-yloxy)-[1,2,4]triazolo[4,3-b]pyridazine;
Cpd.4-59: 3-chloro-6-(5-hydroxycarbonyl-biphenyl-2-yloxy)-[1,2,4]triazolo[4,3-b]pyridazine;
Cpd.4-60: 3-chloro-6-(4-N-methyl-N-benzylaminomethyl-biphenyl-2-yloxy)-[1,2,4]triazolo[4,3-b]pyridazine;
Cpd.4-61: 3-trifluoromethyl-6-(4,5-difluorobiphenyl-2-yloxy)-[1,2,4]triazolo[4,3-b]pyridazine;
Cpd.4-62: 3-chloro-6-(5-morpholinomethyl-biphenyl-2-yloxy)-[1,2,4]triazolo[4,3-b]pyridazine;
Cpd.4-63: 3-chloro-6-(5-N,N-dimethylaminomethyl-biphenyl-2-yloxy)-[1,2,4]triazolo[4,3-b]pyridazine;
Cpd.4-64: 3-chloro-6-(4-morpholinomethyl-biphenyl-2-yloxy)-[1,2,4]triazolo[4,3-b]pyridazine;
Cpd.4-65: 3-chloro-6-(4-aminomethyl-biphenyl-2-yloxy)-[1,2,4]triazolo[4,3-b]pyridazine;

Cpd.4-66: 3-chloro-6-(5-hydroxymethyl-biphenyl-2-yloxy)-[1,2,4]triazolo[4,3-b]pyridazine;
Cpd.4-67: 3-chloro-6-(5-isobutylamino-biphenyl-2-yloxy)-[1,2,4]triazolo[4,3-b]pyridazine;
Cpd.4-68: 3-chloro-6-(4-trifluoromethyloxy-biphenyl-2-yloxy)-[1,2,4]triazolo[4,3-b]pyridazine;
Cpd.4-69: 3-chloro-6-(5-methyloxycarbonyl-biphenyl-2-yloxy)-[1,2,4]triazolo[4,3-b]pyridazine;
Cpd.4-70: 3-chloro-6-(5-aminocarbonyl-biphenyl-2-yloxy)-[1,2,4]triazolo[4,3-b]pyridazine;
Cpd.4-71: 3-chloro-6-(3'-methoxy-4-trifluoromethyl-biphenyl-2-yloxy)-[1,2,4]triazolo[4,3-b]pyridazine;
Cpd.4-72: 3-chloro-6-(4-trifluoromethyl-3'-aminocarbonyl-biphenyl-2-yloxy)-[1,2,4]triazolo[4,3-b]pyridazine;
Cpd.4-73: 3-chloro-6-(3'-(bromomethyl)-4-(trifluoromethyl)-biphenyl-2-yloxy)-[1,2,4]triazolo[4,3-b]pyridazine hydrochloride;
Cpd.4-74: 3-chloro-6-(3'-carboxy-5-fluoro-2-yloxy)]-[1,2,4]triazolo[4,3-b]pyridazine;
Cpd.4-75: 3-chloro-6-(3'-methanoate-5-fluoro-2-yloxy)]-[1,2,4]triazolo[4,3-b]pyridazine;
Cpd.4-76: 3-chloro-6-(5-fluoro-3' methoxy-biphenyl-2-yloxy)-[1,2,4]triazolo[4,3-b]pyridazine;
Cpd.4-77: 3-chloro-6-(5-fluoro-3'-hydroxy-biphenyl-2-yloxy)-[1,2,4]triazolo[4,3-b]pyridazine;
Cpd.4-78: 3-chloro-6-(2-(2-fluoropyridin-3-yl)-5-(trifluoromethyl)phenoxy)-[1,2,4]triazolo[4,3-b]pyridazine;
Cpd.4-79: 3-chloro-6-(2-(pyridin-4-yl)-5-(trifluoromethyl)phenoxy)-[1,2,4]triazolo[4,3-b]pyridazine hydrochloride;
Cpd.4-80: 3-chloro-6-(2-(2-methoxypyridin-3-yl)-5-(trifluoromethyl)phenoxy)-[1,2,4]triazolo[4,3-b]pyridazine hydrochloride;
Cpd.4-81: 3-chloro-6-(2-(6-methoxypyridin-3-yl)-5-(trifluoromethyl)phenoxy)-[1,2,4]triazolo[4,3-b]pyridazine;
Cpd.4-82: 3-chloro-6-(2-(5-methoxypyridin-3-yl)-5-(trifluoromethyl)phenoxy)-[1,2,4]triazolo[4,3-b]pyridazine;
Cpd.4-83: 5-(2-(3-chloro-[1,2,4]triazolo[4,3-b]pyridazin-6-yloxy)-4-(trifluoromethyl)phenyl)pyridin-2(1H)-one;
Cpd.4-84: 3-chloro-6-(2-(6-ethoxypyridin-3-yl)-5-(trifluoromethyl)phenoxy)-[1,2,4]triazolo[4,3-b]pyridazine;
Cpd.4-85: 3-(2-(3-chloro-[1,2,4]triazolo[4,3-b]pyridazin-6-yloxy)-4-(trifluoromethyl)phenyl)pyridin-2(1H)-one;
Cpd.4-86: 5-(2-(3-chloro-[1,2,4]triazolo[4,3-b]pyridazin-6-yloxy)-4-(trifluoromethyl)phenyl)-1-methylpyridin-2(1H)-one;
Cpd.4-87: 3-chloro-6-(2-(6-fluoropyridin-3-yl)-5-(trifluoromethyl)phenoxy)-[1,2,4]triazolo[4,3-b]pyridazine;
Cpd.4-88: 5-(2-(3-chloro-[1,2,4]triazolo[4,3-b]pyridazin-6-yloxy)-4-(trifluoromethyl)phenyl)-1-propylpyridin-2(1H)-one;
Cpd.4-89: 1-butyl-5-(2-(3-chloro-[1,2,4]triazolo[4,3-b]pyridazin-6-yloxy)-4-(trifluoromethyl)phenyl)pyridin-2(1H)-one;
Cpd.4-90: 5-(2-(3-chloro-[1,2,4]triazolo[4,3-b]pyridazin-6-yloxy)-4-(trifluoromethyl)phenyl)-1-(2-hydroxyethyl)pyridin-2(1H)-one;
Cpd.4-91: 3-chloro-6-(2-(6-cyclohexanoxypyridin-3-yl)-5-(trifluoromethyl)phenoxy)-[1,2,4]triazolo[4,3-b]pyridazine;
Cpd.4-92: 3-chloro-6-(2-(6-propoxypyridin-3-yl)-5-(trifluoromethyl)phenoxy)-[1,2,4]triazolo[4,3-b]pyridazine hydrochloride;
Cpd.4-93: 6-(2-(6-butoxypyridin-3-yl)-5-(trifluoromethyl)phenoxy)-3-chloro-[1,2,4]triazolo[4,3-b]pyridazine hydrochloride;
Cpd.4-94: 3-chloro-6-(2-(6-isopropoxypyridin-3-yl)-5-(trifluoromethyl)phenoxy)-[1,2,4]triazolo[4,3-b]pyridazine;
Cpd.4-95: 3-chloro-6-(2-(6-hexyloxypyridin-3-yl)-5-(trifluoromethyl)phenoxy)-[1,2,4]triazolo[4,3-b]pyridazine hydrochloride;
Cpd.4-96: 5-(2-(3-chloro-[1,2,4]triazolo[4,3-b]pyridazin-6-yloxy)-4-(trifluoromethyl)phenyl)pyridin-3-ol;
Cpd.4-97: 3-chloro-6-(2-(pyridin-2-yl)-5-(trifluoromethyl)phenoxy)-[1,2,4]triazolo[4,3-b]pyridazine hydrochloride;
Cpd.4-98: 3-chloro-6-(2-(pyridin-3-yl)phenoxy)-[1,2,4]triazolo[4,3-b]pyridazine hydrochloride;
Cpd.4-99: 3-chloro-6-(2-(pyrimidin-5-yl)-5-(trifluoromethyl)phenoxy)-[1,2,4]triazolo[4,3-b]pyridazine;
Cpd.4-100: 3-chloro-6-(2-(4-methoxypyridin-3-yl)-5-(trifluoromethyl)phenoxy)-[1,2,4]triazolo[4,3-b]pyridazine;
Cpd.4-101: 3-chloro-6-(2-(6-chloropyridin-3-yl)-5-(trifluoromethyl)phenoxy)-[1,2,4]triazolo[4,3-b]pyridazine;
Cpd.4-102: 5-(2-(3-chloro-[1,2,4]triazolo[4,3-b]pyridazin-6-yloxy)-4-(trifluoromethyl)phenyl)-N,N-dimethylpyridin-2-amine;
Cpd. 4-103: 3-chloro-6-(2-(thiazol-4-yl)phenoxy)-[1,2,4]triazolo[4,3-b]pyridazine;
Cpd.4-104: 3-chloro-6-(2-(thiazol-2-yl)phenoxy)-[1,2,4]triazolo[4,3-b]pyridazine;
Cpd.4-105: 3-chloro-6-(2-(thiazol-2-yl)-5-(trifluoromethyl)phenoxy)-[1,2,4]triazolo[4,3-b]pyridazine;
Cpd.4-106: 3-chloro-6-(2-(thiazol-4-yl)-5-(trifluoromethyl)phenoxy)-[1,2,4]triazolo[4,3-b]pyridazine;
Cpd.4-107: 3-chloro-6-(4-fluoro-2-(pyridin-3-yl)phenoxy)-[1,2,4]triazolo[4,3-b]pyridazine;
Cpd.4-108: 3-chloro-6-(2-(thiophen-3-yl)phenoxy)-[1,2,4]triazolo[4,3-b]pyridazine;
Cpd.4-109: 3-chloro-6-(2-(3,5-dimethylisoxazol-4-yl)phenoxy)-[1,2,4]triazolo[4,3-b]pyridazine;
Cpd.4-110: 6-(2-(benzo[d]thiazol-5-yl)phenoxy)-3-chloro-[1,2,4]triazolo[4,3-b]pyridazine;
Cpd.4-111: 3-chloro-6-(2'-methoxybiphenyl-2-yloxy)-[1,2,4]triazolo[4,3-b]pyridazine;
Cpd.4-112: 3-chloro-6-[(3'-fluoro-4-methoxybiphenyl-2-yl)oxy]-[1,2,4]triazolo[4,3-b]pyridazine;
Cpd.4-113: 3-chloro-6-{[4-methoxy-3'-(trifluoromethyl)biphenyl-2-yl]oxy}-[1,2,4]triazolo[4,3-b]pyridazine;
Cpd.4-114: 3-chloro-6-[5-chloro-2-(2,4-dichloro-phenoxy)-phenoxy]-[1,2,4]triazolo[4,3-b]pyridazine;
Cpd.4-115: 3-chloro-6-(5,3',4'-trifluorobiphenyl-2-yloxy)-[1,2,4]triazolo[4,3-b]pyridazine;
Cpd.4-116: 3-chloro-6-(5,4'-difluorobiphenyl-2-yloxy)-[1,2,4]triazolo[4,3-b]pyridazine;
Cpd.4-117: 3-chloro-6-(4'-chlorobiphenyl-2-yloxy)-[1,2,4]triazolo[4,3-b]pyridazine;
Cpd.4-118: 3-chloro-6-(4'-chloro-5-fluorobiphenyl-2-yloxy)-[1,2,4]triazolo[4,3-b]pyridazine;
Cpd.4-119: 3-chloro-6-(3'-amino-5-fluorobiphenyl-2-yloxy)-[1,2,4]triazolo[4,3-b]pyridazine;
Cpd. 4-120: 3-chloro-6-(3',5-difluorobiphenyl-2-yloxy)-[1,2,4]triazolo[4,3-b]pyridazine;
Cpd.4-121: 3-chloro-6-(2',5-difluorobiphenyl-2-yloxy)-[1,2,4]triazolo[4,3-b]pyridazine;
Cpd.4-122: 3-chloro-6-(2-(morpholinomethyl)-5-(trifluoromethyl)phenoxy)-[1,2,4]triazolo[4,3-b]pyridazine;
Cpd.4-123: 3-chloro-6-(2-(2-methylpyridin-3-yl)-5-(trifluoromethyl)phenoxy)-[1,2,4]triazolo[4,3-b]pyridazine;
Cpd.4-124: 3-chloro-6-(2-((4-methylpiperazin-1-yl)methyl)-5-(trifluoromethyl)phenoxy)-[1,2,4]triazolo[4,3-b]pyridazine;
Cpd.4-125: 3-chloro-6-(4-N-hexylaminobiphenyl-2-yloxy)-[1,2,4]triazolo[4,3-b]pyridazine;
Cpd.4-126: 3-(trifluoromethyl)-6-(2-(pyridin-3-yl)-5-(trifluoromethyl)phenoxy)-[1,2,4]triazolo[4,3-b]pyridazine;

Cpd.4-127: 3-chloro-6-((2-(2-methoxypyrimidin-5-yl))-5-(trifluoromethyl)phenoxy)-[1,2,4]triazolo[4,3-b]pyridazine;
Cpd.4-128: 3-chloro-6-((2-(4-isopropylpyrimidin-5-yl))-5-(trifluoromethyl)phenoxy)-[1,2,4]triazolo[4,3-b]pyridazine;
Cpd.4-129: 3-chloro-6-(2-(pyridin-3-yl)-3-(trifluoromethyl)phenoxy)-[1,2,4]triazolo[4,3-b]pyridazine;
Cpd.4-130: 3-chloro-6-((2-(2-methoxy-4-methylpyridin-3-yl))-5-(trifluoromethyl)phenoxy)-[1,2,4]triazolo[4,3-b]pyridazine;
Cpd.4-131: 3-chloro-6-((2-(2-methoxy-5-fluoropyridin-3-yl))-5-(trifluoromethyl)phenoxy)-[1,2,4]triazolo[4,3-b]pyridazine;
Cpd.4-132: 3-chloro-6-(3'-methylbiphenyl-2-yloxy)-[1,2,4]triazolo[4,3-b]pyridazine;
Cpd.4-133: 3-(trifluoromethyl)-6-(3'-methylbiphenyl-2-yloxy)-[1,2,4]triazolo[4,3-b]pyridazine;
Cpd.4-134: 3-chloro-6-(5-nitrobiphenyl-2-yloxy)-[1,2,4]triazolo[4,3-b]pyridazine;
Cpd.4-135: 3-chloro-6-(5-fluoro-3'-methylbiphenyl-2-yloxy)-[1,2,4]triazolo[4,3-b]pyridazine;
Cpd.4-136: 3-(trifluoromethyl)-6-(5-fluoro-3'-methylbiphenyl-2-yloxy)-[1,2,4]triazolo[4,3-b]pyridazine;
Cpd.4-137: 3-(trifluoromethyl)-6-(3'-methoxy-4-(trifluoromethyl)biphenyl-2-yloxy)-[1,2,4]triazolo[4,3-b]pyridazine;
Cpd.4-138: 3-(trifluoromethyl)-6-(3'-hydroxy-4-(trifluoromethyl)biphenyl-2-yloxy)-[1,2,4]triazolo[4,3-b]pyridazine;
Cpd.4-139: 3-chloro-6-(5-ethoxybiphenyl-2-yloxy)-[1,2,4]triazolo[4,3-b]pyridazine;
Cpd.4-140: 3-Chloro-6-(3'-(methyloxycarbonyl)biphenyl-2-yloxy)-[1,2,4]triazolo[4,3-b]pyridazine;
Cpd.4-141: 3-(trifluoromethyl)-6-(5-fluorobiphenyl-2-yloxy)-[1,2,4]triazolo[4,3-b]pyridazine;
Cpd.4-142: 3-(trifluoromethyl)-6-(5-fluoro-4'-methylbiphenyl-2-yloxy)-[1,2,4]triazolo[4,3-b]pyridazine;
Cpd.4-143: 3-chloro-6-(5-fluoro-4'-methylbiphenyl-2-yloxy)-[1,2,4]triazolo[4,3-b]pyridazine;
Cpd.4-144: 3-chloro-6-(2-benzoyl-5-methoxy-phenoxy)-[1,2,4]triazolo[4,3-b]pyridazine;
Cpd.4-145: 3-chloro-6-(4-bromo-2-benzoyl-phenoxy)-[1,2,4]triazolo[4,3-b]pyridazine;
Cpd.4-146: 6-(2-benzyl-4-chloro-phenoxy)-3-chloro-[1,2,4]triazolo[4,3-b]pyridazine;
Cpd.4-147: 3-chloro-6-(4-fluoro-3'-piperidin-1-ylmethylbiphenyl-2-yloxy)-[1,2,4]triazolo[4,3-b]pyridazine, hydrochloride;
Cpd.4-148: 3-chloro-6-(5-fluoro-3'-(trifluoromethyl)biphenyl-2-yloxy)-[1,2,4]triazolo[4,3-b]pyridazine;
Cpd.4-149: 3-(trifluoromethyl)-6-(5-fluoro-3'-methoxybiphenyl-2-yloxy)-[1,2,4]triazolo[4,3-b]pyridazine;
Cpd.4-150: 3-(trifluoromethyl)-6-(4,5-difluoro-3'-methoxybiphenyl-2-yloxy)-[1,2,4]triazolo[4,3-b]pyridazine;
Cpd.4-151: 3-(trifluoromethyl)-6-(4,5-difluoro-3'-hydroxybiphenyl-2-yloxy)-[1,2,4]triazolo[4,3-b]pyridazine;
Cpd.4-152: 3-chloro-6-(4,5-difluoro-3'-methoxybiphenyl-2-yloxy)-[1,2,4]triazolo[4,3-b]pyridazine;
Cpd.4-153: 3-chloro-6-(4,5-difluoro-3'-hydroxybiphenyl-2-yloxy)-[1,2,4]triazolo[4,3-b]pyridazine;
Cpd.4-154: 3-chloro-6-(5-cyanobiphenyl-2-yloxy)-[1,2,4]triazolo[4,3-b]pyridazine;
Cpd.4-155: 3-chloro-6-(4-(hydroxymethyl)biphenyl-2-yloxy)-[1,2,4]triazolo[4,3-b]pyridazine;
Cpd.4-156: 3-chloro-6-(5-piperidin-1-ylmethylbiphenyl-2-yloxy)-[1,2,4]triazolo[4,3-b]pyridazine;
Cpd.4-157: 3-chloro-6-(5-diethylaminomethylbiphenyl-2-yloxy)-[1,2,4]triazolo[4,3-b]pyridazine;
Cpd.4-158: 3-chloro-6-(5-(benzylmethylaminomethyl)biphenyl-2-yloxy)-[1,2,4]triazolo[4,3-b]pyridazine;
Cpd.4-159: 3-chloro-6-(5-(4-methylpiperazin-1-ylmethyl)biphenyl-2-yloxy)-[1,2,4]triazolo[4,3-b]pyridazine;
Cpd.4-160: 3-chloro-6-(5-(cyclopentylaminomethyl)biphenyl-2-yloxy)-[1,2,4]triazolo[4,3-b]pyridazine;
Cpd.4-161: 3-chloro-6-(5-(cyclopropylaminomethyl)biphenyl-2-yloxy)-[1,2,4]triazolo[4,3-b]pyridazine;
Cpd.4-162: 3-chloro-6-(5-((cyclohexylmethyl)aminomethyl)biphenyl-2-yloxy)-[1,2,4]triazolo[4,3-b]pyridazine;
Cpd.4-163: 3-chloro-6-(5-(tetrahydrofurfurylaminomethyl)biphenyl-2-yloxy)-[1,2,4]triazolo[4,3-b]pyridazine;
Cpd.4-164: 3-chloro-6-(5-(4-methanesulfonyl-piperazin-1-ylmethyl)biphenyl-2-yloxy)-[1,2,4]triazolo[4,3-b]pyridazine;
Cpd.4-165: 3-chloro-6-(5-(methylphenethylaminomethyl)biphenyl-2-yloxy)-[1,2,4]triazolo[4,3-b]pyridazine;
Cpd.4-166: 3-chloro-6-(5-(diisopropylaminomethyl)biphenyl-2-yloxy)-[1,2,4]triazolo[4,3-b]pyridazine;
Cpd.4-167: 3-chloro-6-(5-(methyl-cyclohexylaminomethyl)biphenyl-2-yloxy)-[1,2,4]triazolo[4,3-b]pyridazine;
Cpd.4-168: 3-chloro-6-(4-(trifluoromethyl)-3'-(cyclopropylaminomethyl)biphenyl-2-yloxy)-[1,2,4]triazolo[4,3-b]pyridazine, hydrochloride;
Cpd.4-169: 3-chloro-6-(4-cyanobiphenyl-2-yloxy)-[1,2,4]triazolo[4,3-b]pyridazine;
Cpd.4-170: 3-chloro-6-(5-(tertbutyloxycarbonylaminomethyl)biphenyl-2-yloxy)-[1,2,4]triazolo[4,3-b]pyridazine;
Cpd.4-171: 3-chloro-6-(5-aminomethylbiphenyl-2-yloxy)-[1,2,4]triazolo[4,3-b]pyridazine, trifluoroacetic acid salt;
Cpd.4-172: 3-chloro-6-(4-methylcarbonyloxymethylbiphenyl-2-yloxy)-[1,2,4]triazolo[4,3-b]pyridazine;
Cpd.4-173: 3-chloro-6-(5-methylsulfonamidobiphenyl-2-yloxy)-[1,2,4]triazolo[4,3-b]pyridazine;
Cpd.4-174: 3-chloro-6-(5-acetamidobiphenyl-2-yloxy)-[1,2,4]triazolo[4,3-b]pyridazine;
Cpd.4-175: 3-chloro-6-(4-((3-methylbutyl)amino)biphenyl-2-yloxy)-[1,2,4]triazolo[4,3-b]pyridazine;
Cpd.4-176: 3-chloro-6-(4-(cyclohexylmethyl)aminomethyl-biphenyl-2-yloxy)-[1,2,4]triazolo[4,3-b]pyridazine;
Cpd.4-177: 3-chloro-6-(4-(1-methylpiperazin-4-ylmethyl)biphenyl-2-yloxy)-[1,2,4]triazolo[4,3-b]pyridazine;
Cpd.4-178: 3-chloro-6-(4-cyclopropylaminomethylbiphenyl-2-yloxy)-[1,2,4]triazolo[4,3-b]pyridazine;
Cpd.4-179: 3-chloro-6-(4-cyclopentylaminomethylbiphenyl-2-yloxy)-[1,2,4]triazolo[4,3-b]pyridazine;
Cpd.4-180: 3-chloro-6-(4-tetrahydrofurfurylaminomethyl)biphenyl-2-yloxy)-[1,2,4]triazolo[4,3-b]pyridazine;
Cpd.4-181: 3-chloro-6-(4-(methylphenethylaminomethyl)biphenyl-2-yloxy)-[1,2,4]triazolo[4,3-b]pyridazine;
Cpd.4-182: 3-chloro-6-(4-(4-methanesulfonylpiperazin-1-ylmethyl)biphenyl-2-yloxy)-[1,2,4]triazolo[4,3-b]pyridazine;
Cpd.4-183: 3-chloro-6-(4-piperidin-1-ylmethylbiphenyl-2-yloxy)-[1,2,4]triazolo[4,3-b]pyridazine;
Cpd.4-184: 3-chloro-6-(4-diethylaminomethylbiphenyl-2-yloxy)-[1,2,4]triazolo[4,3-b]pyridazine;
Cpd. 4-185: 3-chloro-6-(4-((cyclohexylethyl)amino)biphenyl-2-yloxy)-[1,2,4]triazolo[4,3-b]pyridazine;
Cpd.4-186: 3-chloro-6-(4-tertbutyloxycarbonylaminomethylbiphenyl-2-yloxy)-[1,2,4]triazolo[4,3-b]pyridazine;
Cpd.4-187: 3-chloro-6-(5-fluoro-3'-nitrobiphenyl-2-yloxy)-[1,2,4]triazolo[4,3-b]pyridazine;
Cpd.4-188: 3-chloro-6-(5,2',4'-trifluorobiphenyl-2-yloxy)-[1,2,4]triazolo[4,3-b]pyridazine;

Cpd.4-189: 3-chloro-6-(4-isopropylamino-biphenyl-2-yloxy)-[1,2,4]triazolo[4,3-b]pyridazine;
Cpd.4-190: 3-chloro-6-(5-methyloxycarbonylethylamino-biphenyl-2-yloxy)-[1,2,4]triazolo[4,3-b]pyridazine;
Cpd.4-191: 3-chloro-6-(5-ethylcarbonylamino-biphenyl-2-yloxy)-[1,2,4]triazolo[4,3-b]pyridazine;
Cpd.4-192: 3-chloro-6-(5-isopropylcarbonylamino-biphenyl-2-yloxy)-[1,2,4]triazolo[4,3-b]pyridazine;
Cpd.4-193: 3-chloro-8-methyl-6-((2-(2-methoxy-5-fluoropyridin-3-yl))-5-(trifluoromethyl)-phenoxy)-[1,2,4]triazolo[4,3-b]pyridazine;
Cpd.4-194: 3-chloro-6-(4-chloro-2-(pyrimidin-5-yl)phenoxy)-[1,2,4]triazolo[4,3-b]pyridazine;
Cpd.4-195: 3-chloro-6-(4-chloro-2-(2-methoxypyrimidin-5-yl)phenoxy)-[1,2,4]triazolo[4,3-b]pyridazine;
Cpd.4-196: 3-chloro-6-(2-(6-methylpyridin-3-yl)-5-(trifluoromethyl)phenoxy)-[1,2,4]triazolo[4,3-b]pyridazine;
Cpd.4-197: 3-chloro-6-(5-(5-methyl-1,2,4-oxadiazol-3-yl)-2-(phenyl)phenoxy)-[1,2,4]triazolo[4,3-b]pyridazine;
Cpd.4-198: 3-chloro-6-(4-(5-methyl-1,2,4-oxadiazol-3-yl)-2-(phenyl)phenoxy)-[1,2,4]triazolo[4,3-b]pyridazine;
Cpd.4-199: 3-chloro-6-(5-(5-methyl-1,2,4-oxadiazol-3-yl)-2-(pyridin-3-yl)phenoxy)-[1,2,4]triazolo[4,3-b]pyridazine;
Cpd.5-1: 3-chloro-6-(4-trifluoromethyl-biphenyl-2-yloxy)-[1,2,4]triazolo[3,4-a]phthalazine;
Cpd.5-2: 3-chloro-6-(4-trifluoromethyl-biphenyl-2-yloxy)-9-fluoro-[1,2,4]triazolo[3,4-a]phthalazine;
Cpd.5-3: 3-chloro-6-(4-trifluoromethyl-biphenyl-2-yloxy)-8-fluoro-[1,2,4]triazolo[3,4-a]phthalazine;
Cpd.5-4: 3-chloro-8-phenyl-6-(4-trifluoromethyl-biphenyl-2-yloxy)-[1,2,4]triazolo[4,3-b]pyridazine;
Cpd.5-5: 3-chloro-7-phenyl-6-(4-trifluoromethyl-biphenyl-2-yloxy)-[1,2,4]triazolo[4,3-b]pyridazine;
Cpd.5-6: 3-chloro-8-methyl-6-(4-trifluoromethyl-biphenyl-2-yloxy)-[1,2,4]triazolo[4,3-b]pyridazine;
Cpd.5-7: 3-chloro-7-methyl-6-(4-trifluoromethyl-biphenyl-2-yloxy)-[1,2,4]triazolo[4,3-b]pyridazine;
Cpd.5-8: 3-chloro-8-isopropyl-6-(4-trifluoromethyl-biphenyl-2-yloxy)-[1,2,4]triazolo[4,3-b]pyridazine;
Cpd.5-9: 3-chloro-6-(4-trifluoromethyl-biphenyl-2-yloxy)-9-methyl-[1,2,4]triazolo[3,4-a]phthalazine;
Cpd.5-10: 3-chloro-6-(4-trifluoromethyl-biphenyl-2-yloxy)-8-methyl-[1,2,4]triazolo[3,4-a]phthalazine;
Cpd.5-11: 3-chloro-7-isopropyl-6-(4-trifluoromethyl-biphenyl-2-yloxy)-[1,2,4]triazolo[4,3-b]pyridazine;
Cpd.5-12: 3-chloro-7,8-diethyl-6-(4-trifluoromethyl-biphenyl-2-yloxy)-[1,2,4]triazolo[4,3-b]pyridazine;
Cpd.5-13: 3-chloro-8-ethyl-6-(4-trifluoromethyl-biphenyl-2-yloxy)-[1,2,4]triazolo[4,3-b]pyridazine;
Cpd.5-14: 3-chloro-7-cyclopropyl-6-(4-trifluoromethyl-biphenyl-2-yloxy)-[1,2,4]triazolo[4,3-b]pyridazine;
Cpd.5-15: 3-chloro-6-(2-(pyridin-3-yl)-5-(trifluoromethyl)phenoxy)-[1,2,4]triazolo[3,4-a]phthalazine;
Cpd.5-16: 3-chloro-8-methyl-6-(2-(6-methylpyridin-3-yl)-5-(trifluoromethyl)phenoxy)-[1,2,4]triazolo[4,3-b]pyridazine;
Cpd.5-17: 3-chloro-7-methyl-6-(2-(6-methylpyridin-3-yl)-5-(trifluoromethyl)phenoxy)-[1,2,4]triazolo[4,3-b]pyridazine;
Cpd.5-18: 3-chloro-6-(2-(6-methylpyridin-3-yl)-5-(trifluoromethyl)phenoxy)-[1,2,4]triazolo[3,4-a]phthalazine;
Cpd.5-19: 3-chloro-8-methyl-6-(2-(2-methylpyridin-3-yl)-5-(trifluoromethyl)phenoxy)-[1,2,4]triazolo[4,3-b]pyridazine;
Cpd.5-20: 3-chloro-7-methyl-6-(2-(2-methylpyridin-3-yl)-5-(trifluoromethyl)phenoxy)-[1,2,4]triazolo[4,3-b]pyridazine;
Cpd.5-21: 3-chloro-6-(2-(2-methylpyridin-3-yl)-5-(trifluoromethyl)phenoxy)-[1,2,4]triazolo[3,4-a]phthalazine;
Cpd.5-22: 3-chloro-6-(2-(pyrimidin-5-yl)-5-(trifluoromethyl)phenoxy)-[1,2,4]triazolo[3,4-a]phthalazine;
Cpd.5-23: 3-chloro-6-(2-(2-methoxypyridin-3-yl))-5-(trifluoromethyl)phenoxy)-8-methyl-[1,2,4]triazolo[4,3-b]pyridazine;
Cpd.5-24: 3-chloro-7-methyl-6-((2-(2-methoxypyridin-3-yl))-5-(trifluoromethyl)phenoxy)-[1,2,4]triazolo[4,3-b]pyridazine;
Cpd.5-25: 3-chloro-7,8-dimethyl-6-((2-(2-methoxypyridin-3-yl))-5-(trifluoromethyl)phenoxy)-[1,2,4]triazolo[4,3-b]pyridazine;
Cpd.5-26: 3-chloro-7-methyl-6-((2-(2-methoxy-5-(trifluoromethyl)pyridin-3-yl))-5-(trifluoromethyl)phenoxy)-[1,2,4]triazolo[4,3-b]pyridazine;
Cpd.5-27: 3-chloro-8-methyl-6-((2-(2-methoxy-5-methylpyridin-3-yl))-5-(trifluoromethyl)phenoxy)-[1,2,4]triazolo[4,3-b]pyridazine;
Cpd.5-28: 3-chloro-7-methyl-6-((2-(2-methoxy-5-methylpyridin-3-yl))-5-(trifluoromethyl)phenoxy)-[1,2,4]triazolo[4,3-b]pyridazine;
Cpd.5-29: 3-chloro-7-methyl-6-(2-(pyrimidin-5-yl)-5-(trifluoromethyl)phenoxy)-[1,2,4]triazolo[4,3-b]pyridazine;
Cpd.5-30: 3-chloro-8-methyl-6-(2-(pyrimidin-5-yl)-5-(trifluoromethyl)phenoxy)-[1,2,4]triazolo[4,3-b]pyridazine;
Cpd.5-31: 3-chloro-6-(2-fluoro-6-(pyrimidin-5-yl)-3-(trifluoromethyl)phenoxy)-7-methyl-[1,2,4]triazolo[4,3-b]pyridazine;
Cpd.5-32: 8-methyl-6-(2-(pyridin-3-yl)-5-(trifluoromethyl)phenoxy)-3-(trifluoromethyl)-[1,2,4]triazolo[4,3-b]pyridazine;
Cpd.5-33: 7-methyl-6-(2-(pyridin-3-yl)-5-(trifluoromethyl)phenoxy)-3-(trifluoromethyl)-[1,2,4]triazolo[4,3-b]pyridazine;
Cpd.5-34: 3-chloro-8-methyl-6-((2-(2-methoxypyrimidin-5-yl))-5-(trifluoromethyl)phenoxy)-[1,2,4]triazolo[4,3-b]pyridazine;
Cpd.5-35: 3-chloro-7-methyl-6-((2-(2-methoxypyrimidin-5-yl))-5-(trifluoromethyl)phenoxy)-[1,2,4]triazolo[4,3-b]pyridazine;
Cpd.5-36: 3-chloro-6-((2-(2-methoxypyrimidin-5-yl))-5-(trifluoromethyl)phenoxy)-[1,2,4]triazolo[3,4-a]phthalazine;
Cpd.5-37: 3-chloro-8-methyl-6-((2-(2-methylpyrimidin-5-yl))-5-(trifluoromethyl)phenoxy)-[1,2,4]triazolo[4,3-b]pyridazine;
Cpd.5-38: 3-chloro-8-methyl-6-((2-(4-isopropylpyrimidin-5-yl))-5-(trifluoromethyl)phenoxy)-[1,2,4]triazolo[4,3-b]pyridazine;
Cpd.5-39: 3-chloro-8-methyl-6-((2-(2-methoxy-4-methylpyridin-3-yl))-5-(trifluoromethyl)phenoxy)-[1,2,4]triazolo[4,3-b]pyridazine;
Cpd.5-40: 3-chloro-7-methyl-6-((2-(2-methoxy-4-methylpyridin-3-yl))-5-(trifluoromethyl)phenoxy)-[1,2,4]triazolo[4,3-b]pyridazine;
Cpd.5-41: 3-chloro-7-methyl-6-((2-(2-methoxy-5-fluoropyridin-3-yl))-5-(trifluoromethyl)phenoxy)-[1,2,4]triazolo[4,3-b]pyridazine;
Cpd.5-42: 3-chloro-8-methyl-6-(2-(pyrimidin-5-yl)-3-(trifluoromethyl)phenoxy)-[1,2,4]triazolo[4,3-b]pyridazine;
Cpd.5-43: 3-ethyl-7-methyl-6-(2-(pyrimidin-5-yl)-5-(trifluoromethyl)phenoxy)-[1,2,4]triazolo[4,3-b]pyridazine;

Cpd.5-44: 7-methyl-6-(2-(pyrimidin-5-yl)-5-(trifluoromethyl)phenoxy)-[1,2,4]triazolo[4,3-b]pyridazine;
Cpd.5-45: 3-chloro-8-methyl-6-(2-(4-methylpyrimidin-5-yl)-5-(trifluoromethyl)phenoxy)-[1,2,4]triazolo[4,3-b]pyridazine;
Cpd.5-46: 8-methyl-6-(2-(pyrimidin-5-yl)-5-(trifluoromethyl)phenoxy)-[1,2,4]triazolo[4,3-b]pyridazine;
Cpd.5-47: 3-chloro-7-methyl-6-(2-(4-methylpyrimidin-5-yl)-5-(trifluoromethyl)phenoxy)-[1,2,4]triazolo[4,3-b]pyridazine;
Cpd.5-48: 3-ethyl-8-methyl-6-(2-(pyrimidin-5-yl)-5-(trifluoromethyl)phenoxy)-[1,2,4]triazolo[4,3-b]pyridazine;
Cpd.5-49: 3-ethyl-7-methyl-6-(2-(pyridin-3-yl)-5-(trifluoromethyl)phenoxy)-[1,2,4]triazolo[4,3-b]pyridazine;
Cpd.5-50: 3-chloro-6-(2-(2,4-dimethoxypyrimidin-5-yl)-5-(trifluoromethyl)phenoxy)-8-methyl-[1,2,4]triazolo[4,3-b]pyridazine;
Cpd.5-51: 3-chloro-6-(2-(2,4-dimethoxypyrimidin-5-yl)-5-(trifluoromethyl)phenoxy)-7-methyl-[1,2,4]triazolo[4,3-b]pyridazine;
Cpd.5-52: 3-chloro-6-(2-(4-ethylpyrimidin-5-yl)-5-(trifluoromethyl)phenoxy)-7-methyl-[1,2,4]triazolo[4,3-b]pyridazine;
Cpd.5-53: 3-chloro-6-(2-(4-ethylpyrimidin-5-yl)-5-(trifluoromethyl)phenoxy)-8-methyl-[1,2,4]triazolo[4,3-b]pyridazine;
Cpd.5-54: 3-chloro-6-(2-(2,4-dimethoxypyrimidin-5-yl)-5-(trifluoromethyl)phenoxy)-[1,2,4]triazolo[3,4-a]phthalazine;
Cpd.5-55: 3-chloro-6-(4-chloro-2-(2-methoxypyrimidin-5-yl)phenoxy)-8-methyl-[1,2,4]triazolo[4,3-b]pyridazine;
Cpd.5-56: 3-chloro-6-(4-chloro-2-(2-methoxypyrimidin-5-yl)phenoxy)-7-methyl-[1,2,4]triazolo[4,3-b]pyridazine;
Cpd.5-57: 3-chloro-6-(4-chloro-2-(2-methoxypyrimidin-5-yl)phenoxy)-[1,2,4]triazolo[3,4-a]phthalazine;
Cpd.5-58: 3-chloro-6-(4-chloro-2-(pyrimidin-5-yl)phenoxy)-8-methyl-[1,2,4]triazolo[4,3-b]pyridazine;
Cpd.5-59: 3-chloro-6-(4-chloro-2-(pyrimidin-5-yl)phenoxy)-7-methyl-[1,2,4]triazolo[4,3-b]pyridazine;
Cpd.5-60: 3-chloro-6-(4-chloro-2-(pyrimidin-5-yl)phenoxy)-[1,2,4]triazolo[3,4-a]phthalazine;
Cpd.5-61: 7-methyl-6-(2-(pyrimidin-5-yl)-5-(trifluoromethyl)phenoxy)-3-(trifluoromethyl)-[1,2,4]triazolo[4,3-b]pyridazine;
Cpd.5-62: 6-(2-(pyrimidin-5-yl)-5-(trifluoromethyl)phenoxy)-3-(trifluoromethyl)-[1,2,4]triazolo[3,4-a]phthalazine;
Cpd.5-63: 8-methyl-6-(2-(pyrimidin-5-yl)-5-(trifluoromethyl)phenoxy)-3-(trifluoromethyl)-[1,2,4]triazolo[4,3-b]pyridazine;
Cpd.5-64: 6-(2-(pyrimidin-5-yl)-5-(trifluoromethyl)phenoxy)-[1,2,4]triazolo[3,4-a]phthalazine;
Cpd.5-65: 3-chloro-7-methyl-6-(4-(5-methyl-1,2,4-oxadiazol-3-yl)-2-(phenyl)phenoxy)-[1,2,4]triazolo[4,3-b]pyridazine.

Alternative compounds of General Formula (I) can be produced by selecting specific combinations of the groups indicated above and tested in a relevant assay for Rev-Erb activation as disclosed in the literature and in the Examples for characterizing them as Rev-Erb agonist, and consequently as having medical uses associated to inflammatory disorders and circadian rhythm-related disorders.

The term "alkyl" refers to a saturated hydrocarbon radical that is linear or branched, having preferably from one to seven, and even more preferably from one to four carbon atoms, such as methyl, ethyl, n-propyl, isopropyl, n-butyl, isobutyl, tert-butyl, or sec-butyl.

The term "alkoxy" or "alkylthio" refers to an alkyl group that is linked to the remainder of the compound by an oxygen atom or a sulfur atom (as a thioether bond or a sulfone group), respectively.

The term "alkylamino" refers to monoalkylamino (—NHR) or dialkylamino (—NRR') group where a NH group or a nitrogen atom linked to the remainder of the compound is substituted by one or two alkyl groups, respectively, said alkyl groups being substituted or not with a cycloalkyl group, an aryl group, a heterocyclic group, or an alkyloxycarbonyl group.

The term "cycloalkylamino" refers to a —NH-cycloalkyl group or a —N(alkyl)cycloalkyl group.

The term "amino group" designates a —NH$_2$ group.

The term "alkylcarbamate" designates a —NH—COO-alkyl group.

The term "alkylsulfonamide" designates a —NH—SO$_2$-alkyl group.

The term "alkylsulfonyl" designates a —SO$_2$-alkyl group.

The term "cycloalkyl" designates an alkyl group that forms one cycle having preferably from three to fourteen carbon atoms, and more preferably five to six carbon atoms, such as cyclopentyl and cyclohexyl.

The term "cycloalkyloxy" refers to a cycloalkyl group that is linked to the remainder of the compound by an oxygen atom.

The term "aryl" designates an aromatic group, substituted or not, having preferably from six to fourteen carbon atoms such as phenyl, a-naphtyl, b-naphtyl, or biphenyl.

The term "heterocyclic" refers to a heterocycloalkyl group or a heteroaryl group.

The term "heterocycloalkyl" group refers to a cycloalkyl as indicated above that further comprises one or several heteroatoms selected among nitrogen, oxygen or sulfur. They generally comprise from four to fourteen carbon atoms, such as morpholinyl, piperidinyl, tetrahydropyranyl, dithiolanyl.

The term "heteroaryl" refers to an aryl group as indicated above that further comprises one or several heteroatoms selected among nitrogen, oxygen or sulfur. They generally comprise from four to fourteen carbon atoms, such as furanyl, thiophenyl, pyridinyl, pyrimidinyl, quinoleinyl, or isoquinoleinyl.

By halogen atom, an atom of bromine, chlorine, fluorine or iodine is understood.

In the context of the present invention, when R2 and R3, together with the carbon atoms to which they are attached, form a 5- to 8-membered cycle, the compound of formula (I) can be represented by formula (I') below:

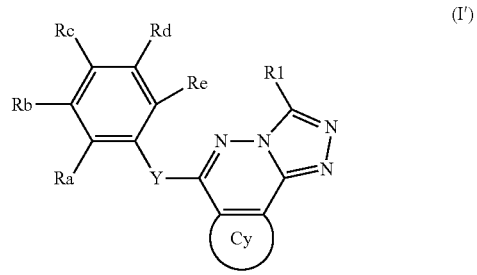

(I')

wherein Cy is a cycle such as a cycloalkyl, heterocycloalkyl, aryl or heteroaryl. Said cycle may be either unsubstituted, or substituted with at least one substituent selected in the group consisting of a hydrogen atom, a halogen atom, a hydroxyl group, a COOH group, a CO-alkyl group, a COO-alkyl group, a CONH2 group, an amino group, an alkyl group, a cycloalkyl group, an alkoxy group, an alkylthio group, an alkylamino group or a dialkylamino group. For example, when R2 and R3, together with the carbon atoms to which they are attached, form a phenyl group, the corresponding compounds is represented by formula (I"):

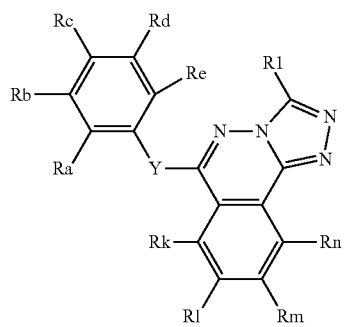

In formula (I"), Rk, Rl, Rm and Rn represent indepentyl a hydrogen atom, a halogen atom, a hydroxyl group, a COOH group, a CO-alkyl group, a COO-alkyl group, a CONH2 group, an amino group, an alkyl group, a cycloalkyl group, an alkoxy group, an alkylthio group, an alkylamino group or a dialkylamino group. In a particular embodiment, either R1 or Rm, or both, represents a halogen atom, an alkyl group or a cycloalkyl group and Rk and Rn represent hydrogen atoms.

The term "Rev-Erb agonist" refers to a compound that, following the binding to a Rev-Erb isoform, for example Rev-Erb alpha and/or Rev-Erb beta, exhibits modulation of the expression of a gene that is under the control of said Rev-Erb isoform. In particular, the term "Rev-Erb alpha agonist" or "Rev-Erb dual agonist" refers to a compound that, following the binding to Rev-Erb-Alpha or Rev-Erb alpha and beta, exhibits modulation of the expression of a gene that is under the control of Rev-Erb alpha or Rev-Erb beta. In vitro, the Rev-Erb alpha agonist, such as a compound of General Formula (I), exhibits an $EC_{50}$ equal or below 10 µM, preferably equal or below around 6 µM, and more preferably equal or below 1 µM, or a 130% fold activation when compared to the control condition (DMSO) by specifically binding Rev-Erb alpha or Rev-Erb alpha and beta and inhibiting (when comparing the basal level of transcription that is measured in absence of such agonist) the transcription of genes that are under the control of Rev-Erb response elements, such as Bmal-1 and other genes that are described in the literature as presenting a promoter that is modulated by Rev-Erbs. A Rev-Erb agonist exerts its action in a tissue, an organ, or an organism by specifically repressing the expression of specific genes and, by means of this modulation, improving biochemical and/or physiological indexes having medical relevance.

Thus, Rev-Erb agonists can be used as medicinal products. Consequently, the present invention provides novel pharmaceutical compositions comprising a compound of General Formula (I) and a pharmaceutically acceptable carrier. Such pharmaceutical compositions, optionally in combination with one or more other therapeutically active substances and/or substances providing appropriate pharmaceutical formulations, can be used in methods for treating diseases for which the activation of Rev-Erb, in particular Rev-Erb alpha or Rev-Erb alpha and beta, has positive effects in a subject. In this regard, reference is made to the literature (such as WO 2011/022619, Grant D et al., 2010, and publications cited above) about the use of Rev-Erb alpha agonists for treating inflammatory disorders and circadian rhythm-related disorders including sleep-related disorders. In addition to the compounds of formula (I), it is herein shown that compounds of formula (Ia) are Rev-Erb agonists, in particular Rev-Erb alpha agonists. Accordingly, the invention also provides a compound of formula (Ia) for use in a method for treating a disease for which activation of Rev-Erb, in particular Rev-Erb alpha or Rev-Erb alpha and beta, has positive effects:

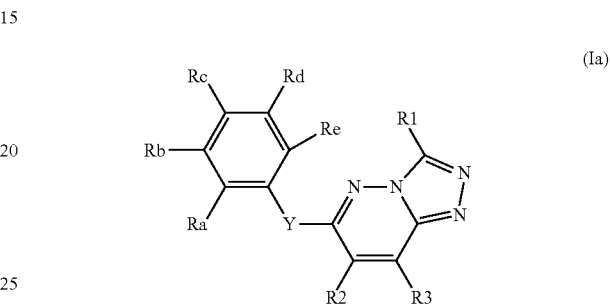

wherein

R1 represents a hydrogen atom, a halogen atom, an amino group, a hydroxyl group, a COOH group, a CO-alkyl group, a COO-alkyl group, a CONH2 group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a 5- to 8-membered cycle.

Ra, Rb, Rc, Rd, and Re represent independently a hydrogen atom, a halogen atom, a hydroxyl group, a COOH group, a CO-alkyl group, a COO-alkyl group, a CONH2 group, an amino group, an alkylcarbonylamino group, a nitro group, a cyano group, an alkoxy group, an alkylthio group, an alkylcarbamate group, an alkylamino group, a W or W—Z group, a heterocyclic group, an alkylsulfonamide group, or an alkyl group substituted or not with one or more halogen atoms, an hydroxyl group, an alkylcarbonyloxy group, an amino group, an alkylamino group, a cycloalkylamino group, an alkylcarbamate group, an alkylsulfonyl group or a heterocyclic group substituted or not with an alkyl group;

wherein one of Ra, Rb, Rc, Rd and Re is a W or W—Z group;

W represents a cyclic group selected from a cycloalkyl, aryl and heterocyclic group, W being substituted or not with one or more substituent groups chosen from a halogen atom, a hydroxyl group, a COOH group, a CO-alkyl group, a COO-alkyl group, a CONH2 group, an amino group, a nitro group, an alkylcarbamate group, an alkylcarbonylamino group, an alkoxy group, a cycloalkyloxy group, an alkylthio group, an alkylamino group or an alkyl group substituted or not with one or more halogen atoms, a cycloalkylamino group, a heterocyclic group substituted or not with an alkyl group;

each of Y and Z represents independently an oxygen atom, a sulphur atom, a $CH_2$, or a carbonyl group; and wherein any of the alkyl, alkoxy, alkylamino, and alkylthio group in R1, R2, R3; Ra, Rb, Rc, Rd, Re, or within W is substituted or not with one or more halogen atoms, an aryl group, an heterocyclic group, an alkylamino group, an amino group or a hydroxy group.

In a particular embodiment, the invention provides a compound of formula (Ia) for use in a method for treating a disease for which activation of Rev-Erb, in particular Rev-Erb alpha, has positive effects:

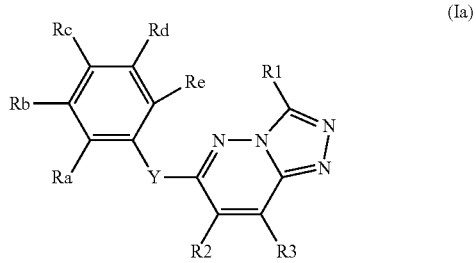

(Ia)

wherein

R1 represents a hydrogen atom, a halogen atom, a hydroxyl group, a COOH group, a CO-alkyl group, a COO-alkyl group, a $CONH_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a 5- to 8-membered cycle.

Ra, Rb, Rc, Rd, and Re represent independently a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group, a W or W—Z group;

wherein one of Ra, Rb, Rc, Rd and Re is a W or W—Z group;

W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a $CONH_2$ group, an amino group, an alkyl group, an alkoxy group, an alkylthio group, or an alkylamino group;

each of Y and Z represents independently an oxygen atom, a sulphur atom, a $CH_2$, or a carbonyl group; and wherein any of the alkyl, alkoxy, alkylamino, and alkylthio group in R1, R2, R3; Ra, Rb, Rc, Rd, Re, or within W is substituted or not with one or more halogen atoms, an aryl group, an heterocyclic group, an alkylamino group, an amino group or a hydroxy group.

In a further particular embodiment, the invention provides a compound of formula (Ia) for use in a method for treating a disease for which activation of Rev-Erb, in particular Rev-Erb alpha or Rev-Erb alpha and beta, has positive effects wherein R1 represents a hydrogen atom, a halogen atom, a hydroxyl group, a COOH group, a CO-alkyl group, a COO-alkyl group, a $CONH_2$ group, an alkyl group, an alkoxy group, an alkylthio group, or an alkylamino group;

R2 and R3 are hydrogen atoms.

Ra, Rb, Rc, Rd, and Re represent independently a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group, a W or W—Z group;

wherein one of Ra, Rb, Rc, Rd and Re is a W or W—Z group;

W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a $CONH_2$ group, an amino group, an alkyl group, an alkoxy group, an alkylthio group, or an alkylamino group;

each of Y and Z represents independently an oxygen atom, a sulphur atom, a $CH_2$, or a carbonyl group; and wherein any of the alkyl, alkoxy, alkylamino, and alkylthio group in R1, R2, R3; Ra, Rb, Rc, Rd, Re, or within W is substituted or not with one or more halogen atoms, an aryl group, an heterocyclic group, an alkylamino group, an amino group or a hydroxy group.

The present invention also relates to particular embodiments of a compound of formula (Ia), wherein Ra, Rb, Rc, Rd, Rf, Rg, Rh, Ri, Rj, R1, R2, R3, W, Y, and Z have the same definitions as provided above for the particular or preferred embodiments of compounds of formula (I).

In a particular embodiment, the compound of formula (Ia) is a compound of formula (I) as defined above.

In a particular embodiment, the expression "wherein one of Ra, Rb, Rc, Rd and Re is a W or W—Z group" refers to the fact that one, and only one of these positions is a W or W—Z group.

A non-exhaustive list of inflammatory disorders in mammals includes skin diseases (inter alia eczema, psoriasis, dermatitis and pruritus); conjunctivitis, hypersensitivity reactions; lung disorders such as asthma, rhinitis, chronic obstructive pulmonary disease, interstitial lung disease and fibrosis; ulcerative colitis and Crohn's disease; auto-immune diseases such as rheumatoid arthritis.

Sleep related disorders are disorders displaying sleep disruption as a cause or as a symptom. A non exhaustive list of sleep related disorders includes fatigue accumulation-preventing activity; insomnia, hypersomnia; autonomic dystonia, bipolar disorder, mood disorders such as atypical depression; and parasomnias. A non exhaustive list of metabolic diseases includes cardiometabolic diseases, such as insulin resistance, impaired glucose tolerance, prediabetes, type 2 diabetes, obesity, abdominal obesity, atherosclerosis, non-alcoholic steatohepatitis, non-alcoholic fatty liver diseases, and ensuing cardiovascular diseases such as coronary heart disease, cardiomyopathy, hypertensive heart disease, cardiac dysrhythmias, Inflammatory heart diseases, valvular heart disease, stroke, cerebrovascular disease, peripheral arterial disease. A non-exhaustive list of pathological bacteria, which may induce increased host mortality upon infection are *Campylobacter jejuni, Clostridium perfringens, Salmonella* spp, enterohemorrhagic *Escherichia coli* O157:H7, *Bacillus cereus, Escherichia coli* spp, *Listeria monocytogenes, Shigella* spp, *Staphylococcus aureus, Staphylococcal enteritis, Streptococcus, Vibrio cholerae, Vibrio parahaemolyticus, Vibrio vulnificus, Yersinia enterocolitica* and *Yersinia pseudotuberculosis, Brucella* spp, *Corynebacterium ulcerans, Coxiella burnetii, Plesiomonas shigelloides.*

A non-exhaustive list of pathological viruses, which may induce increased host mortality upon infection are HIV, hepatitis B virus, hepatitis C virus, West Nile virus, Chikungunya virus, Dengue fever virus and the hemorrhagic fever viruses, such as those from the families Arenaviridae, Filoviridae, Bunyaviridae and Flaviviridae.

A non-exhaustive list of pathological parasites, which may induce increased host mortality upon infection are *Babesia microti* and *Babesia divergens, Trypanosoma cruzi, Leishmania major, Leishmania braziliensis, Leishmania*

*donovani, Leishmania infantum, Plasmodium falciparum, Plasmodium malariae, Plasmodium vivax,* and *Plasmodium ovale.*

The term "treatment" or "treating" refers to therapy, prevention, or prophylaxis of a disorder, in particular of an inflammatory or circadian rhythm-related disorder or metabolic disorder, in a subject in need thereof. The treatment involves the administration of a pharmaceutical composition to subjects (e.g. patients) having a declared disorder to prevent, cure, delay, reverse, or slow down the progress of the disorder, improving thereby the condition of patients. A treatment may be also administered to subjects that are either healthy or at risk of developing a disorder such as an inflammatory disorder or a circadian rhythm-related disorder or metabolic disorder.

The term "subject" refers to a mammal and more particularly a human. The subjects to be treated according to the invention can be appropriately selected on the basis of several criteria associated to circadian or inflammatory pathological processes such as previous and/or present drug treatments, associated pathologies, genotype, exposure to risk factors, as well as any other relevant biomarker that can be evaluated by means of any suitable immunological, biochemical, or enzymatic method.

The Examples show how Compounds of General Formula (I) and (Ia) can be produced and tested for establishing structure-activity relationships that apply to said compounds. The skilled person can use technical details and general knowledge in the literature for generating additional compounds of General Formula (I) and (Ia) and testing their structural and biological properties.

Figure 1A:
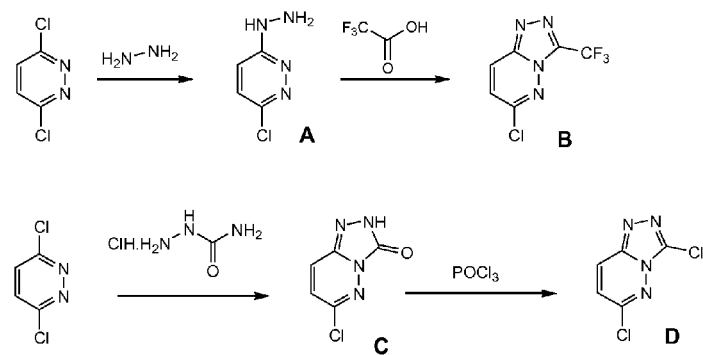
FIG. 1a) and substituted phenyl group (2-aryl phenol or 2-heteroaryle phenol, according to Protocol SA.
Figure 1B:
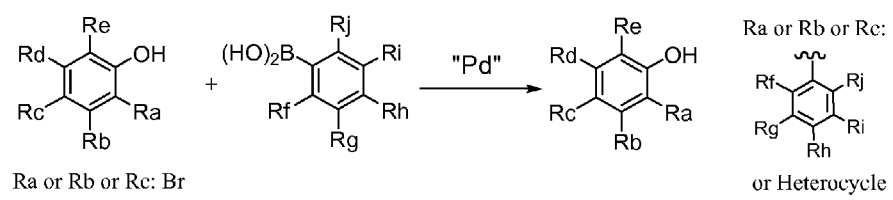
FIG. 1b).

The details of the general methods of synthesis and purification of intermediate and final reaction products for Compounds of General Formula (I) and (Ia) are provided in Example 1. Specific reaction intermediates can be synthesized and purified from compounds that may be already available commercially or that can readily be synthesized. General scheme of synthesis of the compounds of General Formula (I) and (Ia) is presented in FIGS. 1-2. However, additional chemical reactions can be implemented for the preparation of compounds of General Formula (I) and (Ia), including those already known to a person skilled in the art who will be able to synthesize said compounds, notably to obtain reaction intermediates and/or compounds with specific combinations of R1, W, Z, Y, and/or Ra-Rj groups within 6-substituted [1,2,4]triazolo[4,3-b]pyridazines.

These alternative methods of producing compounds of General Formula (I) and (Ia) can be established by applying technologies that allow simplifying synthetic protocols, such as polymer-assisted solution-phase synthesis or microwave-assisted organic synthesis, thus establishing a workflow for medicinal chemists to identify drug candidate molecules (Carey J et al., 2006; Colombo M and Peretto I, 2008; Roughley S and Jordan A, 2011). Moreover, cheminformatics and computer-aided drug design techniques may allow a more systematic qualitative and quantitative evaluation of chemical libraries of 6-substituted [1,2,4]triazolo[4,3-b]pyridazines (Di L et al., 2009; Zhao H and Guo Z, 2009; Villar H and Hansen M, 2009; Wishart D, 2008; Mayr L and Bojanic D, 2009).

The functional groups optionally present in the reaction intermediates that are generated for obtaining the desired compounds of General Formula (I) and (Ia) can be protected, either permanently, or temporarily, by protective groups, which ensure unequivocal synthesis of the desired compounds. The reactions of protection and deprotection are carried out according to techniques well known by a person skilled in the art or such as those described in the literature, as in the book "Greene's Protective Groups in Organic Synthesis" (4th edition, 2007; edited by Wuts P G and Greene T W; published by John Wiley and Sons).

The compounds according to the invention may contain one or more asymmetric centres that are associated to specific R1, W, and/or Ra-Rj groups. The present invention includes stereoisomers (diastereoisomers, enantiomers), pure or mixed, as well as racemic mixtures and geometric isomers, or tautomers of compounds of General Formula (I) and (Ia). When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are described in the literature, such as in the book "Chirality in Drug Design and Development" (2004; edited by Reddy I K et al.; Published by CRC Press).

The compounds of General Formula (I) and (Ia) can be purified by precipitation or solid/liquid extraction after evaporation of the reaction medium. Further or other purification step can be performed by chromatography over silica gel or by crystallization, when the compound is stable as a solid form, by applying techniques well known in the literature for 6-substituted [1,2,4]triazolo[4,3-b]pyridazines or, more in general, for chemicals ("Purification of Laboratory Chemicals", 2009, ed. Armarego W and Chai C; Elsevier). Moreover, the required purification and/or (re-)crystallization steps that are appropriate for isolating compounds of General Formula (I) from the reaction mixture, can be used for obtaining amorphous, polymorphous, mono- or poly-crystalline forms. Such polymorphisms may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids.

The (re-)crystallisation assays can be performed in panels of different solvents (such as isopropanol, acetone, methanol, diisopropyl ether, or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms (Erdemir D et al., 2007; Bauer M, 2004; Morissette S et al., 2004; Yin S and Grosso J, 2008). Such a polymorphism study allows characterizing the crystalline form of a compound that is pharmaceutically acceptable for both pharmacological and manufacturing points of view. Certain compounds of General Formula (I) can be isolated in the form of zwitterions and each of these forms is included in the invention, as well as mixtures thereof.

Compounds of General Formula (I) and (Ia) and their salts can be stable in liquid or solid forms. The present invention includes all solid and liquid forms of General Formula (I) and (Ia), which includes the amorphous, polymorphic, mono- and poly-crystalline forms. In particular, the compounds of General Formula (I) and (Ia) can exist in the free form or in the solvated form, i.e. in the form of associations or combinations with one or more molecules of a solvent, for example with pharmaceutically acceptable solvents such as water (hydrates) or ethanol. The present invention also includes the prodrugs of the compounds according to the invention which, after administration to a subject, are converted to the compounds as described in the invention or to their metabolites having therapeutic activities comparable to the compounds according to the invention.

Specific compounds of General Formula (I) and (Ia) can comprise at least one atom of the structure that is replaced by an isotope (radioactive or not). Examples of isotopes that can be included in the structure of the compounds according to the invention can be selected from hydrogen, carbon, nitrogen, oxygen, sulphur such as $^2H$, $^3H$, $^{13}C$, $^{14}C$, $^{15}N$, $^{18}O$, $^{17}O$, $^{35}S$ respectively. When non-radioactive, the stable isotope can be selectively incorporated in the structure in place of hydrogen (in the case of deuterium) or carbon (in the case of $^{13}C$) not only as means of performing absorption, distribution, metabolism, and excretion (ADME) studies but also as means for obtaining compounds that may retain the desired biochemical potency and selectivity of the original compound while the metabolic fate is substantially altered. In some favourable cases, this modification has the potential to have a positive impact effect on safety, efficacy and/or tolerability of the original compound (Mutlib A, 2008; O'Driscoll C, 2009). Otherwise radioactive isotopes $^3H$ and $^{14}C$ are particularly preferred as they are easy to prepare and detect in studies of the bioavailability in vivo of the substances. The heavy isotopes (such as $^2H$) are particularly preferred as they are used as internal standards in analytical studies and as possible variants of pharmaceutical interest.

Compounds of General Formula (I) and (Ia) can be obtained as specific salts, hydrates, and polymorphs that can be obtained during the final purification step of the compound or, in the case of salts, by incorporating the salt into the previously purified compound. The selection of a compound of General Formula (I) and (Ia) that is produced according to the methods of the Invention as an optimal candidate for drug development can be automated for a comprehensive biopharmaceutical characterization at the scale-up stage and for the solid or liquid formulation that is appropriate for the desired route of administration and therapeutic indication (Kumar L et al., 2007; <<Handbook of Pharmaceutical Salts: Properties, Selection, and Use>> 2002, edit. Stahl P and Wermuth G, Viley-VCH Germany; <<Pharmaceutical Dosage Forms and Drug Delivery>> 2007, ed. Mahato R, CRC Press).

In view of their use as medicinal products, the compounds of General Formula (I) and (Ia) can be formulated as pharmaceutically acceptable salts obtained from organic or inorganic bases or acids of such compounds. Alternatively, the compounds of General Formula (I) and (Ia) can be formulated as pharmaceutically acceptable hydrates or polymorphs of such compounds. These salts, hydrates, and polymorphs can be obtained during the final purification step of the compound or, in the case of salts, by incorporating the salt into the previously purified compound (Handbook of Pharmaceutical Salts: Properties, Selection, and Use, 2002; edited by Stahl P H and Wermuth G H; published by VHCA Switzerland and Wiley-VCH Germany). These salts can be prepared with pharmaceutically acceptable acids but the salts of other acids useful for purifying or isolating the compounds of general formula (I) and (Ia) also form part of the invention. In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

The present invention further provides pharmaceutical compositions comprising a compound of General Formula (I) or (Ia), or its pharmaceutically acceptable salt, and optionally at least one pharmaceutically acceptable carrier or diluent. The pharmaceutical compositions comprising a compound of General Formula (I) or (Ia) may comprise one or several excipients or vehicles acceptable within a pharmaceutical context (e.g., for liquid formulations, saline solutions, physiological solutions, isotonic solutions).

A further object of the invention are methods of preparing such pharmaceutical compositions, comprising admixing a compound of General Formula (I) or (Ia), with at least one pharmaceutically acceptable carrier, vehicle, or diluent. These methods involve, for example, conventional mixing, dissolving, granulation, dragee-making, levigating, emulsifying, encapsulating, entrapping, lyophilizing processes or spray drying (Remington: The Science and Practice of Pharmacy, 20th Ed., 2000, Lippincott Williams & Wilkins; Handbook of Pharmaceutical Excipients, 4th Ed., 2003, Pharmaceutical Press).

The phrase "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "carrier", "vehicle", or "excipient" refers to any substance, not itself a therapeutic agent, that is added to a pharmaceutical composition to be used as a carrier, vehicle, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, polysorbate 80, mannitol, gelatin, lactose, vegetable oils, liposomes, etc. Acceptable excipients can be chosen among disintegrants, binding agents, adhesives, wetting agents, lubricants, glidants, flavors, dyes, fragrances, stearic acid, magnesium oxide, sodium and calcium salts of phosphoric and sulfuric acids, magnesium carbonate, talc, gelatin, lactose, sucrose, starches, polymers, such as polyvinyl alcohol and polytheylene glycols, and other pharmaceutically acceptable materials added to improve taste, odor or appearance of the composition.

The compounds can be made up in solid or liquid form, such as tablets, capsules, powders, syrups, elixirs and the like, aerosols, sterile solutions, suspensions or emulsions, and the like. The composition may be presented in a solid preformulation composition wherein the active ingredients are dispersed evenly throughout the composition so that the composition may be readily subdivided into equally effective dosage forms such as tablets, pills and capsules. Additionally, the combined compositions may be delivered using sustained-release formulations.

The compositions can be formulated as injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used. The compositions of the present invention can also be formulated in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phophatidylcholines, cardiolipins, phosphatidylethanolamines, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

The pharmaceutical combination of the invention can be administered in a systematic or parenteral way, by using oral, topical, perlingual, nasal, rectal, transmucosal, transdermal, intestinal, intramuscular, intravenously, subcutaneous, intraarterial, intraperitoneal, intrapulmonary or intraocular route, by using methods known in the art.

Oral administration is the preferential route of administration for pharmaceutical compositions comprising a compound of General Formula (I) or (Ia) for the treatment of inflammatory or circadian rhythm-related disorders. Formulations for oral administration may be in the form of aqueous solutions and suspensions, in addition to solid tablets and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers.

For administration by inhalation, the pharmaceutical compositions comprising a compound of General formula (I) or (Ia) are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, 1,1,1,2-tetrafluoroethane, 1,1,1,2,3,3,3-heptafluoropropane, carbon dioxide or other suitable gas, alone or in combination. Pressurized aerosols may be formulated as suspensions or solutions, and include an appropriate propellant formulation, and various excipients, such as surfactants, co-solvents, etc. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such as shellac and cellulose acetate.

The liquid forms in which the pharmaceutical compositions can be incorporated for oral administration or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. A person skilled in the art will take care to select the possible compound or compounds to be added to these compositions in such a way that the advantageous properties intrinsically attaching to the present invention are not or substantially not altered by the addition envisaged, as is also explained in the literature, for example in the book "Pharmaceutical Dosage Forms and Drug Delivery" (2007; edited by Mahato R; published by CRC Press).

A pharmaceutical composition as disclosed herein is understood to be useful for treating or preventing an inflammatory, or circadian rhythm-related disorder or cardiometabolic diseases or infectious diseases, that is, the active ingredients are contained in an amount to achieve their intended purpose. At this scope, a compound of General Formula (I) or (Ia) should be administered in an effective amount by using a pharmaceutical composition as above-defined. Administration can be performed daily or even several times per day, if necessary, and in an amount that can be optimal or suboptimal, if they are compared with dosages that are normally used for such compounds.

The term "an effective amount" refers to an amount of the compound sufficient to produce the desired therapeutic result; in particular the compounds of General Formula (I) or (Ia) are administered in amounts that are sufficient to display desired effect.

Optimal dosages of compounds of General Formula (I) or (Ia) to be administered may be readily determined by those skilled in the art, and will vary with the particular compound used, the strength of the preparation, the mode of administration, and the severity of the condition to be treated. In addition, factors associated with the particular patient being treated, including patient age, weight, diet and time of administration, will result in the need to adjust dosages and interval. The frequency and/or dose relative to the simultaneous or separate administrations can be adapted by one of ordinary skill in the art, in function of the patient, the pathology, the form of administration, etc. For instance, a compound of General Formula (I) should be provided in a dosage that allows its administration in the amount 0.01 mg/day to 1000 mg/day, preferably from 0.1 mg/day to 10 mg/day.

The compounds of General Formula (I) or (Ia) can advantageously be formulated and/or administered in combination with one or more other therapeutically active substances, marketed or under development, that are selected according to a specific circadian rhythm-related or inflammatory disorder or any other disorders that may be found associated to said disorder in medical settings and that should be also treated. Such a combined administration includes two possibilities: the two agents are administered to a subject at substantially similar times; or the two agents are administered to a subject at different times, at independent intervals that may or may not overlap or coincide.

A non-exhaustive list of therapeutically active substances that may be advantageously formulated and/or administered with compounds of General Formula (I) or (Ia) includes:
  Anti-inflammatory and anti-oxidant agents;
  Agents used in the treatment of heart failure or coronary insufficiency Anti-hypertensive and hypotensive agents;
  Anti-coagulant, vasodilators, and anti-ischemic agents;

Anti-diabetic, hypolipemic, hypocholesterolemic, and anti-obesity agents;

substances useful for treating infectious diseases.

A further embodiment of the invention is a method of treating circadian rhythm-related disorders comprising the administration of a compound of General Formula (I) or (Ia) to a patient in need thereof. Given the specific features of such disorders, the methods may involve selecting preferred hours of the day and/or frequency by which a compound of General Formula (I) or (Ia) should be administered, alone or in combination with another compound that is administered simultaneously, or at a different time of the day. Another embodiment of the invention is a method of treating inflammatory disorders comprising the administration of a compound of General Formula (I) or (Ia) to a patient in need thereof.

All references cited herein are fully incorporated by reference in their entirety. Having now fully described the invention, it will be understood by those of ordinary skill in the art that the invention may be practiced within a wide and equivalent range of conditions, parameters and the like, without affecting the spirit or scope of the invention or any embodiment thereof. Several other advantages of the invention will rise in the reading of the following examples; they should be considered as illustrative data and not as limitative ones.

EXAMPLES

Example 1

General Protocols

Compounds provided herein may generally be prepared using standard synthetic methods. Starting materials are generally readily available from commercial sources, such as Interchim, Sigma-Aldrich or Carlo-Erba, or may be prepared as described herein, or using standard synthetic methods known by the person skilled in the art. For example, specific bromophenol intermediates can be prepared using bromination protocols that are described in the literature. Moreover, some compounds are available from commercial libraries such as KeyOrganics Library (Cpd.1-5), Maybridge (Cpd.1-6) or Enamine (Cpd.2-2).

The compounds of the invention are prepared according to the general methods and general protocols of synthesis given below. Representative procedures suitable for the preparation of compounds of General Formula (I) are outlined in the Reaction Schemes for intermediate (FIG. 1) and final (FIG. 2) compounds. Reagents and conditions may be adapted and additional steps employed to produce further compounds encompassed in the present invention having alternative substituent groups, or for achieving such compounds at higher yield and/or of higher purity. The final and intermediate compounds were characterized structurally by proton Nuclear Magnetic Resonance ($^1$H NMR; 300 MHz; δ in ppm).

Intermediate A (3-chloro-6-hydrazinopyridazine)

3,6-Dichloropyridazine (1 eq) was dissolved in tetrahydrofuran (0.33 mol/L), then potassium carbonate (0.1 eq) and hydrazine monohydrate (1.6 eq) were added. The reaction mixture was heated to reflux for 48 hours. The reaction mixture was evaporated to half volume, and hydrazine monohydrate (1 eq) was added to the residue. The mixture was stirred overnight at reflux. The hot suspension was filtered. The filtrate was cooled to 0° C. and filtered. The filtrate was concentrated and it was cooled at 0° C., the solid was filtered, to give Intermediate A (75% yield). Appearance: off-white solid. $^1$H NMR (MeOD-d$_4$): 7.18 (d, 1H, J=9.4 Hz); 7.40 (d, 1H, J=9.4 Hz).

Intermediate B (6-Chloro-3-trifluoromethyl-[1,2,4] triazolo[4,3-b]pyridazine)

3-Chloro-6-hydrazinopyridazine (1 eq) was dissolved in trifluoroacetic acid (5 eq mol). The reaction mixture was placed in a sealed tube at 110° C. for 2 hours. The reaction mixture was evaporated to dryness. Ethyl acetate (AcOEt) (1.5 mol/L) and potassium carbonate (50 eq) were added to the residue. The organic layer was dried over Na$_2$SO$_4$, filtered and evaporated to dryness to give Intermediate B (quantitative yield). Appearance: off-white solid. $^1$H NMR (MeOD-d$_4$): 7.65 (d, 1H, J=9.8 Hz); 8.45 (d, 1H, J=9.8 Hz).

Intermediate C (6-chloro-[1,2,4]triazolo[4,3-b] pyridazin-3(2H)-one)

3,6-Dichloropyridazine (1 eq) was dissolved in ethanol (0.43 mol/L) under stirring. Water (1.72 mol/L) and semicarbazide hydrochloride (2 eq) were added to the reaction. A solution of 35% hydrogen chloride in water (0.005 eq) was added to the mixture. The reaction was heated to reflux for 24 hours. The reaction was kept at room temperature for 3 days and then was evaporated to dryness. The residue was recrystallised from ethanol (5 mL) to give Intermediate C (97% yield). Appearance: light yellow solid. $^1$H NMR (MeOD-d$_4$): 7.16 (d, 1H, J=9.9 Hz); 7.76 (d, 2H, J=9.9 Hz).

Intermediate D (3,6-Dichloro-[1,2,4]triazolo[4,3-b]pyridazine)

6-Chloro-[1,2,4]triazolo[4,3-b]pyridazin-3(2H)-one (1 eq) was added to phosphoryl chloride (10 eq). The mixture was heated to reflux for 20 hours. The mixture was evaporated to dryness. The reaction was dissolved in ethyl acetate and washed by K$_2$CO$_3$ saturated aqueous solution. The organic layer was dried over Na$_2$SO$_4$, filtered and evaporated to dryness to give Intermediate D (93% yield). Appearance: light yellow solid. $^1$H NMR (MeOD-d$_4$): 7.51 (dd, 1H, J=9.6 Hz J=0.9 Hz); 8.30 (dd, 1H, J=9.6 Hz J=0.9 Hz).

Protocol SA

The palladium-catalysed synthesis of bicycle groups (biphenyl or phenyl-heteroaryl groups) was performed by using the appropriate bromophenol (1 eq) and phenyl- or heteroaryl-boronic acid (2 eq), or the appropriate 2-hydroxyphenylboronic acid (2 eq) and brominated aryl/heteroaryl group (1 eq). The reagents were dissolved in solvent. Toluene (0.42 mol/L) and base were added. The reaction was degased 10 minutes with nitrogen. Catalyst and ligand were added and the mixture was bubbled again with nitrogen during 5 minutes. The reaction was heated under microwave or on reflux. The reaction was filtered. The filtrate was extracted with dichloromethane and the organic layer was washed with brine. This layer was dried over Na$_2$SO$_4$, filtered and evaporated. The crude reaction product was purified on silica gel, precipitated, or triturated in the appropriate solvent to obtain the desired hydroxybiphenyl or heteroaryl-phenol.

This reaction was performed using different combinations of solvent, catalyst, ligand, base, bromoderivatives for distinct Compounds of General Formula (I), as summarized below (but further information about reaction conditions and purification are reported in Tables of Example 2)

1—toluene/water (4/1, v/v, 0.35 mol/L); palladium 5% wt on carbon powder, 50% Wt water (0.02 eq); triphenylphosphine (0.04 eq); potassium carbonate (2 eq)

2—toluene/ethanol (4/1, v/v, 0.42 mol/L); palladium (II) chloride (dppf) in dichloromethane (0.025 eq); sodium carbonate 2M (3 eq)

3—dioxanne/water (2/1, v/v, 0.67 mol/L); Pd2 dBa3 (0.01 eq); tricyclohexyllphosphine or XPhos (0.024 eq); potassium phosphate (2-2.5 eq).

Protocol SB

Appropriate 6-chloro-[1,2,4]triazolo[4,3-b]pyridazine (1 eq) or 6-chloro-[1,2,4]triazolo[3,4-a]phtalazine (1 eq), potassium carbonate (3 to 4 eq) and the appropriate phenol, thiophenol (1 to 4 eq, 1 eq is preferentially used when R1=Cl) were dissolved in N,N-dimethylformamide under nitrogen atmosphere. The reaction mixture was stirred overnight at room temperature or at 100-110° C., or 5-30 minutes at 100-170° C. on microwave irradiation. The reaction mixture was diluted with ethyl acetate and washed with brine. The organic layer was dried over $Na_2SO_4$, filtered and evaporated to dryness. The residue was purified by chromatography on silica gel, precipitated, triturated in the appropriate solvent, or used without further purification to obtain the desired 6-aryl-[1,2,4]triazolo[4,3-b]pyridazine, or 6-aryl-[1,2,4]triazolo[3,4-a]phtalazine.

This protocol was used to prepare the following compounds: Cpd.1-1, Cpd.1-3, Cpd.1-4, Cpd.1-7, Cpd.1-8, Cpd.1-9, Cpd.1-10, Cpd.1-11, Cpd.1-12, Cpd.1-13, Cpd.1-14, Cpd.2-1, Cpd.2-3, Cpd.2-4 and other compounds of the invention that contain a biphenyloxy, a pyridinylphenyloxy, a thiazolylphenyloxy, or a thiopenylphenyloxy group in the 6-substituted position of the [1,2,4]triazolo[4,3-b]pyridazines or 6-substituted position of the [1,2,4]triazolo[3,4-a]phthalazine (but further information about conditions and purification are reported in Tables of Example 2).

Protocol SC

The appropriate (([1,2,4]triazolo[4,3-b]pyridazin-6-yloxy)phenyl)phenyl-methanone (1 eq) was dissolved in dichloromethane (0.13 mol/L) and trifluoroacetic acid (52 eq) was added. The reaction mixture was cooled at 0° C. then sodium tetrahydroborate (6 eq) was added. The reaction mixture was stirred 3 hours at 0° C. and 2 hours at room temperature. The reaction mixture was hydrolysed with ice and dichloromethane was added. The organic layer was washed twice with water, twice with $NaHCO_3$ 5% and with water until pH 7. The organic layer was dried on $Na_2SO_4$, filtered and evaporated to obtain the desired 6-benzylphenoxy-[1,2,4]triazolo[4,3-b]pyridazine.

This protocol was used to prepare Cpd.3-5 starting from Cpd.3-4 (see Table 1-1), and it can be adapted for preparing other Compounds of General Formula (I) wherein Z is modified from carbonyl to $CH_2$ group.

Protocol SD

Appropriate [1,2,4]triazolo[4,3-b]pyridazine (or intermediate compound) bearing a methoxy group (1 eq) was dissolved in dichloromethane (0.14 mol/L) under nitrogen atmosphere. The mixture was cooled down to −78° C. A 1M solution of $BBr_3$ in dichloromethane (2-2.5 eq) was added to the reaction. The reaction was allowed to warm at room temperature for 2.5 to 4 hours and quenched with methanol (MeOH). Water was added and the mixture was diluted in dichloromethane. The organic layer was extracted twice with saturated NaCl aqueous solution. The organic layer was dried over $Na_2SO_4$, filtered and evaporated to dryness. The crude was purified by chromatography on silica gel to obtain the desired [1,2,4]triazolo[4,3-b]pyridazine (or intermediate compound) bearing a hydroxyl group.

This protocol was used to prepare Cpd.4-21 starting from Cpd.4-16, Cpd.4-32 from Cpd.4-14, Cpd.4-37 from Cpd.4-71, Cpd.4-77 from Cpd.4-76, Cpd.4-138 from Cpd.4-137, Cpd.4-151 and Cpd.4-153 from Cpd.4-150 and Cpd.4-152 respectively (see Tables 2-2, 2-3, and 2-4).

This protocol was also used to prepare intermediates of Cpd.4-45, Cpd.4-48, Cpd.4-65, Cpd.4-122, Cpd.4-124, Cpd.4-169, Cpd.4-170 and Cpd.4-185 (see Table 2-3 and it can be adapted for preparing other Compounds of General Formula (I) wherein any of Ra-Rj group is modified from O-methyl to hydroxy group.

Protocol SE

This protocol was used to prepare Cpd.1-2 from Cpd.1-5. 6-substituted-2H-[1,2,4]triazolo[4,3-b]pyridazin-3-one (1 eq) was dissolved in phosphorylchloride (68 eq). The reaction mixture was heated 1 h30 on microwave irradiation at 170° C. The reaction mixture was evaporated to dryness and 5.0 mL of methanol was added and it was evaporated. The resulting solid was dissolved in dichloromethane and saturated aqueous sodium bicarbonate solution. The organic layer was washed twice with saturated aqueous sodium bicarbonate solution and dried on $Na_2SO_4$, filtered and evaporated. The residue was purified by chromatography on silica gel to obtain the desired product.

Protocol SF

The appropriate nitro-substituted biphenyl-2-ol was dissolved in ethanol (0.5 mol/L) and Pd/C (0.05 eq) was added. The reaction was stirred under hydrogen at room temperature during 16 hours. The reaction mixture was filtered and residue was washed with tetrahydrofuran. The filtrate was evaporated to dryness and the resulting solid was triturated with diethyl ether to obtain the desired amino compound to be used in Protocol SB.

This protocol can also be used for debenzylation (see intermediate of Cpd.4-78).

This protocol was used to prepare intermediates of Cpd.4-36, Cpd.4-48, Cpd.4-78 and Cpd.4-185 (see Tables 2-3 and 2-4), and can be adapted for preparing Compounds of General Formula (I) wherein one of Ra-Rj group is an amino group.

Protocol SG

Appropriate 2-(biphenyl-2-yl)acetonitrile (1 eq) was dissolved in tetrahydrofuran (1.5 mol/L) under nitrogen atmosphere. Sodium hydride (1.1 eq) was added to the solution (red coloration). The solution was stirred 10 min at room temperature and poured slowly over a solution of 3,6-dichloropyridazine (preparation of Cpd.4-9) or Intermediate B (preparation of Cpd.4-12) (1 eq) in tetrahydrofuran (1.5 mol/L) under nitrogen. The mixture was stirred at RT for 20 hours. The reaction was diluted in dichloromethane and washed twice with saturated aqueous sodium chloride solution. The organic layer was dried over $Na_2SO_4$, filtered and evaporated to dryness. The residue was purified by chromatography on silica gel to obtain the 2-(biphenyl-2-yl)-2-(6-chloropyridazin-3-yl)acetonitrile (preparation of Cpd.4-9) or 2-(biphenyl-2-yl)-2-[3-trifluoromethyl-[1,2,4]triazolo[4,3-b]pyridazin-6-yl]acetonitrile (preparation of Cpd.4.12) (20-25% yield).

Protocol SH

The 2-(biphenyl-2-yl)-2-(6-chloropyridazin-3-yl)acetonitrile (preparation of Cpd.4-9) or 2-(biphenyl-2-yl)-2-[3-trifluoromethyl-[1,2,4]triazolo[4,3-b]pyridazin-6-yl]acetonitrile (preparation of Cpd.4-12) (1 eq) obtained by Protocol SG was introduced in the kettle and a mixture 10/2/1 v/v/v (0.3 mol/L) of HCl 35% in water, acetic acid 10% in water and water was added. The reaction was heated to reflux during 5 days and evaporated to dryness. Residue was dissolved in ethyl acetate and washed by aqueous saturated soldium chlorure solution. Organic layer was evaporated to dryness and residue was purified by chromatography on silica gel to obtain the desired 6-(biphenyl-2-ylmethyl)-pyridazin-3(2H)-one (preparation of Cpd.4-9) or 6-(biphenyl-2-ylmethyl)-3-(trifluoromethyl)-[1,2,4]triazolo[4,3-b]pyridazine (Cpd.4-12) (35% yield).

Protocol SI

The appropriate pyridazinone or phtalazinone (1 eq) was dissolved in phosphoryl chloride (60 eq). The reaction mixture was stirred overnight at 105° C. The mixture was cooled at room temperature; dichloromethane was added and evaporated to dryness. The residue was diluted in dichloromethane and cooled to 5° C. and saturated aqueous $K_2CO_3$ was added dropwise. The organic layer was dried on $Na_2SO_4$, filtered and evaporated to dryness to obtain the desired pyridazine or phtalazine.

This protocol was used to prepare 3,6-dichloro-4-phenylpyridazine from 4-phenylpyridazine-3,6-dione, intermediates of Cpd.5-4.

According to this protocol, various substituted 1,4-dichloro-phthalazines were prepared from 2,3-dihydrophthalazine-1,4-diones and used as intermediates of Cpd.5-2, and Cpd.5-9.

This protocol was also used in the preparation of intermediate of Cpd.4-9.

Protocol SJ

The appropriate dichloropyridazine or dichlorophtalazine (1 eq) was dissolved in ethanol (0.3 mol/L). Semicarbazide hydrochloride (2 eq) and water (1.6 mol/L) were added. A solution of 35% HCl in water (0.08 eq) was added to the mixture. The reaction was stirred 4 days at reflux. The reaction was kept at RT for 2 days and then was evaporated to dryness, to the desired 6-(biphenyl-2-ylmethyl)-[1,2,4]triazolo[4,3-b]pyridazin-3(2H)-one (80% yield).

According to that protocol 3,6-dichloro-4-methyl-pyridazine gave 6-chloro-7-methyl-[1,2,4]triazolo[4,3-b]pyridazin-3(2H)-one and 6-chloro-8-methyl-[1,2,4]triazolo[4,3-b]pyridazin-3(2H)-one, theses intermediates were used for the preparation of Cpd.5-6, Cpd.5-7 and Cpd.5-10.

In the same manner were prepared intermediates of Cpd.5-4, Cpd.5-5, Cpd.5-9, Cpd.5-11, and Cpd.5-14.

Starting from 1,4-dichlorophthalazine was prepared 6-chloro-[1,2,4]triazolo[3,4-a]phthalazin-3(2H)-one. This intermediate was used in the preparation of Cpd.5-1.

Starting from 1,4-dichloro-6-fluorophthalazine, 6-chloro-9-fluoro-[1,2,4]triazolo[3,4-a]phthalazin-3(2H)-one and 6-chloro-8-fluoro-[1,2,4]triazolo[3,4-a]phthalazin-3(2H)-one were obtained. After separation by chromatography on silica gel these intermediates were used to prepare Cpd.5-2 and Cpd.5-3.

Protocol SK

Appropriate 6-(biphenyl-2-ylmethyl)-[1,2,4]triazolo[4,3-b]pyridazin-3(2H)-one (1 eq) was dissolved in phosphoryl chloride (70 eq). The reaction mixture was stirred overnight at 110° C. The mixture was cooled at room temperature. Dichloromethane was added and evaporated to dryness. The residue was cooled to 5° C. and diluted in dichloromethane and saturated aqueous $K_2CO_3$ was added dropwise. The organic layer was dried on $Na_2SO_4$, filtered and evaporated to dryness. The crude compound was purified by chromatography on silica gel to obtain the desired 6-(biphenyl-2-ylmethyl)-3-chloro-[1,2,4]triazolo[4,3-b]pyridazine (Cpd.4-9) (10% yield).

According to this protocol were prepared various substituted 3,6-dichloro[1,2,4]triazolo[4,3-b]pyridazine, intermediates of Cpd.5-4, Cpd.5-5, Cpd.5-6, Cpd.5-7, Cpd.5-11 and Cpd.5-14.

This protocol was also adapted to prepare various 3,6-dichloro-[1,2,4]triazolo[3,4-a]phthalazine from 6-chloro-[1,2,4]triazolo[3,4-a]phthalazin-3(2H)-one, intermediates of Cpd.5-1, Cpd.5-2, Cpd.5-3, Cpd.5-9 and Cpd.5-10.

Protocol SL 4-(methyloxycarbonyl)biphenyl-2-ol (1 eq) was obtained by protocol SA, and was dissolved in anhydrous tetrahydrofuran. The reaction mixture was cooled to 0° C. and $LiAlH_4$ (1.2 eq) was added by small portions. The reaction mixture was stirred and allowed to reach room temperature during 2 hours then additional $LiAlH_4$ (1.2 eq) was added. The reaction mixture was stirred during 60 hours, and was diluted with ethyl acetate and water. Lithium salts were filtered and washed with water and ethyl acetate. Filtrate was extracted three times with ethyl acetate. Combined organic layers were washed with brine, dried over $MgSO_4$, filtered and evaporated to dryness. The residue was purified by chromatography on silica gel. (cyclohexane/AcOEt 7/3 v/v) to give 4-phenyl-3-hydroxybenzyl alcohol an off-white solid. (84% yield). $^1H$ NMR (DMSO $d_6$): 4.44 (d, 2H, J=5.6 Hz); 5.13 (t, 1H, J=5.8 Hz); 6.80 (d, 1H, J=7.6 Hz); 6.92 (s, 1H); 7.18 (d, 1H, J=7.9 Hz); 7.26 (t, 1H, J=7.3 Hz); 7.37 (t, 2H, J=7.3 Hz); 7.52 (d, 2H, J=7.3 Hz); 9.43 (s, 1H).

In the same manner was prepared 3-phenyl-4-hydroxybenzyl alcohol from 5-(methyloxycarbonyl)biphenyl-2-ol with 70% yield.

The same protocol was also used to prepare intermediate of Cpd.4-41, Cpd.4-65, Cpd.4-66, and Cpd.4-170.

Protocol SM 3-chloro-6-(4-hydroxymethyl-biphenyl-2-yloxy)-[1,2,4]triazolo[4,3-b]pyridazine (1 eq.) was obtained by protocol SB and was dissolved in dichloromethane stabilized with amylene (0.034 mol/L). Lithium bromide (1 eq) and phosphorus tribromide (1 eq) were added dropwise and the reaction mixture was stirred at room temperature during 2 hours. The reaction mixture was diluted with water. Aqueous layer was extracted twice with dichloromethane. Combined organics layers were washed with water, dried over $MgSO_4$, filtered and evaporated to dryness. The residue was purified by chromatography on silica gel (cyclohexane/AcOEt 8/2 v/v) to give the desired 3-chloro-6-(4-bromomethyl-biphenyl-2-yloxy)-[1,2,4]triazolo[4,3-b]pyridazine. (81% yield). Appearance: white solid. $^1H$ NMR (DMSO $d_6$): 4.77 (s, 2H); 7.26-7.35 (m, 4H); 7.41-7.44 (m, 2H); 7.52-7.57 (m, 3H); 8.36 (d, 1H, J=9.9 Hz).

In the same manner was synthesized 3-chloro-6-(5-bromomethyl-biphenyl-2-yloxy)-[1,2,4]triazolo[4,3-b]pyridazine (intermediate of Cpd.4-62) from Cpd.4-66 with 93% yield, and intermediate of Cpd.4-41.

Protocol SN 3-chloro-6-(4-bromomethyl-biphenyl-2-yloxy)-[1,2,4]triazolo[4,3-b]pyridazine (1 eq) was dissolved in dimethylformamide (0.24 mol/L). Carbonate potassium (4 eq) was added and the reaction mixture was stirred at room temperature for 5 minutes. Then, dimethylamine hydrochloride (2 eq) was added and the reaction mixture was heated on microwave 10 minutes at 120° C. The reaction mixture was diluted with water. Aqueous layer was extracted twice with dichloromethane. Combined organics layers were washed with water, dried over $MgSO_4$, filtered and evaporated to dryness. The residue was purified by chromatography on silica gel (automatic column $CH_2Cl_2$ 95/MeOH 5) to obtain the desired compound (Cpd.4-41; 18% yield).

From 3-chloro-6-(4-bromomethyl-biphenyl-2-yloxy)-[1,2,4]triazolo[4,3-b]pyridazine and various amines were prepared Cpd.4-64 and Cpd.4-60 with 45 and 17% yield respectively.

According to this protocol starting from 3-chloro-6-(5-bromomethyl-biphenyl-2-yloxy)-[1,2,4]triazolo[4,3-b]pyridazine were prepared Cpd.4-62, Cpd.4-63, Cpd.4-156, Cpd.4-157, Cpd.4-158, Cpd.4-159, Cpd.4-160, Cpd.4-161, Cpd.4-162, Cpd.4-163, Cpd.4-164, Cpd.4-165, Cpd.4-166, and Cpd.4-167 with yields ranging from 9.6% and 91%.

According to this protocol starting from 3-chloro-6-(4-(trifluoromethyl)-3'-(bromomethyl)biphenyl-2-yloxy)-[1,2,4]triazolo[4,3-b]pyridazine was prepared Cpd.4-168 with 16% yield.

According to this protocol starting from 3-chloro-6-(4-bromomethylbiphenyl-2-yloxy)-[1,2,4]triazolo[4,3-b]pyridazine were prepared Cpd.4-176, Cpd.4-177, Cpd.4-178, Cpd.4-179, Cpd.4-180, Cpd.4-181, Cpd.4-182, Cpd.4-183 and Cpd.4-184 with yields ranging from 5% and 88%.

The same protocol was also used to prepare intermediates of Cpd.4-73, Cpd.4-122, Cpd.4-124, and Cpd.4-147.

Protocol SO

The 3-chloro-6-(5-aminobiphenyl-2-yloxy)-[1,2,4]triazolo[4,3-b]pyridazine (1 eq), and potassium carbonate (3 eq) were added to N,N-dimethylformamide. Appropriate halogenated derivative (3 eq.) was added and the reaction mixture was heated 15 minutes at 110° C. on microwave. The reaction mixture was diluted with ethyl acetate and washed with brine. The organic layer was dried over MgSO$_4$, filtered and evaporated to dryness. The residue was purified by chromatography on silica gel to obtain pure mono and dialkylated amino derivatives.

Starting from Cpd.4-36 was prepared a series of mono and dialkylated amino compounds: Cpd.4-46, Cpd.4-47, Cpd.4-53, Cpd.4-54, Cpd.4-55, Cpd.4-56, Cpd.4-57, Cpd.4-58, Cpd.4-67, and Cpd. 4-190 with yields ranging from 8 to 33%.

In the same manner, were prepared Cpd.4-86, Cpd.4-88, Cpd.4-89, Cpd.4-90, Cpd.4-92 and Cpd.4-93 from Cpd.4-83 with yields ranging from 8 to 30%.

According to this protocol starting from Cpd.4-48 were prepared Cpd.4-52 and Cpd.4-125 with 3% and 40% yield respectively.

According to this protocol was also prepared an intermediate of Cpd.4-45, Cpd.4-185, and Cpd.4-189 with 61%, 51% and 72% yield respectively.

Protocol SP 4-amino-2-hydroxybiphenyl derivative (1 eq), and potassium carbonate (4.5 eq.) were dissolved in N,N-dimethylformamide. Acetyl bromide (2.3 eq.) was added and the reaction mixture was heated 15 minutes at 110° C. on microwave irradiation. Pyridine (2 eq.) and additional acetyl bromide (1.5 eq.) were added and the reaction mixture was heated 15 more minutes at 110° C. on microwave irradiation. The reaction mixture was partitioned between water and ethyl acetate. Organic layer was washed with brine, dried over MgSO$_4$, filtered and evaporated to dryness. The residue was purified by chromatography on silica gel to afford 4-N-(2-hydroxy-biphenyl)acetamide derivative. This protocol was used to prepare intermediate of Cpd.4-49.

Protocol SQ

Copper(II) acetate (4 eq.) was added to a mixture of 3-chloro-6-(4-amino-biphenyl-2-yloxy)-[1,2,4]triazolo[4,3-b]pyridazine (1 eq.) and pyridine (4 eq.) in dioxane. The mixture was heated 15 minutes at 100° C. and appropriate alkyl boronic acid (4 eq.) was added. The reaction mixture was heated at 100° C. during 7 hours before cooling to room temperature.

Water was added and the reaction mixture was extracted with ethyl acetate. The organic layer was washed with brine, dried over MgSO$_4$, filtered and evaporated. The residue was purified by chromatography on silica gel and trituration in cyclohexane.

This protocol was used to prepare Cpd.4-50, Cpd.4-51, and Cpd.4-175 from Cpd.4-48 with yields ranging from 8 and 16%.

Protocol SR

The carboxylic acid (1 eq.) was dissolved in methanol (0.1 mol/L). Concentrated H$_2$SO$_4$ (0.05 eq.) was added. The reaction mixture was heated at 80° C. for 6 hours before cooling to room temperature.

The reaction mixture was evaporated. Water and dichloromethane were added to the residue. The organic layer was washed with brine, dried over MgSO$_4$, filtered and evaporated. The residue was purified by chromatography on silica gel to obtain the corresponding ester.

This protocol was used to prepare the ester Cpd.4-75 form the corresponding carboxylic acid Cpd.4-74 with 14% yield.

This protocol was also used to prepare an intermediate of Cpd.4-140 with 53% yield.

Protocol SS 4-aminomethyl-biphenyl-2-ol (1 eq.) was dissolved in dichloromethane (0.375 mol/L). Triethylamine (2.5 eq.) and BOC anhydride (2 eq.) were added in small portions. The reaction mixture was stirred for 1 hour, washed twice with water, dried on over MgSO$_4$, filtered and evaporated. The residue was purified by chromatography on silica gel to provide 2-(tertbutyloxycarbonyloxy)-4-(tertbutyloxycarbonylaminomethyl)-biphenyl-2-ol with 53% yield, an intermediate of Cpd.4-65.

In a same manner from 4-aminomethyl-biphenyl-2-ol was prepared an intermediate of Cpd.4-170 with 41% yield.

Protocol ST

3-Chloro-6-(4-tertbutyloxycarbonylaminomethyl-biphenyl-2-yloxy)-[1,2,4]triazolo[4,3-b]pyridazine (1 eq.) was dissolved in dichloromethane. Trifluoroacetic acid (10 eq.) was added. The reaction was stirred at room temperature for 5 hours.

The reaction mixture was washed with water and the pH adjusted to 7-8 with 1N NaOH and extracted with dichloromethane. The organic layers were combined and washed with brine, dried over MgSO$_4$, filtered and evaporated. The residue was purified by chromatography on silica gel. The residue was triturated in diethyl oxide, filtered and dried to afford 3-chloro-6-(4-aminomethyl-biphenyl-2-yloxy)-[1,2,4]triazolo[4,3-b]pyridazine, an intermediate of Cpd.4-65, with 29% yield.

Cpd.4-171 was prepared from Cpd.4-170 according to this protocol with 56% yield.

Protocol SU 2-(Tertbutyloxycarbonyloxy)-4-(tertbutyloxycarbonylaminomethyl)-biphenyl (1 eq.) was dissolved in methanol. 2N NaOH (10 eq.) was added and the reaction was stirred at room temperature for 48 hours. Methanol was evaporated. The aqueous layer was extracted with dichloromethane. Organics layers were combined and washed with water, dried over MgSO$_4$, filtered and evaporated. The residue was purified by chromatography on silica gel to obtain 4-tertbutyloxycarbonylaminomethyl-biphenyl-2-ol, an intermediate of Cpd.4-65 with 61% yield.

Protocol SV 5-(Methyloxycarbonyl)biphenyl-2-ol (1 eq.) was dissolved methanol. An aqueous sodium hydroxide 2N solution (2 eq.) was added. The mixture was heated 5 minutes at 60° C. on microwave irradiation. The reaction mixture was diluted with water and acidified by with HCl 1N (pH 3-4) and extracted with ethyl acetate. Organic layers were combined and washed with brine, dried over MgSO$_4$, filtered and evaporated to dryness. The residue was purified by chromatography on silica gel to provide 5-(hydroxycarbonyl)biphenyl-2-ol, an intermediate of Cpd.4-59 with 53% yield.

Protocol SW

3-Chloro-6-(2-(6-methoxypyridin-3-yl)-5-(trifluoromethyl)phenoxy)-[1,2,4]triazolo[4,3-b]pyridazine (1 eq.), lithium chloride (2 eq.) and p-toluene sulfonic acid monohydrate (2 eq.) were dissolved in N-methyl-2-pyrrolidone. The reaction mixture was heated 15 minutes at 120° C. on microwave irradiation. The reaction was poured into water and ethyl acetate was added. The precipitate was filtered, washed and dried to provide desired 5-(2-(3-chloro-[1,2,4]triazolo[4,3-b]pyridazin-6-yloxy)-4-(trifluoromethyl)phenyl)pyridin-2(1H)-one. In the case of Cpd.4-83, and Cpd.4-96, compounds were obtained after extraction with ethyl acetate then the crude products were precipitated in the appropriate solvent.

This protocol was used to prepare Cpd.4-83 from Cpd.4-81 with 27% yield, Cpd.4-85 from Cpd.4-80 with 76% yield and Cpd.4-96 from Cpd.4-82 with 31% yield.

Protocol SX 5-(2-(3-Chloro-[1,2,4]triazolo[4,3-b]pyridazin-6-yloxy)-4-(trifluoromethyl)phenyl)pyridin-2(1H)-one (1 eq.), silver oxide (3 eq.) and iodoethane (3 eq.) were dissolved in toluene/dichloromethane 1/1 v/v (15 mol/L). The reaction mixture was heated at 50° C. for 12 hours before cooling to room temperature. The reaction was filtered and residue was washed with dichloromethane and methanol. The filtrate was evaporated to dryness and the resulting solid was purified by chromatography on silica gel, triturated in diethyl ether to obtain 3-chloro-6-(2-(6-ethoxypyridin-3-yl)-5-(trifluoromethyl)phenoxy)-[1,2,4]triazolo[4,3-b]pyridazine.

This protocol was used to prepare Cpd.4-84, Cpd.4-91, Cpd.4-94 and Cpd.4-95 from Cpd.4-83 with yields ranging from 19 to 68%.

Protocol SY

To a solution of hydrazine hydrate (1.2 eq.) in water (6 mol/L) cooled at 0° C. was slowly added concentrated HCl (1 eq.) and appropriate phthalic anhydride (1 eq.). The mixture was heated under reflux for 18 hours before cooling to room temperature. The resulting precipitate was filtered, washed with diethyl oxide to afford the desired 2,3-dihydrophthalazine-1,4-dione.

Starting form 4-fluorophthalic anhydride was prepared 6-fluoro-2,3-dihydrophthalazin-1,4-dione, intermediate of Cpd.5-2 with 74% yield.

Starting form 4-methylphtalic anhydride was prepared 6-methyl-2,3-dihydrophtalazin-1,4-dione, intermediate of Cpd.5-9 with 92% yield.

This protocol allowed also the preparation of 4-phenylpyridazin-3,6-dione, intermediate of Cpd.5-4 with 83% yield.

Protocol SZ

Intermediate D (1 eq.), silver nitrate (1 eq.), and the appropriate carboxylic acid (1 eq.) were dissolved in water. The reaction mixture was heated to 50° C. and concentrated sulfuric acid (3 eq.) was added. The reaction mixture was heated to 60° C. and aqueous ammonium per sulphate (3 eq.) was added. The reaction mixture was kept at 70° C. for 30 minutes before cooling to room temperature. pH was adjusted to 8 with 1N NaOH. The mixture was extracted with ethyl acetate, dried over MgSO$_4$, filtered and evaporated. The residue was purified by chromatography on silica gel to provide the desired mono or di substituted 3,6-dichloro-[1,2,4]triazolo[4,3-b]pyridazine.

Reaction of intermediate D with propionic acid gave a mixture of compounds. Purification on silica gel yielded 6% of 3,6-dichloro-7,8-diethyl-[1,2,4]triazolo[4,3-b]pyridazine and 5% of 3,6-dichloro-8-ethyl-[1,2,4]triazolo[4,3-b]pyridazine. These intermediates were used to prepare Cpd.5-12 and Cpd.5-13 respectively.

Intermediate of Cpd.5-8 was obtained in the same manner with 15% yield.

This protocol was also used to prepare intermediate of Cpd.5-14, Cpd.5-11 from 3,6-dichloropyridazine with appropriate carboxylic acid with 42% and 81% yields respectively.

Protocol TA

The appropriate phenol (1 eq.) was dissolved in dichloromethane and cooled a 0° C. Bromine (1 eq.) in dichloromethane was added. The reaction mixture was allowed to reach room temperature and kept under stirring for 18 hours. The reaction mixture was washed with aqueous Na$_2$SO$_3$, brine, dried over MgSO$_4$, filtered and evaporated. The residue was purified by chromatography on silica gel to provide the desired bromophenols with yields ranging from 3 to 76%.

Bromination of 3-trifluoromethylphenol gave a mixture of isomers. Separation on silica gel afforded 2-bromo-3-trifluoromethylphenol, intermediate of Cpd.4-44 and 2-bromo-5-trifluoromethylphenol, intermediate of Cpd.4-73.

This protocol was also used to prepare intermediates of Cpd.4-68, and Cpd.4-70.

Protocol TB

A solution of 3-chloro-6-(2-(6-chloropyridin-3-yl)-5-(trifluoromethyl)phenoxy)-[1,2,4]triazolo[4,3-b]pyridazine (1 eq), cesium carbonate (3 eq) and dimethylamine hydrochloride (2 eq) in tetrahydrofuran. was degased 10 minutes with nitrogen. Pd(OAc)$_2$ (0.05 eq) and BINAP (0.1 eq) were added and the mixture was bubbled again with nitrogen during 5 minutes. The reaction was heated 12 hours at 60° C.

The reaction mixture was diluted with ethyl acetate and washed with brine and water. The organic layer was dried over MgSO$_4$, filtered and evaporated to dryness. The residue was purified by chromatography on silica gel. Trituration in diethylether, afforded 5-(2-(3-chloro-[1,2,4]triazolo[4,3-b]pyridazin-6-yloxy)-4-(trifluoromethyl)phenyl)-N,N-dimethylpyridin-2-amine.

According to that protocol was prepared Cpd.4-102 from Cpd.4-101.

Protocol TC

Step 1: Synthesis of Intermediate Benzamidine

In a sealed tube, a mixture of appropriate benzonitrile (1 eq.), hydroxylamine hydrochloride (3 eq.) and sodium hydrogenocarbonate (2 eq.) in absolute ethanol (5 mol/L) was heated at 80 to 90° C. for 12 hours. After cooling to room temperature, the reaction mixture was diluted with water and extracted with ethyl acetate or/and dichloromethane. Combined organic layers were dried over MgSO$_4$, filtered, and concentrated under reduced pressure. Intermediate benzamidine was isolated by flash chromatography on silica gel, eluent:dichloromethane/ethyl acetate 5/5, and engaged in a step 2.

Step 2: Synthesis of Oxadiazole Derivative

A solution of intermediate benzamidine (1 eq.) and acetic anhydride (5 eq.) in N,N-dimethylformamide (1 mL) was heated at 120° C. After 12 hours the reaction mixture was diluted with water. The precipitate was filtered, washed thoroughly with water and dried to give the desired oxadiazole derivative. Alternatively, pH was adjusted to pH=7-8 with a solution of sodium hydrogenocarbonate 10% and extracted with ethyl acetate or diethyl ether. The combined organic layers were washed with brine and concentrated under reduced pressure. The crude was purified by flash chromatography on silica gel, eluent:dichloromethane/ethyl acetate/methanol:6.5/3.5/0.5 to afford title compound. Further purification step may be performed by trituration of the solid in diethyl ether or dichloromethane/ethanol.

According to that protocol was prepared Cpd.4-199.
Protocol TD

A solution of 6-arylamino-triazolopyridazine (1 eq.) and pyridine (40 eq.) in dichloromethane (0.6 mol/L) was placed at 0° C. before acyl or sulfonyl chloride was added dropwise under stirring. After 16 hours of stirring at room temperature, the reaction mixture was diluted with brine and extracted with dichloromethane. Combined organic layers were dried over MgSO4, filtered, and concentrated under reduced pressure. The crude was purified by flash chromatography on silica gel to give the desired compound.

According to that protocol was prepared Cpd.4-172, Cpd.4-173, Cpd.4-191, and Cpd.4-192.

As specified in tables, some compounds were purified preparative HPLC according to the following conditions: Column type: LiChrospher 100 RP-18 12_m—Merck NW25 250×25 mm—RT, detection 220 & 254 nm, solvent A (MeOH/HCOOH 0.1%) 70 to 40%) solvent B (water/HCOOH 0.1%): 30 to 60%.

See purification of Cpd.4-53, Cpd.4-54, Cpd.4-55, and Cpd.4-56.

Example 2

Synthesis of the Compounds According to the Invention

Synthesis of the compounds according to the invention as listed in FIGS. 4-9 requires specific reaction schemes (as single, two, three, four, or five steps) and conditions, as well as the means for purifying the compounds in a satisfactory manner by chromatography on silica gel (unless otherwise indicated) before proceeding to the evaluation of their biological activities, are summarized in following Tables 1-1 and 1-2 (for compounds having R2=R3=H and W or W—Z— as Rb), Tables 2-1 to 2-4 (for compounds having R2=R3=H and W or W—Z— as Ra), and Tables 3-1 and 3-2 (for compounds substituted by at least one R2 or R3 different of hydrogen and W or W—Z— as Ra).

TABLE 1-1

Rb is W or W-Z- and Ra and Rc-Rj are hydrogen, R2 and R3 are hydrogen

| Cpd. | Reagents and conditions for reaction; Chromatography on silica gel (yield) | Appearance, $^1$H NMR (solvent) data, Mass (ES+) data (MP) |
|---|---|---|
| 3-1 | Intermediate D and biphenyl-3-ol (Protocol SB; RT o/n) Eluent: cyclohexane/AcOEt 10/0 to 6/4 v/v (Yield: 20%) | White solid (MeOD-d$_4$): 7.26-7.45 (m, 5H); 7.53-7.69 (m, 5H); 8.22 (d, 1H, J = 9.8 Hz) Mass: 323.3 [M + H]+ |
| 3-2 | Intermediate D and (3-hydroxyphenyl)(phenyl)methanone (Protocol SB; 100° C. o/n) Eluent: cyclohexane/AcOEt 5/5 to 4/6 v/v (Yield: 40%) | White solid (MeOD-d$_4$): 7.36 (d, 1H, J = 10.0 Hz); 7.52-7.57 (m, 2H); 7.66-772 (m, 3H); 7.76-7.79 (m, 2H); 7.83-7.87 (m, 2H); 8.27 (d, 1H, J = 9.8 Hz) Mass: 351.2 [M + H]+ (MP: 148° C.) |
| 3-3 | Intermediate B and [1,1'-biphenyl]-3-ol (Protocol SB; 100° C., o/n) Eluent: cyclohexane/AcOEt 8/2 to 3/7 v/v (Yield: 47%) | White solid (MeOD-d$_4$): 7.28-7.73 (m, 10H); 8.38 (d, 1H, J = 9.8 Hz) Mass: 357.3 [M + H]+ (MP: 140.2° C.) |
| 3-4 | Intermediate B and (3-hydroxyphenyl)(phenyl)methanone (Protocol SB; 100° C. o/n) Eluent: cyclohexane/AcOEt 9/1 to 5/5 v/v (Yield: 57%) | Off-white solid (MeOD-d$_4$): 7.48 (d, 1H, J = 10.0 Hz); 7.52 (t, 2H, J = 7.7 Hz); 7.62-7.81 (m, 7H); 8.40 (d, 1H, J = 10.0 Hz) Mass: 385.3 [M + H]+ (MP: 94.4° C.) |
| 3-5 | From Cpd.3-4 (Protocol SC: 3 hours at 0° C. and 2 hours RT) Eluent: (Yield: 31%) | White solid (MeOD-d$_4$): 3.91 (s, 2H); 6.96-7.18 (m, 8H); 7.26-7.31 (m, 2H); 8.23 (d, 1H, J = 9.8 Hz) Mass: 371.3 [M + H]+ (MP: 115° C.) |

TABLE 1-2

Rb is W or W-Z- and at least one of Rf, Rg, or Rh is other than hydrogen atom, R2 and R3 are hydrogen.

| Cpd. | Reagents and conditions for reaction; Chromatography on silica gel (yield) | Appearance, $^1$H NMR (solvent) data, Mass (ES+ or ES−) data (MP) |
|---|---|---|
| 3-6 | 3'-fluorobiphenyl-3-ol from 3-bromophenol and 3-fluorophenyl boronic acid.(Protocol SA; 110° C. o/n) | Colourless oil (CDCl$_3$): 5.97 (s, 1H); 6.93 (dd, 1H, J = 8.1 Hz J = 2.5 Hz); 7.05-7.11 (m, 2H); |

TABLE 1-2-continued

Rb is W or W-Z- and at least one of Rf, Rg, or Rh is other than hydrogen atom, R2 and R3 are hydrogen.

| Cpd. | Reagents and conditions for reaction; Chromatography on silica gel (yield) | Appearance, $^1$H NMR (solvent) data, Mass (ES+ or ES−) data (MP) |
|---|---|---|
| | Eluent: cyclohexane/dichloromethane 8/2 to 6/4 v/v (Yield: 92%) | 7.19-7.43 (m, 5H) Mass: 187.1 [M + H]+ |
| | Intermediate D and 3'-fluorobiphenyl-3-ol (Protocol SB; 100° C. o/n) Eluent: cyclohexane/AcOEt 7/3 to 5/5 v/v (Yield: 85%) | Colourless amorphous solid (CDCl$_3$): 7.06-7.13 (m, 2H); 7.29-7.32 (m, 2H); 7.38-7.46 (m, 2H); 7.53-7.58 (m, 3H); 8.12 (d, 1H, J = 9.8 Hz) Mass: 341.1 [M + H]+ |
| 3-7 | 4'-methoxy-biphenyl-3-ol from 3-bromophenol and 4-methoxyphenyl-boronic acid (Protocol SA; reflux heating o/n) Eluent: cyclohexane/dichloromethane 10/0 to 0/10 v/v (Yield: 83%) | Colourless oil (CDCl$_3$): 3.87 (s, 3H); 4.90 (s, 1H); 6.87 (dd, 1H, J = 7.9 Hz J = 2.4 Hz); 6.98-7.05 (m, 3H); 7.15 (d, 1H, J = 7.7 Hz); 7.32 (d, 1H, J = 7.7 Hz); 7.52 (d, 2H, J = 8.8 Hz) |
| | Intermediate D and 4'-methoxy-biphenyl-3-ol (Protocol SB; 100° C. o/n) Eluent: cyclohexane/AcOEt 10/0 to 6/4 v/v (Yield: 60%) | White solid (CDCl$_3$): 3.87 (s, 3H); 7.01 (d, 2H, J = 8.9 Hz); 7.10 (d, 1H, J = 9.0 Hz); 7.22 (m, 1H); 7.48-7.59 (m, 5H); 8.10 (d, 1H, J = 9.8 Hz) Mass: 353.1 [M + H]+ (MP: 124.0; 137.8° C.) |
| 3-8 | 2'-methoxybiphenyl-3-ol from 3-bromophenol and 2-methoxyphenyl-boronic acid (Protocol SA; reflux heating o/n) Eluent: cyclohexane/AcOEt 10/0 to 8/2 v/v (Yield: 70%.) | Colourless oil (CDCl$_3$): 3.88 (s, 3H); 6.98 (dd, 2H, J = 8.6 Hz J = 2.3 Hz); 7.11 (d, 1H, J = 8.5 Hz); 7.17 (t, 1H, J = 7.3 Hz); 7.24-7.28 (m, 2H); 7.40 (d, 1H, J = 7.7 Hz); 7.44-7.49 (m, 2H) |
| | Intermediate D and 2'-methoxybiphenyl-3-ol (Protocol SB; 100° C. o/n) Eluent: cyclohexane/AcOEt 10/0 to 4/6 v/v (Yield: 60%) | Yellow solid (CDCl$_3$): 3.84 (s, 3H); 7.00-7.10 (m, 3H); 7.25 (m, 1H); 7.36 (m, 2H); 7.49 (m, 3H); 8.08 (d, 1H, J = 9.8 Hz) Mass: 353.1 [M + H]+ (MP: 82.5° C.) |
| 3-9 | 4'-fluorobiphenyl-3-ol from 3-bromophenol and 4-fluorophenyl-boronic acid (Protocol SA; 5 min at 150° C. on microwave) Eluent: cyclohexane/AcOEt 10/0 to 8/2 v/v (Yield: 89%) | White solid (CDCl$_3$): 4.88 (s, 1H); 6.83 (dd, 1H, J = 7.9 Hz J = 1.7 Hz); 7.03 (s, 1H); 7.13 (m, 3H); 7.32 (t, 1H, J = 7.7 Hz); 7.54 (m, 2H) |
| | Intermediate D and 4'-fluorobiphenyl-3-ol (Protocol SB; 100° C. o/n) Eluent: cyclohexane/AcOEt 8/2 to 5/5 v/v (Yield: 43%) | White solid (MeOD-d$_4$): 7.22 (t, 2H, J = 8.7 Hz); 7.34 (m, 1H); 7.38 (d, 1H, J = 9.8 Hz); 7.58-7.63 (m, 3H); 7.68-7.73 (m, 2H); 8.29 (d, 1H, J = 10.0 Hz Mass: 341.1 [M + H]+ (MP: 88.0° C.) |
| 3-10 | 2'-fluorobiphenyl-3-ol from 3-bromophenol and 2-fluorophenyl-boronic acid (Protocol SA; 110° C. o/n) Eluent: cyclohexane/AcOEt 10/0 to 8/2 v/v (Yield: 80%) | White solid (CDCl$_3$): 4.89 (s, 1H); 6.88 (d, 1H, J = 7.7 Hz); 7.06 (s, 1H); 7.13-7 36 (m 5H); 7.45 (t, 1H, J = 6.8 Hz) |
| | Intermediate D and 2'-fluorobiphenyl-3-ol (Protocol SB; 100° C. o/n) Eluent: cyclohexane/AcOEt 8/2 to 5/5 v/v (Yield: 64%) | White solid (MeOD-d$_4$): 7.20-7.44 (m, 5H); 7.53-7.63 (m, 4H); 8.28 (d, 1H, J = 9.8 Hz) Mass: 341.1 [M + H]+ ((MP: 128.6° C.) |
| 3-11 | 2'-chlorobiphenyl-3-ol from 3-bromophenol and 2-chlorophenyl-boronic acid (Protocol SA; 110° C. o/n) Eluent: cyclohexane/AcOEt 10/0 to 9/1 v/v (Yield: 85%) | Colourless oil (CDCl$_3$): 4.81 (s, 1H); 6.88 (m, 1H); 6.94 (t, 1H, J = 1.5 Hz); 7.03 (dt, 1H, J = 7.7 Hz J = 1.5 Hz); 7.29-7.37 (m, 4H); 7.47 (m, 1H) |
| | Intermediate D and 2'-chlorobiphenyl-3-ol (Protocol SB; 100° C. o/n) Eluent: cyclohexane/AcOEt 8/2 to 6/4 v/v (Yield: 83%) | White solid (MeOD-d$_4$): 7.34-7.46 (m, 7H); 7.52 (m, 1H); 7.58 (t, 1H, J = 7.9 Hz); 8.27 (d, 1H, J = 10.0 Hz) Mass: 357.1 [M + H]+ (MP: 82.4° C.) |
| 3-12 | 4'-chlorobiphenyl-3-ol from 3-bromophenol and 4-chlorophenyl-boronic acid (Protocol SA; 110° C. o/n) Eluent: cyclohexane/AcOEt 10/0 to 9/1 v/v (Yield: 95%) | Yellow solid (CDCl$_3$): 4.89 (s, 1H); 6.85 (dd, 1H, J = 8.1 Hz J = 1.9 Hz); 7.05 (s, 1H); 7.14 (d, 1H, J = 7.7 Hz); 7.33 (t, 1H, J = 7.9 Hz); 7.41 (d, 2H, J = 8.7 Hz); 7.51 (d, 2H, J = 8.7 Hz) |
| | Intermediate D and 4'-chlorobiphenyl-3-ol (Protocol SB; 100° C. o/n) Eluent: cyclohexane/AcOEt 8/2 to 6/4 v/v (Yield: 40%) | White solid (MeOD-d$_4$): 7.34 (m, 1H); 7.36 (d, 1H, J = 10.0 Hz); 7.47 (m, 2H); 7.58-7.69 (m, 5H); 8.27 (d, 1H, J = 9.8 Hz) Mass: 357.1 [M + H]+ (MP: 128° C.) |
| 3-13 | 3'-Chlorobiphenyl-3-ol from 3-bromophenol and 3-chlorophenyl- | (CDCl$_3$): 6.49 (s (large), 1H); 6.92-6.95 (m, 1H); 7.10 (s (large), 1H); 7.16 (d, |

TABLE 1-2-continued

Rb is W or W-Z- and at least one of Rf, Rg, or Rh is other than hydrogen atom, R2 and R3 are hydrogen.

| Cpd. | Reagents and conditions for reaction; Chromatography on silica gel (yield) | Appearance, $^1$H NMR (solvent) data, Mass (ES+ or ES−) data (MP) |
|---|---|---|
| | boronic acid. (Protocol SA; 110° C. o/n). Eluent: cyclohexane/AcOEt 1/0 to 6/4 v/v (Yield: 51%). | 1H, J = 8.1 Hz); 7.32-738 (m, 3H); 7.40-7.45 (m, 1H); 7.56 (m, 1H) |
| | Intermediate D and 3'-chlorobiphenyl-3-ol (Protocol SB; K2CO3 (2 eq); 110° C. o/n). Eluent: cyclohexane/AcOEt 5/5 v/v (Yield: 54%). | White solid (CDCl$_3$): 7.11 (d, 1H, J = 9.8 Hz); 7.29-7.34 (m, 1H); 7.35-7.44 (m, 2H); 7.50 (t, 1H, J = 1.9 Hz); 7.51-7.57 (m, 3H); 7.62 (t, 1H, J = 1.7 Hz); 8.12 (d, 1H, J = 9.8 Hz) Mass: 357.1 [M + H]+ (MP: 77.5-123.8° C.-DSC) |
| 3-14 | 3'-Methoxybiphenyl-2-ol from 3-methoxyphenylboronic acid and 3-bromophenol (Protocol SA; 110° C. o/n). Eluent: cyclohexane/AcOEt 1/0 to 8/2 v/v (Yield: 50%). Intermediate D and 3'-methoxy-biphenyl-2-ol (Protocol SB; K2CO3 (2 eq); 110° C. o/n). Eluent: cyclohexane/AcOEt 1/0 to 6/4 v/v (Yield: 52%). | (CDCl$_3$): 3.90 (s, 3H); 6.20 (s (large), 1H); 6.91 (dd, 1H, J = 7.9 Hz, J = 1.5 Hz); 6.97 (dd, 1H, J = 8.3 Hz, J = 1.7 Hz); 7.17 (d, 2H, J = 11.7 Hz); 7.20 (d, 2H, J = 8.9 Hz); 7.32-7.42 (m, 2H) White solid (CDCl$_3$): 3.85 (s, 3H); 6.91 (dd, 1H, J = 8.1 Hz, J = 1.9 Hz); 7.07 (d, 1H, J = 9.8 Hz); 7.12 (s, 1H); 7.18 (d, 1H, J = 7.7 Hz); 7.23-7.27 (m, 1H); 7.33 (t, 1H, J = 7.9 Hz); 7.48-7.53 (m, 3H); 8.06 (d, 1H, J = 9.8 Hz) Mass: 353.1 [M + H]+ (MP: 91.46° C.) |

TABLE 2-1

Ra is W or W-Z- and Rb-Rj are hydrogen, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-1 | Intermediate D and biphenyl-2-ol (Protocol SB; 100° C. o/n) Recrystallization in methanol or elution with cyclohexane/AcOEt 8/2 to 0/10 v/v (Yield: 67%) | White solid (MeOD-d$_4$): 7.17 (d, 1H, J = 9.8 Hz); 7.19-7.24 (m, 1H); 7.28-7.33 (m, 2H); 7.38-7.54 (m, 6H); 8.09 (d, 1H, J = 10.0 Hz) Mass: 323.2 [M + H]+ (MP: 163° C.) |
| 4-2 | Intermediate B and biphenyl-2-ol (Protocol SB; 100° C. o/n) Eluent: cyclohexane/AcOEt 8/2 to 3/7 v/v (Yield: 7%) | Brown oil (MeOD-d$_4$): 7.17-7.30 (m, 4H); 7.35-7.52 (m, 6H); 8.20 (d, 1H, J = 10.0 Hz) Mass: 357.2 [M + H]+ |
| 4-4 | Intermediate D and 2-benzylphenol (Protocol SB; 100° C. o/n) Eluent: cyclohexane/AcOEt 10/0 to 5/5 v/v (Yield: 10%) | White solid (MeOD-d$_4$): 3.99 (s, 2H); 6.83 (t, 1H, J = 7.2 Hz); 6.95-7.05 (m, 4H); 7.21 (d, 1H, J = 9.8 Hz); 7.24 (dd, 1H, J = 7.7 Hz J = 1.7 Hz); 7.32-7.42 (m, 2H); 7.46 (dd, 1H, J = 6.8 Hz J = 1.9 Hz); 8.10 (d, 1H, J = 9.8 Hz) Mass: 337.2 [M + H]+ (MP: 113.7° C.) |
| 4-5 | Intermediate B and 2-benzylphenol (Protocol SB; 110° C. o/n) Eluent: (Yield: 70%) | White solid (MeOD-d$_4$): 4.00 (s, 2H); 6.84 (t, 1H, J = 7.2 Hz); 6.95-7.05 (m, 4H); 7.24 (dd, 1H, J = 7.7 Hz J = 1.9 Hz); 7.29 (d, 1H, J = 10.0 Hz); 7.34-7.39 (m, 2H, J = 7.2 Hz J = 2.3 Hz); 7.44 (dd, 1H, J = 6.8 Hz J = 1.9 Hz); 8.21 (d, 1H, J = 10.0 Hz) Mass: 371.2 [M + H]+ (MP: 128.8° C.) |
| 4-8 | Intermediate B and (2-hydroxyphenyl)(phenyl)methanone (Protocol SB; 4 h at 100° C.) Eluent: (Yield: 30%) | Orange solid (MeOD-d$_4$): 7.12 (d, 1H, J = 10.0 Hz); 7.37 (t, 2H, J = 7.7 Hz); 7.51-7.56 (m, 3H); 7.65-7.70 (m, 3H); 7.73-7.77 (m, 1H); 8.24 (d, 1H, J = 9.8 Hz) Mass: 385.1 [M + H]+ (MP: 112.1° C.) |
| 4-9 | This compound was prepared starting from 2-(biphenyl-2-yl)acetonitrile using 5 steps (Protocols SG, SH, SI, SJ, and SK) | Off-white solid (MeOD-d$_4$): 4.24 (s 2H); 6.90 (d, 1H, J = 9.8 Hz); 7.15-7.69 (m, 9H); 7.92 (d, 1H, J = 9.8 Hz) Mass: 321.2 [M + H]+ |
| 4-11 | Intermediate D and (2-hydroxyphenyl)(phenyl)methanone (Protocol SB; RT o/n) | White solid (MeOD-d$_4$): 7.04 (d, 1H, J = 9.8 Hz); 7.41 (t, 2H, J = 7.5 Hz); 7.50-7.59 (m, 3H); |

TABLE 2-1-continued

Ra is W or W-Z- and Rb-Rj are hydrogen, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | Precipitation in diethyl ether (Yield: 60%) | 7.64 (dd, 1H, J = 8.1 Hz J = 1.9 Hz); 7.72-7.78 (m, 3H); 8.11 (d, 1H, J = 9.8 Hz) Mass: 351.1 [M + H]+ (MP: 137.9° C.) |
| 4-12 | This compound was prepared starting from intermediate B and 2-(biphenyl-2-yl)acetonitrile (Protocols SG and SH) | White solid (MeOD-d$_4$): 4.32 (s, 2H); 7.09 (d, 1H, J = 9.8 Hz); 7.20-7.31 (m, 6H); 7.37-7.42 (m, 3H); 8.12 (d, 1H, J = 9.6 Hz) Mass: 355.3 [M + H]+ (MP: 117.4° C.) |
| 4-98 | 2-(Pyridin-3-yl)phenol from 2-bromophenol and pyridin-3-yl-boronic acid (Protocol SA; boronic acid (2 eq), PCy$_3$ (0.024 eq), PdDBa$_3$ (0.01 eq), K$_3$PO$_4$ (2.0 eq)-dioxane/water - 10 min at 120° C. on microwave.) Eluent: dichloromethane/AcOEt 5/5 v/v (Yield: 40%) | White solid (DMSO-d$_6$): 6.91 (td, 1H, J = 7.6 Hz, J = 1.0 Hz); 6.96 (dd, 1H, J = 7.6 Hz, J = 1.0 Hz); 7.22 (td, 1H, J = 7.9 Hz, J = 1.7 Hz); 7.30 (dd, 1H, J = 7.6 Hz, J = 1.0 Hz); 7.42 (td, 1H, J = 7.6 Hz, J = 1.0 Hz); 7.93 (tt, 1H, J = 7.9 Hz, J = 1.7 Hz); 8.48 (dd, 1H, J = 4.7 Hz, J = 1.7 Hz); 8.72 (d, 1H, J = 1.7 Hz); 9.75 (s, 1H) |
| | Intermediate D and 2-(pyridin-3-yl)phenol (Protocol SB; 10 min at 170° C. on microwave) Eluent: dichloromethane/MeOH 95/5 v/v (Yield: 71%). | White solid (DMSO-d$_6$): 5.60 (s, 1H); 7.31 (d, 1H, J = 9.9 Hz); 7.45-7.65 (m, 3H); 7.70 (dd, 1H, J = 7.6 Hz, J = 1.4 Hz); 7.22 (m, 1H); 7.93 (tt, 1H, J = 7.9 Hz); 8.42 (d, 1H, J = 9.9 Hz); 8.70 (d, 1H, J = 4.9 Hz); 8.72 (s, 1H) Mass (ES+): 324/326 (M + H) (MP: 192.0-197.0° C.) |
| 4-103 | 2-(thiazol-4-yl)phenol from 2-hydroxyphenylboronic acid and 4-bromothiazole (Protocol SA, boronic acid (2 eq,) potassium phosphate (2.40 eq), Pd$_2$dBa$_3$ (0.01 eq) and XPHOS (0.04 eq) in dioxane/water; 15 min at 120° C. on microwave) Eluent: cyclohexane/dichloromethane 7/3 v/v (Yield: 57%) | Colorless liquid (DMSO-d$_6$): 6.90 (t, 1H, J = 7.9 Hz); 6.95 (d, 1H, J = 7.9 Hz); 7.19 (td, 1H, J = 7.9 Hz, J = 1.5 Hz); 8.02 (dd, 1H, J = 7.9 Hz, J = 1.5 Hz); 8.24 (d, 1H, J = 2.0 Hz); 9.24 (d, 1H, J = 2.0 Hz); 10.83 (s, 1H) |
| | 2-(thiazol-4-yl)phenol and intermedidiate D, (Protocol SB; 120° C. microwave 10 min) Eluent: dichloromethane/AcOEt 8/2 v/v (Yield: 36%) | White solid (DMSO-d$_6$): 7.4-7.55 (m, 4H); 8.02 (d, 1H, J = 2.0 Hz); 8.12 (d, 1H, J = 7.9 Hz); 8.47 (d, 1H, J = 9.9 Hz); 9.13 (d, 1H, J = 2.0 Hz) Mass (ES+): 330/332 (M + H) (MP: 132.0-134.0° C.) |
| 4-104 | 2-(thiazol-2-yl)phenol from 2-hydroxyphenylboronic acid, 2-bromothiazole (Protocol SA, boronic acid (2 eq,), potassium phosphate (2.40 eq), Pd$_2$dBa$_3$ (0.01 eq) and XPHOS (0.04 eq) in dioxane/water; 15 min at 120° C. on microwave) Eluent: cyclohexane/dichloromethane 7/3 v/v (Yield: 3%) | Colorless liquid (DMSO-d$_6$): 6.90 (t, 1H, J = 7.9 Hz); 6.95 (d, 1H, J = 7.9 Hz); 7.19 (td, 1H, J = 7.9 Hz, J = 1.5 Hz); 8.02 (dd, 1H, J = 7.9 Hz, J = 1.5 Hz); 8.24 (d, 1H, J = 2.0 Hz); 9.24 (d, 1H, J = 2.0 Hz); 10.83 (s, 1H) |
| | 2-(thiazol-2-yl)phenol and intermediate D (Protocol SB; 10 min at 120° C. on microwave) Eluent: dichloromethane/AcOEt 8/2 v/v and trituration in diethyl ether (Yield: 63%) | White solid (DMSO-d$_6$): 7.4-7.7 (m, 4H); 7.85 (d, 1H, J = 3.2 Hz); 7.97 (d, 1H, J = 3.2 Hz); 8.34 (dd, 1H, J = 8.0 Hz, J = 1.3 Hz); 8.56 (d, 1H, J = 9.9 Hz) Mass (ES+): 330/332 (M + H) (MP: 174.0-176.0° C.) |
| 4-108 | 2-(Thiophen-3-yl)phenol from 2-bromophenol and thiophen-3-yl-boronic acid (Protocol SA; boronic acid (2 eq), PCy$_3$ (0.024 eq), PdDBa$_3$(0.01 eq), K$_3$PO$_4$(2.0 eq)-dioxane/water - 15 min at 120° C. on microwave.) Eluent cyclohexane/dichloromethane 7/3 v/v (Yield: 16%) | White solid (DMSO-d$_6$): 6.83 (td, 1H, J = 7.6 Hz, J = 1.2 Hz); 6.93 (dd, 1H, J = 7.6 Hz, J = 1.2 Hz); 7.10 (td, 1H, J = 7.6 Hz, J = 1.0 Hz); 7.49 (dd, 1H, J = 7.6 Hz, J = 1.0 Hz); 7.50-7.55 (m, 2H); 7.82 (t, 1H, J = 2.0 Hz); 9.74 (s, 1H) |
| | Intermediate D and 2-(thiophen-3-yl)phenol (Protocol SB; 10 min at 120° C. on microwave) (Yield: 80%) | Beige solid (DMSO-d$_6$): 7.36 (m, 1H, J = 7.6 Hz); 7.39 (d, 1H, J = 9.9 Hz); 7.35-7.5 (m, 3H); 7.55 (dd, 1H, J = 7.6 Hz); 7.69 (d, 1H, J = 7.6 Hz); 7.72 (m, 1H); 8.42 (d, 1H, J = 9.9 Hz) |

TABLE 2-1-continued

Ra is W or W-Z- and Rb-Rj are hydrogen, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-109 | 2-(3,5-Dimethylisoxazol-4-yl)phenol from 2-bromophenol and 3,5-dimethylisoxazol-4-ylboronic acid (Protocol SA; boronic acid (2 eq), PCy$_3$ (0.024 eq), PdDBa$_3$(0.01 eq), K$_3$PO$_4$ (2.0 eq)-dioxane/water - microwave 15 min at 120° C. on microwave) Eluent: dichloromethane/AcOEt 9/1 v/v (Yield: 12%) | Mass (ES+): 329/331 (M + H) (MP: 176.0-178.0° C.) White solid (DMSO-d$_6$): 2.10 (s, 3H); 2.26 (s, 3H); 6.86 (td, 1H, J = 7.6 Hz, J = 1.2 Hz); 6.94 (dd, 1H, J = 7.6 Hz, J = 1.2 Hz); 7.13 (dd, 1H, J = 7.6 Hz, J = 1.2 Hz); 7.21 (td, 1H, J = 7.6 Hz, J = 1.2 Hz); 9.65 (s, 1H) |
| | Intermediate D and 2-(3,5-dimethylisoxazol-4-yl)phenol (Protocol SB; 10 min at 120° C. on microwave) Eluent: dichloromethane/AcOEt 9/1 v/v (Yield: 43%) | White solid (DMSO-d$_6$): 2.10 (s, 3H); 2.26 (s, 3H); 7.36 (d, 1H, J = 9.9Hz); 7.45-7.55 (m, 3H); 7.55-7.65 (m, 1H); 8.40 (d, 1H, J = 9.9 Hz) Mass (ES+): 342/344 (M + H) (MP: 144.0-146.0° C.) |
| 4-110 | 2-(benzo[d]thiazol-5-yl)phenol, from 2-hydroxyphenylboronic acid, and 5-bromobenzo[d]thiazole (Protocole SA, boronic acid (2 eq), potassium phosphate (2.40 eq), Pd$_2$dBa$_3$ (0.01 eq) and XPHOS (0.04 eq) in dioxane/water; 15 min at 120° C. on microwave) Eluent: dichloromethane 100%(Yield: 77%) | White Solid (DMSO-d$_6$): 6.91 (t, 1H, J = 7.6 Hz); 7.00 (d, 1H, J = 7.6 Hz); 7.20 (td, 1H, J = 7.6 Hz, J = 1.5 Hz); 7.36 (dd, 1H, J = 7.6 Hz, J = 1.5 Hz); 7.66 (dd, 1H, J = 8.4 Hz, J = 1.7 Hz); 8.16 (d, 1H, J = 8.4 Hz, J = 1.7 Hz); 8.21 (d, 1H, J = 1.7 Hz); 9.40 (s, 1H); 11.47 (s, 1H) |
| | 2-(benzo[d]thiazol-5-yl)phenol, intermedidiate D (Protocole SB; 120° C. microwave 10 min) Eluent: dichloromethane/AcOEt 8/2 v/v and trituration in diethyl ether and recrystallized from methanol (Yield: 78%) | White solid (DMSO-d$_6$): 7.28 (d, 1H, J = 9.9 Hz); 7.45-7.6 (m, 4H); 7.65 (dd, 1H); 8.1-8.2 (m, 2H); 8.56 (d, 1H, J = 9.9 Hz); 9.40 (s, 1H) Mass (ES+): 380/382 (M + H) MP: 158.0-160.0° C. |

TABLE 2-2

Ra is W, Rb-Re are hydrogen and at leastone of Rf-Rj is other than hydrogen atom, R2 and R3 are hydrogen.

| Cpd. | Starting compounds, Reaction conditions and purification | Appearance, $^1$H NMR (solvent) data, Mass (ES+ or ES−) data (MP) |
|---|---|---|
| 4-3 | 3'-fluorobiphenyl-2-ol from 2-bromophenol and 3-fluorophenyl-boronic acid (Protocol SA; 110° C. o/n) Eluent: cyclohexane/AcOEt 10/0 to 9/1 v/v (Yield: 38%.) | Colourless oil (DMSO-d$_6$): 6.90 (td, 1H, J = 7.3 Hz J = 1.1 Hz); 6.97 (dd, 1H, J = 8.1 Hz J = 1.0 Hz); 7.10-.724 (m, 2H); 7.31 (dd, 1H, J = 7.6 Hz J = 1.7 Hz); 7.37-7.49 (m, 3H); 9.68 (s, 1H) |
| | Intermediate D and 3'-fluorobiphenyl-2-ol (Protocol SB; 3 hours at 100° C.) Eluent: cyclohexane/AcOEt 8/2 to 7/3 v/v (Yield: 61%) | White solid (MeOD-d$_4$): 6.95-7.01 (m, 1H); 7.18-7.57 (m, 8H); 8.14 (d, 1H, J = 10.0 Hz) Mass: 341.1 [M + H]+ (MP: 97.3° C.) |
| 4-10 | 4'-fluorobiphenyl-2-ol from 2-bromophenol and 4-fluorophenyl-boronic acid (Protocol SA; 110° C. o/n) Eluent: cyclohexane/AcOEt 10/0 to 9/1 v/v (Yield: 38%) | Colourless oil (DMSO-d$_6$): 6.89 (td, 1H, J = 7.5 Hz J = 0.9 Hz); 6.96 (dd, 1H, J = 7.9 Hz J = 0.9 Hz); 7.15-7.27 (m, 4H); 7.59 (m, 2H); 9.58 (s, 1H) Mass: 187.1 [M − H]− |
| | Intermediate D and 4'-fluorobiphenyl-2-ol (Protocol SB; 100° C. o/n) Eluent: cyclohexane/AcOEt 80/20 to 75/35 v/v (Yield: 98%) | White solid (MeOD-d$_4$): 7.06 (t, 2H, J = 8.7 Hz); 7.19 (d, 1H, J = 10.0 Hz); 7.38-7.53 (m, 6H); 8.13 (d, 1H, J = 10.0 Hz) Mass: 341.1 [M + H]+ (MP: 144.4° C.) |
| 4-13 | 2',4'-difluoro-biphenyl-2-ol from 2-bromophenol and 2,4-difluorophenyl-boronic acid (Protocol SA; 110° C. o/n) Eluent: cyclohexane/dichloromethane 8/2 to 6/4 v/v (Yield: 56%) | White solid (CDCl$_3$): 4.99 (s (large), 1H); 6.95-7.07 (m, 4H); 7.24-7.43 (m, 3H) |

TABLE 2-2-continued

Ra is W, Rb-Re are hydrogen and at least one of Rf-Rj is other than hydrogen atom, R2 and R3 are hydrogen.

| Cpd. | Starting compounds, Reaction conditions and purification | Appearance, $^1$H NMR (solvent) data, Mass (ES+ or ES−) data (MP) |
|---|---|---|
|  | Intermediate D and 2',4'-difluoro-biphenyl-2-ol (Protocol SB; 2 hours at 100° C.) Eluent: cyclohexane/AcOEt 8/2 to 5/5 v/v (Yield: 90%) | Colourless amorphous solid (CDCl$_3$): 6.79-6.91 (m, 3H); 7.26-7.33 (m, 1H); 7.38 (d, 1H, J = 7.9 Hz); 7.44-7.47 (m, 2H); 7.51-7.57 (m, 1H); 7.96 (d, 1H, J = 9.8 Hz) Mass: 359.1 [M + H]+ |
| 4-16 | 3'-methoxybiphenyl-2-ol from 2-bromophenol and 3-methoxyphenyl boronic acid. Protocol SA; 110° C. o/n Eluent: cyclohexane/dichloromethane 8/2 to 6/4 v/v (Yield: 58%) | White solid (CDCl$_3$): 3.87 (s, 3H); 5.35 (s, 1H); 6.96-7.09 (m, 5H); 7.27-7.30 (m, 2H); 7.43 (t, 1H, J = 7.9 Hz) |
|  | Intermediate D and 3'-methoxy-biphenyl-2-ol (Protocol SB; 2 hours at 100° C.) Eluent: cyclohexane/AcOEt 8/2 to 5/5 v/v (Yield: 85%) | Colourless amorphous solid (CDCl$_3$): 3.76 (s, 3H); 6.76-6.80 (m, 1H); 6.89 (d, 1H, J = 9.8 Hz); 6.96 (t, 1H, J = 2.5 Hz); 6.97-7.01 (m, 1H); 7.21 (t, 1H, J = 7.9 Hz); 7.30-7.33 (m, 1H); 7.40-7.52 (m, 3H); 7.92 (d, 1H, J = 9.8 Hz) Mass: 353.1 [M + H]+ |
| 4-17 | 2'-fluorobiphenyl-2-ol from 2-bromo-phenol and 2-fluorophenyl-boronic acid (Protocol SA; 110° C. o/n) Eluent: cyclohexane/dichloromethane 10/0 to 6/4 v/v (Yield: 15%) | Colourless oil (CDCl$_3$): 4.94 (s, 1H); 7.04 (t, 2H, J = 7.7 Hz); 7.20-7.46 (m, 6H) |
|  | Intermediate D and 2'-fluorobiphenyl-2-ol (Protocol SB: 100° C. o/n) Eluent: cyclohexane/AcOEt 10/0 to 6/4 v/v (Yield: 35%) | White solid (CDCl$_3$): 6.88 (d, 1H, J = 9.8 Hz); 7.0-7.11 (m, 2H); 7.22-7.55 (m, 6H); 7.92 (d, 1H, J = 9.8 Hz) Mass: 341.1 [M + H]+ (MP: 95.9° C.) |
| 4-20 | 3',4'-difluoro-biphenyl-2-ol from 2-bromophenol and 3,4-difluorophenyl boronic acid (Protocol SA; 110° C. o/n) Eluent: cyclohexane/dichloromethane 7/3 v/v (Yield: 70%) | White solid (CDCl$_3$): 5.06 (s, 1H); 6.96 (dd, 1H, J = 8.1 Hz J = 0.8 Hz); 7.02 (td, 1H, J = 7.6 Hz J = 1.1 Hz); 7.21-7.39 (m, 5H) |
|  | Intermediate D and 3',4'-difluorobiphenyl-2-ol (Protocol SB; 3 hours at 100° C.) Eluent: cyclohexane/AcOEt 7/3 to 6/4 v/v (Yield: 87%) | White solid (MeOD-d$_4$): 7.18-7.26 (m, 3H); 7.35-7.56 (m, 5H); 8.17 (d, 1H, J = 9.8 Hz) Mass: 359.0 [M + H]+ (MP: 129.3° C.) |
| 4-21 | Cpd 4-16 (Protocol SD: RT o/n) Eluent: cyclohexane/AcOEt 7/3 to 5/5 v/v (Yield: 32%) | White solid (MeOD-d$_4$): 6.65 (dd, 1H, J = 8.3 Hz J = 1.5 Hz); 6 84 (s, 1H); 6.87 (d, 1H, J = 7.71 Hz); 7.11 (t, 1H, J = 7.9 Hz); 7.17 (d, 1H, J = 10.0 Hz); 7.37-7.51 (m, 4H); 8.11 (d, 1H, J = 10.0 Hz) Mass: 339.1 [M + H]+ (MP: 203.7° C.) |
| 4-22 | 4'-methoxybiphenyl-2-ol from 2-bromo-phenol and 4-methoxyphenyl-boronic acid (Protocol SA; 110° C. o/n) Eluent: cyclohexane/dichloromethane 8/2 to 6/4 v/v (Yield: 30%) | White solid (CDCl$_3$): 3.90 (s, 3H); 5.62 (s, 1H); 7.03-7.09 (m, 4H); 7.28-7.33 (m, 2H); 7.49 (d, 2H, J = 8.6 Hz) |
|  | Intermediate D and 4'-methoxybiphenyl-2-ol (Protocol SB; 100° C. o/n) Eluent: cyclohexane/AcOEt 10/0 to 6/4 v/v (Yield: 52%) | Off-white solid (CDCl$_3$): 3.78 (s, 3H); 6.82-6.85 (m, 2H); 6.89 (d, 1H, J = 9.8 Hz); 7.30-7.49 (m, 6H); 7.92 (d, 1H, J = 9.8 Hz) Mass: 353.1 [M + H]+ (MP: 138.1° C.) |
| 4-23 | 4'-methylbiphenyl-2-ol from 2-bromo-phenol and 4-methylphenyl-boronic acid (Protocol SA: 110° C. o/n) Eluent: cyclohexane/dichloromethane 10/0 to 5/5 v/v (Yield: 70%) | White solid (CDCl$_3$): 2.49 (s, 3H); 5.38 (s, 1H); 7.04-7.08 (m, 2H); 7.31 (d, 2H, J = 7.4 Hz); 7.37 (d, 2H, J = 7.9 Hz); 7.44 (d, 2H, J = 8.1 Hz) |
|  | Intermediate D and 4'-methylbiphenyl-2-ol (Protocol SB: 100° C. o/n) Eluent: cyclohexane/AcOEt 10/0 to 5/5 v/v (Yield: 54%) | White solid (CDCl$_3$): 2.31 (s, 3H); 6.88 (d, 1H, J = 9.8 Hz); 7.11 (d, 2H, J = 7.9 Hz); 7.29-7.32 (m, 3H); 7.39-7.50 (m, 3H); 7.91 (d, 1H, J = 9.8 Hz) Mass: 337.1 [M + H]+ (MP: 166.9-173.4° C.) |
| 4-24 | 4'-(trifluoromethyl)-biphenyl-2-ol from 2-bromophenol and 4-(trifluoromethyl)phenyl-boronic acid (Protocol SA; 110° C. o/n) Eluent: cyclohexane/dichloromethane 8/2 to 6/4 v/v (Yield: 43%) | White solid (CDCl$_3$): 5.02 (s, 1H); 6.99 (dd, 1H, J = 7.9 Hz J = 0.8 Hz); 7.05 (td, 1H, J = 7.5 Hz J = 1.1 Hz); 7.29-7.34 (m, 2H); 7.66 (d, 2H, J = 8.1 Hz); 7.76 (d, 2H, J = 8.1 Hz) |
|  | Intermediate D and 4'-(trifluoromethyl)-biphenyl-2-ol | White solid (CDCl$_3$): 6.91 (d, 1H, J = 9.8 Hz); 7.35 (d, |

TABLE 2-2-continued

Ra is W, Rb-Re are hydrogen and at leastone of Rf-Rj is other than hydrogen atom, R2 and R3 are hydrogen.

| Cpd. | Starting compounds, Reaction conditions and purification | Appearance, $^1$H NMR (solvent) data, Mass (ES+ or ES−) data (MP) |
|---|---|---|
| | (Protocol SB: 90 min. at 100° C.) Eluent: cyclohexane/AcOEt 8/2 to 6/4 v/v (Yield: 73%) | 1H, J = 8.1 Hz); 7.43-7.62 (m, 7H); 7.97 (d, 1H, J = 10.0 Hz) Mass: 391.1 [M + H]+ (MP: 185.8° C.) |
| 4-25 | 2'-chlorobiphenyl-2-ol from 2-bromophenol and 2-chlorophenyl-boronic acid (Protocol SA; 110° C. o/n) Eluent: cyclohexane/dichloromethane 8/2 to 6/4 v/v (Yield: 20%.) | Yellow oil (CDCl$_3$): 5.37 (s, 1H); 7.03-7.10 (m, 2H); 7.24 (dd, 1H, J = 7.5 Hz J = 1.5 Hz); 7.34-7.43 (m, 4H); 7.56-7.60 (m, 1H) |
| | Intermediate D and 2'-chlorobiphenyl-2-ol (Protocol SB: 100° C. o/n) Eluent: cyclohexane/AcOEt 10/0 to 5/5 v/v (Yield: 16%) | Yellow solid (CDCl$_3$): 6.82 (d, 1H, J = 9.8 Hz); 7.13-7.19 (m, 2H); 7.25 (m, 1H); 7.33-7.46 (m, 4H); 7.53 (m, 1H); 7.87 (d, 1H, J = 9.8 Hz) Mass: 357.1 [M + H]+ (MP: 81.9° C.) |
| 4-28 | 3'-(trifluoromethyl)-biphenyl-2-ol from 2-bromophenol and 3-(trifluoromethyl)phenylboronic acid (Protocol SA; 110° C. o/n) Eluent: cyclohexane/AcOEt 100/0 to 95/5 v/v (Yield: 26%) | Yellow oil (DMSO-d$_6$): 7.89 (d, 1H); 6.90-7.00 (m, 2H); 7.24 (m, 1H); 7.34 (dd, 1H, J = 7.5 Hz J = 1.7 Hz); 7.67 (m, 1H); 7.85-7.89 (m, 2H); 9.77 (s, 1H) |
| | Intermediate D and 3'-(trifluoromethyl)-biphenyl-2-ol (Protocol SB; 100° C. o/n) Eluent: cyclohexane/AcOEt 8/2 to 5/5 v/v (Yield: 53%) | Brown oil (DMSO-d$_6$): 7.24-7.27 (d, 1H, J = 9.9 Hz); 7.46-7.74 (m, 8H); 8.34-8.38 (d, 1H, J = 9.9 Hz) Mass: 391 [M + H]+; 413 [M + Na]+ |
| 4-29 | 3'-chlorobiphenyl-2-ol from 2-bromo phenol and 3-chlorophenylboronic acid (Protocol SA; 110° C. o/n) (Yield: 52%) | Yellow oil (CDCl$_3$): 6.90 (t, 1H, J = 7.5 Hz); 6.99 (d, 1H, J = 7.3 Hz); 7.21 (td, 1H, J = 8.3 Hz J = 1.5 Hz); 7.30 (dd, 1H, J = 7.5 Hz J = 1.5 Hz); 7.35-7.54 (m, 3H); 7.62 (m, 1H); 9.70 (s, large), 1H) |
| | Intermediate D and 3'-chlorobiphenyl-2-ol (Protocol SB; 100° C. o/n) Eluent: cyclohexane/AcOEt 80/20 to 75/35 v/v (Yield: 53%) | White solid (DMSO-d$_6$): 7.27-7.39 (m, 4H); 7.43-7.58 (m, 5H); 8.36-8.39 (d, 1H, J = 9.9 Hz) Mass: 357 [M + H]+; 379 [M + Na]+ (MP: 89.8° C.) |
| 4-111 | 2'-Methoxybiphenyl-2-ol from 2-bromophenol and 2-methoxybenzene-boronic acid (Protocol SA; 110° C. o/n). Eluent: cyclohexane/AcOEt 1/0 to 6/4 v/v (Yield: 40%). | (CDCl$_3$): 3.98 (s, 3H); 7.14 (dd, 1H, J = 8.3 Hz, J = 1.1 Hz); 7.19 (m, 1H, J = 8.5 Hz, J = 1.1 Hz); 7.25 (m, 1H, J = 8.1 Hz, J = 1.0 Hz); 7.45 (d, 2H, J = 7.4 Hz); 7.49-7.54 (m, 2H) |
| | Intermediate D and 2'-methoxy-biphenyl-2-ol (Protocol SB; K$_2$CO$_3$ (1.3 eq); 5 hours at 100° C.). Eluent: cyclohexane/AcOEt 9/1 to 6/4 v/v (Yield: 54%). | White solid (CDCl$_3$): 3.61 (s, 3H); 6.81 (d, 1H, J = 9.8 Hz); 6.83 (d, 1H, J = 6.8 Hz); 6.90 (m, 1H, J = 7.3 Hz, J = 0.7 Hz); 7.19 (dd, 1H, J = 7.5 Hz, J = 1.7 Hz); 7.22-7.25 (m, 1H); 7.34-7.51 (m, 4H); 7.88 (d, 1H, J = 9.8 Hz) Mass: 353.1 [M + H]+ |
| 4-117 | 4'-Chlorobiphenyl-2-ol from 2-bromophenol and 4-chlorophenyl-boronic acid (Protocol SA; 110° C. o/n). Eluent: cyclohexane/dichoromethane 8/2 to 5/5 v/v (Yield: 50%). | (CDCl$_3$): 5.10 (s, 1H); 6.99 (dd, 1H, J = 8.1 Hz, J = 0.7 Hz); 7.03 (m, 1H, J = 7.5 Hz, J = 1.1 Hz); 7.24-7.33 (m, 2H); 7.44-7.51 (m, 4H) |
| | Intermediate D and 4'-chlorobiphenyl-2-ol (Protocol SB; K$_2$CO$_3$ (1.2 eq); 110° C. o/n). Eluent: cyclohexane/AcOEt 1/0 to 7/3 v/v (Yield: 18%). | Beige solid (CDCl$_3$): 6.90 (d, 1H, J = 9.8 Hz); 7.29-7.39 (m, 5H); 7.43-7.49 (m, 3H); 7.96 (d, 1H, J = 9.8 Hz) Mass: 357.1 [M + H]+ (MP: 173° C.) |
| 4-132 | 3'-Methylbiphenyl-2-ol | (DMSO-d$_6$): 2.44 (s, 3H); 5.28 (s, 1H); 6.99-7.03 (m, 2H); 7.23-7.28 (m, 5H); 7.38 (t, 1H, J = 7.5 Hz) DMSO d6: 2.44 (s, 3H); 5.28 (s, 1H); 6.99-7.03 (m, 2H); 7.23-7.28 (m, 5H); 7.38 (t, 1H, J = 7.5 Hz) |
| | Intermediate D and 3'-methylbiphenyl-2-ol (Protocol SB; K$_2$CO$_3$ (2 eq); 10 min at 120° C. on microwave). Eluent: cyclohexane/AcOEt 1/1 v/v (Yield: 74%). | White solid (DMSO-d$_6$): 2.24 (s, 3H); 7.04-7.07 (m, 1H); 7.17-7.21 (m, 3H); 7.25 (d, 1H, J = 9.9 Hz); 7.40-7.52 (m, 4H); 8.34 (d, 1H, J = 9.9 Hz) Mass: 337 [M + H]+ (MP: 51° C.) |

TABLE 2-2-continued

Ra is W, Rb-Re are hydrogen and at leastone of Rf-Rj is other than hydrogen atom, R2 and R3 are hydrogen.

| Cpd. | Starting compounds, Reaction conditions and purification | Appearance, $^1$H NMR (solvent) data, Mass (ES+ or ES−) data (MP) |
|---|---|---|
| 4-133 | Intermediate B and 3'-methylbiphenyl-2-ol (Protocol SB; K$_2$CO$_3$ (2 eq); 10 min at 170° C. on microwave). Eluent: cyclohexane/AcOEt 1/1 v/v (Yield: 73%). | Colorless amorphous solid (DMSO-d$_6$): 2.22 (s, 3H); 7.04-7.06 (m, 1H); 7.17-7.19 (m, 3H); 7.41-7.52 (m, 5H); 8.50 (d, 1H, J = 9.9 Hz) Mass: 371 [M + H]+ |
| 4-140 | 3'-Carboxybiphenyl-2-ol from 2-bromophenol and 3-carboxybenzene-boronic acid (Protocol SA; 5 min at 150° C. on microwave). Eluent: dichloromethane/AcOEt 8/2 v/v (Yield: 5%) | (DMSO-d$_6$): 6.90 (t, 1H, J = 7.6 Hz); 6.96 (d, 1H, J = 7.6 Hz); 7.19 (td, 1H, J = 7.9 Hz, J = 1.5 Hz); 7.28 (dd, 1H, J = 7.6 Hz, J = 1.5 Hz); 7.52 (t, 1H, J = 7.6 Hz); 7.77 (d, 1H, J = 7.9 Hz); 7.87 (d, 1H, J = 7.6 Hz); 8.13 (s, 1H); 9.62 (s, 1H); 12.94 (s, 1H) |
| | Intermediate D and 3'-carboxybiphenyl-2-ol (Protocol SB; K$_2$CO$_3$ (4 eq); 10 min at 170° C. on microwave). Acidification of aqueous layer with 1M HCl, filtration (Yield: 70%) | White solid (DMSO-d$_6$): 7.24 (d, 1H, J = 9.9 Hz); 7.51 (m, 5H); 7.64 (d, 1H, J = 7.9 Hz); 7.83 (d, 1H, J = 7.9 Hz); 7.95 (s, 1H); 8.35 (d, 1H, J = 9.9 Hz); 12.96 (s, 1H) Mass: 367 [M + H]+ (MP: 236-246° C.) |
| | From 3-chloro-6-(3'carboxy-biphenyl-2-yloxy)-[1,2,4]triazolo[4,3-b]pyridazine (Protocol SR). Eluent: dicholoromethane/AcOEt 7/3 v/v (Yield: 53%) | White solid (DMSO-d$_6$): 3.77 (s, 3H); 7.24 (d, 1H, J = 9.9 Hz); 7.52 (m, 5H); 7.70 (dt, 1H, J = 7.9 Hz, J = 1.5 Hz); 7.85 (d, 1H, J = 7.9 Hz); 7.95 (st, 1H, J = 1.4 Hz); 8.35 (d, 1H, J = 9.9 Hz) Mass: 381 [M + H]+ (MP: 155-158° C.) |

TABLE 2-3

Ra is W or W-Z, Rf-Rj are hydrogen, and at least one of Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-6 | 4-methoxybiphenyl-2-ol from 2-bromo-5-methoxyphenol and phenylboronic acid (Protocol SA; 110° C. o/n) Eluent: cyclohexane/AcOEt 100/0 to 95/5 v/v (Yield: 91%) | Yellow solid (CDCl$_3$): 3.84 (s, 3H); 5.30 (s, 1H); 6.58-6.61 (m, 2H); 7.18 (d, 1H, J = 9.0 Hz); 7.39-7.50 (m, 5H) |
| | Intermediate D and 4-methoxy-biphenyl-2-ol (Protocol SB; 3 hours at 100° C.) Eluent: cyclohexane/AcOEt 8/2 to 7/3 v/v (Yield: 69%) | White solid (CDCl$_3$): 3.90 (s, 3H); 6.85-6.89 (m, 2H); 6.98 (dd, 1H, J = 8.5 Hz J = 2.6 Hz); 7.20-7.30 (m, 3H); 7.36-7.39 (m, 2H); 7.41 (d, 1H, J = 8.5 Hz); 7.90 (d, 1H, J = 9.8 Hz) Mass: 353.2 [M + H]+ (MP: 128.1° C.) |
| 4-7 | 4-fluorobiphenyl-2-ol from 2-bromo-5-fluorophenol and phenylboronic acid (Protocol SA; 110° C. o/n) Eluent: cyclohexane/AcOEt 10/0 to 9/1 v/v (Yield: 20%) | Yellow oil (DMSO-d$_6$): 6.72 (m, 2H); 7.28-7.51 (m, 6H); 10.07 (s, 1H) |
| | Intermediate D and 4-fluorobiphenyl-2-ol (Protocol SB; 100° C. o/n) Eluent: cyclohexane/AcOEt 7/3 to 5/5 v/v (Yield: 45%) | Off-white solid (DMSO-d$_6$): 7.30-7.45 (m, 7H); 7.53 (dd, 1H, J = 9.8 Hz J = 2.6 Hz); 7.61 (dd, 1H, J = 8.7 Hz J = 6.6 Hz); 8.41 (d, 1H, J = 9.8 Hz) Mass: 341.1 [M + H]+ (MP: 180.7° C.) |
| 4-14 | 5-methoxybiphenyl-2-ol from 2-bromo-4-methoxyphenol and phenylboronic acid (Protocol SA; 100° C. o/n) Eluent: cyclohexane/dichloromethane 10/0 to 5/5 v/v (Yield: 36%) | Brown oil (MeOD-d$_4$): 3.81 (s, 3H); 4.88 (s, 1H); 6.82-6.87 (m, 2H); 6.93-6.95 (m, 1H); 7.04-7.54 (m, 5H) |
| | Intermediate D and 5-methoxy-biphenyl-2-ol (Protocol SB; 100° C. o/n) Eluent: cyclohexane/AcOEt 8/2 to 5/5 v/v (Yield: 70%) | Off-white solid (CDCl$_3$): 3.91 (s, 3H); 6.85 (d, 1H, J = 9.8 Hz); 6.98-7.0 (m, 2H); 7.22-7.31 (m, 5H); 7.41 (dd, 1H, J = 7.9 Hz J = 1.3 Hz); 7.89 (d, 1H, J = 9.8 Hz) Mass: 353.1 [M + H]+ (MP: 164.6° C.) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-15 | 5-fluorobiphenyl-2-ol from 2-bromo-4-fluorophenol and phenylboronic acid (Protocol SA; 100° C. o/n) Eluent: cyclohexane/dichloromethane 10/0 to 5/5 v/v (Yield: 11%) | Brown oil (CDCl$_3$): 5.04 (s (large), 1H); 6.92-7.00 (m, 3H); 7.42-7.56 (m, 5H) |
|  | Intermediate D and 5-fluorobiphenyl-2-ol (Protocol SB; 100° C. o/n) Eluent: cyclohexane/AcOEt 8/2 to 5/5 v/v (Yield: 20%) | White solid (MeOD-d$_4$): 7.18 (d, 1H, J = 9.8 Hz); 7.23-7.36 (m, 5H); 7.41-7.46 (m, 3H); 8.11 (d, 1H, J = 10.0 Hz) Mass: 341.1 [M + H]+ (MP: 148.4° C.) |
| 4-18 | 4,5-dimethylbiphenyl-2-ol from 2-bromo-4,5-dimethylphenol and phenylboronic acid (Protocol SA; 110° C. o/n) Eluent: cyclohexane/AcOEt (Yield: 13%) | White solid (MeOD-d$_4$): 2.25 (s, 3H); 2.31 (s, 3H); 5.01 (s, 1H); 6.82 (s, 1H); 7.03 (s, 1H); 7.37-7.42 (m, 1H); 7.46-7.52 (m, 4H) Mass: 199.1 [M + H]+ |
|  | Intermediate D and 4,5-dimethyl-biphenyl-2-ol (Protocol SB; 100° C. o/n) Eluent: cyclohexane/AcOEt 8/2 to 5/5 v/v (Yield: 22%) | Off-white solid (MeOD-d$_4$): 2.37 (s, 3H); 2.38 (s, 3H); 7.14 (d, 1H, J = 9.8 Hz); 7.15-7.21 (m, 1H); 7.25-7.30 (m, 4H); 7.38-7.41 (m, 2H); 8.07 (d, 1H, J = 10.0 Hz) Mass: 351.1 [M + H]+ (MP: 147.5° C.) |
| 4-19 | 5-tert-butyl-biphenyl-2-ol from 4-tert-butyl-2-bromophenol and phenyl boronic acid (Protocol SA; 110° C. o/n) Eluent: cyclohexane/AcOEt 100/0 to 98/2 v/v (Yield: 13%) | Yellow oil (CDCl$_3$): 1.40 (s, 9H); 6.98 (d, 1H, J = 8.5 Hz); 7.32-7.37 (m, 2H); 7.43-7.49 (m, 1H); 7.61-7.64 (m, 4H) |
|  | Intermediate D and 5-tert-butyl-biphenyl-2-ol (Protocol SB; 100° C. o/n) Eluent: cyclohexane/AcOEt 10/0 to 6/4 v/v (Yield: 42%) | White solid (CDCl$_3$): 6.86 (d, 1H, J = 9.8 Hz); 7.10-7.26 (m, 2H); 7.31-7.34 (m, 2H); 7.41-7.44 (m, 2H); 7.46-7.50 (m, 2H); 7.90 (d, 1H, J = 9.8 Hz) Mass: 379.2 [M + H]+ (MP: 199.1° C.) |
| 4-26 | 4,5-difluorobiphenyl-2-ol from 2-bromo-4,5-difluorophenol and phenylboronic acid (Protocol SA; 110° C. o/n) Eluent: cyclohexane/AcOEt 10/0 to 9/1 v/v (Yield: 52%) | Yellow oil (CDCl$_3$): 5.17 (s (large), 1H); 6.83 (dd, 1H, J = 11.3 Hz J = 7.0 Hz); 7.07 (dd, 1H, J = 10.7 Hz J = 8.9 Hz); 7.40-7.55 (m, 5H) |
|  | Intermediate D and 4,5-difluoro-biphenyl-2-ol (Protocol SB; 100° C. o/n) Eluent: cyclohexane/AcOEt 8/2 to 6/4 v/v (Yield: 26%) | White solid (MeOD-d$_4$): 7.20 (d, 1H, J = 10.0 Hz); 7.25-7.37 (m, 3H); 7.42-7.54 (m, 4H); 8.15 (d, 1H, J = 10.0 Hz) Mass: 359.1 [M + H]+ (MP: 125.6° C.) |
| 4-27 | 5-methylbiphenyl-2-ol from 2-bromo-4-methylphenol and phenylboronic acid (Protocol SA; 110° C. o/n) Eluent: cyclohexane/dichloromethane 10/0 to 4/6 v/v (Yield: 60%) | White solid (MeOD-d$_4$): 2.34 (s, 3H); 5.05 (s, 1H); 6.89-6.92 (m, 1H); 7.08-7.10 (m, 2H); 7.37-7.58 (m, 5H) |
|  | Intermediate D and 5-methylbiphenyl-2-ol (Protocol SB; 100° C. o/n) Eluent: cyclohexane/AcOEt 8/2 to 6/4 v/v (Yield: 33%) | White solid (MeOD-d$_4$): 2.48 (s, 3H); 7.15 (d, 1H, J = 9.8 Hz); 7.19-7.33 (m, 6H); 7.40-7.44 (m, 2H); 8.09 (d, 1H, J = 10.0 Hz) Mass: 337.1 [M + H]+ (MP: 144.5° C.) |
| 4-32 | Cpd. 4-14 (Protocol SD: RT o/n) Eluent: cyclohexane/AcOEt 7/3 to 5/5 v/v (Yield: 18%) | White solid (MeOD-d$_4$): 6.86-6.89 (m, 2H); 7.12 (d, 1H, J = 10.0 Hz); 7.18-7.23 (m, 2H); 7.26-7.31 (m, 2H); 7.39-7.42 (m, 2H); 8.06 (d, 1H, J = 10.0 Hz) Mass: 339.1 [M + H]+ (MP: 267.7° C.) |
| 4-33 | 4-(trifluoromethyl)biphenyl-2-ol from 2-bromo-5-(trifluoromethyl)phenol and phenylboronic acid (Protocol SA; 110° C. o/n) Eluent: cyclohexane/AcOEt 10/0 to 7/3 v/v (Yield: 59%) | White solid (CDCl$_3$): 5.41 (s, 1H); 7.35-7.38 (m, 2H); 7.45-7.58 (m, 7H) |
|  | Intermediate D and 4-(trifluoromethyl)biphenyl-2-ol (Protocol SB; 100° C. o/n) Eluent: cyclohexane/AcOEt 8/2 to 5/5 v/v (Yield: 12%) | White solid (MeOD-d$_4$): 7.22 (d, 1H, J = 9.8 Hz); 7.33-7.35 (m, 3H); 7.47-7.49 (m, 2H); 7.73-7.82 (m, 3H); 8.14 (d, 1H, J = 9.8 Hz) Mass: 391.1 [M + H]+ (MP: 138.9° C.) |
| 4-35 | 5-chlorobiphenyl-2-ol from 2-bromo-4-chlorophenol and phenylboronic acid (Protocol SA; 2 h 30 at 100° C.) | Colorless oil (CDCl$_3$): 5.23 (s, 1H); 6.92-6.96 (m, 1H); 7.22-7.25 (m, 2H); 7.42-7.56 (m, 5H) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | Eluent: cyclohexane/dichloromethane: 80/20 to 60/40 v/v (Yield: 72%) Intermediate D and 5-chlorobiphenyl-2-ol (Protocol SB; 100° C. o/n) Eluent: cyclohexane/AcOEt 90/10 to 60/40 v/v (Yield: 50%) | White solid (CDCl$_3$): 6.88 (d, 1H, J = 9.8 Hz); 7.28-7.49 (m, 8H); 7.92 (d, 1H, J = 9.9 Hz) Mass: 357 [M + H]+ (MP: 166.2° C.) |
| 4-36 | 5-nitrobiphenyl-2-ol from 2-bromo-4-nitrophenol and phenylboronic acid (Protocol SA; 5 min at 150° C. on microwave) Eluent: cyclohexane/AcOEt 60/40 v/v (Yield: 74%) | Yellow solid (DMSO-d$_6$): 7.12 (d, 1H, J = 8.7 Hz); 7.35-7.47 (m, 3H); 7.57-7.60 (m, 2H); 8.09-8.14 (m, 2H); 11.26 (s, 1H) |
| | 5-aminobiphenyl-2-ol from 5-nitro-biphenyl-2-ol (Protocol SF: 16 h at RT) (Yield: 75%) | White solid (DMSO-d$_6$): 4.48 (s, 2H); 6.41 (dd, 1H, J = 8.4 Hz, J = 2.9 Hz); 6.52 (d, 1H, J = 2.9 Hz); 6.64 (d, 1H, J = 8.4 Hz); 7.24 (t, 1H, J = 7.3 Hz); 7.35 (t, 2H, J = 7.6 Hz); 7.47-7.49 (m, 2H); 8.41 (s, 1H) |
| | Intermediate D and 5-aminobiphenyl-2-ol (Protocol SB; 10 min at 170° C. on microwave) Eluent: dichloromethane/MeOH 95/5, NH$_4$OH 0.5% v/v (Yield: 46%) | White solid (DMSO-d$_6$): 5.26 (s, 2H); 6.61-6.64 (m, 2H); 7.06 (d, 1H, J = 9.0 Hz); 7.15 (d, 1H, J = 9.9 Hz); 7.19-7.34 (m, 5H); 8.28 (d, 1H, J = 9.9 Hz) Mass: 338[M + H]+; 360[M + Na]+ (MP: 79-82° C.) |
| 4-38 | 4-(trifluoromethyl)biphenyl-2-ol from 2-bromo-5-(trifluoromethyl)phenol and phenylboronic acid (Protocol SA; 110° C. o/n) Eluent: cyclohexane/dichloromethane 7/3 (Yield: 83%) | Yellow solid (DMSO-d$_6$): 7.19-7.22 (m, 2H); 7.34-7.47 (m, 4H); 7.55-7.58 (m, 2H); 10.25 (s, 1H) |
| | Intermediate B and 4-(trifluoromethyl)biphenyl-2-ol (Protocol SB; 10 min at 170° C. on microwave) Eluent: cyclohexane/AcOEt 60/40 v/v (Yield: 76%) | White solid (DMSO-d$_6$): 7.35-7.51 (m, 6H); 7.77-7.80 (m, 2H); 8.02 (s, 1H); 8.56 (d, 1H, J = 10.2 Hz) Mass: 425 [M + H]+; 447 [M + Na]+ (MP: 150° C.) |
| 4-39 | 2-(Pyridin-3-yl)-5-(trifluoromethyl)-phenol from 2-bromo-5-(trifluoro-methyl)phenol and 3-pyridineboronic acid (Protocol SA, 10 min at 120° C. on microwave) Eluent: dichloromethane/AcOEt 50/50 v/v (Yield: 46%) | White solid (DMSO-d$_6$): 7.2-7.3 (m, 2H); 7.30 (dd, 1H, J = 7.9 Hz); 7.42 (td, 1H, J = 7.6 Hz); 7.93 (tt, 1H, J = 7.9 Hz, J = 1.7 Hz); 8.55 (dd, 1H, J = 4.7 Hz, J = 1.7 Hz); 8.76 (d, 1H, J = 1.7 Hz); 10.50 (s (large), 1H) |
| | Intermediate D and 2-(pyridin-3-yl)-5-(trifluoromethyl)phenol (Protocol SB; 10 min at 150° C. on microwave) Eluent: dichloromethane/MeOH 95/5 v/v (Yield: 93%) | White solid (DMSO-d$_6$): 7.35 (d, 1H); 7.66 (m, 1H); 7.85-7.95 (m, 2H); 8.11 (s, 1H); 8.21(m, 1H); 8.43 (d, 1H); 8.68 (d, 1H); 8.86 (s, 1H) Mass: 323 [M + H]+ (MP: 215-220° C.) |
| 4-40 | 5-(trifluoromethyl)biphenyl-2-ol from 2-bromo-4-(trifluoromethyl)phenol and phenylboronic acid (Protocol SA; 15 min at 150° C. on microwave) Eluent cyclohexane/dichloromethane 70/30 v/v (Yield: 20%) | Colorless oil (CDCl$_3$): 5.51 (s, 1H); 7.08 (d, 1H, J = 8.7 Hz); 7.45-7.56 (m, 7H) |
| | Intermediate D and 5-(trifluoromethyl) biphenyl-2-ol (Protocol SB; 10 min at 170° C. on microwave) Eluent: dichloromethane/MeOH 99/1 v/v (Yield: 28%) | White solid (DMSO-d$_6$): 7.32-7.40 (m, 4H); 7.49 (m, 2H); 7.75 (d, 1H, J = 8.5 Hz); 7.87-7.92 (m, 2H); 8.40 (d, 1H, J = 9.9 Hz) Mass: 391 [M + H]$^+$; 413 [M + Na]$^+$ (MP: 123-125° C.) |
| 4-41 | This compound was prepared starting from methyl-4-bromo-3-hydroxybenzoate and phenylboronic acid using 5 steps (Protocols SA, SL, SB, SM, and SN) | Off-white solid (DMSO-d$_6$): 2.20 (s, 6H); 3.47 (s, 2H); 7.26-7.50 (m, 9H); 8.37 (d, 1H, J = 10.1 Hz) Mass: 380 [M + H]$^+$ (MP: 141-144° C.) |
| 4-42 | Intermediate D and 5-chloro-2-hydroxybenzophenone (Protocol SB; microwave 10 min 170° C.) Eluent: cyclohexane/AcOEt 6/4 v/v (Yield: 16%) | white solid (DMSO-d$_6$): 7.15 (d, 1H, J = 9.9 Hz); 7.45 (m, 2H); 7.64 (m, 4H); 7.73 (d, 1H, J = 2.6 Hz); 7.84 (dd, 1H, J = 2.6 Hz, J = 11.4 Hz); 8.35 (d, 1H, J = 9.8 Hz) Mass: 385 [M + H]+; 407 [M + Na]+ (MP: 141-142° C.) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-43 | 4-(Methyloxycarbonyl)-2-hydroxybiphenyl from methyl 4-bromo-3-hydroxybenzoate and phenylboronic acid (Protocol SA; 10 min at 150° C. on microwave) Eluent: cyclohexane/AcOEt 8/2 v/v (Yield: 18%) | White solid (DMSO-$d_6$): 3.86 (s, 3H); 7.41 (m, 3H); 7.60 (m, 5H); 10.04 (s, 1H) |
|  | Intermediate D and 4-(methyloxy-carbonyl)-2-hydroxybiphenyl (Protocol SB; 10 min at 120° C. on microwave) Eluent: cyclohexane/AcOEt 8/2 v/v (Yield: 46%) | White solid (DMSO-$d_6$): 3.89 (s, 3H); 7.35 (m, 4H); 7.47 (m, 2H); 7.71 (d, 1H, J = 8.2 Hz); 8.02 (m, 2H); 8.38 (d, 1H, J = 9.9 Hz) Mass: 381 [M + H]+; 403 [M + Na]+ (MP: 172-175° C.) |
| 4-44 | 2-Bromo-3-(trifluoromethyl)phenol from 3-hydroxybenzotrifluroride (Protocol TA; bromine (1 eq), dichloromethane, 18 h at RT) Eluent: dicholromethane/cyclohexane 4/6 v/v and cyclohexane/AcOEt 9/1 v/v (Yield: 3%) | Colorless oil (DMSO-$d_6$): 7.20-7.25 (m, 2H); 7.37 (d, 1H, J = 7.9 Hz); 10.97 (s, 1H) |
|  | 6-(Trifluromethyl)biphenyl-2-ol from 2-bromo-3-(trifluoromethyl)phenol and phenylboronic acid (Protocol SA; boronic acid (1.1 eq), 5 min at 150° C. on microwave) Eluent: dicholromethane/cyclohexane 3/7 v/v (Yield: 100%) | White solid (DMSO-$d_6$): 7.15-7.25 (m, 4H); 7.34-7.47 (m, 4H); 9.94 (s, 1H) |
|  | Intermediate D and 6-(trifluromethyl)biphenyl-2-ol (Protocol SB; 10 min at 120° C. on microwave) Precipitation (Yield: 46%) | White solid (DMSO-$d_6$): 7.06 (d, 1H, J = 9.9 Hz); 7.15-7.25 (m, 2H); 7.25-7.35 (m, 4H); 7.75-7.85 (m, 2H); 7.88 (dd, 1H, J = 7.0 Hz, J = 2.0 Hz); 8.30 (d, 1H, J = 9.9 Hz) Mass: 391 [M + H]+; 413 [M + Na]+ (MP: 186-187° C.) |
| 4-45 | 4-N,N-dimethylamino-2-methoxy-biphenyle from 4-amino-2-methoxy-biphenyle (Protocol SO; CH$_3$I) Precipitation (Yield: 61%) | White solid (DMSO-$d_6$): 3.75 (s, 3H); 6.35-6.38 (m, 2H); 7.10 (d, 1H, J = 9.3 Hz); 7.20 (td, 1H, J = 7.3 Hz, J = 1.5 Hz); 7.30-7.35 (m, 2H); 7.40-7.43 (m, 2H) |
|  | 4-N,N-dimethyl-biphenyl-2-ol from 4-N,N-dimethylamino-2-methoxy-biphenyle (Protocol SD; BBr$_3$ (10 eq)) (Yield: 61%) | White solid (DMSO-$d_6$): 2.87 (s, 6H); 6.28 (m, 2H, J = 2.3 Hz); 7.09 (m, 1H, J = 9.0 Hz); 7.17 (t, 1H, J = 7.3 Hz); 7.31 (m, 2H, J = 7.6 Hz); 7.49 (m, 2H, J = 7.6 Hz); 9.22 (s, 1H) |
|  | Intermediate D and 4-N,N-dimethyl-2-hydroxy-biphenyle (Protocol SB; 20 min at 120° C. on microwave) Eluent: cyclohexane/AcOEt 7/3 v/v (Yield: 12%) | White solid (DMSO-$d_6$): 2.94 (s, 6H); 6.74-6.78 (m, 2H); 7.13-7.37 (m, 7H); 8.32 (d, 1H, J = 9.9 Hz) J = 9.9 Hz) Mass: 388 [M + H]+; 404 [M + Na]+ (MP: 180-185° C.) |
| 4-46 | Cpd. 4-36 (Protocol SO, CH$_3$I). Eluent: cyclohexane/AcOEt 1/1 v/v (Yield: 41%) | Yellow solid (DMSO-$d_6$): 2.97 (s, 6H); 6.71 (d, 1H, J = 3.2 Hz); 6.81 (dd, 1H, J = 9.0 Hz, J = 3.2 Hz); 7.18 (d, 1H, J = 9.9 Hz); 7.21-7.34 (m, 4H); 7.39-7.41 (m, 2H); 8.30 (d, 1H, J = 9.9 Hz) Mass: 366 [M + H]+ (MP: 148-149° C.) |
| 4-47 | Cpd. 4-36 (Protocol SO, CH$_3$I) Eluent: cyclohexane/AcOEt 1/1 v/v (Yield: 33%) | Yellow solid (DMSO-$d_6$): 2.73 (d, 3H, J = 5.0 Hz); 5.85-5.87 (m, 1H); 6.56 (d, 1H, J = 2.6 Hz); 6.61 (dd, 1H, J = 8.7 Hz, J = 2.6 Hz); 7.14 (d, 1H, J = 3.5 Hz); 7.16 (d, 1H, J = 4.7 Hz); 7.22-7.38 (m, 5H); 8.28 (d, 1H, J = 9.9 Hz) Mass: 352 [M + H]+ (MP: 157-158° C.) |
| 4-48 | 4-Nitro-2-methoxybiphenyle from 1-bromo-2-methoxy-4-nitrobenzene and phenylboronic acid (Protocol SA; 5 min at 150° C. on microwave) Eluent: cyclohexane/AcOEt 99/1 v/v (Yield: 86%) | White solid (DMSO-$d_6$): 3.91 (s, 3H); 7.45 (m, 3H); 7.54 (m, 2H); 7.58 (d, 1H, J = 8.4 Hz); 7.87 (d, 1H, J = 2.0 Hz); 7.91 (dd, 1H, J = 8.2 Hz, J = 2.0 Hz) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | 4-Amino-2-methoxy-biphenyle from 4-nitro-2-methoxybiphenyle (Protocol SF; H$_2$ Pd/C, EtOH; 7 h RT) Eluent: cyclohexane/AcOEt 8/2 v/v (Yield: 67%) | Brown oil (DMSO-d$_6$): 3.67 (s, 3H); 5.21 (s, 2H); 6.22 (dd, 1H, J = 8.2 Hz, J = 2.0 Hz); 6.31 (d, 1H, J = 1.7 Hz); 6.94 (d, 1H, J = 7.9 Hz); 7.17 (t, 1H, J = 7.3 Hz); 7.34 (m, 4H) |
| | 4-Amino-biphenyl-2-ol from 4-amino-2-methoxybiphenyle (Protocol SD; BBr$_3$ (10 eq), dichloromethane; 2 h at RT) Precipitation (Yield: 57%) | White solid (DMSO-d$_6$): 5.04 (s, 2H); 6.11 (d, 1H, J = 8.2 Hz); 6.16 (s, 1H); 6.92 (d, 1H, J = 8.1 Hz); 7.14 (t, 1H, J = 7.3 Hz); 7.29 (m, 2H, J = 7.6 Hz); 7.44-7.47 (m, 2H); 9.04 (s, 1H) |
| | Intermediate D and 4-amino-biphenyl-2-ol (Protocol SB; 20 min at 120° C. on microwave) Eluent: cyclohexane/dichloromethane 7/3 to 5/5 v/v (Yield 20%) | Beige solid (DMSO-d$_6$): 5.49 (s, 2H); 6.51 (s, 1H); 6.62 (dd, 1H, J = 8.5 Hz, J = 1.8 Hz); 7.10-7.32 (m, 7H); 8.31 (d, 1H, J = 9.9 Hz) Mass: 338 [M + H]+; 360 [M + Na]+ (MP: 183-187° C.) |
| 4-49 | 4-(Methylcarbonylamino)-biphenyl-2-ol from 4-amino-biphenyl-2-ol and acetyl bromide (Protocol SP) Eluent: cyclohexane/dichloromethane 5/5 v/v (Yield: 41%) | White solid (DMSO-d$_6$): 2.05 (s, 3H); 7.00 (d, 1H, J = 6.7 Hz); 7.16-7.54 (m, 7H); 9.58 (s, 1H); 9.90 (s, 1H) Mass: 228 [M + H]+; 250 [M + Na]+; 266 [M + K]+ |
| | Intermediate D and 4-(methylcarbonylamino)-biphenyl-2-ol (Protocol SB; Intermediate D (1.3 eq); 30 min at 120° C. on microwave) Eluent: cyclohexane/AcOEt 1/9 v/v (Yield: 37%) | White solid (DMSO-d$_6$): 2.07 (s, 3H); 7.18-7.39 (m, 6H); 7.45-7.56 (m, 2H); 7.75 (m, 1H); 8.34 (d, 1H, J = 9.9 Hz); 10.24 (s, 1H) Mass: 380 [M + H]+; 402 [M + Na]+ (MP: 190-194° C.) |
| 4-50 | Cpd. 4-48 (Protocol SQ; butylboronic acid) Eluent: cyclohexane/AcOEt 7/3 v/v (Yield: 8%) | Yellow solid (DMSO-d$_6$): 0.89 (t, 3H, J = 7.3 Hz); 1.38 (m, 2H, J = 9.9 Hz); 1.54 (quint, 2H, J = 7.0 Hz); 3.02 (q, 2H, J = 4.7 Hz); 6.03 (s, 1H); 6.53(s, 1H); 6.63 (dd, 1H, J = 8.7 Hz, J = 2.0 Hz); 7.11-7.34 (m, 7H); 8.32 (d, 1H, J = 9.9 Hz) Mass: 394 [M + H]+; 416 [M + Na]+; 432 [M + K]+ (MP: 132-135° C.) |
| 4-51 | Cpd. 4-48 (Protocol SQ; 2-methylpropylboronic acid) Eluent: cyclohexane/AcOEt 7/3 v/v (Yield: 16%) | Yellow solid (DMSO-d$_6$): 0.92 (d, 6H, J = 6.1 Hz); 1.86 (m, 1H, J = 6.4 Hz); 2.85 (t, 2H, J = 6.1 Hz); 6.11 (s, 1H); 6.54 (s, 1H); 6.64 (d, 1H, J = 8.4 Hz); 7.11-7.33 (m, 7H); 8.32 (d, 1H, J = 9.9 Hz) Mass: 394 [M + H]+ (MP: 124-128° C.) |
| 4-52 | Cpd. 4-48 (Protocol SO; CH$_3$I) Eluent: cyclohexane/AcOEt 6/4 v/v (Yield: 3%) | Yellow solid (DMSO-d$_6$): 2.71 (d, 3H, J = 3.5 Hz); 6.09 (m, 1H, J = 5.0 Hz); 6.52 (d, 1H, J = 2.3 Hz); 6.62 (dd, 1H, J = 8.4 Hz, J = 2.3 Hz); 7.12-7.36 (m, 7H); 8.33 (d, 1H, J = 9.9 Hz) Mass: 352 [M + H]+; 374 [M + Na]+ |
| 4-53 | Cpd. 4-36 (Protocol SO, 1-bromopropane). Eluent: cyclohexane/AcOEt 7/3 v/v Preparative HPLC (Yield: 9%) | Yellow solid (DMSO-d$_6$): 0.90 (t, 6H, J = 7.3 Hz); 1.52-1.62 (m, 4H); 3.29 (t, 4H, J = 7.6 Hz); 6.59 (d, 1H, J = 2.9 Hz); 6.71 (dd, 1H, J = 9.0 Hz, J = 3.2 Hz); 7.16 (d, 1H, J = 9.9 Hz); 7.20 (d, 1H, J = 9.0 Hz); 7.23-7.39 (m, 5H); 8.29 (d, 1H, J = 9.9 Hz) Mass: 422 [M + H]+ (MP: 106-109° C.) |
| 4-54 | Cpd. 4-36 (Protocol SO iodoethane). Eluent: cyclohexane/AcOEt 7/3 v/v Preparative HPLC (Yield: 8%) | Yellow solid (DMSO-d$_6$): 1.19 (t, 3H, J = 7.0 Hz); 3.04-3.13 (m, 2H); 5.76 (t, 1H, J = 4.9 Hz); 6.58 (d, 1H, J = 2.6 Hz); 6.62 (dd, 1H, J = 8.7 Hz, J = 2.6 Hz); 7.11 (d, 1H, J = 7.0 Hz); 7.16 (d, 1H, J = 8.2 Hz); 7.2-7.37 (m, 5H); 8.28 (d, 1H, J = 9.9 Hz) Mass: 366 [M + H]+ (MP: 72-77° C.) |
| 4-55 | Cpd. 4-36 (Protocol SO iodoethane). Eluent: cyclohexane/AcOEt 7/3 v/v Preparative HPLC (Yield: 9%) | Yellow solid (DMSO-d$_6$): 1.13 (t, 6H, J = 7.0 Hz); 3.39 (q, 4H, J = 6.7 Hz); 6.62 (d, 1H, J = 3.2 Hz); 6.73 (dd, 1H, J = 9.0 Hz, |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | | J = 2.9 Hz); 7.16 (d, 1H, J = 9.9 Hz); 7.21 (d, 1H, J = 9.0 Hz); 7.23-7.40 (m, 5H); 8.29 (d, 1H, J = 9.9 Hz) Mass: 394 [M + H]+ (MP: 55-58° C.) |
| 4-56 | Cpd. 4-36 (Protocol SO, 1-bromopropane). Eluent: cyclohexane/AcOEt 7/3 v/v Preparative HPLC (Yield: 22%) | Yellow solid (DMSO-d$_6$): 0.96 (t, 3H, J = 7.3 Hz); 1.55-1.63 (m, 2H, J = 7.0 Hz); 3.01 (q, 2H, J = 6.7 Hz); 5.81 (t, 1H, J = 5.5 Hz); 6.59 (d, 1H, J = 2.6 Hz); 6.63 (dd, 1H, J = 8.7 Hz, J = 2.9 Hz); 7.11-7.17 (m, 2H); 7.22-7.37 (m, 5H); 8.28 (d, 1H, J = 9.9 Hz) Mass: 380 [M + H]+ (MP: 55-58° C.) |
| 4-57 | Cpd. 4-36 (Protocol SO, 1-bromobutane). Eluent: cyclohexane/AcOEt 1/1 v/v | Yellow oil (DMSO-d$_6$): 0.92 (t, 6H, J = 7.3 Hz); 1.27-1.40 (m, 4H, J = 7.3 Hz); 1.49-1.59 (m, 4H, J = 7.0 Hz); 3.29-3.34 (m, 4H); 6.59 (d, 1H, J = 2.9 Hz); 6.70 (dd, 1H, J = 9.0 Hz, J = 2.9 Hz); 7.15-7.21 (m, 2H); 7.23-7.39 (m, 5H); 8.29 (d, 1H, J = 9.9 Hz) Mass: 450 [M + H]+ |
| 4-58 | Cpd. 4-36 (Protocol SO, 1-bromobutane). Eluent: cyclohexane/AcOEt 1/1 v/v (Yield: 11%) | Salmon solid (DMSO-d$_6$): 0.93 (t, 3H, J = 7.3 Hz); 1.35-1.47 (m, 2H); 1.52-1.61 (m, 2H); 3.01-3.07 (m, 2H); 5.77 (t, 1H, J = 5.3 Hz); 6.59 (d, 1H, J = 2.6 Hz); 6.62 (dd, 1H, J = 8.7 Hz, J = 2.9 Hz); 7.14 (t, 2H, J = 9.0 Hz); 7.20-7.37 (m, 5H); 8.28 (d, 1H, J = 9.9 Hz) Mass: 394 [M + H]+ (MP: 85-88° C.) |
| 4-59 | 5-(Hydroxycarbonyl)biphenyl-2-ol from 5-(methyloxycarbonyl)biphenyl-2-ol (Protocol SV) Eluent: cyclohexane/AcOEt 5/5 v/v (Yield: 53%) | White solid (DMSO d$_6$): 7.02 (d, 1H, J = 8.5 Hz); 7.33 (m, 1H); 7.42 (m, 2H); 7.54 (m, 2H); 7.78 (dd, 1H, J = 8.4 Hz, J = 2.3 Hz); 7.83 (d, 1H, J = 2.1 Hz); 10.43 (s, 1H); 12.52 (s, 1H) |
| | Intermediate D and 5-(hydroxycarbonyl)biphenyl-2-ol (Protocol SB; 10 min at 120° C. on microwave) Eluent: dichloromethane/MeOH 98/2 v/v (Yield: 15%) | White powder (DMSO-d$_6$): 7.30-7.39 (m, 4H); 7.44-7.47 (m, 2H); 7.61 (d, 1H, J = 9.0 Hz); 8.03-8.06 (m, 2H); 8.39 (d, 1H, J = 9.9 Hz); 13.20 (s, 1H) Mass (ES+): 367 (M + H); 389 (M + Na) (MP: 266.9-267.7° C.) |
| 4-60 | 3-Chloro-6-(4-bromomethyl-biphenyl-2-yloxy)-[1,2,4]triazolo[4,3-b]pyridazine and N-methylbenzylamine (Protocol SN; K$_2$CO$_3$ (3 eq), N-methylbenzylamine (2 eq), DMF, microwave 10 min 120° C.) Eluent: dichloromethane/MeOH 6/4 v/v (Yield: 17%) | White solid (DMSO-d$_6$): 2.14 (s, 3H); 3.56 (d, 4H, J = 10.2 Hz); 7.20-7.36 (m, 9H); 7.39-7.45 (m, 4H); 7.50 (d, 1H, J = 9.9 Hz); 8.36 (d, 1H, J = 7.9 Hz) Mass: 456 [M + H]+ (MP: 119-122° C.) |
| 4-61 | Intermediate B and 4,5-difluoro-biphenyl-2-ol (Protocol SB; 15 min at 150° C. microwave) Eluent: cyclohexane/AcOEt 4/6 v/v (Yield: 43%) | White Solid (DMSO-d$_6$): 7.29-7.38 (m, 4H); 7.42-7.45 (m, 2H); 7.67-7.73 (dd, 1H, J = 11.1 Hz, J = 8.7 Hz); 7.76-7.82 (dd, 1H, J = 11.1 Hz, J = 7.3 Hz); 8.39 (d, 1H, J = 9.6 Hz) Mass (ES+): 393 (M + H) (MP: 164.3-164.8° C.) |
| 4-62 | 3-Chloro-6-(5-bromomethyl-biphenyl-2-yloxy)-[1,2,4]triazolo[4,3-b]pyridazine from Cpd. 4-66 (Protocol SM; 3.5 h) Eluent: cyclohexane/AcOEt 5/5 v/v (Yield: 87%) | Yellow powder (DMSO-d$_6$, d en ppm): 4.82 (s, 2H); 7.62-7.48 (m, 7H); 7.56-7.63 (m, 2H); 8.36 (d, 1H, J = 9.9 Hz) |
| | 3-Chloro-6-(5-bromomethyl-biphenyl-2-yloxy)-[1,2,4]triazolo[4,3-b]pyridazine and morpholine (Protocol SN) Eluent: dichloromethane/MeOH 100/0 to 98/2 v/v (Yield: 16%) | White solid (DMSO-d$_6$): 2.41 (m, 4H); 3.59 (m, 6H); 7.25 (d, 1H, J = 9.9 Hz); 7.28-7.35 (m, 3H); 7.40-7.42 (m, 5H); 8.35 (d, 1H, J = 9.9 Hz) Mass (ES+): 422 (M + H) (MP: 70.8-72.6° C.) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-63 | 3-Chloro-6-(5-bromomethyl-biphenyl-2-yloxy)-[1,2,4]triazolo[4,3-b]pyridazine and dimethylamine hydrochloride (Protocol SN) Eluent: dichloromethane/MeOH 100/0 to 98/2 v/v (Yield: 51%) | Yellowish solid (DMSO-d$_6$): 2.19 (s, 6H); 3.48 (s, 2H); 7.25 (d, 1H, J = 9.9 Hz); 7.26-7.35 (m, 3H); 7.40-7.42 (m, 5H); 8.34 (d, 1H, J = 9.9 Hz) Mass (ES+): 380 (M + H) (MP: 131.8° C.). |
| 4-64 | 3-Chloro-6-(4-bromomethyl-biphenyl-2-yloxy)-[1,2,4]triazolo[4,3-b]pyridazine and morpholine (Protocol SN; K$_2$CO$_3$ (4 eq), morpholine (2 eq), DMF, 10 min at 120° C. on microwave) Eluent: dichloromethane/MeOH 9/1 v/v (Yield: 45%) | White solid (DMSO-d$_6$): 2.42 (s, 4H); 3.59 (m, 6H); 7.35 (m, 8H); 7.50 (d, 1H, J = 7.7 Hz); 8.37 (d, 1H, J = 9.8 Hz) Mass: 422 [M + H]+ (MP: 162-163° C.) |
| 4-65 | 4-Cyano-2-methoxy-biphenyl from 4-cyano-2-methoxybromophenyl and phenylboronic acid (Protocol SA, boronic acid (1.1 eq.), palladium (II) chloride (dppf) (0.025 eq.) and sodium carbonate (3 eq.) 45 min at 150° C. on microwave) Eluent: cyclohexane/AcOEt 95/5 v/v (Yield: 79%) | Green oil (DMSO-d$_6$): 3.82 (s, 3H); 7.34-7.51 (m, 7H); 7.58 (s, 1H) |
|  | 4-Aminomethyl-2-methoxybiphenyl from 4-cyano-2-methoxybiphenyl (Protocol SL, 3 h at RT) (Yield: 66%) | Pale yellow oil (DMSO-d$_6$): 3.74 (s, 2H); 3.75 (s, 3H); 6.97 (d, 1H, J = 7.9 Hz); 7.10 (s, 1H); 7.18 (d, 1H, J = 7.6 Hz); 7.28 (t, 1H, J = 7.0 Hz); 7.35-7.49 (m, 4H) |
|  | 4-Aminomethyl-biphenyl-2-ol from 4-aminomethyl-2-methoxybiphenyl (Protocol SD) (Yield: quantitative) | Beige powder (DMSO-d$_6$): 3.97 (m, 2H); 6.96-69.8 (m, 2H); 7.28-7.32 (m, 2H); 7.39 (t, 2H, J = 7.3 Hz); 7.52 (d, 2H, J = 7.3 Hz); 8.12 (s, 2H); 9.77 (s, 1H) |
|  | 2-(Tertbutyloxycarbonyloxy)-4-(tertbutyloxycarbonylaminomethyl)-biphenyl from 4-aminomethyl-biphenyl-2-ol (Protocol SS) Eluent: dichloromethane/MeOH 95/5 v/v (Yield: 53%) | Colorless oil (DMSO-d$_6$): 1.25 (s, 9H); 1.40 (s, 9H); 4.17 (d, 2H, J = 6.1 Hz); 7.09 (s, 1H); 7.23 (d, 1H, J = 7.9 Hz); 7.34-7.46 (m, 7H) |
|  | 4-(Tertbutyloxycarbonylaminomethyl)-biphenyl-2-ol from 2-(tertbutyloxycarbonyloxy)-4-(tertbutyloxycarbonylaminomethyl)-biphenyl (Protocol SU) Eluent: cyclohexane/AcOEt 8/2 v/v (Yield: 61%) | Colorless oil (DMSO-d$_6$): 1.40 (s, 9H); 4.06 (d, 2H, J = 6.1 Hz); 6.74 (d, 1H, J = 7.6 Hz); 6.82 (s, 1H); 7.17 (d, 1H, J = 7.9 Hz); 7.26 (t, 1H, J = 7.3 Hz); 7.37 (t, 3H, J = 7.6 Hz); 7.51 (d, 2H, J = 7.3 Hz); 9.47 (s, 1H) |
|  | 3-Chloro-6-(4-tertbutyloxycarbonyl-aminomethyl-biphenyl-2-yloxy)-[1,2,4]triazolo[4,3-b]pyridazine from intermediate D and 4-(tertbutyloxycarbonylaminomethyl)-biphenyl-2-ol (Protocol SB; 10 min at 120° C. on microwave) Eluent: cyclohexane/AcOEt 7/3 v/v (Yield: 79%) | White solid (DMSO-d$_6$): 1.37 (s, 9H); 4.20 (d, 2H, J = 6.1 Hz); 7.23-7.33 (m, 6H); 7.38-7.40 (m, 2H); 7.46-7.49 (m, 2H); 8.34 (d, 1H, J = 9.6 Hz) Mass (MALDI+): 451/453 (M + H); 473/475 (M + Na); 489/491 (M + K) (MP: 160.9-162.0° C.). |
|  | 3-Chloro-6-(4-(tertbutyloxycarbonylaminomethyl)-biphenyl-2-yloxy)-[1,2,4]triazolo[4,3-b]pyridazine, (Protocol ST) Eluent: dichloromethane/MeOH 95/5 v/v (Yield: 29%) | White powder (DMSO-d$_6$): 3.48 (s, 2H); 3.86 (s, 2H); 7.26-7.44 (m, 9H); 8.37 (d, 1H, J = 9.9 Hz) Mass (MALDI+): 352/354 (M + H); 374/376 (M + Na) (MP: 164.6-167.7° C.) |
| 4-66 | 5-(Methyloxycarbonyl)biphenyl-2-ol from methyl-3-bromo-4-hydroxybenzoate and phenylboronic acid (Protocol SA, boronic acid (1.1 eq.), palladium (II) chloride (dppf), (0.025 eq.) and sodium carbonate (3 eq.); 5 min at 150° C. on microwave). Eluent: cyclohexane/dichloromethane/AcOEt 6/3.5/0.5 v/v/v (Yield: 70%) | White solid (CDCl$_3$): 3.90 (s, 3H); 5.62 (s, 1H); 7.03 (d, 1H, J = 9.0 Hz); 7.44-7.55 (m, 5H); 7.96-7.98 (m, 2H) |
|  | 3-Phenyl-4-hydroxybenzyl alcohol from 5-(methyloxycarbonyl)biphenyl-2-ol (Protocol SL; LiAlH$_4$ (2.4 eq.) 16 h at 70° C.) | White solid (DMSO-d$_6$): 4.41 (d, 2H, J = 5.2 Hz); 4.98 (t, 1H, J = 5.5 Hz); 6.88 (d, 1H, J = 8.2 Hz); 7.09 (dd, 1H, J = 8.2 Hz, |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
|  | Eluent: cyclohexane/AcOEt 57/3 v/v (Yield: 70%) | J = 2.0 Hz); 7.18 (d, 1H, J = 2.0 Hz); 7.27 (t, 1H, J = 7.3 Hz); 7.38 (m, 2H); 7.52 (m, 2H); 9.38 (s, 1H) |
|  | Intermediate D and 3-phenyl-4-hydroxybenzyl alcohol (Protocol SB; 10 min at 120° C. on microwave) Eluent: cyclohexane/AcOEt 5/5 v/v (Yield: 57%) | White powder (DMSO-$d_6$): 4.59 (d, 2H, J = 5.8 Hz); 5.32 (t, 1H, J = 5.6 Hz); 7.24-7.28 (m, 2H); 7.30-7.35 (m, 2H); 7.39-7.45 (m, 5H); 8.35 (d, 1H, J = 9.9 Hz) Mass (ES+): 353 (M + H); 375 (M + Na) (MP: 72° C.) |
| 4-67 | Cpd. 4-36 (Protocol SO, isobutylbromide (1 eq)) Eluent: cyclohexane/AcOEt 1/1 v/v (Yield: 33%) | Yellow solid (DMSO-$d_6$): 0.87 (d, 6H, J = 6.8 Hz); 1.80-1.93 (m, 1H, J = 6.4 Hz); 2.87 (t, 2H, J = 6.1 Hz); 5.84 (t, 1H, J = 5.5 Hz); 6.60 (d, 1H, J = 2.6 Hz); 6.64 (dd, 1H, J = 8.7 Hz, J = 2.9 Hz); 7.12 (d, 1H, J = 8.7 Hz); 7.15 (d, 1H, J = 9.9 Hz); 7.2-7.37 (m, 5H); 8.28 (d, 1H, J = 9.9 Hz) Mass: 394 [M + H]+ (MP: 62-67° C.) |
| 4-68 | 2-Bromo-5-(trifluoromethyloxy)phenol from 3-(trifluoromethyloxy)phenol (Protocol TA) Eluent: cyclohexane/AcOEt 8/2 (Yield: 76%) | Yellow oil (DMSO-$d_6$): 5.91 (s, 1H); 7.10 (d, 1H, J = 8.7 Hz); 7.50 (dd, 1H, J = 8.4 Hz, J = 1.4 Hz); 7.75 (d, 1H, J = 1.4 Hz) |
|  | 4-(Trifluoromethyloxy)biphenyl-2-ol from 2-bromo-5-(trifluoromethyloxy)-phenol, phenylboronic acid (Protocole SA (1.1 eq.), palladium (II) chloride (dppf) (0.025 eq.) and sodium carbonate (3 eq.); 5 min at 150° C. on microwave) Eluent: cyclohexane/dichloromethane 7/3 v/v (Yield: 45%) | Colorless oil (DMSO-$d_6$): 5.37 (s, 1H); 6.86-6.92 (m, 2H); 7.25 (d, 1H, J = 8.1 Hz); 7.41-7.45 (m, 3H); 7.50-7.54 (m, 2H) |
|  | 4-(Trifluoromethyloxy)biphenyl-2-ol and intermediate D (Protocol SB; 10 min at 170° C. on microwave) Eluent: cyclohexane/AcOEt 7/3 (Yield: 46%) | White solid (DMSO-$d_6$): 7.29-7.47 (m, 7H); 7.66-7.69 (m, 2H); 8.40 (d, 1H, J = 9.9 Hz) Mass (QTOF+): 407 (M + H); 429 (M + Na) (MP: 225.4-228.2° C.) |
| 4-69 | 5-(methyloxycarbonyl)biphenyl-2-ol from methyl-3-bromo-4-hydroxybenzoate, phenylboronic acid (Protocol SA; boronic acid (1.1 eq.), palladium (II) chloride (dppf) (0.025 eq.) and sodium carbonate (3 eq.), 5 min at 150° C. on microwave) Eluent: cyclohexane/dichloromethane 7/3 v/v (Yield: 51%) | White solid (DMSO-$d_6$): 3.90 (s, 3H); 5.64 (s, 1H); 7.03 (d, 1H, J = 9.0 Hz); 7.42-7.55 (m, 5H); 7.94-7.96 (m, 2H) |
|  | 5-(Methyloxycarbonyl)biphenyl-2-ol and intermediate D (Protocol SB; 10 min at 170° C. on microwave) Eluent: cyclohexane/dichloromethane/AcOEt 6/3.5/0.5 v/v (Yield: 13%) | White solid (DMSO-$d_6$): 3.89 (s, 3H); 7.29-7.40 (m, 4H); 7.44-7.47 (m, 2H); 7.65 (d, 1H, J = 8.4 Hz); 8.04-8.09 (m, 2H); 8.40 (d, 1H, J = 9.9 Hz) Mass (QTOF+): 381 (M + H); 403 (M + Na) (MP: 75.9-78.8° C.) |
| 4-70 | 3-Bromo-4-hydroxybenzamide from 4-hydroxybenzamide (Protocol TA) Eluent: cyclohexane/MeOH 95/5 (Yield: 37%) | White solid (DMSO-$d_6$): 6.96 (d, 1H, J = 8.5 Hz); 7.22 (s, 1H); 7.72(dd, 1H, J = 8.4 Hz, J = 2.0 Hz); 7.84 (s, 1H); 8.02 (d, 1H, J = 2.0 Hz); 10.84 (s, 1H) |
|  | 5-(Aminocarbonyl)biphenyl-2-ol from 3-bromo-4-hydroxybenzamide, phenylboronic acid (Protocol SA, boronic acid (1.1 eq.), palladium (II) chloride (dppf) (0.025 eq.) and sodium carbonate (3 eq.); 10 min at 150° C. on microwave) Eluent: dichloromethane/MeOH 98/2 v/v (Yield: 46%) | Yellow oil (DMSO-$d_6$): 6.98 (d, 1H, J = 8.4 Hz); 7.11 (s, 1H); 7.31 (t, 1H, J = 7.0 Hz); 7.41 (t, 2H, J = 7.3 Hz); 7.56 (d, 2H, J = 7.0 Hz); 7.70 (dd, 1H, J = 8.4 Hz, J = 2.3 Hz); 7.82 (d, 1H, J = 2.3 Hz); 7.82 (s 1H); 10.12 (s, 1H) |
|  | 5-(Aminocarbonyl)biphenyl-2-ol and intermediate D (Protocol SB; 10 min at 120° C. microwave) Eluent: dichloromethane/MeOH 98/2 (Yield: 53%) | Beige solid (DMSO-$d_6$): 7.27-7.39 (m, 4H); 7.46-7.49 (m, 2H); 7.50 (s, 1H); 7.56 (d, 1H, J = 8.5 Hz); 7.97 (dd, 1H, J = 8.7 Hz, J = 2.3 Hz); 8.04 (d, 1H, J = 2.0 Hz); 8.14 (s, 1H); 8.39 (d, 1H, J = 9.9 Hz) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-79 | 2-(Pyridin-4-yl)-5-(trifluoromethyl) phenol from 2-bromo-5-(trifluoromethyl) phenol and pyridin-4-ylboronic acid (Protocol SA; boronic acid (2 eq), PCy$_3$ (0.024 eq), PdDBa$_3$ (0.01 eq), K$_3$PO$_4$(2 eq) - dioxane/water 48 H at 120° C.) Eluent: cyclohexane/AcOEt 9/1 v/v (Yield: 65%) | Mass (QTOF+): 366 (M + H); 388 (M + Na) (MP: 196.5-198.4° C.) White solid (DMSO-d$_6$): 5.33 (s, 2H); 7.27 (dd, 1H, J = 8.3 Hz, J = 1.3 Hz); 7.3-7.55 (m, 6H); 7.86 (d, 1H, J = 8.3 Hz) |
|  | Intermediate D and 2-(pyridin-4-yl)-5-(trifluoromethyl)phenol (Protocol SB; 2 H at 120° C.) Eluent: dichloromethane/MeOH 95/5 (Yield: 66%) | White solid (DMSO-d$_6$): 7.38 (d, 1H, J = 9.9 Hz); 7.9-8.0 (m, 4H); 8.16 (s, 1H); 8.46 (d, 1H, J = 9.9 Hz); 8.81 (d, 2H, J = 6.1 Hz) Mass (ES+): 392/394 (M + H) (MP: 255.0-262.0° C.) |
| 4-97 | 2-(Pyridin-2-yl)-5-(trifluoromethyl)phenol from 2-hydroxy-4-(trifluoromethyl)-phenylboronic acid and 2-bromopyridine (Protocol SA; boronic acid (2 eq), PCy$_3$ (0.024 eq), PdDBa$_3$ (0.01 eq), K$_3$PO$_4$ (2 eq)-dioxane/water-15 min at 120° C. on microwave) Eluent: cyclohexane/AcOEt 8/2 v/v (Yield: 29%) | White solid (DMSO-d$_6$): 7.2-7.3 (m, 2H); 7.46 (dd, 1H, J = 7.9 Hz, J = 4.7 Hz); 8.09 (tt, 1H, J = 7.9 Hz, J = 1.7 Hz); 8.25 (d, 1H, J = 8.5 Hz); 8.31 (d, 1H, J = 8.2 Hz); 8.69 (d, 1H, J = 4.7 Hz); 14.46 (s, 1H) |
|  | Intermediate D and 2-(pyridin-2-yl)-5-(trifluoromethyl)phenol (Protocol SB; 15 min at 120° C. on microwave) Eluent: dichloromethane/MeOH 95/5 (Yield: 70%) | White solid (DMSO-d$_6$): 6.40 (s); 7.3-7.45 (m, 2H); 7.79 (d, 1H, J = 7.9 Hz); 7.84-7.95 (m, 2H); 8.05-8.10 (m, 2H); 8.43 (d, 1H, J = 9.9 Hz); 8.63 (d, 1H, J = 5.0 Hz) Mass (MALDI+): 392/394 (M + H) (MP: 221.0-231.0° C.) |
| 4-99 | 2-(Pyrimidin-5-yl)-5-(trifluoromethyl)-phenol from 2-bromo-5-(trifluoromethyl)phenol and pyrimidin-5-yl-boronic acid hemihydrates (Protocol SA; boronic acid (2 eq), PCy$_3$ (0.024 eq), PdDBa$_3$ (0.01 eq), K$_3$PO$_4$ (2 eq)-dioxane/water- 10 min at 120° C. on microwave) Trituration in diethyl ether (Yield: 69%) | Grey solid (DMSO-d$_6$): 7.25-7.35 (m, 2H); 7.65 (d, 1H, J = 7.9 Hz); 9.02 (s, 2H); 9.17 (s, 1H); 10.76 (s, 1H) |
|  | Intermediate D and 2-(pyrimidin-5-yl)-5-(trifluoromethyl)phenol (Protocol SB; 10 min at 120° C. on microwave) Trituration in diethyl ether the recrystallization in EtOH (Yield: 64%) | White solid (DMSO-d$_6$): 7.42 (d, 1H, J = 9.9 Hz); 7.90 (dd, 1H, J = 8.1 Hz, J = 1.1 Hz); 7.98 (d, 1H, J = 8.1 Hz); 8.15 (s, 1H); 8.46 (d, 1H, J = 9.9 Hz); 9.03 (s, 2H); 9.21 (s, 1H) Mass (ES+): 392/394 (M + H) (MP: 130.0-132.0° C.) |
| 4-105 | 2-(thiazol-2-yl)-5-(trifluoromethyl)-phenol from 2-bromothiazole and 2-hydroxy-4-(trifluoromethyl)phenyl-boronic acid (Protocol SA, boronic acid (2 eq), potassium phosphate (2.40 eq), Pd$_2$dBa$_3$ (0.01 eq) and XPHOS (0.04 eq) in dioxane/water; 15 min at 120° C. on microwave) Eluent: dichloromethane/cyclohexane 3/7 v/v (Yield: 13%) | White solid (DMSO-d$_6$): 7.28 (d, 1H, J = 8.5 Hz); 7.31 (s, 1H); 7.88 (d, 1H, J = 3.2 Hz); 8.01 (d, 1H, J = 3.2 Hz); 8.34 (d, 1H, J = 8.5 Hz); 11.90 (s, 1H) |
|  | Intermediate D and 2-(thiazol-2-yl)-5-(trifluoromethyl)phenol (Protocol SB; Intermediate D (1.05 eq), microwave 10 min 120° C.) Trituration in diethyl ether (Yield: 41%) | White solid (DMSO-d$_6$): 7.62 (d, 1H, J = 9.9 Hz); 7.88 (dd, 1H, J = 8.3 Hz, J = 1.2 Hz); 7.99 (d, 1H, J = 3.2 Hz); 8.08 (d, 1H, J = 3.2 Hz); 8.17 (d, 1H, J = 1.2 Hz); 8.59 (m, 2H) Mass: 398 [M + H]+ (MP: 171-173° C.) |
| 4-106 | 2-(thiazol-4-yl)-5-(trifluoromethyl)-phenol from 4-bromothiazole and 2-hydroxy-4-(trifluoromethyl)phenyl-boronic acid (Protocol SA, boronic acid (2 eq), Potassium phosphate (2.40 eq), Pd2dBa3 (0.01 eq) and XPHOS (0.04 eq) in dioxane/water; | White solid (DMSO-d$_6$): 7.2-7.3 (m, 2H); 8.29 (d, 1H, J = 7.9 Hz); 8.41 (d, 1H, J = 2.0 Hz); 9.25 (d, 1H, J = 2.0 Hz); 11.35 (s, 1H) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | 15 min at 120° C. on microwave) Eluent: dicholromethane/cyclohexane 3/7 v/v (Yield: 40%) | |
| | Intermediate D and 2-(thiazol-4-yl)-5-(trifluoromethyl)phenol (Protocol SB; microwave 10 min 120° C.) Trituration in diethyl ether (Yield: 73%) | White solid (DMSO-d$_6$): 7.54 (d, 1H, J = 9.9 Hz); 7.82 (dd, 1H, J = 7.9 Hz, J = 1.2 Hz); 8.04 (s, 1H); 8.25 (d, 1H, J = 1.7 Hz); 8.37 (d, 1H, J = 7.9 Hz); 8.51 (d, 1H, J = 9.9 Hz); 9.20 (d, 1H, J = 1.7 Hz) Mass: 398 [M + H]+ (MP: 191-192° C.) |
| 4-107 | 2-bromo-4-fluorophenol and pyridin-3-ylboronic acid (Protocol SA; boronic acid (2 eq), PCy$_3$ (0.024 eq), PdDBa$_3$ (0.01 eq), K$_3$PO$_4$ (2.5 eq) - dioxane/water- 15 min at 120° C. on microwave Eluent: dichloromethane/AcOEt 7/3 v/v (Yield: 81%) | White solid (DMSOd$_6$): 6.95 (q, 1H, J = 9.0 Hz, J = 5.0 Hz); 7.03 (td, 1H, J = 9.0 Hz, J = 2.9 Hz); 7.15 (dd, 1H, J = 9.0 Hz, J = 2.9 Hz); 7.40 (dd, 1H, J = 8.0 Hz, J = 5.0 Hz); 7.96 (td, 1H, J = 8.0 Hz, J = 1.5 Hz); 8.50 (tt, 1H, J = 5.0 Hz, J = 1.5 Hz); 8.75 (d, 1H, J = 1.5 Hz); 9.57 (s, 1H) |
| | Intermediate D and 4-fluoro-2-(pyridin-3-yl)phenol (Protocol SB; 10 min at 120° C. on microwave) Trituration in diethyl ether (Yield: 69%) | White solid (DMSO-d$_6$): 7.30 (d, 1H, J = 9.9 Hz); 7.35-7.45 (m, 2H); 7.54 (dd, 1H, J = 8.0 Hz, J = 5.0 Hz); 7.57 (td, 1H, J = 9.0 Hz, J = 2.9 Hz); 7.88 (td, 1H, J = 8.0 Hz, J = 1.5 Hz); 8.38 (d, 1H, J = 9.9 Hz); 8.50 (dd, 1H, J = 5.0 Hz, J = 1.5 Hz); 8.66 (d, 1H, J = 1.5 Hz) Mass (ES+): 342/344 (M + H) (MP: 140.0-142.0° C.) |
| 4-122 | 4-(2-Methoxy-4-(trifluoromethyl)-benzyl)morpholine from 2-methoxy-4-(trifluoromethyl)benzylbromide and morpholine (2 eq) (Protocol SN; 110° C.). Eluent: cyclohexane/AcOEt 1/1 v/v (Yield: 86%). | (DMSO-d$_6$): 2.38-2.41 (m, 4H); 3.51 (s, 2H); 3.57-3.61 (m, 4H); 3.87 (s, 3H); 7.25 (s, 1H); 7.29 (d, 1H, J = 7.9 Hz); 7.56 (d, 1H, J = 7.7 Hz) |
| | 4-(2-Hydroxy-4-(trifluoromethyl)-benzyl)morpholine from 4-(2-methoxy-4-(trifluoromethyl)benzyl)-morpholine (Protocol SD; BBr$_3$ (1.2 eq)) (Yield: 72%). | (DMSO-d$_6$): 2.40-2.50 (m, 4H); 3.60-3.63 (m, 4H); 3.68 (s, 2H); 7.51 (s, 1H); 7.15 (d, 1H, J = 7.9 Hz); 7.41 (d, 1H, J = 7.8 Hz); 10.73 (s (large), 1H) |
| | Intermediate D and 4-(2-hydroxy-4-(trifluoromethyl)benzyl)morpholine (Protocol SB; 15 min at 110° C. on microwave). Eluent: cyclohexane/AcOEt 1/1 then dichloromethane/MeOH 9/1 v/v (Yield: 78%). | Yellow solid (DMSO-d$_6$): 2.26 (t, 4H, J = 4.5 Hz); 3.22-3.34 (m, 4H); 3.54 (s, 2H); 7.48 (d, 1H, J = 9.8 Hz); 7.71-7.79 (m, 2H); 7.84 (s, 1H); 8.51 (d, 1H, J = 9.9 Hz) Mass: 413.8 [M + H]+ (MP: 55-58° C.) |
| 4-124 | 1-(2-Methoxy-4-(trifluoromethyl)benzyl)-4-methylpiperazine from 2-methoxy-4-(trifluoromethyl)benzylbromide and 1-methylpiperazine (Protocol SN; 10 min at 110° C. on microwave). Eluent: dichloromethane/MeOH 9/1 v/v (Yield: 62%). | (DMSO-d$_6$): 2.16 (s, 3H); 2.34-2.40 (m, 8H); 3.50 (s, 2H); 3.86 (s, 3H); 7.24 (s, 1H); 7.29 (d, 1H, J = 8.0 Hz); 7.53 (d, 1H, J = 8.0 Hz) |
| | 2-((4-Methylpiperazin-1-yl)methyl)-5-(trifluoromethyl)phenol from 1-(2-methoxy-4-(trifluoromethyl)benzyl)-4-methylpiperazine (Protocol SD; BBr$_3$ (1.2 eq)). Precipitation in MeOH (Yield: 61%). | (DMSO-d$_6$): 2.27-2.50 (m, 4H); 2.82-3.52 (m, 7H); 3.53 (s, 2H); 7.19-7.24 (m, 2H); 7.58 (m, 1H) |
| | Intermediate D and 2-((4-methyl-piperazin-1-yl)methyl)-5-(trifluoromethyl)phenol (Protocol SB; 15 min at 110° C. on microwave) Eluent: dichloromethane/MeOH 9/1 v/v (Yield: 14%). | Beige solid (DMSO-d$_6$): 1.8-1.92 (m, 7H); 2.23 (m, 4H); 3.51 (s, 2H); 7.47 (d, 1H, J = 9.9 Hz); 7.72 (s, 2H); 7.83 (s, 1H); 8.51 (d, 1H, J = 9.9 Hz) |
| 4-125 | Cpd. 4-48 and iodohexane (3 eq) (Protocol SO; 15 min at 110° C. on microwave) Eluent: cyclohexane/AcOEt 6/4 v/v (Yield: 40%). | Brown oil (DMSO-d$_6$): 0.86 (m, 3H, J = 6.7 Hz); 1.27-1.35 (m, 6H); 1.55 (quin, 2H, J = 7.1 Hz); 3.02 (q, 2H, J = 6.7 Hz); 6.04 (t, 1H, J = 5.3 Hz); 6.53 (d, 1H, J = 2.2 Hz); |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | | 6.63 (dd, 1H, J = 8.5 Hz, J = 2.3 Hz); 7.14 (m, 1H, J = 7.2 Hz); 7.28 (m, 6H); 8.33 (d, 1H, J = 9.8 Hz) Mass: 421 [M + H]+ |
| 4-126 | Intermediate B and 2-(pyridin-3-yl)-5-(trifluoromethyl)phenol (Protocol SB; 10 min at 120° C. on microwave) Eluent: cyclohexane/AcOEt 7/3 v/v (Yield: 77%). | White solid (DMSO-d$_6$): 7.45 (m, 1H, J = 8.1 Hz, J = 1.3 Hz); 7.55 (d, 1H, J = 16.5 Hz); 7.83-7.89 (m, 2H); 7.95 (td, 1H, J = 13.3 Hz, J = 2.9 Hz); 8.10 (s, 1H); 8.57-8.62 (m, 2H); 8.72 (d, 1H, J = 2.7 Hz) Mass: 425 [M + H]+ (MP: 69-70° C.) |
| 4-129 | 2-(Pyridin-3-yl)-3-(trifluoromethyl)phenol from 2-bromo-3-(trifluoromethyl)phenol and pyridin-3-ylboronic acid (Protocol SA; 15 min at 120° C. on microwave) From aqueous pahses by acido-basic treatment (Yield: 89%). | (DMSO-d$_6$): 7.25-7.35 (m, 2H); 7.65 (d, 1H, J = 7.9 Hz); 9.02 (s, 2H); 9.17 (s, 1H); 10.76 (s, 1H) |
| | Intermediate D and 2-(pyridin-3-yl)-3-(trifluoromethyl)phenol (Protocol SB; K$_2$CO$_3$ (3 eq); 10 min at 100° C. on microwave). Eluent: dichloromethane/MeOH 96/4 v/v (Yield: 25%). | White solid (DMSO-d$_6$): 7.39 (d, 1H, J = 9.9 Hz); 7.35 (qd, 1H, J = 8.2 Hz, J = 1.3 Hz); 7.67 (dt, 1H, J = 8.2 Hz); 7.8-7.9 (m, 2H); 7.92 (dd, 1H, J = 8.2 Hz, J = 4.1 Hz); 8.33 (d, 1H, J = 9.9 Hz); 8.41 (d, 1H, J = 1.3 Hz); 8.52 (dd, 1H, J = 8.2 Hz, J = 2.3 Hz) Mass: 391/393 [M + H]+ (MP: 158-160° C.) |
| 4-134 | 5-Nitrobiphenyl-2-ol Intermediate D and 5-nitrobiphenyl-2-ol (Protocol SB; K$_2$CO$_3$ (2 eq); 100° C. o/n). Eluent: cyclohexane/AcOEt 4/6 then cyclohexane/acetone 1/1 v/v (Yield: 64%). | White solid (DMSO-d$_6$): 7.36-7.44 (m, 4H); 7.52-7.55 (m, 2H); 7.82 (d, 1H, J = 9.0 Hz); 8.33 (d, 1H, J = 2.6 Hz); 8.37 (dd, 1H, J = 9.0 Hz, J = 2.9 Hz); 8.44 (d, 1H, J = 9.9 Hz) Mass: 368 [M + H]+ (MP: 182.7-183.4° C.). |
| 4-139 | 5-Ethoxybiphenyl-2-ol from 2-bromo-4-ethoxyphenol and phenylboronic acid (Protocol SA; 5 min at 150° C. on microwave). Eluent: cyclohexane/dichloromethane 7/3 to 6/4 (Yield: 34%) | (CDCl$_3$): 1.41 (t, 3H, J = 7.0 Hz); 4.02 (q, 2H, J = 7.0 Hz); 4.84 (s (large), 1H); 6.81-6.85 (m, 2H); 6.91 (dd, 1H, J = 7.6 Hz, J = 1.7 Hz); 7.40 (m, 1H); 7.467.52 (m, 4H) |
| | Intermediate D and 5-ethoxybiphenyl-2-ol (Protocol SB; K$_2$CO$_3$ (3 eq); 10 min at 170° C. on microwave). Eluent: cyclohexane/AcOEt 7/3 v/v (Yield: 68%). | White solid (DMSO-d$_6$): 1.36 (t, 3H, J = 7.0 Hz); 4.11 (q, 2H, J = 7.0 Hz); 6.99-7.06 (m, 2H); 7.20-7.42 (m, 7H); 8.32 (d, 1H, J = 9.6 Hz) Mass: 367 [M + H]+ (MP: 89.7-90.8° C.). |
| 4-141 | Intermediate B and 5-fluorobiphenyl-2-ol (Protocol SB; K$_2$CO$_3$ (3 eq); 10 min at 170° C. on microwave). Eluent: cyclohexane/dichloromethane/AcOEt 6/3.5/0.5 v/v (Yield: 57%) | White solid (DMSO-d$_6$): 1.36 (t, 3H, J = 7.0 Hz); 4.11 (q, 2H, J = 7.0 Hz); 6.99-7.06 (m, 2H); 7.20-7.42 (m, 7H); 8.32 (d, 1H, J = 9.6 Hz) Mass: 375 [M + H]+ (MP: 85.3-87.7° C.). |
| 4-144 | Intermediate D and 2-hydroxy-4-methoxybenzophenone (Protocol SB; K$_2$CO$_3$ (3 eq); 10 min at 120° C. on microwave) Trituration in diethyl ether (Yield: 59%). | White solid (DMSO-d$_6$): 3.88 (s, 3H); 7.06 (dd, 1H, J = 8.7 Hz, J = 2.6 Hz); 7.14 (d, 1H, J = 11.9 Hz); 7.15 (s, 1H); 7.43 (m, 2H, J = 7.6 Hz); 7.59 (m, 4H); 8.34 (d, 1H, J = 9.9 Hz) Mass: 381 [M + H]+ (MP: 175-176° C.). |
| 4-145 | Intermediate D and 5-bromo-2-hydroxybenzophenone (Protocol SB; K$_2$CO$_3$ (3 eq); 10 min at 120° C. on microwave) Precipitation from AcOEt/cyclohexane (Yield: 44%). | White solid (DMSO-d$_6$): 7.12 (d, 1H, J = 9.9 Hz); 7.44 (m, 2H, J = 7.9 Hz); 7.61 (m, 4H); 7.83 (d, 1H, J = 2.6 Hz); 7.95 (dd, 1H, J = 8.7 Hz, J = 2.6 Hz); 8.33 (d, 1H, J = 9.9 Hz) Mass: 429 [M + H]+ (MP: 135-137° C.). |
| 4-146 | Intermediate D and 2-benzyl-4-chlorophenol (Protocol SB; K$_2$CO$_3$ (3 eq); 15 min at 120° C. on microwave) Trituration in diethyl ether (Yield: 68%) | White solid (DMSO-d$_6$): 3.93 (s, 2H); 6.97 (m, 1H, J = 4.4 Hz); 7.10 (m, 4H, J = 4.4 Hz); 7.38 (m, 3H); 7.52 (d, 1H, J = 2.3 Hz); 8.39 (d, 1H, J = 9.9 Hz) Mass: 371 [M + H]+ (MP: 161-162° C.). |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-154 | Intermediate D and 5-cyanobiphenyl-2-ol (Protocol SA; 10 min at 170° C. on microwave). Eluent: cyclohexane/AcOEt 1/1 and trituration in methanol (Yield: 39%) | White solid (DMSO-d$_6$): 7.33-7.41 (m, 4H); 7.47-7.49 (m, 2H); 7.73 (d, 1H, J = 8.5 Hz); 8.01 (dd, 1H, J = 8.7 Hz, J = 2.0 Hz); 8.08 (d, 1H, J = 1.7 Hz); 8.41 (d, 1H, J = 9.6 Hz) Mass: 348 [M + H]+ (MP: 208-209° C.) |
| 4-155 | Intermediate D and 4-(hydroxymethyl)biphenyl-2-ol (1 eq) (Protocol SB; K$_2$CO$_3$ (3 eq); 10 min at 120° C. on microwave). Eluent: cyclohexane/AcOEt 5/5 v/v (Yield: 62%). | White solid (DMSO-d$_6$): 4.58 (d, 2H, J = 5.5 Hz); 5.36 (t, 1H, J = 5.8 Hz); 7.20-7.41 (m, 8H); 7.48 (d, 1H, J = 7.6 Hz); 8.33 (d, 1H, J = 9.9 Hz) Mass: 353 [M + H]+ (MP: 187.0-189.2° C.) |
| 4-156 | 3-Chloro-6-(5-bromomethylbiphenyl-2-yloxy)[1,2,4]triazolo[4,3-b]pyridazine and piperidine (Protocol SN, K$_2$CO$_3$ (3 eq)) Eluent: dichloromethane/MeOH 95/5 v/v (Yield: 44%) | White solid (DMSO-d$_6$): 1.40 (m, 1H); 1.71 (m, 3H); 1.82 (m, 2H); 2.92 (m, 2H); 3.35 (m, 2H); 4.37 (d, 2H, J = 5.0 Hz); 7.29-7.40 (m, 4H); 7.47-7.49 (m, 2H); 7.58 (d, 1H, J = 8.4 Hz); 7.66 (d, 1H, J = 8.5 Hz); 7.76 (s, 1H); 8.40 (d, 1H, J = 9.9 Hz); 9.76 (s (large), 1H) Mass: 420 [M + H]+ (MP: 70-70.4° C.). |
| 4-157 | 3-Chloro-6-(5-bromomethylbiphenyl-2-yloxy)[1,2,4]triazolo[4,3-b]pyridazine and diethylamine (Protocol SN; K$_2$CO$_3$ (3 eq)) Eluent: dichloromethane/MeOH 99/1 to 95/5 v/v (Yield: 67%) | Yellow oil (MeOD-d$_4$): 1.27 (t, 6H, J = 7.0 Hz); 2.64 (q, 4H, J = 7.0 Hz); 3.72 (s, 2H); 7.15 (d, 1H, J = 9.9 Hz); 7.19-7.36 (m, 4H); 7.41-7.49 (m, 4H); 8.08 (d, 1H, J = 9.9 Hz) Mass: 408 [M + H]+ |
| 4-158 | 3-Chloro-6-(5-bromomethylbiphenyl-2-yloxy)[1,2,4]triazolo[4,3-b]pyridazine and N-methylbenzylamine (Protocol SN) Eluent: dichloromethane/MeOH 99/1 v/v (Yield: 91%) | White solid (MeOD-d$_4$): 1.27 (t, 6H, J = 7.0 Hz); 2.64 (q, 4H, J = 7.0 Hz); 3.72 (s, 2H); 7.15 (d, 1H, J = 9.9 Hz); 7.19-7.36 (m, 4H); 7.41-7.49 (m, 4H); 8.08 (d, 1H, J = 9.9 Hz) Mass: 456 [M + H]+ (MP: 60.8-62.5° C.) |
| 4-159 | 3-Chloro-6-(5-bromomethylbiphenyl-2-yloxy)[1,2,4]triazolo[4,3-b]pyridazine and 1-methylpiperazine (2.5 eq) (Protocol SN, K$_2$CO$_3$ (3 eq)) Eluent: dichloromethane/MeOH 96/4 v/v (Yield: 63.7%) | White solid (DMSO-d$_6$): 2.14 (s, 3H); 2.33 (m, 4H); 2.42 (m, 4H); 3.55 (s, 2H); 7.23-7.35 (m, 4H); 7.40-7.42 (m, 5H); 8.34 (d, 1H, J = 9.9 Hz) Mass: 435 [M + H]+ (MP: 184.4-186.5° C.). |
| 4-160 | 3-Chloro-6-(5-bromomethylbiphenyl-2-yloxy)[1,2,4]triazolo[4,3-b]pyridazine and cyclopentylamine (4 eq) (Protocol SN, K$_2$CO$_3$ (3 eq)) Eluent: dichloromethane/MeOH 99/1 to 96/4 v/v (Yield: 66%) | Yellow oil (DMSO-d$_6$): 1.33-1.48 (m, 4H); 1.60-1.75 (m, 4H); 2.18 (s (large), 1H); 3.04 (t, 1H, J = 5.8 Hz); 3.75 (s, 2H); 7.23-7.35 (m, 5H); 7.38-7.42 (m, 3H); 7.45-7.46 (m, 1H); 8.34 (d, 1H, J = 9.9 Hz) Mass: 420 [M + H]+ |
| 4-161 | 3-Chloro-6-(5-bromomethylbiphenyl-2-yloxy)[1,2,4]triazolo[4,3-b]pyridazine and cyclopropylamine (4 eq) (Protocol SN, K$_2$CO$_3$ (3 eq)) Eluent: dichloromethane/MeOH 100/0 to 98/2 v/v (Yield: 13%) | Yellow solid (DMSO-d$_6$): 0.27 (m, 2H); 0.35 (m, 2H); 2.09 (m, 1H); 3.81 (s, 2H); 7.22-7.45 (m, 9H); 8.34 (d, 1H, J = 9.9 Hz) Mass: 392 [M + H]+ (MP: 62.2-64.9° C.). |
| 4-162 | 3-Chloro-6-(5-bromomethylbiphenyl-2-yloxy)[1,2,4]triazolo[4,3-b]pyridazine and cyclohexanemethylamine (4 eq) (Protocol SN) Eluent: dichloromethane/MeOH 98/2 v/v (Yield: 46%) | Yellowish solid (DMSO-d$_6$): 0.88 (m, 2H); 1.17 (m, 4H); 1.40 (m, 1H); 1.63 (m, 3H); 1.76 (m, 2H); 2.37 (d, 2H, J = 6.7 Hz); 3.75 (s, 2H); 7.22-7.46 (m, 9H); 8.34 (d, 1H, J = 9.9 Hz) Mass: 448 [M + H]+ (MP: 53.4-55.7° C.). |
| 4-163 | 3-Chloro-6-(5-bromomethylbiphenyl-2-yloxy)[1,2,4]triazolo[4,3-b]pyridazine and tetrahydrofurfurylamine (4 eq) (Protocol SN) Eluent: cyclohexane/AcOEt 7/3 then dichloromethane/MeOH 98/2 v/v (Yield: 63%) | White oil (DMSO-d$_6$): 1.50-1.59 (m, 1H); 1.73-1.82 (m, 2H); 1.85-1.93 (m, 1H); 2.26 (s (large), 1H); 2.59 (m, 2H); 3.59 (q, 1H, J = 7.0 Hz); 3.70 (q, 1H, J = 6.7 Hz); 3.81 (s, 2H); 3.88 (quint, 1H, J = 6.7 Hz); 7.23-7.36 (m, 5H); 7.39-7.42 (m, 3H); 7.45-7.46 (m, 1H); 8.34 (d, 1H, J = 9.9 Hz) Mass: 436 [M + H]+ |
| 4-164 | 3-Chloro-6-(5-bromomethylbiphenyl-2-yloxy)[1,2,4]triazolo[4,3-b]pyridazine and 1-methanesulfanylpiperazine | Beige solid (DMSO-d$_6$): 2.51 (m, 4H); 2.86 (s, 3H); 3.13 (m, 4H); 3.64 (s, 2H); 7.23-7.36 |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | (1 eq) (Protocol SN) Eluent: dichloromethane/MeOH 98/2 v/v (Yield: 9.6%) | (m, 4H); 7.40-7.44 (m, 5H); 8.35 (d, 1H, J = 9.9 Hz) Mass: 499 [M + H]+ (MP: 188.0-193.2° C.). |
| 4-165 | 3-Chloro-6-(5-bromomethylbiphenyl-2-yloxy)[1,2,4]triazolo[4,3-b]pyridazine and methylphenylethylamine (Protocol SN) Eluent: dichloromethane/MeOH 1/0 to 98/2 v/v (Yield: 77%) | White solid (DMSO-$d_6$): 2.25 (s, 3H); 2.63 (t, 2H, J = 7.9 Hz); 2.79 (t, 2H, J = 7.6 Hz); 3.62 (s, 2H); 7.12-7.38 (m, 14H); 8.32 (d, 1H, J = 9.9 Hz) Mass: 470 [M + H]+ (MP: 114.3-117-7° C.). |
| 4-166 | 3-Chloro-6-(5-bromomethylbiphenyl-2-yloxy)[1,2,4]triazolo[4,3-b]pyridazine and diisopropylamine (Protocol SN) Eluent: dichloromethane/MeOH 1/0 to 98/2 v/v (Yield: 19%) | White solid (DMSO-$d_6$): 1.02 (d, 12H, J = 6.4 Hz); 3.01 (m, 2H, J = 6.4 Hz); 3.71 (s, 2H); 7.21 (d, 1H, J = 9.9 Hz); 7.23-7.47 (m, 8H); 8.31 (d, 1H, J = 9.9 Hz) Mass: 435 [M + H]+ (MP: 59.1° C.). |
| 4-167 | 3-Chloro-6-(5-bromomethylbiphenyl-2-yloxy)[1,2,4]triazolo[4,3-b]pyridazine and methylcyclohexylamine (Protocol SN) Eluent: dichloromethane/MeOH 1/0 to 98/2 v/v (Yield: 51%) | Beige solid (DMSO-$d_6$): 1.06-1.35 (m, 5H); 1.58 (d, 1H, J = 10.5 Hz); 1.78 (t, 4H, J = 13.1 Hz); 2.15 (s, 3H); 2.44 (m, 1H); 3.63 (s, 2H); 7.21-7.36 (m, 4H, J = 9.9 Hz); 7.39-7.41 (m, 5H); 8.32 (d, 1H, J = 9.9 Hz) Mass: 447 [M + H]+ (MP: 50.6° C.). |
| 4-169 | 2-Methoxy-4-cyanobiphenyl from 4-bromo-3-methoxybenzonitrile and phenylboronic acid (Protocol SA; 80° C. o/n). Eluent: cyclohexane/AcOEt 95/5 v/v (Yield: 93%). | (DMSO-$d_6$): 3.82 (s, 3H); 7.34-7.51 (m, 7H); 7.58 (s, 1H) |
| | 4-Cyanobiphenyl-2-ol from 2-methoxy-4-cyanobiphenyl (Protocol SD). Eluent: cyclohexane/AcOEt 8/2 v/v (Yield: 89%). | (DMSO-$d_6$): 7.25 (d, 1H, J = 1.5 Hz); 7.31-7.38 (m, 2H); 7.40-7.45 (m, 3H); 7.55-7.57 (m, 2H); 10.40 (s, 1H) |
| | Intermediate D and 4-cyanobiphenyl-2-ol (1 eq) (Protocol SB; K$_2$CO$_3$ (3 eq); 10 min at 120° C. on microwave). Eluent: cyclohexane/AcOEt 6/4 v/v (Yield: 23%). | White solid (DMSO-$d_6$): 7.34-7.43 (m, 4H); 7.48-7.51 (m, 2H); 7.77 (d, 1H, J = 8.0 Hz); 7.93 (dd, 1H, J = 8.0 Hz, J = 1.6 Hz); 8.12 (d, 1H, J = 1.4 Hz); 8.42 (d, 1H, J = 9.8 Hz) Mass: 348/350 [M + H]+ (MP: 216.6-218.4° C.). |
| 4-170 | 5-Cyano-2-methoxybiphenyl from 3-bromo-4-methoxybenzonitrile and phenylboronic acid (Protocol SA; 5 min at 150° C. on microwave). Eluent: cyclohexane/AcOEt 9/1 v/v and trituration in cyclohexane (Yield: 65%) | (DMSO-$d_6$): 3.85 (s, 3H); 7.29 (d, 1H, J = 8.4 Hz); 7.34-7.51 (m, 5H); 7.72 (d, 1H, J = 2.0 Hz); 7.84 (dd, 1H, J = 8.7 Hz, J = 2.0 Hz) |
| | 5-(Aminomethyl)-2-methoxybiphenyl from 5-cyano-2-methoxybiphenyl (Protocol SL) Hydrolysis with NaOH 2N, evaporation - used without further purification | (DMSO-$d_6$): 3.68 (s, 2H); 3.73 (s, 3H); 7.03 (d, 1H, J = 8.1 Hz); 7.25-7.47 (m, 7H) |
| | 5-(Aminomethyl)biphenyl-2-ol from 5-(aminomethyl)-2-methoxybiphenyl (Protocol SD) Used without further purification: (Yield: 98%). | (DMSO-$d_6$): 3.96 (q, 2H, J = 5.8 Hz); 6.96 (d, 1H, J = 8.2 Hz); 7.24 (dd, 1H, J = 8.2 Hz, J = 2.3 Hz); 7.31 (t, 1H, J = 7.3 Hz); 7.38-7.43 (m, 3H); 7.54-7.57 (m, 2H); 8.06 (s (large), 2H); 9.77 (s, 1H) |
| | 5-(Tertiobutyloxycarbonylamino methyl)biphenyl-2-ol from 5-(aminomethyl)biphenyl-2-ol (Protocol SS) Eluent: dichloromethane/MeOH 99/1 v/v (Yield: 41%) | DMSO-$d_6$: 1.37 (s, 9H); 4.04 (d, 2H, J = 5.8 Hz); 6.86 (d, 1H, J = 8.1 Hz); 7.02 (d, 1H, J = 8.5 Hz); 7.12 (s, 1H); 7.25-7.30 (m, 2H); 7.38 (t, 2H, J = 7.3 Hz); 7.51 (d, 2H, J = 7.3 Hz); 9.41 (s, 1H) |
| | Intermediate D and 5-(tertiobutyloxy-carbonylaminomethyl)biphenyl-2-ol (1 eq) (Protocol SB; K$_2$CO$_3$ (3 eq); 10 min at 120° C. on microwave). Eluent: cyclohexane/AcOEt 5/5 v/v (Yield: 88%). | White solid (DMSO-$d_6$): 1.39 (s, 9H); 4.23 (d, 2H, J = 6.1 Hz); 7.24-7.48 (m, 10H); 8.35 (d, 1H, J = 9.6 Hz) Mass: 452/454 [M + H]+ (MP: 63.4-67.2° C.). |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| 4-171 | Cpd. 4-170 (Protocol ST) Precipitation in dichloromethane (Yield: 56%). | White solid (DMSO-$d_6$): 4.16 (s, 2H); 7.29-7.45 (m, 6H); 7.55 (m, 2H); 7.67 (s, 1H); 8.24 (s (large), 3H); 8.40 (d, 1H, J = 9.9 Hz) Mass: 352/354 [M + H]+ (MP: 124.0-125.2° C.). |
| 4-172 | (Methylcarbonyloxymethyl)biphenyl-2-ol from 4-methyloxycarbonylbiphenyl-2-ol Intermediate D and 4-(methylcarbonyloxymethyl)biphenyl-2-ol (1 eq) (Protocol SB; K$_2$CO$_3$ (3 eq); 10 min at 120° C. on microwave). Eluent: cyclohexane/AcOEt 6/4 v/v (Yield: 72%). | White solid (DMSO-$d_6$): 2.08 (s, 3H); 5.14 (s, 2H); 7.22-7.35 (m, 4H); 7.39-7.47 (m, 4H); 7.53 (d, 1H, J = 7.9 Hz); 8.35 (d, 1H, J = 9.9 Hz) Mass: 395/397 [M + H]+ (MP: 129.5-131.4° C.). |
| 4-173 | Cpd. 4-36 and methanesulfonyl chloride (Protocol TD) Trituration in diethyl ether (Yield: 38%). | Salmon-colored solid (DMSO-$d_6$): 3.09 (s, 3H); 7.23-7.46 (m, 9H); 8.34 (d, 1H, J = 9.9 Hz); 9.96 (s, 1H) Mass: 416/418 [M + H]+ (MP: 112-116° C.). |
| 4-174 | Cpd. 4-36 and acetic anhydride (Protocol TD) Trituration in diethyl ether (Yield: 66%). | Salmon-colored solid (DMSO-$d_6$): 2.08 (s, 3H); 7.22-7.39 (m, 7H); 7.65 (dd, 1H, J = 9.0 Hz, J = 2.6 Hz); 7.75 (d, 1H, J = 2.3 Hz); 8.33 (d, 1H, J = 9.9 Hz); 10.14 (s, 1H) Mass: 380/382 [M + H]+ (MP: 186-187° C.). |
| 4-175 | Cpd. 4-48 (Protocol SQ; 100° C. o/n) Eluent: cyclohexane/AcOEt 5/5 v/v (Yield: 8%). | Yellow solid (DMSO-$d_6$): 0.90 (d, 6H, J = 6.7 Hz); 1.45 (q, 2H, J = 7.0 Hz); 1.68 (m, 1H, J = 6.7 Hz); 3.03 (q, 2H, J = 6.4 Hz); 5.97 (t, 1H, J = 5.3 Hz); 6.52 (d, 1H, J = 2.0 Hz); 6.63 (dd, 1H, J = 6.4 Hz); 7.11-7.34 (m, 7H); 8.31 (d, 1H, J = 9.9 Hz) Mass: 408 [M + H]+ (MP: 145-150° C.). |
| 4-176 | 3-Chloro-6-(4-bromomethylbiphenyl-2-yloxy)-[1,2,4]triazolo[4,3-b]pyridazine and cyclohexane-methylamine (2.5 eq) (Protocol SN; K$_2$CO$_3$ (3 eq), 10 min at 120° C. on microwave) Eluent: dichloromethane/MeOH 98/2 v/v | White solid (DMSO-$d_6$): 0.82 (m, 2H); 1.13 (m, 3H); 1.38 (m, 1H); 1.59 (m, 3H); 1.73 (m, 2H); 2.33 (d, 2H, J = 6.5 Hz); 3.75 (s, 2H); 7.25-7.47 (m, 10H); 8.37 (d, 1H, J = 9.9 Hz) Mass: 448/449 [M + H]+ (MP: 141.4-143.8° C.). |
| 4-177 | 3-Chloro-6-(4-bromomethylbiphenyl-2-yloxy)-[1,2,4]triazolo[4,3-b]pyridazine and 1-methylpiperazine (2.5 eq) (Protocol SN; K$_2$CO$_3$ (3 eq)) Eluent: dichloromethane/MeOH 98/2 v/v (Yield: 9.5%) | Beige solid (DMSO-$d_6$): 2.14 (s, 3H); 2.42 (m, 8H); 3.52 (s, 2H); 7.24-7.42 (m, 8H); 7.48 (d, 1H, J = 7.9 Hz); 8.65 (d, 1H, J = 9.9 Hz) Mass: 435/437 [M + H]+ (MP: 137.5-139.9° C.). |
| 4-178 | 3-Chloro-6-(4-bromomethylbiphenyl-2-yloxy)-[1,2,4]triazolo[4,3-b]pyridazine and cyclopropylamine (2.5 eq) (Protocol SN; K$_2$CO$_3$ (3 eq)) Eluent: dichloromethane/MeOH/NH$_4$OH 99/1/0.1 v/v (Yield: 32%) | White solid (DMSO-$d_6$): 0.22-025 (m, 2H); 0.27-0.31 (m, 2H); 2.06 (m, 1H); 3.78 (s, 2H); 7.24-7.46 (m, 10H); 8.35 (d, 1H, J = 9.6 Hz) Mass: 392/394 [M + H]+ (MP: 140.2-13.2° C.). |
| 4-179 | 3-Chloro-6-(4-bromomethylbiphenyl-2-yloxy)-[1,2,4]triazolo[4,3-b]pyridazine and cyclopentylamine (2.5 eq) (Protocol SN; K$_2$CO$_3$ (3 eq)) Eluent: dichloromethane/MeOH 98/2 v/v (Yield: 5%) | White solid (DMSO-$d_6$): 1.35-1.44 (m, 4H); 1.61 (m, 4H); 3.00 (m, 1H); 3.74 (s, 2H); 7.24-7.34 (m, 4H); 7.40-7.46 (m, 6H); 8.35 (d, 1H, J = 9.9 Hz) Mass: 420/422 [M + H]+ |
| 4-180 | 3-Chloro-6-(4-bromomethylbiphenyl-2-yloxy)-[1,2,4]triazolo[4,3-b]pyridazine and tetrahydrofurfuryl-amine (2.5 eq) (Protocol SN; K$_2$CO$_3$ (3 eq)) Eluent: dichloromethane/MeOH 98/2 v/v (Yield: 67%) | White oil (DMSO-$d_6$): 1.51 (m, 1H); 1.72-1.91 (m, 3H); 2.55 (d, 2H, J = 4.8 Hz); 3.57 (m, 1H); 3.66 (m, 1H); 3.80 (s, 2H); 3.87 (t, 1H, J = 5.8 Hz); 7.23-7.48 (m, 10H); 8.36 (d, 1H, J = 9.9 Hz) Mass: 436/438 [M + H]+ |
| 4-181 | 3-Chloro-6-(4-bromomethylbiphenyl-2-yloxy)-[1,2,4]triazolo[4,3-b]pyridazine and methylphenethyl-amine (2.5 eq) (Protocol SN; K$_2$CO$_3$ | Yellow oil (DMSO-$d_6$): 2.26 (s, 3H); 2.63 (t, 2H, J = 8.0 Hz); 2.78 (t, 2H, J = 7.9 Hz); 3.61 (s, 2H); 7.10 (m, 1H); 7.18 (m, 4H); |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
| | (3 eq))<br>Eluent: dichloromethane/MeOH 98/2 v/v (Yield: 88%) | 7.26-7.36 (m, 6H)); 7.40-7.47 (m, 3H); 8.37 (d, 1H, J = 9.9 Hz)<br>Mass: 467/469 [M + H]+ |
| 4-182 | 3-Chloro-6-(4-bromomethylbiphenyl-2-yloxy)-[1,2,4]triazolo[4,3-b]pyridazine and 1-methanesulfonylpiperazine (2.5 eq) (Protocol SN; K$_2$CO$_3$ (3 eq))<br>Trituration in diethyl ether (Yield: 78%) | White solid<br>(DMSO-d$_6$): 2.50 (m, 4H); 2.85 (s, 3H); 3.12 (m, 4H); 3.62 (s, 2H); 7.25-7.42 (m, 8H); 7.50 (d, 1H, J = 7.9 Hz); 8.37 (d, 1H, J = 9.9 Hz)<br>Mass: 499 [M + H]+ (MP: 117.8-120.4° C.). |
| 4-183 | 3-Chloro-6-(4-bromomethylbiphenyl-2-yloxy)-[1,2,4]triazolo[4,3-b]pyridazine and piperidine (Protocol SN; K$_2$CO$_3$ (3 eq))<br>Eluent: dichloromethane/MeOH 95/5 v/v (Yield: 52%) | White solid<br>(DMSO-d$_6$): 3.93 (s, 2H); 6.97 (m, 1H, J = 4.4 Hz); 7.10 (m, 4H, J = 4.4 Hz); 7.38 (m, 3H); 7.52 (d, 1H, J = 2.3 Hz); 8.39 (d, 1H, J = 9.9 Hz)<br>Mass: 420 [M + H]+ (MP: 163-164° C.). |
| 4-184 | 3-Chloro-6-(4-bromomethylbiphenyl-2-yloxy)-[1,2,4]triazolo[4,3-b]pyridazine and diethylamine (Protocol SN)<br>Eluent: dichloromethane/MeOH 96/4 v/v (Yield: 41%) | White solid<br>(DMSO-d$_6$): 1.11 (t, 6H, J = 7.0 Hz); 3.96 (q, 4H, J = 7.3 Hz); 3.72 (s, 2H); 7.15-7.32 (m, 4H); 7.40-7.49 (m, 5H); 8.09 (d, 1H, J = 9.9 Hz)<br>Mass: 408 [M + H]+ (MP: 110-112° C.). |
| 4-185 | 2-Methoxy-4-nitrobiphnenyl from 1-bromo-2-methoxy-4-nitrobenzene and phenylboronic acid (Protocol SA, 2.5 hours at 80° C.).<br>Eluent: cyclohexane/AcOEt 99/1 v/v (Yield: 60%)<br>2-Methoxy-4-aminobiphenyl from 2-methoxy-4-nitrobiphenyl (Protocol SF, purification by extraction in acidic media)<br>Eluent: cyclohexane/AcOEt 5/5 v/v (Yield: 40%).<br>4-((Cyclohexylethyl)amino)-2-methoxybiphenyl from 2-methoxy-4-aminobiphenyl and 1-bromo-2-cyclohexylethane (Protocol SO, 30 min at 120° C. on microwave).<br>Eluent: cyclohexane/AcOEt 9/1 v/v (Yield: 51%).<br><br>4-((Cyclohexylethyl)amino)biphenyl-2-ol from 4-((cyclohexylethyl)aminomethyl)-2-methoxybiphenyl (Protocol SD; BBr$_3$ (10 eq))<br>Trituration in dichloromethane: (Yield: 78%).<br><br>Intermediate D and 4-(cyclohexylethylamino)biphenyl-2-ol (Protocol SB; K$_2$CO$_3$ (3 eq); 20 min at 120° C. on microwave).<br>Eluent: cyclohexane/AcOEt 7/3 v/v (Yield: 45%). | (DMSO-d$_6$): 0.93 (m, 5H, J = 11.0 Hz); 1.20 (m, 3H, J = 11.9 Hz); 1.46 (m, 3H, J = 7.3 Hz); 1.70 (m, 2H, J = 14.0 Hz); 3.05 (q, 2H, J = 6.4 Hz); 3.69 (s, 3H); 6.66 (t, 1H, J = 5.3 Hz); 6.21 (dd, 1H, J = 8.5 Hz, J = 2.0 Hz); 6.28 (d, 1H, J = 2.0 Hz); 7.00 (d, 1H, J = 8.5 Hz); 7.17 (t, 1H, J = 7.0 Hz); 7.28-7.40 (m, 4H)<br><br>(DMSO-d$_6$): 0.91 (m, 2H, J = 11.3 Hz); 1.06-1.25 (m, 4H); 1.41-1.84 (m, 3H); 1.65-1.74 (m, 5H); 2.99 (t, 2H, J = 7.0 Hz); 6.13-6.16 (m, 2H); 6.98 (d, 1H, J = 8.2 Hz); 7.14 (t, 1H, J = 7.3 Hz); 7.29 (t, 2H, J = 7.6 Hz); 7.45-7.48 (m, 2H); 9.08 (s, 1H)<br>White solid<br>(DMSO-d$_6$): 0.89 (m, 2H, J = 10.8 Hz); 1.06-1.25 (m, 3H); 1.39-1.48 (m, 3H); 1.62-1.72 (m, 5H); 3.03 (q, 2H, J = 6.1 Hz); 5.97 (t, 1H, J = 10.5 Hz); 6.51 (d, 1H, J = 2.0 Hz); 6.62 (dd, 1H, J = 8.5 Hz, J = 2.3 Hz); 7.11-7.34 (m, 7H); 8.32 (d, 1H, J = 9.9 Hz)<br>Mass: 448 [M + H]+ (MP: 154-159° C.). |
| 4-186 | 3-Chloro-6-(4-tertbutyloxycarbonyl-aminomethyl-biphenyl-2-yloxy)-[1,2,4]triazolo[4,3-b]pyridazine from intermediate D and 4-(tertbutyloxycarbonylaminomethyl)-biphenyl-2-ol (Protocol SB; 10 min at 120° C. on microwave)<br>Eluent: cyclohexane/AcOEt 7/3 v/v (Yield: 79%)<br>(Cf intermediate of Cpd. 4-65) | White solid<br>(DMSO-d$_6$): 1.37 (s, 9H); 4.20 (d, 2H, J = 6.1 Hz); 7.23-7.33 (m, 6H); 7.38-7.40 (m, 2H); 7.46-7.49 (m, 2H); 8.34 (d, 1H, J = 9.6 Hz)<br>Mass: 451/453 [M + H]+ (MP: 160.9-162.0° C.). |
| 4-189 | 4-Nitro-2-methoxybiphenyle from 1-bromo-2-methoxy-4-nitrobenzene and phenylboronic acid (Protocol SA, 2 hours 30 min at 80° C.); dissolution in dichloromethane/cyclohexane, evaporation. | (DMSO-d$_6$): 3.91 (s, 3H); 7.45 (m, 3H); 7.54 (m, 2H); 7.58 (d, 1H, J = 8.4 Hz); 7.87 (d, 1H, J = 2.0 Hz); 7.91 (dd, 1H, J = 8.2 Hz, J = 2.0 Hz) |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
|  | Eluent: cyclohexane/AcOEt: 99/1 v/v (Yield: 60%). |  |
|  | 4-Amino-2-methoxy-biphenyle from 4-nitro-2-methoxybiphenyle (Protocol SF, 24 h at RT); extraction in acidic medium. Eluent: cyclohexane/AcOEt: 5/5 v/v (Yield: 40%). | (DMSO-d$_6$): 3.67 (s, 3H); 5.21 (s, 2H); 6.22 (dd, 1H, J = 8.2 Hz, J = 2.0 Hz); 6.31 (d, 1H, J = 1.7 Hz); 6.94 (d, 1H, J = 7.9 Hz); 7.17 (t, 1H, J = 7.3 Hz); 7.34 (m, 4H) |
|  | 4-Amino-2-methoxy-biphenyle and isopropylbromide (Protocol SO). Eluent: cyclohexane/AcOEt: 9/1 v/v (Yield: 72%). | (DMSO-d$_6$): 1.16 (d, 6H, J = 6.3 Hz); 3.59 (m, 1H, J = 6.3 Hz); 3.70 (s, 3H); 5.56 (d, 1H, J = 8.1 Hz); 6.22 (dd, 1H, J = 8.3 Hz, J = 2.0 Hz); 6.29 (d, 1H, J = 2.0 Hz); 7.01 (d, 1H, J = 8.3 Hz); 7.18 (td, 1H, J = 7.2 Hz, J = 1.4 Hz); 7.29-7.42 (m, 4H) |
|  | 4-(Isopropylamino)-2-hydroxy-biphenyl from 4-(isopropylamino)-2-methoxy-biphenyle (Protocole SD; BBr$_3$ (10 eq), 30 min at RT) Trituration in dichloromethane (Yield: 40%). | (DMSO-d$_6$): 1.13 (d, 6H, J = 6.4 Hz); 3.47 (m, 1H, J = 5.6 Hz); 5.39 (s, 1H); 6.11-6.14 (m, 2H); 6.97 (d, 1H, J = 8.2 Hz); 7.14 (t, 1H, J = 7.3 Hz); 7.29 (t, 2H, J = 7.6 Hz); 7.46 (d, 2H, J = 7.6 Hz); 9.06 (s, 1H) |
|  | Intermediate D and 4-(isopropylamino)-2-hydroxy-biphenyle (Protocole SB) Eluent: cyclohexane/AcOEt: 5/5 v/v (Yield: 31%). | Yellow solid (DMSO-d$_6$): 1.14 (d, 6H, J = 6.1 Hz); 3.55 (m, 1H, J = 6.4 Hz); 5.84 (d, 1H, J = 7.9 Hz); 6.53 (d, 1H, J = 2.0 Hz); 6.62 (dd, 1H, J = 8.5 Hz, J = 2.0 Hz); 7.11-7.34 (m, 7H); 8.32 (d, 1H, J = 9.3 Hz) Mass: 380 [M + H]+ (MP: 170-175° C.) |
| 4-190 | Cpd. 4-36 and methyl-3-bromopropionate (Protocol SO) Eluent: cyclohexaneAcOEt: 5/5 v/v (Yield: 5%) | Yellow solid (DMSO-d$_6$): 2.63 (t, 2H, J = 6.6 Hz); 3.36 (t, 2H, J = 6.8 Hz); 3.63 (s, 3H); 5.92 (t, 1H, J = 5.5 Hz); 6.62 (d, 1H, J = 2.6 Hz); 6.66 (dd, 1H, J = 8.8 Hz, J = 2.8 Hz); 7.15 (d, 1H, J = 5.6 Hz); 7.18 (d, 1H, J = 6.8 Hz); 7.21-7.39 (m, 5H); 8.30 (d, 1H, J = 9.9 Hz) Mass: 424 [M + H]+ (MP: 52-57° C.) |
| 4-191 | Cpd. 4-36 and propionyl chloride (Protocol TD) Eluent: dichloromethane/MeOH: 9/1 v/v (Yield: 30%) | White solid (DMSO-d$_6$): 1.10 (t, 3H, J = 7.6 Hz); 2.37 (q, 2H, J = 7.6 Hz); 7.22-7.39 (m, 7H); 7.68 (dd, 1H, J = 8.7 Hz, J = 2.3 Hz); 7.78 (d, 1H, J = 2.3 Hz); 8.33 (d, 1H, J = 9.6 Hz); 10.07 (s, 1H) Mass: 394 [M + H]+ (MP: 163-165° C.). |
| 4-192 | Cpd. 4-36 and isobutyryl chloride (Protocol TD) Eluent: dichloromethane/MeOH: 9/1 v/v (Yield: 31%). | White solid (DMSO-d$_6$): 1.12 (d, 6H, J = 7.0 Hz); 2.57-2.66 (m, 1H, J = 6.7 Hz); 7.22-7.39 (m, 7H); 7.68 (dd, 1H, J = 9.0 Hz, J = 2.3 Hz); 7.80 (d, 1H, J = 2.6 Hz); 8.33 (d, 1H, J = 9.9 Hz); 10.03 (s, 1H) Mass: 408/410 [M + H]+ (MP: 222-224° C.) |
| 4-194 | 3,6-Dichloro-[1,2,4]triazolo[4,3-b]pyridazine and 4-chloro-2-(pyrimidin-5-yl)phenol (Protocol SB; K$_2$CO$_3$ (3 eq); 10 min at 110° C. on microwave) Precipitation with water; washings with diethyl ether (Yield: 48%) | White solid (DMSO-d$_6$): 7.38 (d, 1H, J = 9.9 Hz); 7.64-7.73 (m, 2H); 7.87 (d, 1H, J = 2.3 Hz); 8.44 (d, 1H, J = 9.9 Hz); 8.97 (s, 2H); 9.17(s, 1H) Mass: 359 [M + H]+ (MP: 152-155° C.). |
| 4-197 | 3-Chloro-6-(4-cyanobiphenyl-2-yloxy)-[1,2,4]triazolo[4,3-b]pyridazine Cpd. 4-169 (Protocol TC) Trituration dichloromethane/ethanol) (Yield: 11%) | White solid (DMSO-d$_6$): 2.69 (s, 3H); 7.3-7.45 (m, 4H); 7.50 (d, 2H, J = 7.0 Hz); 7.75 (d, 1H, J = 8.2 Hz); 8.05-8.15 (m, 2H); 8.38 (d, 1H, J = 9.9 Hz) Mass: 380/382 [M + H]+ (MP: 159-161° C.) |
| 4-198 | 2-Methoxy-5-(5-methyl-1,2,4-oxadiazol-3-yl)-biphenyl from 5-cyano-2-methoxybiphenyl (Protocol TC) (Yield 24%) | (DMSO-d$_6$): 2.66 (s, 3H); 3.86 (s, 3H); 7.30 (d, 1H, J = 8.4 Hz); 7.35-7.4 (m, 1H); 7.40-7.50 (m, 2H); 7.50-7.55 (m, 2H); 7.86 (d, 1H, J = 2.0 Hz); 7.85 (dd, 1H, J = 8.4 Hz, J = 2.0 Hz) |
|  | 5-(5-Methyl-1,2,4-oxadiazol-3-yl)biphenyl-2-ol from 5-(5-methyl-1,2,4-oxadiazol-3-yl)-2-methoxybiphenyl (Protocol SD; | (DMSO-d$_6$): 2.66 (s, 3H); 7.10 (d, 1H, J = 8.4 Hz); 7.35-7.4 (m, 1H); 7.40-7.50 (m, 2H); 7.50-7.55 (m, 2H); 7.82 (dd, 1H, J = 8.4 Hz, J = 2.0 Hz); 7.85 (d, 1H, |

TABLE 2-3-continued

Ra is W or W-Z, Rf-Rj are hydrogen, and at least one of
Rb-Re is other than hydrogen atom, R2 and R3 are hydrogen

| Cpd. | Starting compounds, Reaction conditions and purification | Appearance, $^1$H NMR (solvent) data, Mass (ES+ or ES−) data (MP) |
|---|---|---|
|  | CHCl$_3$; BBr$_3$ (2.5 eq); RT; 16 hours) Trituration in diethyl ether (Yield: 84%). Intermediate D and 5-(5-methyl-1,2,4-oxadiazol-3-yl)biphenyl-2-ol (Protocol SB; K$_2$CO$_3$ (3 eq); 10 min at 120° C. on microwave) Trituration in diethyl ether (Yield: 61%) | J = 2.0 Hz); 10.31 (s large, 1H)<br><br>Beige solid<br>(DMSO-d$_6$): 2.71 (s, 3H); 7.10 (d, 1H, J = 9.9 Hz); 7.35-7.45 (m, 3H); 7.45-7.55 (m, 2H); 7.70 (d, 1H, J = 8.4 Hz); 8.05-8.15 (m, 2H); 8.41 (d, 1H, J = 9.9 Hz)<br>Mass: 404/406 [M + H]+ (MP: 171-173° C.). |

TABLE 2-4

Ra is W or W-Z-, at least one of Rb-Re is either than hydrogen; at
least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
| 4-30 | 3',4-difluorobiphenyl-2-ol from 2-bromo-5-fluorophenol and 3-fluorophenyl-boronic acid (Protocol SA; 110° C. o/n) Eluent: dichloromethane/cyclohexane 5/5 v/v (Yield: 76%) | Colorless oil<br>(CDCl$_3$): 5.32 (s, 1H); 6.72-6.78 (m, 2H); 7.09-7.25 (m, 4H); 7.44-7.51 (m, 1H) |
|  | Intermediate D and 3',4-difluoro-biphenyl-2-ol (Protocol SB; 3 hours at 100° C.) Eluent: cyclohexane/AcOEt 7/3 to 6/4 v/v (Yield: 33%) | White solid<br>(MeOD-d$_4$): 6.97-7.02 (m, 1H); 7.16-7.35 (m, 6H); 7.57 (dd, 1H, J = 8.5 Hz, J = 6.2 Hz); 8.16 (d, 1H, J = 9.8 Hz)<br>Mass: 359.1 [M + H]+ (MP: 123.4° C.) |
| 4-31 | 4,4'-difluoro-biphenyl-2-ol from 2-bromo-5-fluorophenol and 4-fluoro-phenylboronic acid (Protocol SA; 110° C. o/n) Eluent: dichloromethane/cyclohexane 5/5 v/v (Yield: 72%) | White solid<br>(CDCl$_3$): 5.21 (s, 1H); 6.71-6.76 (m, 2H); 7.15-7.23 (m, 3H); 7.4-7.44 (m, 2H) |
|  | Intermediate D and 4,4'-difluoro-biphenyl-2-ol (Protocol SB; 100° C. o/n) Eluent: cyclohexane/AcOEt 7/3 to 6/4 v/v (Yield: 21%) | White solid<br>(MeOD-d$_4$): 7.03-7.09 (m, 2H); 7.20 (d, 1H, J = 9.8 Hz); 7.23-7.31 (m, 2H); 7.41-7.46 (m, 2H); 7.53 (dd, 1H, J = 8.7 Hz, J = 6.4 Hz); 8.16 (d, 1H, J = 10.0 Hz)<br>Mass: 359.1 [M + H]+ (MP: 129.7° C.) |
| 4-34 | 4'-Fluoro-4-methoxybiphenyl-2-ol from 2-bromo-5-methoxyphenol and 4-fluorophenylboronic acid (Protocol SA; 110° C. o/n) Eluent: cyclohexane/dichloromethane 8/2 to 3/7 v/v (Yield: 49%) | White solid<br>(CDCl$_3$): 3.84 (s, 3H); 5.13 (s, 1H); 6.57-6.60 (m, 2H); 7.13-7.20 (m, 2H); 7.40-7.44 (m, 2H) |
|  | Intermediate D and 4'-fluoro-4-methoxybiphenyl-2-ol (Protocol SB; 110° C. o/n) Eluent: cyclohexane/AcOEt 8/2 to 6/4 v/v (Yield: 48%) | White solid<br>(DMSO-d$_6$): 3.86 (s, 3H); 6.98-7.04 (m, 4H); 7.17 (d, 1H, J = 10.0 Hz); 7.37-7.41 (m, 3H); 8.11 (d, 1H, J = 9.8 Hz)<br>Mass: 371.1 [M + H]+ (MP: 171.7° C.) |
| 4-71 | 3'-Methoxy-4-(trifluoromethyl)-biphenyl-2-ol from 2-bromo-5-(trifluoromethyl) phenol and 3-methoxybenzeneboronic acid (Protocol SA; 110° C. o/n) Eluent: cyclohexane/AcOEt 1/1 v/v (Yield: 66%) | White solid<br>(DMSO-d$_6$): 3.78 (s, 3H); 6.91-6.95 (m, 1H); 7.11-7.22 (m, 4H); 7.34 (t, 1H, J = 8.4 Hz); 7.47 (d, 1H, J = 7.9 Hz); 10.27 (s, 1H) |
|  | Intermediate D and 3'-methoxy-4-(trifluoromethyl) biphenyl-2-ol. (Protocol SB; 10 min at 170° C. on microwave) Eluent: cyclohexane/AcOEt 1/1 v/v (Yield: 70%) | White solid<br>(DMSO-d$_6$): 3.71 (s, 3H); 6.89 (dd, 1H, J = 8.2 Hz, J = 2.3 Hz); 7-7.04 (m, 2H); 7.28 (t, 1H, J = 7.9 Hz); 7.35 (d, 1H, J = 9.9 Hz); 7.77-7.82 (m, 2H); 7.99 (s, 1H); 8.39 (d, 1H, J = 9.9 Hz)<br>Mass: 421 [M + H]+; 443 [M + Na]+ (MP: 44-47° C.) |
| 4-37 | Cpd. 4-71 (Protocol SD) Eluent: cyclohexane/AcOEt 20/80 v/v (Yield: 41%) | White solid<br>(DMSO-d$_6$): 6.71 (dd, 1H, J = 8.1 Hz, J = 1.5 Hz); 6.82-6.88 (m, 2H); 7.18 (t, 1H, J = 7.9 Hz); 7.31 (d, 1H, J = 9.9 Hz); |

TABLE 2-4-continued

Ra is W or W-Z-, at least one of Rb-Re is either than hydrogen; at
least one of Rf-Rj is either than hydrogen, R2 and R3 are hydrogen.

| Cpd. | Starting compounds<br>Reaction conditions and purification | Appearance, $^1$H NMR (solvent) data,<br>Mass (ES+ or ES−) data (MP) |
|---|---|---|
| | | 7.71-7.80 (m, 2H); 7.97 (s, 1H); 8.42<br>(d, 1H, J = 9.9 Hz); 9.50 (s, 1H)<br>Mass: 407 [M + H]+; 429 [M + Na]+ (MP:<br>76-79° C.) |
| 4-72 | 4-(Trifluoromethyl)-3'-<br>(aminocarbonyl)-biphenyl-2-ol from 2-<br>bromo-5-(trifluoromethyl)phenol and<br>3-aminocarbonylboronic acid<br>(Protocol SA; boronic acid (1.1 eq.),<br>palladium (II) chloride (dppf)<br>(0.025 eq.) and sodium carbonate<br>(3 eq.) 5 min at 150° C. on microwave)<br>Eluent: cyclohexane/AcOEt 5/5<br>v/v(Yield: 92%) | Beige solid<br>(DMSO-d$_6$): 7.23-7.25 (m, 2H); 7.41-<br>7.55 (m, 2H); 7.74 (d, 1H, J = 8.0 Hz);<br>7.84-7.88 (m, 2H); 8.03-8.05 (m, 2H);<br>10.38 (s, 1H) |
| | Intermediate D and 4-<br>(trifluoromethyl)-3'-(aminocarbonyl)-<br>biphenyl-2-ol (Protocol SB; 5 min at<br>150° C. on microwave)<br>Eluent: dichloromethane/MeOH 98/2<br>v/v (Yield: 85%) | Beige powder<br>(DMSO-d$_6$): 7.32 (d, 1H, J = 9.8 Hz);<br>7.41 (s, 1H); 7.46 (t, 1H, J = 7.7 Hz); 7.65<br>(d, 1H, J = 8.1 Hz); 7.83-7.86 (m, 3H);<br>7.99 (t, 1H, J = 1.5 Hz); 8.01 (s, 1H); 8.05<br>(s, 1H); 8.41 (d, 1H, J = 9.9 Hz)<br>Mass (ES+): 434.1 (M + H); 456.1<br>(M + Na) (MP: 217.7-220.0° C.) |
| 4-73 | 2-Bromo-5-(trifluoromethyl)phenol<br>from 3-(trifluoromethyl)phenol<br>(Protocol TA)<br>Eluent: dichloromethane/cyclohexane<br>4/6 v/v and cyclohexane/AcOEt 9/1 v/v<br>(Yield: 40%) | Colorless oil<br>(DMSO-d$_6$): 7.06 (dd, 1H, J = 8.2 Hz,<br>J = 1.4 Hz); 7.18 (d, 1H, J = 1.7 Hz); 7.72<br>(d, 1H, J = 8.2 Hz); 11.05 (s, 1H) |
| | 3'-(hydroxymethyl)-4-(trifluoromethyl)-<br>biphenyl-2-ol from 2-bromo-5-<br>(trifluoromethyl)phenol and 3-<br>(hydroxymethyl)phenylboronic acid<br>(Protocol SA; boronic acid (1.5 eq), 5<br>min at 150° C. on microwave)<br>Eluent: dichloromethane/AcOEt 7/3<br>v/v (Yield: 74%) | Ocher oil<br>(DMSO-d$_6$): 4.54 (d, 2H, J = 5.6 Hz);<br>5.21 (t, 1H, J = 5.6 Hz); 7.15-7.25 (m,<br>2H); 7.29 (d, 1H); 7.38 (t, 1H); 7.39-<br>7.48 (m, 2H); 7.50 (s, 1H); 10.25 (s,<br>1H) |
| | 3-Chloro-6-(3'-(hydroxymethyl)-4-<br>(trifluoromethyl)-biphenyl-2-yloxy)-<br>[1,2,4]triazolo[4,3-b]pyridazine from<br>Intermediate D and 3'-<br>(hydroxymethyl)-4-(trifluoromethyl)-<br>biphenyl-2-ol (Protocol SB,<br>acetonitrile, 30 min at 80° C. on<br>microwave)<br>Eluent: AcOEt (Yield: 81%) | Yellow oil<br>(DMSO-d$_6$): 4.45 (d, 2H, J = 5.6 Hz);<br>5.17 (t, 1H, J = 5.6 Hz); 7.25-7.38 (m,<br>4H); 7.42 (s, 1H); 7.70-7.85 (m, 2H);<br>8.00 (s, 1H); 10.25 (d, 1H, J = 9.9 Hz) |
| | 3-Chloro-6-(3'-(bromomethyl)-4-<br>(trifluoromethyl)-biphenyl-2-yloxy)-<br>[1,2,4]triazolo[4,3-b]pyridazine from 3-<br>chloro-6-(3'-(hydroxymethyl)-4-<br>(trifluoromethyl)-biphenyl-2-yloxy)-<br>[1,2,4]triazolo[4,3-b]pyridazine<br>(Protocol SN; phosphoryl tribromide<br>(1.5 eq), dichloromethane<br>stabilized/amylene, 1 h RT° C.)<br>(Yield: 100%) | Yellow oil |
| | 3-Chloro-6-(3'-(bromomethyl)-4-<br>(trifluoromethyl)-biphenyl-2-yloxy)-<br>[1,2,4]triazolo[4,3-b]pyridazine<br>(Protocol SM; dimethylamine<br>hydrochloride (1.5 eq), triethylamine<br>(2 eq), dichloromethane, microwave 5<br>min at 45° C. on microwave)<br>Eluent: dichloromethane/MeOH 9/1<br>v/v (Yield: 38%) | White solid<br>(DMSO-d$_6$): 2.62 (s, 6H); 4.25 (s, 2H);<br>7.37 (d, 1H, J = 9.9 Hz); 7.47 (q, 1H);<br>7.53-7.63 (m, 2H); 7.70 (s, 1H); 7.85 (s,<br>2H); 8.05 (s, 1H); 8.41 (d, 1H,<br>J = 9.9 Hz); 10.68 (s, 1H)<br>Mass: 448 [M + H]+ (MP: 181-184° C.) |
| 4-74 | 3'-Carboxy-5-fluoro-biphenyl-2-ol from<br>4-fluoro-2-bromophenol and 3-<br>carboxybenzeneboronic (Protocol SA;<br>microwave 5 min at 150° C. on<br>microwave)<br>Eluent: dichloromethane/MeOH 96/4<br>v/v (Yield: 44%) | White solid<br>(DMSO-d$_6$): 6.96 (d, 1H, J = 5.0 Hz);<br>7.04 (td, 1H, J = 8.7 Hz, J = 3.2 Hz); 7.14<br>(dd, 1H, J = 9.6 Hz, J = 2.9 Hz); 7.54 (t,<br>1H, J = 7.6 Hz); 7.79 (d, 1H, J = 7.9 Hz);<br>7.89 (d, 1H, J = 7.6 Hz); 8.15 (s, 1H);<br>9.65 (s, 1H); 12.97 (s, 1H) |
| | Intermediate D and 3'-carboxy-5-<br>fluoro-biphenyl-2-ol (Protocol SB; 10<br>min at 170° C. on microwave) | White solid<br>(DMSO-d$_6$): 7.29 (d, 1H, J = 9.8 Hz);<br>7.36 (td, 1H, J = 8.4 Hz, J = 2.6 Hz); 7.48 |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
| | (Yield: 38%) | (t, 1H, J = 7.7 Hz); 7.54 (dd, 1H, J = 9.7 Hz, J = 2.6 Hz); 7.65 (m, 2H); 7.85 (d, 1H, J = 7.7 Hz); 7.94 (st, 1H, J = 1.4 Hz); 8.41 (d, 1H, J = 9.9 Hz); 13.04 (s, 1H) (MP: 266-276° C.) |
| 4-75 | Cpd. 4-74 (Protocol SR; 8 h at 80° C.) Eluent: dichloromethane/AcOEt 9/1 v/v (Yield: 14%) | White solid (DMSO-$d_6$): 3.78 (s, 3H); 7.27 (d, 1H, J = 9.9 Hz); 7.35 (t, 1H, J = 8.2 Hz); 7.59 (m, 4H); 7.86 (d, 1H, J = 7.6 Hz); 7.93 (s, 1H); 8.39 (d, 1H, J = 9.9 Hz) Mass: 399 [M + H]+; 421 [M + Na]+ (MP: 172-173° C.) |
| 4-76 | 5-Fluoro-3'-methoxy-biphenyl-2-ol from 2-bromo-4-fluorophenol and 3-methoxyphenylboronic acid (Protocol SA, boronic acid (1.1 eq), palladium (II) chloride (dppf) (0.025 eq.) and sodium carbonate(3 eq.), 5 min at 150° C. on microwave) Eluent: cyclohexane/dichloromethane 8/2 to 5/5 v/v (Yield: 70%) | Yellow solid (DMSO-$d_6$): 3.86 (s, 3H); 5.13 (s, 1H); 6.92-7.04 (m, 6H); 7.42 (m, 1H) |
| | 5-fluoro-3'-methoxy-biphenyl-2-ol and intermediate D (Protocol SB; 10 min at 170° C. on microwave) Eluent: cyclohexane/AcOEt 3/7 v/v (Yield: 100%) | White solid (DMSO-$d_6$): 3.69 (s, 3H); 6.85 (d, 1H, J = 7.9 Hz); 6.96-7.00 (m, 2H); 7.24 (t, 1H, J = 7.6 Hz); 7.30 (d, 1H, J = 9.9 Hz); 7.37-7.44 (m, 2H); 7.53 (m, 1H); 8.36 (d, 1H, J = 9.9 Hz) Mass (ES+): 371 (M + H); 393 (M + Na) (MP: 91.3-93.4° C.) |
| 4-77 | Cpd. 4-76 (Protocol SD) Eluent: cyclohexane/AcOEt 3/7 v/v (Yield: 46%) | White solid (DMSO-$d_6$): 6.67 (dd, 1H, J = 8.2 Hz, J = 1.4 Hz); 6.77 (s, 1H); 6.82 (d, 1H, J = 7.9 Hz); 7.14 (t, 1H, J = 7.9 Hz); 7.27 (d, 1H, J = 9.9 Hz); 7.32-7.37 (m, 2H); 7.50 (m, 1H); 8.39 (d, 1H, J = 9.9 Hz); 9.42 (s, 1H) Mass (QTOF+): 357 (M + H); 379 (M + Na) (MP: 241.3-244.5° C.) |
| 4-78 | 2-(Benzyloxy)-1-bromo-4-(trifluoromethyl)benzene from 2-bromo-5-(trifluoromethyl)phenol (Protocol SB; benzylbromide, $K_2CO_3$, DMF, microwave 10 min at 120° C.). Eluent: cyclohexane/AcOEt 95/5 v/v (Yield: 92%) | White solid (DMSO-$d_6$): 5.33 (s, 2H); 7.27 (dd, 1H, J = 8.3 Hz, J = 1.3 Hz); 7.3-7.55 (m, 6H); 7.86 (d, 1H, J = 8.3 Hz) |
| | 3-((2-(Benzyloxy)-4-(trifluoromethyl))phenyl)-2-fluoropyridine from 2-(benzyloxy)-1-bromo-4-(trifluoromethyl)benzene and 2-fluoropyridin-3-ylboronic acid (Protocol SA; boronic acid (2 eq) Eluent: cyclohexane/AcOEt 9/1 v/v (Yield: 65%) | White solid (DMSO-$d_6$): 5.33 (s, 2H); 7.27 (dd, 1H, J = 8.3 Hz, J = 1.3 Hz); 7.3-7.55 (m, 6H); 7.86 (d, 1H, J = 8.3 Hz) |
| | 2-(2-Fluoropyridin-3-yl)-5-(trifluoromethyl)phenol from 3-((2-(benzyloxy)-4-(trifluoromethyl)-phenyl)-2-fluoropyridine (Protocol SF; Pd/C 5%/50% wet, MeOH/THF/DCM) Eluent: cyclohexane/AcOEt 8/2 (Yield: 96%). | Yellow solid (DMSO-$d_6$): 7.2-7.25 (m, 2H); 7.4-7.5 (m, 2H); 7.99 (td, 1H, J = 7.6 Hz, J = 1.7 Hz); 8.25 (d, 1H, J = 4.4 Hz); 10.51 (s, 1H) |
| | Intermediate D and 2-(2-fluoropyridin-3-yl)-5-(trifluoromethyl)phenol (Protocol SB; 10 min at 80° C. on microwave) Eluent: dichloromethane/AcOEt 7/3 v/v (Yield: 74%) and precipitation. | White solid. (DMSO-$d_6$): 7.2-7.25 (m, 2H); 7.4-7.5 (m, 2H); 7.99 (td, 1H, J = 7.6 Hz, J = 1.7 Hz); 8.25 (d, 1H, J = 4.4 Hz); 10.51 (s, 1H). Mass (MALDI+): 410/412 (M + H) (MP: 180-182° C.) |
| 4-80 | 2-(2-methoxypyridin-3-yl)-5-(trifluoromethyl)phenol from 2-bromo-5-(trifluoromethyl)phenol and 2-methoxy-3-(4,4,5,5-tetramethyl-1,3,2-dioxaborolan-2-yl)pyridine (Protocol SA; boronic acid (2 eq), $PCy_3$ (0.024 eq), $PdDBa_3$ (0.01 eq), $K_3PO_4$ (2 eq)-dioxane/water - 48 H at 120° C.) | Lemon yellow solid (DMSO-$d_6$): 3.81 (s, 3H); 7.05 (dd, 1H, J = 7.3 Hz, J = 4.7 Hz); 7.15-7.20 (m, 2H); 7.34 (d, 1H, J = 7.6 Hz); 7.62 (dd, 1H, J = 7.3 Hz, J = 1.7 Hz); 8.18 (dd, 1H, J = 5.0 Hz, J = 1.7 Hz); 10.50 (s, 1H) |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds<br>Reaction conditions and purification | Appearance, $^1$H NMR (solvent) data,<br>Mass (ES+ or ES−) data (MP) |
|---|---|---|
| | Eluent: dichloromethane/AcOEt 7/3 and dichloromethane/MeOH 95/5 v/v (Yield: 73%)<br>Intermediate D and 2-(2-methoxypyridin-3-yl)-5-(trifluoromethyl)phenol (Protocol SB; 120° C.)<br>Precipitation in ethanol; trituration in diethyl ether (Yield: 54%) | White solid<br>(DMSO-$d_6$): 3.64 (s, 3H); 5.62 (s, 1H); 7.02 (dd, 1H, J = 7.6 Hz, J = 2.0 Hz); 7.25 (d, 1H, J = 9.9 Hz); 7.69 (dd, 1H, J = 7.6 Hz, J = 2.0 Hz); 7.7-7.85 (m, 2H); 8.02 (s, 1H); 8.17 (dd, 1H, J = 5.0 Hz, J = 2.0 Hz); 8.39 (d, 1H, J = 9.9 Hz)<br>Mass (MALDI+): 422/424 (M + H) (MP: 160.0-167.0° C.) |
| 4-81 | 2-(6-Methoxypyridin-3-yl)-5-(trifluoromethyl)phenol from 2-bromo-5-(trifluoromethyl)phenol and 6-methoxypyridin-3-ylboronic acid (Protocol SA; boronic acid (2 eq), PCy$_3$ (0.024 eq), PdDBa$_3$ (0.01 eq), K$_3$PO$_4$ (2 eq)-dioxane/water - 48 H at 120° C.)<br>Trituration in petroleum ether: (Yield: 75%) | Grey solid<br>(DMSO-$d_6$): 3.89 (s, 3H); 6.89 (d, 1H, J = 8.4 Hz); 7.15-7.25 (m, 2H); 7.50 (d, 1H, J = 8.2 Hz); 7.93 (dd, 1H, J = 8.4 Hz, J = 2.0 Hz); 8.76 (d, 1H, J = 2.0 Hz); 10.41 (s, 1H) |
| | Intermediate D and 2-(6-methoxy pyridin-3-yl)-5-(trifluoromethyl)phenol (Protocol SB; 120° C.)<br>Trituration in diethyl ether: (Yield: 60%) | White solid<br>(DMSO-$d_6$): 3.85 (s, 3H); 6.86 (d, 1H, J = 8.5 Hz); 7.39 (d, 1H, J = 9.9 Hz); 7.83 (s, 2H); 7.88 (dd, 1H, J = 8.5 Hz, J = 2.0 Hz); 8.05 (s, 1H); 8.34 (d, 1H, J = 2.0 Hz); 8.45 (d, 1H, J = 9.9 Hz)<br>Mass (MALDI+): 422/424 (M + H) (MP: 137.0-139.0° C.) |
| 4-82 | 2-(5-Methoxypyridin-3-yl)-5-(trifluoromethyl)phenol from 2-bromo-5-(trifluoromethyl)phenol and 5-methoxypyridin-3-ylboronic acid (Protocol SA; boronic acid (2 eq), PCy$_3$ (0.024 eq), PdDBa$_3$ (0.01 eq), K$_3$PO$_4$ (2 eq) - dioxane/water - 48 H at 120° C.).<br>Eluent: dichloromethane/AcOEt 7/3 v/v (Yield: 28%) | White solid<br>(DMSO-$d_6$): 3.87 (s, 3H); 7.2-7.3 (m, 2H); 7.5-7.6 (m, 2H); 8.28 (d, 1H, J = 2.6 Hz); 8.37 (d, 1H, J = 1.5 Hz); 10.52 (s, 1H) |
| | Intermediate D and 2-(5-methoxy pyridin-3-yl)-5-(trifluoromethyl)phenol (Protocol SB; 10 min at 120° C. on microwave)<br>Trituration in diethyl ether; recristallisation in ethanol: (Yield: 54%). | White solid<br>(DMSO-$d_6$): 3.81 (s, 3H); 7.39 (d, 1H, J = 9.9 Hz); 7.50 (q, 1H, J = 2.6 Hz, J = 1.9 Hz); 7.8-7.9 (m, 2H); 8.08 (s, 1H); 8.27 (d, 1H, J = 2.6 Hz); 8.29 (d, 1H, J = 1.9 Hz); 8.43 (d, 1H, J = 9.9 Hz)<br>Mass (MALDI+): 422/424 (M + H) (MP: 189.0-191.0° C.) |
| 4-83 | Cpd. 4-81 (Protocol SW)<br>Precipitation (Yield: 27%). | White solid<br>(DMSO-$d_6$): 6.32 (d, 1H, J = 10.5 Hz); 7.38 (d, 1H, J = 9.9 Hz); 7.55-7.65 (m, 1H); 7.7-7.8 (m, 1H); 7.97 (s, 1H); 8.46 (d, 1H, J = 9.9 Hz); 11.82 (s, 1H)<br>Mass (MALDI+): 408/410 (M + H) (MP: 285.0-287.0° C.) |
| 4-84 | Cpd. 4-83 (Protocol SX).<br>Eluent: dichloromethane/MeOH 95/5 v/v (Yield: 47%). | White solid<br>(DMSO-$d_6$): 1.28 (t, 3H, J = 7.0 Hz); 4.28 (q, 2H, J = 7.0 Hz); 6.81 (d, 1H, J = 8.7 Hz); 7.36 (d, 1H, J = 9.9 Hz); 7.81 (s, 2H); 7.84 (dd, 1H, J = 8.7 Hz, J = 2.0 Hz); 8.05 (s, 1H); 8.30 (d, 1H, J = 2.0 Hz); 8.43 (d, 1H, J = 9.9 Hz)<br>Mass (MALDI+): 436/438 (M + H) (MP: 141.0-143.0° C.) |
| 4-85 | Cpd. 4-80 (Protocol SW)<br>Trituration in diethyl ether (Yield: 76%). | White solid<br>(DMSO-$d_6$): 6.23 (t, 1H, J = 6.4 Hz); 7.28 (d, 1H, J = 9.9 Hz); 7.42 (dd, 1H, J = 6.4 Hz); 7.53 (dd, 1H, J = 6.4 Hz, J = 2.0 Hz); 7.73 (s, 2H); 7.96 (s, 1H); 8.40 (d, 1H, J = 9.9 Hz); 11.87 (s, 1H)<br>Mass (MALDI+): 408/410 (M + H) (MP: 204.0-206.0° C.) |
| 4-86 | Cpd. 4-83 (Protocol SO; CH$_3$I (1.5 eq)/ DMF, 3 h RT° C.) | White solid<br>(DMSO-$d_6$): 3.44 (s, 3H); 6.37 (d, 1H, |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
|  | Eluent: dichloromethane/MeOH 95/5 v/v (Yield: 25%). | J = 9.3 Hz); 7.41 (d, 1H, J = 9.9 Hz); 7.60 (dd, 1H, J = 9.3 Hz, J = 2.6 Hz); 7.77 (s, 2H); 8.00 (m, 2H); 8.46 (d, 1H, J = 9.9 Hz) Mass (MALDI+): 422/424 (M + H) (MP: 246.0-248.0° C.) |
| 4-87 | 2-(6-fluoropyridin-3-yl)-5-(trifluoromethyl)phenol from 2-bromo-5-(trifluoromethyl)phenol and 6-fluoropyridin-3-ylboronic acid (Protocol SA; boronic acid (2 eq), PCy$_3$ (0.024 eq), PdDBa$_3$ (0.01 eq), K$_3$PO$_4$ (2.0 eq) - dioxane/water-microwave 15 min at 120° C. on microwave) Eluent: cyclohexane/AcOEt 8/2 v/v (Yield: 73%). Intermediate D and 2-(6-fluoropyridin-3-yl)-5-(trifluoromethyl)phenol (Protocol SB; 10 min at 120° C. on microwave) Eluent: dichloromethane/AcOEt 9/1 v/v (Yield: 53%) | White solid (DMSO-d$_6$): 7.2-7.3 (m, 3H); 7.42 (d, 1H, J = 8.2 Hz); 7.93 (tt, 1H, J = 8.4 Hz, J = 2.6 Hz); 8.55 (d, 1H, J = 2.6 Hz); 10.62 (s, 1H)<br><br>White solid (DMSO-d$_6$): 7.23 (dd, 1H, J = 8.5 Hz, J = 2.6 Hz); 7.36 (d, 1H, J = 9.9 Hz); 7.85-7.95 (m, 2H); 8.08 (s, 1H); 8.14 (td, 1H, J = 8.5 Hz, J = 2.6 Hz); 8.40 (d, 1H, J = 2.6 Hz); 8.43 (d, 1H, J = 9.9 Hz) Mass (ES+): 410/412 (M + H) (MP: 200.0-202.0° C.) |
| 4-88 | Cpd. 4-83 (Protocol SO; 1-bromopropane (1.5 eq), K$_2$CO$_3$ (2 eq)/DMF, 1 h at RT) Eluent: dichloromethane/MeOH 98/2 to 95/5 v/v (Yield: 20%) | White solid (DMSO-d$_6$): 0.72 (t, 3H, J = 7.3 Hz); 1.58 (m, 2H, J = 7.3 Hz); 3.84 (t, 2H, J = 7.3 Hz); 6.37 (d, 1H, J = 9.6 Hz); 7.40 (d, 1H, J = 9.9 Hz); 7.60 (dd, 1H, J = 9.6 Hz, J = 2.6 Hz); 7.77 (s, 2H); 7.93 (d, 1H, J = 2.6 Hz); 8.00 (s, 1H); 8.46 (d, 1H, J = 9.9 Hz) Mass (MALDI+): 449/451 (M + H) (MP: 173.0-175.0° C.) |
| 4-89 | Cpd. 4-83 (Protocol SO; 1-bromobutane (1.5 eq), K$_2$CO$_3$ (2 eq)/DMF, 1 h at RT) Eluent: dichloromethane/MeOH 98/2 to 95/5 v/v (Yield: 8%) | White solid (DMSO-d$_6$): 0.80 (t, 3H, J = 7.3 Hz); 1.13 (m, 2H, J = 7.3 Hz); 1.52 (m, 2H, J = 7.3 Hz); 3.87 (t, 2H, J = 7.3 Hz); 6.37 (d, 1H, J = 9.6 Hz); 7.40 (d, 1H, J = 9.9 Hz); 7.60 (dd, 1H, J = 9.6 Hz, J = 2.6 Hz); 7.77 (s, 2H); 7.93 (d, 1H, J = 2.6 Hz); 8.00 (s, 1H); 8.46 (d, 1H, J = 9.9 Hz) Mass (MALDI+): 463/465 (M + H) MP: 163.0-173.0° C.) |
| 4-90 | Cpd. 4-83 (Protocol SO; 1-Iodoethanol (2.5 eq), K$_2$CO$_3$ (4 eq)/DMF, 15 min at 80° C. on microwave). Eluent: dichloromethane/MeOH 9/1 v/v (Yield: 30%) | White solid (DMSO d6): 3.57 (m, 2H, J = 7.3 Hz); 3.95 (t, 2H, J = 7.3 Hz); 4.78 (t, 1H, J = 7.3 Hz); 6.39 (d, 1H, J = 9.6 Hz); 7.38 (d, 1H, J = 9.9 Hz); 7.62 (dd, 1H, J = 9.6 Hz, J = 2.6 Hz); 7.77 (s, 2H); 7.90 (d, 1H, J = 2.6 Hz); 8.01 (s, 1H); 8.44 (d, 1H, J = 9.9 Hz) Mass (MALDI+): 451/453 (M + H) (MP: 167.0-169.0° C.) |
| 4-91 | Cpd. 4-83 (Protocol SX; iodocyclohexane (3 eq) Précipitation in ethanol and diethyl ether (Yield: 68%) | White solid (DMSO-d$_6$): 1.15-1.55 (m, 6H); 1.65-1.75 (m, 2H); 1.85-1.95 (m, 2H); 4.30 (s, 1H); 4.96 (m, 1H); 6.77 (d, 1H, J = 8.7 Hz); 7.37 (d, 1H, J = 9.9 Hz); 7.80-7.85 (m, 3H); 8.02 (s, 2H); 8.30 (d, 1H, J = 2.0 Hz); 8.46 (d, 1H, J = 9.9 Hz) Mass (MALDI+): 490/492 (M + H) (MP: 141.0-143.0° C.) |
| 4-92 | Cpd. 4-83 (Protocol SO; 1-bromopropane (1.5 eq), K$_2$CO$_3$ (2 eq)/DMF, 1 h at RT) Eluent: dichloromethane/MeOH 98/2 to 95/5 v/v (Yield: 18%). | White solid (DMSO-d$_6$): 0.92 (t, 3H, J = 7.3 Hz); 1.68 (m, 2H, J = 7.3 Hz); 4.19 (t, 2H, J = 7.3 Hz); 6.81 (d, 1H, J = 8.5 Hz); 7.36 (d, 1H, J = 9.9 Hz); 7.81 (s, 2H); 7.84 (dd, 1H, J = 8.5 Hz, J = 2.0 Hz); 8.02 (s, 1H); 8.30 (d, 1H, J = 2.0 Hz); 8.43 (d, 1H, J = 9.9 Hz) |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
| 4-93 | Cpd. 4-83 (Protocol SO, 1-bromobutane (1.5 eq.), K$_2$CO$_3$ (2 eq)/DMF, 1 h at RT, hydrochloric acid/ethanol, trituration in petroleum ether) Eluent: dichloromethane/MeOH 98/2 to 95/5 v/v (Yield: 8%) | Mass (MALDI+): 449/451 (M + H) (MP: 124.0-126.0° C.) White solid (DMSO-d$_6$): 0.90 (t, 3H, J = 7.3 Hz); 7.00 (m, 2H, J = 7.3 Hz); 1.66 (m, 2H, J = 7.3 Hz); 4.23 (t, 2H, J = 7.3 Hz); 6.80 (d, 1H, J = 8.5 Hz); 7.36 (d, 1H, J = 9.9 Hz); 7.81 (s, 2H); 7.84 (dd, 1H, J = 8.5 Hz, J = 2.0 Hz); 8.02 (s, 1H); 8.30 (d, 1H, J = 2.0 Hz); 8.43 (d, 1H, J = 9.9 Hz) Mass (MALDI+): 463/465 (M + H) (MP: 134.0-136.0° C.) |
| 4-94 | Cpd. 4-83 (Protocol SX; 2-iodopropane (3 eq)). Précipitation in ethanol and diethyl ether (Yield: 21%) | Ocher solid (DMSO-d$_6$): 1.25 (d, 6H, J = 7.3 Hz); 5.20 (m, 1H, J = 7.3 Hz); 6.75(d, 1H, J = 8.7 Hz); 7.37 (d, 1H, J = 9.9 Hz); 7.81 (s, 2H); 7.84 (dd, 1H, J = 8.7 Hz, J = 2.0 Hz); 8.02 (s, 1H); 8.30 (d, 1H, J = 2.0 Hz); 8.43 (d, 1H, J = 9.9 Hz) Mass (MALDI+): 449/451 (M + H) (MP: 141.0-143.0° C.) |
| 4-95 | Cpd. 4-83 (Protocol SX; iodohexane (3 eq), 80° C.) Eluent: dichloromethane/MeOH 98/2; precipitation in ethanol and diethyl ether (Yield: 19%) | Ocher solid (DMSO-d$_6$): 0.85 (t, 3H, J = 7.3 Hz); 1.2-1.4 (m, 6H); 1.65 (qt, 2H, J = 7.3 Hz); 4.23 (t, 2H, J = 7.3 Hz); 6.80 (d, 1H, J = 9.6 Hz); 7.37 (d, 1H, J = 9.9 Hz); 7.81 (s, 2H); 7.84 (dd, 1H, J = 9.6 Hz, J = 2.6 Hz); 8.02 (s, 1H); 8.30 (d, 1H, J = 2.6 Hz); 8.43 (d, 1H, J = 9.9 Hz) Mass (MALDI+): 491/493 (M + H) (MP: 120.0-170.0° C.) |
| 4-96 | Cpd. 4-82 (Protocol SW; LiCl (10 eq) and p-toluene sulfonic acid monohydrate (10 eq)/NMP, 40 min 150° C.-170° C. on microwave) Eluent: dichloromethane/MeOH 95/5 v/v (Yield: 31%). | White solid (DMSO-d$_6$): 7.22 (t, 1H, J = 2.3 Hz); 7.35 (d, 1H, J = 9.9 Hz); 7.82 (s, 2H); 8.03 (s, 1H); 8.08 (d, 1H, J = 2.3 Hz); 8.13 (d, 1H, J = 1.4 Hz); 8.45 (d, 1H, J = 9.9 Hz); 10.10 (s, 1H) Mass (MALDI+): 408/410 (M + H) (MP: 243.0-245.0° C.) |
| 4-100 | 2-(4-Methoxypyridin-3-yl)-5-(trifluoromethyl)phenol from 2-bromo-5-(trifluoromethyl)phenol and 4-methoxypyridin-3-ylboronic acid hydrate (Protocol SA; boronic acid (2 eq),PCy$_3$ (0.024 eq), PdDBa$_3$ (0.01 eq), K$_3$PO$_4$ (2 eq)-dioxane/water - microwave 2 × 10 min at 120° C. on microwave) Trituration in petroleum ether: (Yield: 69%) | Yellow solid (DMSO-d$_6$): 3.80 (s, 3H); 7.1-7.2 (m, 3H); 7.34 (d, 1H, J = 7.6 Hz); 8.24 (s, 1H); 8.45 (dd, 1H, J = 5.8 Hz); 10.14 (s, 1H) |
|  | Intermediate D and 2-(4-methoxypyridin-3-yl)-5-(trifluoromethyl)phenol (Protocol SB; 10 min at 120° C. on microwave) Trituration in diethyl ether: (Yield: 89%) | White solid (DMSO-d$_6$): 3.65 (s, 3H); 7.10 (d, 1H, J = 5.8 Hz); 7.23 (d, 1H, J = 9.9 Hz); 7.73 (d, 1H, J = 8.0 Hz); 7.81 (dd, 1H, J = 8.0 Hz, J = 1.1 Hz); 8.05 (s, 1H); 8.30 (s, 1H); 8.40 (d, 1H, J = 9.9 Hz); 8.44 (d, 1H, J = 5.8 Hz) Mass (ES+): 421/423 (M + H) (MP: 149.0-151.0° C.) |
| 4-101 | 2-(6-Chloropyridin-3-yl)-5-(trifluoromethyl)phenol from 2-bromo-5-(trifluoromethyl)phenol and 6-chloropyridin-3-yl-boronic acid (Protocol SA; boronic acid (2 eq),PCy$_3$ (0.024 eq), PdDBa3 (0.01 eq), K$_3$PO$_4$ (2 eq) - dioxane/water-microwave 15 min at 120° C. microwave) Eluent: cyclohexane/AcOEt 85/15 v/v (Yield: 41%). | White solid (DMSO-d$_6$): 7.2-7.3 (m, 2H); 7.55-7.65 (m, 2H); 8.07 (dd, 1H, J = 8.2 Hz, J = 2.3 Hz); 8.61 (d, 1H, J = 2.3 Hz); 10.63 (s, 1H) |
|  | Intermediate D and 2-(6-chloropyridin-3-yl)-5-(trifluoromethyl)phenol (Protocol SB; microwave 5 min at 80° C.) | White solid (DMSO-d$_6$): 7.36 (d, 1H, J = 9.9 Hz); 7.56 (d, 1H, J = 8.1 Hz); 7.8-7.95 (m, 2H); 8.02 (dd, 1H, J = 8.1 Hz, J = 2.6 Hz); 8.09 |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
| | Eluent: dichloromethane/AcOEt 2/8 v/v (Yield: 21%) | (s, 1H); 8.45 (d, 1H, J = 9.9 Hz); 8.58 (d, 1H, J = 2.6 Hz) Mass (MALDI+): 425/427/429 (M + H) (MP: 198.0-200.0° C.) |
| 4-102 | Cpd. 4-101 (Protocol TB) Eluent: dichloromethane/MeOH 95/5 v/v (Yield: 6%) | Yellow solid (DMSO-d$_6$): 3.02 (s, 6H); 7.24 (d, 1H, J = 9.9 Hz); 7.56 (d, 1H, J = 8.1 Hz); 7.78 (d, 1H, J = 7.9 Hz); 7.86 (d, 1H, J = 7.9 Hz); 7.95 (d, 1H, J = 9.9 Hz); 8.00 (s, 1H); 8.19 (dd, 1H, J = 8.1 Hz, J = 2.0 Hz); 8.75 (d, 1H, J = 2.0 Hz) Mass (MALDI+): 435/437 (M + H) (MP: 181.0-193.0° C.) |
| 4-112 | 3'-Fluoro-4-methoxybiphenyl-2-ol from 2-bromo-5-methoxyphenol and 3-fluorobenzeneboronic acid (Protocol SA; 110° C. o/n) Eluent: cyclohexane/dichloromethane 1/0 to 7/3 v/v (Yield: 33%). Intermediate D and 3'-fluoro-4-methoxybiphenyl-2-ol (Protocol SB; K$_2$CO$_3$ (1.2 eq); 110° C. o/n). Eluent: cyclohexane/AcOEt 8/2 to 4/6 v/v (Yield: 55%). | (CDCl$_3$): 3.85 (s, 3H); 5.20 (s, 1H); 6.56-6.62 (m, 2H); 7.05-7.11 (m, 1H); 7.16-7.20 (m, 2H); 7.23-7.26 (m, 1H); 7.41-7.50 (m, 1H)<br><br>Yellow solid (CDCl$_3$): 3.90 (s, 3H); 6.88-6.95 (m, 3H); 6.99 (dd, 1H, J = 8.6 Hz, J = 2.6 Hz); 7.11-7.14 (m, 1H); 7.16 (d, 1H, J = 8.5 Hz); 7.24 (dd, 1H, J = 7.9 Hz, J = 6.0 Hz); 7.40 (d, 1H, J = 8.5 Hz); 7.95 (d, 1H, J = 9.8 Hz) Mass: 371.1 [M + H]+ |
| 4-113 | 3'-(Trifluoromethyl)-4-methoxy-biphenyl-2-ol from 2-bromo-5-methoxyphenol and 3-(trifluoromethyl)benzeneboronic acid (Protocol SA; 110° C. o/n). Eluent: cyclohexane/dichloromethane 1/0 to 2/8 v/v (Yield: 61%). Intermediate D and 3'-(trifluoromethyl)-4-methoxybiphenyl-2-ol (Protocol SB; K$_2$CO$_3$ (1.2 eq); 3 hours at 110° C.). Eluent: cyclohexane/AcOEt 4/6 v/v (Yield: 71%). | (CDCl$_3$): 3.85 (s, 3H); 5.05 (s, 1H); 6.54 (d, 1H, J = 2.3 Hz); 6.64 (dd, 1H, J = 8.5 Hz, J = 2.5 Hz); 7.20 (d, 1H, J = 8.5 Hz); 7.59-7.69 (m, 3H); 7.75 (s, 1H)<br><br>White solid (CDCl$_3$): 3.91 (s, 3H); 6.88 (d, 1H, J = 10.0 Hz); 6.92 (d, 1H, J = 2.6 Hz); 7.01 (dd, 1H, J = 8.7 Hz, J = 2.6 Hz); 7.39-7.49 (m, 3H); 7.57 (d, 1H, J = 7.3 Hz); 7.70 (s, 1H); 7.94 (d, 1H, J = 9.8 Hz) Mass: 421.1 [M + H]+ (MP: 111.6° C.) |
| 4-114 | Intermediate D and 5-chloro-2-(2,4-dichlorophenoxy)phenol (Protocol SB; K$_2$CO$_3$ (1.3 eq); 2 hours at 100° C.). Eluent: cyclohexane/AcOEt 1/0 to 5/5 v/v (Yield: 78%). | Colorless oil (CDCl$_3$): 6.87 (d, 1H, J = 8.9 Hz); 6.97 (d, 1H, J = 8.8 Hz); 7.06 (d, 1H, J = 9.6 Hz); 7.17 (dd, 1H, J = 8.6 Hz, J = 2.4 Hz); 7.28 (dd, 1H, J = 8.8 Hz); 7.39 (t, 1H, J = 2.3 Hz); 8.08 (d, 1H, J = 9.8 Hz) Mass: 441.0 [M + H]+ |
| 4-115 | 3',4',5-Trifluorobiphenyl-2-ol from 3,4-difluorobenzeneboronic acid and 2-bromo-4-flurophenol (Protocol SA; 110° C. o/n). Eluent: dichloromethane/cyclohexane 5/5 v/v (Yield: 70%) Intermediate D and 3',4',5-trifluorobiphenyl-2-ol (Protocol SB; K2CO3 (1.2 eq); 100° C. o/n). Eluent: cyclohexane/AcOEt 9/1 to 7/3 v/v (Yield: 54%). | (CDCl$_3$): 4.89 (s, 1H); 6.88-7.02 (m, 3H); 7.21-7.39 (m, 3H)<br><br>White solid (MeOD-d$_4$): 7.21-7.29 (m, 4H); 7.33 (dd, 1H, J = 9.2 Hz, J = 3.0 Hz); 7.40-7.49 (m, 2H); 8.18 (d, 1H, J = 10.0 Hz) Mass: 377.1 [M + H]+ (MP: 147.8° C.) |
| 4-116 | 4',5-Difluorobiphenyl-2-ol from 2-bromo-4-fluorophenol and 4-fluorophenylboronic acid (Protocol SA; 110° C. o/n). Eluent: dichloromethane/cyclohexane 3/7 to 35/65 v/v (Yield: 50%). Intermediate D and 4',5-difluoro-biphenyl-2-ol (Protocol SB; K$_2$CO$_3$ (1.2 eq); 2 hours at 100° C.). Eluent: cyclohexane/AcOEt 8/2 to 6/4 v/v (Yield: 59%). | (CDCl$_3$): 4.92 (s, 1H); 6.90-7.00 (m, 3H); 7.18-7.24 (m, 2H); 7.44-7.49 (m, 2H)<br><br>White solid (MeOD-d$_4$): 7.08 (t, 2H, J = 8.9 Hz); 7.19 (d, 1H, J = 9.8 Hz); 7.23-731 (m, 2H); 7.42-7.45 (m, 1H); 7.46-7.51 (m, 2H); 8.15 (d, 1H, J = 10.0 Hz) Mass: 359.1 [M + H]+ (MP: 141.1° C.) |
| 4-118 | 4'-Chloro-5-fluorobiphenyl-2-ol from 2-bromo-4-fluorophenol and 4-chlorophenylboronic acid (Protocol | (CDCl$_3$): 4.93 (s, 1H); 6.89-7.02 (m, 3H); 7.41-7.50 (m, 4H) |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
|  | SA; 110° C. o/n). Eluent: cyclohexane/dichloromethane 8/2 to 6/4 v/v (Yield: 60%). |  |
|  | Intermediate D and 4'-chloro-5-fluorobiphenyl-2-ol (Protocol SB; K$_2$CO$_3$ (1.3 eq); 5 hours at 100° C.). Eluent: cyclohexane/AcOEt 9/1 to 6/4 v/v (Yield: 54%). | White solid (CDCl$_3$): 6.90 (d, 1H, J = 9.8 Hz); 7.16-7.21 (m, 2H); 7.29-7.38 (m, 5H); 7.97 (d, 1H, J = 9.8 Hz) Mass: 375.1 [M + H]+ (MP: 172.0° C.) |
| 4-119 | 3'-Amino-5-fluorobiphenyl-2-ol from 3'-nitro-5-fluorobiphenyl-2-ol (cf Cpd. 4-187) (Protocol SF) Filtration through celite (Yield: 89%). | (MeOD): 4.91 (s, 1H); 6.7-6.74 (m, 1H); 6.83-6.90 (m, 3H); 6.94-6.98 (m, 2H); 7.15 (t, 1H, J = 7.8 Hz) |
|  | Intermediate D and 3'-amino-5-fluorobiphenyl-2-ol (Protocol SB; K$_2$CO$_3$ (1.2 eq); 110° C. o/n). Eluent: cyclohexane/AcOEt 8/2 to 0/1 v/v (Yield: 54%). | Pale yellow solid (CDCl$_3$): 3.66 (s (large), 2H); 6.54-6.58 (m, 1H); 6.69 (t, 1H, J = 1.7 Hz); 6.74-6.77 (m, 1H); 6.89 (d, 1H, J = 9.8 Hz); 7.07 (t, 1H, J = 7.9 Hz); 7.10-7.21 (m, 2H); 7.26 (m, 1H); 7.92 (d, 1H, J = 10.0 Hz) Mass: 356.1 [M + H]+ (MP: 248.2° C.) |
| 4-120 | 3',5-Difluorobiphenyl-2-ol | (CDCl$_3$): 5.22 (s, 3H); 6.89-7.01 (m, 3H); 7.09-7.13 (m, 1H); 7.20-7.25 (m, 1H); 7.26-7.30 (m, 1H); 7.44-7.51 (m, 1H) |
|  | Intermediate D and 3',5-difluoro-biphenyl-2-ol (Protocol SB; K$_2$CO$_3$ (2 eq); 110° C. o/n). Eluent: cyclohexane/AcOEt 1/0 to 4/6 v/v (Yield: 27%). | White solid (CDCl$_3$): 6.92 (d, 1H, J = 9.8 Hz); 6.96 (m, 1H, J = 8.5 Hz, J = 1.7 Hz); 7.12-7.20 (m, 4H); 7.25-7.32 (m, 2H); 7.95 (d, 1H, J = 9.8 Hz) Mass: 359.14 [M + H]+ (MP: 106.2° C.) |
| 4-121 | 2',5-Diflurorobiphenyl-2-ol | (CDCl$_3$): 5.48 (s (large), 1H); 6.90-7.04 (m, 4H); 7.19-7.30 (m, 2H); 7.38-7.45 (m, 1H) |
|  | Intermediate D and 2',5-difluoro-biphenyl-2-ol (Protocol SB; K$_2$CO$_3$ (2 eq); 110° C. o/n). Eluent: cyclohexane/AcOEt 1/0 to 8/2 v/v (Yield: 24%). | White solid (CDCl$_3$): 6.87 (d, 1H, J = 9.8 Hz); 7.01-7.12 (m, 2H); 7.19-7.38 (m, 5H); 7.92 (d, 1H, J = 9.8 Hz) Mass: 359.14 [M + H]+ (MP: 124.3-127.79° C.) |
| 4-123 | 2-(2-Methylpyridin-3-yl)-5-(trifluoromethyl)phenol from 2-methyl-3-(4,4,5,5-tetramethyl-1,3,2-dioxaborolan-2-yl)pyridine and 2-bromo-5-(trifluoromethyl)phenol (Protocol SA; 10 min at 120° C. on microwave). Eluent: dichlorometane/AcOEt 7/3 then dichloromethane/MeOH 95/5 v/v (Yield: 74%). | (DMSO-d$_6$): 2.29 (s, 3H); 7.15-7.35 (m, 4H); 7.53 (dd, 1H, J = 7.9 Hz, J = 1.7 Hz); 8.45 (dd, 1H, J = 7.9 Hz, J = 1.7 Hz); 10.32 (s, 1H). |
|  | Intermediate D and 2-(2-methylpyridin-3-yl)-5-(trifluoromethyl)-phenol (Protocol SB; 10 min at 80° C. on microwave). Eluent: dichloromethane/AcOEt 9/1 v/v (Yield: 48.7%). | White solid (DMSO-d$_6$): 2.34 (s, 3H); 7.20 (q, 1H, J = 7.7 Hz, J = 5.0 Hz); 7.24 (d, 1H, J = 9.9 Hz); 7.58 (dd, 1H, J = 7.7 Hz, J = 2.0 Hz); 7.74 (d, 1H, J = 7.9 Hz); 7.85 (dd, 1H, J = 7.9 Hz); 8.04 (d, 1H); 8.36 (d, 1H, J = 9.9 Hz); 8.40 (dd, 1H, J = 5.0 Hz, J = 1.7 Hz) Mass: 405/407 [M + H]+ (MP: 148-150° C.) |
| 4-127 | 2-(2-Methoxypyrimidin-5-yl)-5-(trifluoromethyl)phenol from 2-bromo-5-(trifluoromethyl)phenol and 2-methoxypyrimidin-5-ylboronic acid (Protocol SA; 10 min at 120° C. on microwave). Eluent: cyclohexane/AcOEt 3/7 v/v (Yield: 39%). | (DMSO-d$_6$): 3.97 (s, 3H); 7.25-7.27 (m, 2H); 7.60 (dd, 1H, J = 8.5 Hz, J = 0.7 Hz); 8.84 (s, 2H); 10.66 (s, 1H) |
|  | Intermediate D and 2-(2-methoxy-pyrimidin-5-yl)-5-(trifluoromethyl)-phenol (Protocol SB; K$_2$CO$_3$ (3 eq); 15 min at 110° C. on microwave). Trituration in diethyl ether (Yield: 75%). | Beige solid (DMSO-d$_6$): 3.92 (s, 3H); 7.42 (d, 1H, J = 9.9 Hz); 7.84-7.93 (m, 2H); 8.10 (s, 1H); 8.46 (d, 1H, J = 9.8 Hz); 8.82 (s, 2H) Mass: 422.8/424.8 [M + H]+ (MP: 186-188° C.) |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, ¹H NMR (solvent) data, Mass (ES+ or ES−) data (MP) |
|---|---|---|
| 4-128 | Intermediate D and 2-(4-isopropyl-pyrimidin-5-yl)-5-(trifluoromethyl)-phenol (Protocol SB; K₂CO₃ (3 eq); 15 min at 110° C. on microwave). Eluent: cyclohexane/AcOEt 3/7 then 0/1 v/v (Yield: 75%). | White solid (DMSO-d₆): 1.00 (d, 3H, J = 6.5 Hz); 1.11 (d, 3H, J = 6.6 Hz); 2.87-2.95 (m, 1H, J = 6.6 Hz); 7.26 (d, 1H, J = 9.9 Hz); 7.80 (d, 1H, J = 7.9 Hz); 7.90 (d, 1H, J = 8.0 Hz, J = 1.1 Hz); 8.10 (d, 1H, J = 0.8 Hz); 8.40 (d, 1H, J = 9.9 Hz); 8.60 (s, 1H); 9.12 (s, 1H) Mass: 434.8/436.8 [M + H]+ (MP: 159-161° C.) |
| 4-130 | Intermediate D and 2-(2-methoxy-4-methylpyridin-3-yl)-5-(trifluoromethyl)phenol (Protocol SB; K₂CO₃ (3 eq); 10 min at 120° C. on microwave). Eluent: cyclohexane/AcOEt 6/4 v/v (Yield: 34%) | White solid (DMSO-d₆): 2.05 (s, 3H); 3.65 (s, 3H); 6.85 (d, 1H, J = 5.4 Hz); 7.14 (d, 1H, J = 9.8 Hz); 7.65 (d, 1H, J = 8.2 Hz); 7.79 (dd, 1H, J = 7.9 Hz, J = 1.0 Hz); 7.98 (d, 1H, J = 5.2 Hz); 8.00 (d, 1H, J = 0.8 Hz); 8.33 (d, 1H, J = 9.8 Hz) Mass: 435.9 [M + H]+ (MP: 129-132° C.) |
| 4-131 | Intermediate D and 2-(2-methoxy-5-fluoropyridin-3-yl)-5-(trifluoromethyl)-phenol (Protocol SB; K₂CO₃ (3 eq); 15 min at 110° C. on microwave). Eluent: cyclohexane/AcOEt 3/7 v/v (Yield: 49%). | White solid (DMSO-d₆): 3.62 (s, 3H); 7.26 (d, 1H, J = 9.8 Hz); 7.76-7.83 (m, 3H); 8.07 (s, 1H); 8.19 (d, 1H, J = 3.0 Hz); 8.42 (d, 1H, J = 9.9 Hz) Mass: 439.8 [M + H]+ (MP: 60-68° C.) |
| 4-135 | 3'-Methyl-5-fluorobiphenyl-2-ol Intermediate D and 3'methyl-5-fluorobiphenyl-2-ol (Protocol SB; K₂CO₃ (2 eq); 10 min at 170° C. on microwave). Eluent: cyclohexane/AcOEt 1/1 v/v (Yield: 51%). | White solid (DMSO-d₆): 2.24 (s, 3H); 7.07-7.10 (m, 1H); 7.17-7.33 (m, 4H); 7.35-7.41 (m, 2H); 7.50-7.55 (m, 1H); 8.35 (d, 1H, J = 9.9 Hz) Mass: 355 [M + H]+ (MP: 94.5-95.1° C.). |
| 4-136 | Intermediate B and 3'methyl-5-fluorobiphenyl-2-ol (Protocol SB; K₂CO₃ (2 eq); 10 min at 170° C. on microwave). Eluent: cyclohexane/AcOEt 1/1 v/v (Yield: 62%). | Colorless amorphous solid (DMSO-d₆): 2.23 (s, 3H); 7.07-7.09 (m, 1H); 7.18-7.22 (m, 3H); 7.31-7.41 (m, 2H); 7.44 (d, 1H, J = 9.9 Hz); 7.48-7.53 (m, 1H); 8.51 (d, 1H, J = 9.9 Hz) Mass: 389 [M + H]+ |
| 4-137 | Intermediate B and -3'methoxy-4-(trifluoromethyl)biphenyl-2-ol (Protocol SB; K₂CO₃ (2 eq); 10 min at 170° C. on microwave). Eluent: cyclohexane/AcOEt 1/1 v/v (Yield: 51%). | White solid (DMSO-d₆): 3.71 (s, 3H); 6.92 (dd, 1H, J = 8.2 Hz, J = 2.6 Hz); 7-7.04 (m, 2H); 7.29 (t, 1H, J = 8.1 Hz); 7.52 (d, 1H, J = 9.9 Hz); 7.79 (s, 2H); 8.01 (s, 1H); 8.57 (d, 1H, J = 9.9 Hz) Mass: 455 [M + H]+ (MP: 102.5° C.). |
| 4-138 | Cpd. 4-137 (Protocol SD) Eluent: cyclohexane/AcOEt 2/8 v/v (Yield: 74%). | White solid (DMSO-d₆): 6.72 (dd, 1H, J = 7.9 Hz, J = 1.8 Hz); 6.81 (s, 1H); 6.86 (d, 1H, J = 7.9 Hz); 7.18 (t, 1H, J = 7.9 Hz); 7.50 (d, 1H, J = 9.9 Hz); 7.71-7.79 (m, 2H); 7.98 (s, 1H); 8.59 (d, 1H, J = 9.9 Hz); 9.50 (s, 1H) Mass: 441 [M + H]+ (MP: 195° C.). |
| 4-142 | 4'-Methyl-5-fluorobiphenyl-2-ol from 2-bromo-4-fluorophenol and 4-methyl-phenylboronic acid (Protocol SA; 5 min at 150° C. on microwave). Eluent: cyclohexane/dichloromethane: 8/2 (Yield: 55%) Intermediate B and 4'-methyl-5-fluorobiphenyl-2-ol (Protocol SB; K₂CO₃ (3 eq); 10 min at 170° C. on microwave). Eluent: cyclohexane/dichloro-methane/AcOEt 6/3.5/0.5 v/v (Yield: 20%). | (CDCl₃): 2.49 (s, 3H); 5.05 (s (large), 1H); 6.92-6.99 (m, 3H); 7.30-7.37 (m, 4H)

White solid (DMSO-d₆): 7.25 (d, 1H, J = 9.9 Hz); 7.33 (s (large), 1H); 7.37-7.60 (m, 6H); 7.77 (d, 1H, J = 7.9 Hz); 7.93 (s, 1H); 7.96 (s (large), 1H); 8.35 (d, 1H, J = 9.9 Hz) Mass: 389 [M + H]+ (MP: 125.5-127.5° C.). |
| 4-143 | Intermediate D and 4'-methyl-5-fluorobiphenyl-2-ol (Protocol SB; K₂CO₃ (3 eq); 10 min at 170° C. on microwave). Eluent: cyclohexane/dichloromethane/AcOEt 6/3.5/0.5 v/v (Yield: 29%) | White solid (DMSO-d₆): 2.25 (s, 3H); 7.16 (m, 2H); 7.28 (d, 1H, J = 9.9 Hz); 7.30-7.39 (m, 4H); 7.52 (dd, 1H, J = 8.7 Hz, J = 5.3 Hz); 8.37 (d, 1H, J = 9.9 Hz) Mass: 355 [M + H]+ (MP: 177.2-179.7° C.) |
| 4-147 | 3-(Piperidin-1-yl-methyl)-phenylboronic acid from 3-(bromomethyl)phenyl-boronic acid | (DMSO-d₆): 1.40 (s (large), 2H); 1.51 (s (large), 4H); 241.00 (s (large), 4H); 3.50 (s (large), 2H); 6.90 (q, 1H, |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, ¹H NMR (solvent) data, Mass (ES+ or ES−) data (MP) |
|---|---|---|
| | and piperidine (protocol SN without K₂CO₃) Extraction (pH = 8-9); no further purification (Yield: 82%) | J = 8.7 Hz, J = 3.5 Hz); 6.99 (td, 1H, J = 8.7 Hz, J = 3.5 Hz); 7.2-7.4 (m, 2H); 7.5-7.9 (m, 2H) |
| | 3'-(Piperidin-1-yl-methyl)-5-fluoro-biphenyl-2-ol from 3-(piperidine-methyl)phenylboronic acid and 2-bromo-4-fluorophenol (Protocol SA; 10 min at 120° C. on microwave). Eluent: dichloromethane/MeOH 95/5 v/v (Yield: 14%) | (DMSO-d₆): 1.38 (m, 2H); 1.48 (m, 4H); 2.34 (m, 4H); 3.46 (s, 2H); 6.90 (q, 1H, J = 8.7 Hz, J = 3.5 Hz); 6.99 (td, 1H, J = 8.7 Hz, J = 3.5 Hz); 7.05 (dd, 1H, J = 8.7 Hz, J = 3.5 Hz); 7.23 (d, 1H, J = 7.6 Hz); 7.33 (t, 1H, J = 7.6 Hz); 7.42 (d, 1H, J = 7.6 Hz); 7.46 (s, 1H); 9.50 (s, 1H) |
| | Intermediate D and 3'-(piperidin-1-ylmethyl)-5-fluorobiphenyl-2-ol (Protocol SB; K₂CO₃ (3 eq); 10 min at 120° C. on microwave) Dissolution in EtOH, HCl, evaporation and trituration in isopropylacetate (Yield: 40%). | Colorless oil (DMSO-d₆): 1.32 (m, 2H); 1.6-1.8 (m, 6H); 2.73 (m, 2H); 3.18 (m, 2H); 4.22 (s, 2H); 7.30 (d, 1H, J = 9.9 Hz); 7.35-7.60 (m, 6H); 7.64 (s (large), 1H); 8.40 (d, 1H, J = 9.9 Hz); 9.99 (s (large), 1H) Mass: 438 [M + H]+ |
| 4-148 | 3'-(Trifluoromethyl)-5-fluoro-biphenyl-2-ol from 2-bromo-4-fluorophenol and 3-(trifluoromethyl)phenylboronic acid (Protocol SA; 10 min at 120° C. on microwave). Eluent: cyclohexane/dichloromethane 75/25 (Yield: 74%) | (CDCl₃): 4.87 (s (large), 1H); 6.89-7.02 (m, 3H); 7.58-7.71 (m, 3H); 7.77 (s, 1H) |
| | Intermediate D and 3'-(trifluoromethyl)-5-fluoro-biphenyl-2-ol (Protocol SB; K₂CO₃ (3 eq); 10 min at 120° C. on microwave). Eluent: cyclohexane/AcOEt 6/4 v/v (Yield: 41%). | Beige solid (DMSO-d₆): 7.26 (d, 1H, J = 9.9 Hz); 7.43 (td, 1H, J = 9.0 Hz, J = 3.2 Hz); 7.53-7.61 (m, 3H); 7.66 (d, 1H, J = 7.9 Hz); 7.74-7.76 (m, 2H); 8.37 (d, 1H, J = 9.9 Hz) Mass: 409 [M + H]+ (MP: 94.5-96.1° C.). |
| 4-149 | Intermediate B and 5-fluoro-3'-methoxybiphenyl-2-ol (Protocol SB; K₂CO₃ (3 eq); 20 min at 170° C. on microwave). Eluent: cyclohexane/AcOEt 5/5 v/v (Yield: 57%). | Beige solid (DMSO-d₆): 3.68 (s, 3H); 6.84 (dd, 1H, J = 8.1 Hz, J = 2.0 Hz); 6.94-6.99 (m, 2H); 7.23 (t, 1H, J = 7.9 Hz); 7.34-7.53 (m, 4H); 8.52 (d, 1H, J = 9.9 Mass: 405 [M + H]+ (MP: 73.7-76.9° C.). |
| 4-150 | 4,5-Difluoro-3'-methoxybiphenyl-2-ol from 2-bromo-4,5-difluorophenol and 3-methoxybenzeneboronic acid (Protocol SA; 5 min at 150° C. on microwave) Eluent: Cyclohexane/AcOEt 8/2 v/v (Yield: 77.9%) | (DMSO-d₆): 3.79 (s, 3H); 6.85-6.91 (m, 2H); 7.09-7.11 (m, 2H); 7.26-7.33 (m, 2H); 9.78 (s (large), 1H) |
| | Intermediate B and 4,5-difluoro-3'-methoxybiphenyl-2-ol (1 eq) (Protocol SB; K₂CO₃ (3 eq); 10 min at 170° C. on microwave). Eluent: cyclohexane/AcOEt 4/6 v/v (Yield: 53%). | White solid (DMSO-d₆): 3.69 (s, 3H); 6.86 (dd, 1H, J = 8.4 Hz, J = 2.3 Hz); 6.95-6.99 (m, 2H); 7.24 (t, 1H, J = 8.2 Hz); 7.50 (d, 1H, J = 9.9 Hz); 7.69-7.79 (m, 2H); 8.57 (d, 1H, J = 10.2 Hz) Mass: 423 [M + H]+ (MP: 52-55° C.). |
| 4-151 | Cpd. 4-150 (Protocol SD) Eluent: cyclohexane/AcOEt 3/7 v/v (Yield: 76%) | White solid (DMSO-d₆): 6.67 (dd, 1H, J = 2.0 Hz); 6.74-6.75 (m, 1H); 6.80 (d, 1H, J = 7.6 Hz); 7.16 (t, 1H, J = 7.9 Hz); 7.47 (d, 1H, J = 9.9 Hz); 7.64 (dd, 1H, J = 11.3 Hz, J = 9.0 Hz); 7.73 (dd, 1H, J = 11.3 Hz, J = 7.3 Hz); 8.58 (d, 1H, J = 9.9 Hz); 9.46 (s (large), 1H) Mass: 409 [M + H]+ (MP: 193-195° C.). |
| 4-152 | Intermediate D and 4,5-difluoro-3'-methoxybiphenyl-2-ol (1 eq) (Protocol SB; K₂CO₃ (3 eq); 10 min at 170° C. on microwave). Eluent: cyclohexane/AcOEt 4/6 v/v (Yield: 66%). | White solid (DMSO-d₆): 3.70 (s, 3H); 6.86 (dd, 1H, J = 8.2 Hz, J = 2.0 Hz); 6.96-7.00 (m, 2H); 7.22-7.27 (m, 1H); 7.33 (d, 1H, J = 9.9 Hz); 7.68-7.82 (m, 2H); 8.40 (d, 1H, J = 9.9 Hz) Mass: 389 [M + H]+ (MP: 102° C.) |
| 4-153 | Cpd. 4-152 (Protocol SD) Eluent: cyclohexane/AcOEt 3/7 v/v (Yield: 20%). | White solid (DMSO-d₆): 6.68 (dd, 1H, J = 8.2 Hz); 6.76 (m, 1H); 6.82 (d, 1H, J = 7.3 Hz); 7.15 (t, 1H, J = 8.4 Hz); 7.30 (d, 1H, J = 9.9 Hz); 7.64 (dd, 1H, J = 11.3 Hz, J = 9.0 Hz); 7.76 (dd, 1H, J = 11.0 Hz, |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds Reaction conditions and purification | Appearance, $^1$H NMR (solvent) data, Mass (ES+ or ES−) data (MP) |
|---|---|---|
| | | J = 7.3 Hz); 8.42 (d, 1H, J = 9.9 Hz); 9.45 (s, 1H)<br>Mass: 375 [M + H]+ (MP: 271.3-277.6° C.). |
| 4-168 | 3-Chloro-6-(4-(trifluoromethyl)-3'-(bromomethyl)biphenyl-2-yloxy)-[1,2,4]triazolo[4,3-b]pyridazine and cyclopropylamine (Protocol SN, triethylamine (2 eq) instead of K$_2$CO$_3$) Eluent: dichloromethane/MeOH 9/1 v/v, trituration in HCl, ethanol then diethyl ether (Yield: 16%) | White solid<br>(DMSO-d$_6$): 0.7-0.8 (m, 4H); 2.54 (m, 2H); 4.23 (s, 2H); 7.36 (d, 1H, J = 9.9 Hz); 7.4-7.6 (m, 3H); 7.67 (s, 1H); 7.75-7.90 (m, 2H); 8.07 (s, 1H); 8.44 (d, 1H, J = 9.9 Hz); 9.08 (s (large), 2H)<br>Mass: 460/462 [M + H]+ (MP: 187.0-189.0° C.). |
| 4-187 | 3'-Nitro-5-fluorobiphenyl-2-ol from 2-bromo-4-fluorophenol and 3-nitrophenylboronic acid (Protocol SA; 110° C. o/n).<br>Eluent: cyclohexane/dichloromethane 1/0 to 0/1 v/v (Yield: 20%).<br>Intermediate D and 3'-nitro-5-fluorobiphenyl-2-ol (Protocol SB; K$_2$CO$_3$ (1.3 eq); 5 hours at 100° C.). Eluent: cyclohexane/AcOEt 9/1 to 6/4 v/v (Yield: 54%). | (CDCl$_3$): 4.88 (s, 1H); 6.92 (dd, 1H, J = 8.7 Hz, J = 4.5 Hz); 7.03 (dd, 1H, J = 4.0 Hz, J = 1.0 Hz); 7.07 (dd, 1H, J = 8.5 Hz, J = 2.8 Hz); 7.66 (t, 1H, J = 8.1 Hz); 7.87-7.90 (m, 1H); 8.25-8.28 (m, 1H); 8.45 (t, 1H, J = 1.9 Hz)<br>Brown solid<br>(CDCl$_3$): 6.93 (d, 1H, J = 9.8 Hz); 7.22-7.28 (m, 2H); 7.37 (dd, 1H, J = 9.6 Hz, J = 4.7 Hz); 7.55 (t, 1H, J = 7.9 Hz); 7.78 (d, 1H, J = 7.9 Hz); 7.98 (d, 1H, J = 9.8 Hz); 8.16 (dd, 1H, J = 8.3 Hz, J = 1.1 Hz); 8.38 (t, 1H, J = 1.7 Hz)<br>Mass: 386.1 [M + H]+ (MP: 190.5° C.) |
| 4-188 | 2',4',5-Trifluorobiphenyl-2-ol from 4-fluoro-2-bromophenol and 2,4-difluorobenzeneboronic acid (Protocol SA; 80° C. o/n).<br>Eluent: dichloromethane/cyclohexane 3/7 v/v (Yield: 30%).<br>Intermediate D and 2',4',5-trifluorobiphenyl-2-ol (Protocol SB; K$_2$CO$_3$ (1.2 eq); 100° C. o/n). Eluent: cyclohexane/AcOEt 9/1 to 7/3 v/v (Yield: 25%) | (CDCl$_3$): 4.77 (s, 1H); 6.91-7.06 (m, 5H); 7.34-7.42 (m, 1H)<br><br>White solid<br>(MeOD-d$_4$): 6.89-7.0 (m, 2H); 7.12 (d, 1H, J = 10.0 Hz); 7.23-7.41 (m, 3H); 7.48 (dd, 1H, J = 8.9 Hz, J = 4.9 Hz); 8.12 (d, 1H, J = 10.0 Hz)<br>Mass: 377.1 [M + H]+ (MP: 143.6° C.) |
| 4-193 | 3,6-Dichloro-8-methyl-[1,2,4]triazolo[4,3-b]pyridazine and 2-(2-methoxy-5-fluoropyridin-3-yl)-5-(trifluoromethyl)phenol (Protocol SB, K$_2$CO$_3$ (3 eq); 15 mn at 110° C. on microwave)<br>Eluent: cyclohexane/AcOEt 3/7 v/v (Yield: 62%). | White solid<br>(DMSO-d$_6$): 2.58 (d, 3H, J = 1.2 Hz); 3.64 (s, 3H); 7.14 (d, 1H, J = 1.3 Hz); 7.74-7.82 (m, 3H); 8.03 (s, 1H); 8.20 (d, 1H, J = 3.0 Hz)<br>Mass = 453.8[M + H]+ (MP: 130-132° C.) |
| 4-195 | 3,6-Dichloro-[1,2,4]triazolo[4,3-b]pyridazine and 4-chloro-2-(2-methoxypyrimidin-5-yl)phenol (Protocol SB; K$_2$CO$_3$ (3 eq); 10 min at 110° C. on microwave).<br>Precipitation with water; washings with diethyl ether: (Yield: 56%) | Beige solid<br>(DMSO-d$_6$): 3.92 (s, 3H); 7.39 (d, 1H, J = 9.9 Hz); 7.60-7.67 (m, 2H); 7.80 (d, 1H, J = 2.0 Hz); 8.44 (d, 1H, J = 9.9 Hz); 8.77 (s, 2H)<br>Mass: 389 [M + H]+ (MP: 210-211° C.). |
| 4-196 | 2-(6-Methylpyridin-3-yl)-5-(trifluoromethyl)phenol from 2-methyl-5-(4,4,5,5-tetramethyl-1,3,2-dioxaborolan-2-yl)pyridine and 2-bromo-5-(trifluoromethyl)phenol (Protocol SA; 64 hours at 120° C.)<br>(Yield: 75%).<br>Intermediate D and 2-(6-methyl-pyridin-3-yl)-5-(trifluoromethyl)phenol (Protocol SB; 10 mn at 80° C. on microwave)<br>Trituration in diethyl ether (Yield 69%) | (DMSO-d$_6$): 2.49 (s, 3H); 7.15-7.25 (m, 2H); 7.31 (d, 1H, J = 8.2 Hz); 7.51 (d, 1H, J = 8.2 Hz); 8.18 (dd, 1H, J = 8.2 Hz, J = 2.3 Hz); 8.62 (d, 1H, J = 2.3 Hz); 10.50 (s (large), 1H)<br><br><br>White solid<br>(DMSO-d$_6$): 2.47 (s, 3H); 7.29 (d, 1H, J = 8.0 Hz); 7.38 (d, 1H, J = 9.9 Hz); 7.9-7.9 (m, 2H); 8.06 (s, 1H); 8.44 (d, 1H, J = 9.9 Hz); 8.59 (d, 1H, J = 2.0 Hz)<br>Mass: 405/407 (MP: 212-214° C.) |
| 4-199 | 3-Methoxy-4-(pyridin-3-yl)benzonitrile from 4-bromo-3-methoxybenzonitrile and 3-pyridineboronic acid (Protocol SA; boronic acid (3 eq); Pd$_2$dBa$_3$ (0.02 eq); PCy$_3$ (0.048 eq); 30 min at 150° C. on microwave)<br>Trituration in diethyl ether (Yield: 94%) | (DMSO-d$_6$): 3.82 (s, 3H); 7.34 (d, 1H); 7.48 (q, 1H, J = 7.7 Hz, J = 4.8 Hz); 7.86 (d, 1H, J = 2.0 Hz); 7.92 (dd, 1H, J = 7.7 Hz, J = 2.2 Hz); 7.94 (d, 1H, J = 8.8 Hz); 8.57 (dd, 1H, J = 4.8 Hz, J = 2.2 Hz); 8.71 (d, 1H, J = 2.2 Hz) |

TABLE 2-4-continued

Ra is W or W-Z-, at least one of Rb-Re is either than hydrogen; at least one of Rf-Rj is either than hydrogen, R2 and R3 are hydrogen.

| Cpd. | Starting compounds<br>Reaction conditions and purification | Appearance, $^1$H NMR (solvent) data,<br>Mass (ES+ or ES−) data (MP) |
|---|---|---|
| | 3-Hydroxy-4-(pyridin-3-yl)benzonitrile from 3-methoxy-4-(pyridin-3-yl)benzonitrile hydrobromide (Protocol SD; toluene/DMF; BBr$_3$ (3 eq); 110° C.; 12 hours); solvent removal to dryness; acido-basic treatments (pH = 12, then 4 then 7) Filtration (Yield: 60%). | (DMSO-d$_6$): 7.12 (d, 1H, J = 8.4 Hz); 7.46 (q, 1H, J = 8.2 Hz, J = 4.8 Hz); 7.69 (dd, 1H, J = 8.4 Hz, J = 2.0 Hz); 7.83 (d, 1H, J = 2.0 Hz); 7.98 (dt, 1H, J = 8.2 Hz); 8.57 (dd, 1H, J = 4.8 Hz, J = 1.7 Hz); 8.71 (d, 1H, J = 1.7 Hz); 12.00 (s (large), 1H) |
| | 3-Chloro-6-(5-cyano-2-(pyridin-3-yl)phenoxy)-[1,2,4]triazolo[4,3-b]pyridazine from intermediate D and 3-hydroxy-4-(pyridin-3-yl)benzonitrile (Protocol SB; 10 min at 120° C. on microwave).<br>Eluent: dichloromethane/EtOAc 95/5 (Yield: 67%) | (DMSO-d$_6$): 7.39 (d, 1H, J = 9.9 Hz); 7.44 (q, 1H, J = 8.2 Hz, J = 4.8 Hz); 7.79 (d, 1H, J = 8.8 Hz); 7.95 (dt, 1H, J = 8.2 Hz, J = 1.7 Hz); 8.08 (dd, 1H, J = 8.8 Hz, J = 2.0 Hz); 8.20 (d, 1H, J = 2.0 Hz); 8.46 (d, 1H, J = 9.9 Hz); 8.56 (dd, 1H, J = 4.8 Hz, J = 1.7 Hz); 8.73 (d, 1H, J = 1.7 Hz) |
| | 3-Chloro-6-(5-cyano-2-(pyridin-3-yl)phenoxy)-[1,2,4]triazolo[4,3-b]pyridazine (Protocol TC) Trituration in diethyl ether (Yield: 41%) | White solid<br>(DMSO d6): 2.71 (s, 3H); 7.37 (d, 1H, J = 9.9 Hz); 7.44 (q, 1H, J = 8.2 Hz, J = 4.8 Hz); 7.76 (d, 1H, J = 8.8 Hz); 7.96 (dt, 1H, J = 8.2 Hz, J = 1.7 Hz); 8.15-8.2 (m, 2H); 8.44 (d, 1H, J = 9.9 Hz); 8.56 (dd, 1H, J = 4.8 Hz, J = 1.7 Hz); 8.73 (d, 1H, J = 1.7 Hz)<br>Mass: 405/407 [M + H]+ (MP: 159-161° C.). |

TABLE 3-1

Ra is W, Rf-Rj are hydrogen, at least one of Rb-Re is other than hydrogen atom, and at least one R2 or R3 is not hydrogen

| Cpd. | Starting compounds<br>Reaction conditions and purification | Appearance, $^1$H NMR (solvent) data,<br>Mass (ES+ or ES−) data (MP) |
|---|---|---|
| 5-1 | 6-chloro-[1,2,4]triazolo[3,4-a]phthalazin-3(2H)-one from 1,4-dichlorophthalazine (Protocol SJ). Used without purification (Yield: 56%) | Yellow solid<br>(DMSO-d$_6$): 7.89-8.02 (m, 2H); 8.13 (d, 1H, J = 7.9 Hz); 8.21 (d, 1H, J = 7.9 Hz); 12.66 (s 1H) |
| | 3,6-dichloro-[1,2,4]triazolo[3,4-a]phthalazine from 6-chloro-[1,2,4]triazolo[3,4-a]phthalazin-3(2H)-one (Protocol SK; POCl$_3$ (160 eq)., 48 h at 150° C.) Used without purification (Yield: 37%) | White solid<br>(DMSO-d$_6$): 8.06 (t, 1H, J = 7.0 Hz); 8.18 (t, 1H, J = 7.3 Hz); 8.35 (d, 1H, J = 8.2 Hz); 8.58 (d, 1H, J = 7.9 Hz) |
| | 3,6-dichloro-[1,2,4]triazolo[3,4-a]phthalazine and 4-(trifluoromethyl)-biphenyl-2-ol (Protocol SB; 10 min at 120° C. on microwave) Eluent: cyclohexane/AcOEt 8/2 to 6/4 v/v (Yield: 31%) | White solid<br>(DMSO-d$_6$): 7.24-7.35 (m, 3H); 7.55-7.58 (m, 2H); 7.82 (m, 2H); 7.97 (t, 1H, J = 7.3 Hz); 8.09-8.14 (m, 2H); 8.32 (d, 1H, J = 7.9 Hz); 8.48 (d, 1H, J = 7.6 Hz)<br>Mass (MALDI+): 440/442 (M + H); 462/464 (M + Na); 478/480 (M + K) (MP: 214.4-215.9° C.) |
| 5-2 | 6-Fluoro-2,3-dihydrophthalazine-1,4-dione from 4-fluorophthalic anhydride (Protocol SY), collected by filtering, washed with ether and dried (Yield: 74%) | White solid<br>(DMSO-d$_6$): 7.71-7.77 (m, 2H); 8.12-8.17 (m, 1H); 11.70 (s (large), 2H) |
| | 1,4-Dichloro-6-fluorophthalazine from 6-fluoro-2,3-dihydrophthalazine-1,4-dione (Protocol SI; 18 h at 110° C.) Collected by filtering, washed with ethanol and dried. (Yield: 86%) | Yellow solid<br>(DMSO-d$_6$): 8.11-8.19 (m, 2H); 8.44 (dd, 1H, J = 9.0 Hz, J = 5.2 Hz) |
| | 6-Chloro-9-fluoro-[1,2,4]triazolo[3,4-a]phthalazin-3(2H)-one from 1,4-dichloro-6-fluorophthalazine (Protocol SJ; 48 h at reflux) Collected by filtering, washed with ethanol and dried. (Yield: 22%) | Yellow solid<br>(DMSO-d$_6$): 7.77 (td, 1H, J = 8.7 Hz, J = 2.6 Hz); 7.85 (dd, 1H, J = 9.3 Hz, J = 2.6 Hz); 8.21 (dd, 1H, J = 9.0 Hz, J = 5.1 Hz); 12.74 (s, 1H) |
| | 3,6-Dichloro-9-fluoro-[1,2,4]triazolo[3,4-a]phthalazine from | Orange solid<br>(DMSO-d$_6$): 7.94 (dt, 1H, J = 8.9Hz, |

TABLE 3-1-continued

Ra is W, Rf-Rj are hydrogen, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | 6-chloro-9-fluoro-[1,2,4]triazolo[3,4-a]phthalazin-3(2H)-one (Protocol SK; 3 h at 150° C.) Eluent: cyclohexane/AcOEt 9/1 v/v (Yield: 13%) | J = 2.7 Hz); 8.38 (dd, 1H, J = 8.4 Hz, J = 2.5 Hz); 8.45 (dd, 1H, J = 9.1 Hz, J = 5.0 Hz) |
| | 3,6-Dichloro-9-fluoro-[1,2,4]triazolo[3,4-a]phthalazine and 4-(trifluoromethyl)biphenyl-2-ol (Protocol SB; 15 min at 150° C. on microwave) Eluent: cyclohexane/AcOEt 7/3 v/v (Yield: 45%) | White solid (DMSO-$d_6$): 7.27-7.32 (m, 3H); 7.59 (d, 2H, J = 8.0 Hz, J = 1.7 Hz); 7.81-7.89 (m, 3H); 8.13 (s, 1H); 8.29 (dd, 1H, J = 8.5 Hz, J = 2.5 Hz); 8.42 (dd, 1H, J = 9.0 Hz, J = 5.2 Hz) Mass (ES+): 459/461(M + H) (MP: 217-219° C.) |
| 5-3 | 6-Chloro-8-fluoro-[1,2,4]triazolo[3,4-a]phthalazin-3(2H)-one from 1,4-dichloro-6-fluorophthalazine (Protocol SJ; 48 h at reflux), collected by filtering, washed with ethanol and dried. (Yield: 30%) | Yellow solid (DMSO-$d_6$): 7.92 (td, 1H, J = 9.3 Hz, J = 2.4 Hz); 8.02 (dd, 1H, J = 8.4 Hz, J = 2.5 Hz); 8.33 (dd, 1H, J = 8.8 Hz, J = 5.5 Hz); 12.97 (s, 1H) |
| | 3,6-Dichloro-8-fluoro-[1,2,4]triazolo[3,4-a]phthalazine from 6-chloro-8-fluoro-[1,2,4]triazolo[3,4-a]phthalazin-3(2H)-one (Protocol SK; 3 h at 150° C.) Eluent: cyclohexane/AcOEt 9/1 v/v (Yield: 28%) | Orange solid (DMSO-$d_6$): 8.08 (dt, 1H, J = 4.7 Hz, J = 2.5 Hz); 8.18 (dd, 1H, J = 9.3 Hz, J = 2.5 Hz); 8.65 (dd, 1H, J = 8.9 Hz, J = 5.3 Hz) |
| | 3,6-Dichloro-8-fluoro-[1,2,4]triazolo[3,4-a]phthalazine and 4-(trifluoromethyl)biphenyl-2-ol (Protocol SB; 15 min at 150° C. on microwave) Eluent: cyclohexane/AcOEt 7/3 v/v (Yield: 29%) | White solid (DMSO-$d_6$): 7.27-7.38 (m, 3H); 7.61 (dd, 2H, J = 8.2 Hz, J = 1.6 Hz); 7.81-7.88 (m, 2H); 8.02 (m, 1H, J = 8.8 Hz, J = 6.2 Hz); 8.13 (s, 1H); 8.16 (dd, 1H, J = 9.1 Hz, J = 2.5 Hz); 8.57 (dd, 1H, J = 8.9 Hz, J = 5.1 Hz) Mass (ES+): 459/461(M + H) (MP: 213-215° C.) |
| 5-4 | 4-Phenylpyridazine-3,6-dione from phenylmaleic acid (Protocol SY) (Yield: 83%) | Colorless liquid (DMSO-$d_6$): 7.54-7.64 (m, 5H); 8.13 (s, 1H) |
| | 3,6-Dichloro-4-phenylpyridazine from 4-phenylpyridazine-3,6-dione (Protocol SI, 18 h at 110° C.) (Yield: 78%) | Yellow solid (DMSO-$d_6$): 7.54-7.64 (m, 5H); 8.13 (s, 1H) |
| | 6-Chloro-8-phenyl-[1,2,4]triazolo[4,3-b]pyridazin-3(2H)-one from 3,6-dichloro-4-phenylpyridazine (Protocol SJ). (Yield: 7%) | Yellow solid (DMSO-$d_6$): 7.56-7.60 (m, 4H); 8.16-8.19 (m, 2H); 12.97 (s, 1H) |
| | 3,6-Dichloro-8-phenyl-[1,2,4]triazolo[4,3-b]pyridazine from 6-chloro-8-phenyl-[1,2,4]triazolo[4,3-b]pyridazin-3(2H)-one (Protocol SK). (Yield: 18%) | Orange solid (DMSO-$d_6$): 7.63-7.65 (m, 3H); 8.00 (s, 1H); 8.43-8.76 (m, 2H) |
| | 3,6-Dichloro-8-phenyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 7/3 v/v (Yield: 3%) | White solid (DMSO-$d_6$): 7.31-7.43 (m, 3H); 7.53-7.63 (m, 5H); 7.76 (s, 1H); 7.80 (s, 2H); 8.03 (s, 1H); 8.38-8.41 (m, 2H) Mass: 467 [M + H]+ (MP: 162-164° C.) |
| 5-5 | 6-Chloro-7-phenyl-[1,2,4]triazolo[4,3-b]pyridazin-3(2H)-one from 3,6-dichloro-4-phenylpyridazine (Protocol SJ). (Yield: 29%) | Yellow solid (DMSO-$d_6$): 7.51-7.53 (m, 5H); 7.91 (s, 1H); 12.97 (s, 1H) |
| | 3,6-Dichloro-7-phenyl-[1,2,4]triazolo[4,3-b]pyridazine from 6-chloro-7-phenyl-[1,2,4]triazolo[4,3-b]pyridazin-3(2H)-one (Protocol SK). (Yield: 71%) | Orange solid (DMSO-$d_6$): 7.55-7.61 (m, 5H); 8.56 (s, 1H) |
| | 3,6-Dichloro-7-phenyl-[1,2,4]triazolo[4,3-b]pyridazine and 4-(trifluoromethyl)biphenyl-2-ol (Protocol SB; 15 min at 150° C. on microwave) | White solid (DMSO-$d_6$): 7.33 (s, 5H); 7.44-7.55 (m, 5H); 7.72-7.80 (m, 2H); 8.11 (s, 1H); 8.43 (s, 1H) Mass: 467 [M + H]+ (MP: 190-192° C.) |

TABLE 3-1-continued

Ra is W, Rf-Rj are hydrogen, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | Eluent: cyclohexane/AcOEt 7/3 v/v (Yield: 13%) | |
| 5-6 | 6-Chloro-8-methyl-[1,2,4]triazolo[4,3-b]pyridazin-3(2H)-one from 3,6-dichloro-4-methylpyridazine (Protocol SJ). Evaporation of ethanol; NaOH 2N to pH 7; filtration of precipitate (Yield: 25%) | Yellow solid (DMSO-$d_6$): 2.32 (d, 3H, J = 1.1 Hz); 7.13 (d, 1H, J = 1.1 Hz); 12.88 (s, 1H) |
| | 3,6-Dichloro-8-methyl-[1,2,4]triazolo[4,3-b]pyridazine from 6-chloro-8-methyl-[1,2,4]triazolo[4,3-b]pyridazin-3(2H)-one (Protocol SK). Eluent: cyclohexane/AcOEt 2/8 v/v (Yield: 57%) | White solid (CDCl$_3$): 2.72 (d, 3H, J = 1.2 Hz); 7.00 (d, 1H, J = 1.2 Hz) |
| | 3,6-Dichloro-8-methyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 1/1 v/v (Yield: 42%) | White solid (DMSO-$d_6$): 2.57 (d, 3H, J = 1.2 Hz); 7.21-7.22 (m, 1H, J = 1.3 Hz); 7.32-7.37 (m, 3H); 7.47-7.50 (m, 2H); 7.75-7.82 (m, 2H); 7.98 (s, 1H) Mass: 405 [M + H]+ (MP: 169-172° C.) |
| 5-7 | 6-Chloro-7-methyl-[1,2,4]triazolo[4,3-b]pyridazin-3(2H)-one from 3,6-dichloro-4-methylpyridazine (Protocol SJ). Evaporation of ethanol; NaOH 2N to pH 7; filtration of precipitate (Yield: 6%) | Yellow solid (DMSO-$d_6$): 2.26 (d, 3H, J = 1.1 Hz); 7.78 (d, 1H, J = 1.2 Hz); 12.73 (s, 1H) |
| | 3,6-Dichloro-7-methyl-[1,2,4]triazolo[4,3-b]pyridazine from 6-chloro-7-methyl-[1,2,4]triazolo[4,3-b]pyridazin-3(2H)-one (Protocol SK). Eluent: cyclohexane/AcOEt 2/8 v/v (Yield: 11%) | White solid (CDCl$_3$): 2.52 (d, 3H, J = 1.1 Hz); 7.00 (d, 1H, J = 1.2 Hz) |
| | 3,6-Dichloro-7-methyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 1/1 v/v (Yield: 30%) | White solid (DMSO-$d_6$): 2.28 (d, 3H, J = 1.2 Hz); 7.30-7.41 (m, 3H); 7.16-7.49 (m, 2H); 7.76-7.83 (m, 2H); 8.02 (s, 1H); 8.19-8.20 (m, 1H, J = 1.3 Hz) Mass: 405 [M + H]+ (MP: 163-165° C.) |
| 5-8 | 3,6-Dichloro-8-isopropyl-[1,2,4]triazolo[4,3-b]pyridazine from intermediate D and isobutyric acid (Protocol SZ) Eluent: cyclohexane/AcOEt 7/3 v/v (Yield: 15%) | Yellow solid (CDCl$_3$): 1.47 (d, 6H, J = 7.0 Hz); 3.60-3.69 (m, 1H, J = 6.7 Hz); 6.96 (s, 1H) |
| | 3,6-dichloro-8-isopropyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 7/3 v/v (Yield: 46%) | White solid (DMSO-$d_6$): 1.35 (d, 6H, J = 6.7 Hz); 3.37-3.44 (m, 1H, J = 5.5 Hz); 7.14 (s, 1H); 7.30-7.41 (m, 5H); 7.74-7.81 (m, 2H); 7.98 (s, 1H) Mass: 432 [M + H]+ (MP: 143.6-144.4° C.) |
| 5-9 | 6-Methyl-2,3-dihydrophthalazine-1,4-dione from 4-methylphthalic anhydride, (Protocol SY) Filtration; mixture washings with diethyl ether (Yield: 92%) | Yellow solid (DMSO-$d_6$): 2.48 (s, 3H); 7.67 (dd, 1H, J = 8.2 Hz, J = 1.4 Hz); 7.85 (s, 1H); 7.95 (d, 1H, J = 8.2 Hz); 11.48 (s (large), 2H) |
| | 1,4-Dichloro-6-methylphthalazine from 6-methyl-2,3-dihydrophthalazine-1,4-dione, (Protocol SI, 110° C., 18 h at 110° C.) Filtration after quenching (Yield: 61%) | Yellow solid (DMSO-$d_6$): 2.66 (s, 3H); 8.08-8.13 (m, 2H); 8.23 (d, 1H, J = 8.5 Hz) |
| | 6-Chloro-9-methyl-[1,2,4]triazolo[3,4-a]phthalazin-3(2H)-one from 1,4-dichloro-6-methylphthalazine (Protocol SJ, 48 h at reflux) Filtration; mixture washings with EtOH (Yield: 31%) | White solid (DMSO-$d_6$): 2.55 (s, 3H); 7.74 (dd, 1H, J = 8.3 Hz, J = 1.2 Hz); 7.94 (s, 1H); 8.00 (d, 1H, J = 8.5 Hz); 12.68 (s, 1H) |
| | 3,6-Dichloro-9-methyl-[1,2,4]triazolo[3,4-a]phthalazine- from | White solid (DMSO-$d_6$): 2.51 (s, 3H); 7.88 (d, 1H, |

TABLE 3-1-continued

Ra is W, Rf-Rj are hydrogen, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | 6-chloro-9-methyl-[1,2,4]triazolo[3,4-a]phthalazin-3(2H)-one (Protocol SK; 3 h at 150° C.) Eluent: cyclohexane/AcOEt 7/3 to 1/1 v/v (Yield: 14%) | J = 8.3 Hz); 8.22 (d, 1H, J = 8.4 Hz); 8.38 (s, 1H) |
| | 3,6-Dichloro-9-methyl-[1,2,4]triazolo[3,4-a]phthalazine and 4-(trifluoromethyl)biphenyl-2-ol, (Protocol SB, 15 min at 150° C. on microwave) Trituration in diethyl ether (Yield: 52%) | White solid (DMSO-$d_6$): 2.62 (s, 3H); 7.28-7.36 (m, 3H); 7.56-7.59 (m, 2H); 7.79-7.87 (m, 2H); 8.12 (s, 1H); 8.21 (d, 1H, J = 8.2 Hz); 8.30 (s, 1H) Mass: 455 [M + H]+ (MP: 229-231° C.) |
| 5-10 | 6-Chloro-8-methyl-[1,2,4]triazolo[3,4-a]phthalazin-3(2H)-one from 1,4-dichloro-6-methylphthalazine (Protocol SJ; 48 h at reflux) Filtration; mixture washings with EtOH (Yield: 31%) | White solid (DMSO-$d_6$): 2.55 (s, 3H); 7.74 (dd, 1H, J = 8.3 Hz, J = 1.2 Hz); 7.94 (s, 1H); 8.00 (d, 1H, J = 8.5 Hz); 12.68 (s, 1H) |
| | 3,6-Dichloro-8-methyl-[1,2,4]triazolo[3,4-a]phthalazine from 6-chloro-8-methyl-[1,2,4]triazolo[3,4-a]phthalazin-3(2H)-one (Protocol SK; 2 h at 150° C.) Eluent: cyclohexane/AcOEt 7/3 to 1/1 v/v (Yield: 18%) | White solid (DMSO-$d_6$): 2.63 (s, 3H); 8.02 (d, 1H, J = 8.1 Hz); 8.15 (s, 1H); 8.46 (d, 1H, J = 8.1 Hz) |
| | 3,6-Dichloro-8-methyl-[1,2,4]triazolo[3,4-a]phthalazine and 4-(trifluoromethyl)biphenyl-2-ol (Protocol SB; 15 min at 150° C. on microwave) Trituration in diethyl ether: (Yield: 46%) | White solid (DMSO-$d_6$): 2.58 (s, 3H); 7.26-7.37 (m, 3H); 7.57-7.6 (dd, 2H, J = 8.2 Hz, J = 1.6 Hz); 7.80-7.87 (m, 2H); 7.95 (dd, 1H, J = 8.2 Hz, J = 1.1 Hz); 8.13 (s, 1H); 8.37 (d, 1H, J = 8.1 Hz) Mass: 455 [M + H]+ (MP: 195-197° C.) |
| 5-11 | 3,6-Dichloro-4-isopropylpyridazine from 3,6-dichloropyridazine and isobutyric acid, (Protocol SZ) Evaporation of ethanol; NaOH 2N to pH 7; filtration of precipitate (Yield: 81%) | Colorless liquid (DMSO-$d_6$): 1.24 (d, 6H, J = 6.7 Hz) 3.08-3.21 (m, 1H, J = 6.7 Hz); 7.97 (s, 1H) |
| | 6-Chloro-7-isopropyl-[1,2,4]triazolo[4,3-b]pyridazin-3(2H)-one from 3,6-dichloro-4-isopropyl-pyridazine (Protocol SJ). Evaporation of ethanol; NaOH 2N to pH 7; filtration of precipitate (Yield: 73%) | Yellow solid |
| | 3,6-Dichloro-7-isopropyl-[1,2,4]triazolo[4,3-b]pyridazine from 6-chloro-7-isopropyl-[1,2,4]triazolo[4,3-b]pyridazin-3(2H)-one, (Protocol SK). (Yield: 21%) | Yellow solid (DMSO-$d_6$): 1.28 (d, 6H, J = 6.7 Hz) 3.80-3.38 (m, 1H); 8.37 (s, 1H) |
| | 3,6-Dichloro-7-isopropyl-[1,2,4]triazolo[4,3-b]pyridazine and 4-(trifluoromethyl)biphenyl-2-ol (Protocol SB; 110° C. microwave 10 min) Eluent: cyclohexane/AcOEt 3/7 (Yield: 9%) | White solid (DMSO-$d_6$): 1.18 (d, 6H, J = 7.0 Hz); 3.08-3.17 (m, 1H, J = 6.7 Hz); 7.32-7.45 (m, 5H); 7.74-7.82 (m, 2H); 8.05 (s, 1H); 8.19 (s, 1H) Mass: 432 [M + H]+ (MP: 55-58° C.) |
| 5-12 | 3,6-Dichloro-7,8-diethyl-[1,2,4]triazolo[4,3-b]pyridazine from intermediate D and propionic acid (Protocol SZ). Eluent: cyclohexane/AcOEt 7/3 v/v (Yield: 6%) | Yellow solid (CDCl$_3$): 1.27 (t, 3H, J = 7.6 Hz); 1.40 (t, 3H, J = 7.6 Hz); 2.87 (q, 2H, J = 7.6 Hz); 3.14 (q, 2H, J = 7.6 Hz) |
| | 3,6-Dichloro-7,8-diethyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 7/3 v/v (Yield: 62%) | White solid (DMSO-$d_6$): 1.02 (t, 3H, J = 7.6 Hz); 1.25 (t, 3H, J = 7.6 Hz); 2.69 (q, 2H, J = 7.6 Hz); 2.97 (q, 2H, J = 7.6 Hz); 7.3-7.46 (m, 5H); 7.73-7.81 (m, 2H); 8.03 (s, 1H) Mass: 446 [M + H]+ (MP: 153.4-155.2° C.) |
| 5-13 | 3,6-Dichloro-8-ethyl-[1,2,4]triazolo[4,3-b]pyridazine from | Yellow solid (DMSO-$d_6$): 1.35 (t, 3H, J = 7.4 Hz); 3.02 |

TABLE 3-1-continued

Ra is W, Rf-Rj are hydrogen, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | intermediate D and propionic acid (Protocol SZ) Eluent: cyclohexane/AcOEt 7/3 v/v (Yield: 5%) | (q, 2H, J = 6.4 Hz); 7.47 (s, 1H) |
| | 3,6-Dichloro-8-ethyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 7/3 v/v (Yield: 17%) | White solid (DMSO-d$_6$): 1.31 (t, 3H, J = 7.6 Hz); 2.96 (q, 2H, J = 7.9 Hz); 7.17 (s, 1H); 7.31-7.39 (m, 3H); 7.46-7.49 (m, 2H); 7.74-7.81 (m, 2H); 7.98 (s, 1H) Mass: 419 [M + H]+ (MP: 139.5-141.8° C.) |
| 5-14 | 3,6-Dichloro-4-cyclopropylpyridazine from 3,6-dichloropyridazine and cyclopropanecarboxylic acid (Protocol SZ) Eluent: cyclohexane/AcOEt 7/3 v/v (Yield: 42%) | Colorless liquid (DMSO-d$_6$): 1.02-1.07 (m, 2H); 1.17-1.24 (m, 2H); 2.10-2.16 (m, 1H); 7.60 (s, 1H) |
| | 6-Chloro-8-cyclopropyl-[1,2,4]triazolo[4,3-b]pyridazin-3(2H)-one from 3,6-dichloro-4-cyclopropylpyridazine, (Protocol SJ; 48 h at reflux) Evaporation of ethanol; washing with water: (Yield: 98%) | Yellow solid |
| | 3,6-Dichloro-8-cyclopropyl-[1,2,4]triazolo[4,3-b]pyridazine from 6-chloro-8-cyclopropyl-[1,2,4]triazolo[4,3-b]pyridazin-3(2H)-one, (Protocol SK; 3 h at 150° C.) Extraction; no further purification (Yield: 85%) | Brown oil (DMSO-d$_6$): 1.30-1.48 (m, 4H); 2.08-2.17 (m, 1H); 7.29 (s, 1H) |
| | 3,6-Dichloro-8-cyclopropyl-[1,2,4]triazolo[4,3-b]pyridazine and 4-(trifluoromethyl)biphenyl-2-ol (Protocol SB; 15 min at 150° C. on microwave) Eluent: cyclohexane/AcOEt 7/3 v/v (Yield: 15%) | Yellow solid (DMSO-d$_6$): 1.22-1.32 (m, 2H); 1.31-1.40 (m, 2H); 2.38-2.45 (m, 1H); 7.04 (s, 1H); 7.32-7.42 (m, 3H); 7.45-7.48 (m, 2H); 7.73-7.80 (m, 2H); 7.94 (s, 1H) Mass: 431 [M + H]+ (MP: 130-133° C.) |
| 5-15 | 2-(Pyridin-3-yl)-5-(trifluoromethyl)phenol from 2-bromo-5-(trifluoromethyl)phenol and pyridin-3-ylboronic acid (Protocol SA; 120° C.) Acido-basic treatment; extraction; precipitation from aqueous phase (Yield: 40%). | White solid (DMSO-d$_6$): 7.2-7.3 (m, 2H); 7.46 (dd, 1H, J = 7.9 Hz, J = 4.7 Hz); 7.54 (d, 1H, J = 7.6 Hz); 7.99 (tt, 1H, J = 7.9 Hz, J = 1.7 Hz); 8.55 (dd, 1H, J = 4.7 Hz, J = 1.7 Hz); 8.76 (d, 1H, J = 1.7 Hz); 10.50 (s, 1H) |
| | 3,6-Dichloro-[1,2,4]triazolo[3,4-a]phthalazine and 2-(pyridin-3-yl)-5-(trifluoromethyl)phenol (Protocol SB; 10 min at 120° C. on microwave) Recristallisation from EtOH (Yield: 41%) | White solid (DMSO-d$_6$): 7.37 (q, 1H, J = 7.6 Hz, J = 4.7 Hz); 7.85-7.95 (m, 2H); 7.99 (td, 1H, J = 7.3 Hz); 8.03 (tt, 1H, J = 8.2 Hz, J = 1.7 Hz); 8.13 (td, 1H, J = 7.3 Hz); 8.20 (s, 1H); 8.32 (d, 1H, J = 8.2 Hz); 8.45-8.55 (m, 2H); 8.81 (d, 1H, J = 1.7 Hz) Mass (ES+): 441/443 (M + H) (MP: 175.0-177.0° C.) |
| 5-22 | 2-(Pyrimidin-5-yl)-5-(trifluoromethyl)-phenol from pyrimidin-5-ylboronic acid and 2-bromo-5-(trifluoromethyl)phenol (Protocol SA; 10 min at 120° C. on microwave) Trituration in diethyl ether (Yield: 78%). | (DMSO-d$_6$): 7.25-7.35 (m, 2H); 7.65 (d, 1H, J = 7.9 Hz); 9.02 (s, 2H); 9.17 (s, 1H); 10.76 (s, 1H) |
| | 3,6-Dichloro-[1,2,4]triazolo[3,4-a]phthalazine and 2-(pyrimidin-5-yl)-5-(trifluoromethyl)phenol (Protocol SB; 10 min at 120° C. on microwave). Eluent: dichloromethane/MeOH 98/2 v/v (Yield: 40%). | White solid (DMSO-d$_6$): 7.93 (dd, 1H, J = 8.3 Hz); 7.95-8.05 (m,2H); 8.15 (t, 1H, J = 7.7 Hz); 8.27 (s, 1H); 8.38 (d, 1H, J = 7.7 Hz); 8.52 (d, 1H, J = 7.7 Hz); 9.13 (s, 2H); 9.16 (s, 1H) Mass: 442/444 [M + H]+ (MP: 222.0-224.0° C.) |
| 5-29 | 3,6-Dichloro-7-methyl-[1,2,4]triazolo[4,3-b]pyridazine and 2-(pyrimidin-5-yl)-5-(trifluoromethyl)-phenol (Protocol SB; 10 min at 120° C. on microwave) Trituration in AcOEt (Yield: 89%). | White solid (DMSO-d$_6$): 2.31 (s, 3H); 7.90 (dd, 1H, J = 8.0 Hz, J = 1.1 Hz); 7.97 (d, 1H, J = 8.0 Hz); 8.19 (s, 1H); 8.27 (d, 1H, J = 1.3 Hz); 9.03 (s, 2H); 9.21 (s, 1H) Mass: 406/408 [M + H]+ (MP: 248-250° C.) |

TABLE 3-1-continued

Ra is W, Rf-Rj are hydrogen, at least one of Rb-Re is other
than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| 5-30 | 3,6-Dichloro-8-methyl-[1,2,4]triazolo[4,3-b]pyridazine and 2-(pyrimidin-5-yl)-5-(trifluoromethyl)-phenol (Protocol SB; 10 min at 120° C. on microwave) Eluent: dichloromethane/MeOH 98/2 v/v (Yield: 50%). | White solid (DMSO-$d_6$): 2.31 (d, 3H, J = 1.3 Hz); 7.29 (d, 1H, J = 1.3 Hz); 7.89 (dd, 1H, J = 8.0 Hz, J = 1.1); 7.96 (d, 1H, J = 8.0 Hz); 8.12 (s, 1H); 9.01 (s, 2H); 9.21 (s, 1H) Mass: 406/408 [M + H]+ (MP: 115-157° C.) |
| 5-31 | 3,6-Dichloro-7-methyl-[1,2,4]triazolo[4,3-b]pyridazine and 2-(pyrimidin-5-yl)-5-(trifluoromethyl)-6-fluoro-phenol (Protocol SB; 15 min at 110° C. on microwave) Eluent: dichloromethane/MeOH 98/2 v/v (Yield: 17%). | White solid (DMSO-$d_6$): 2.34 (d, 3H, J = 0.9 Hz); 7.84 (d, 1H, J = 7.9 Hz); 8.03 (t, 1H, J = 7.6 Hz); 8.34 (d, 1H, J = 1.5 Hz); 9.04 (s, 2H); 9.24 (s, 1H) Mass: 425-427 [M + H]+ (MP: 177-179° C.) |
| 5-32 | 1-(6-Chloro-4-methylpyridazin-3-yl)hydrazine from 3,6-dichloro-4-methylpyridazine (see preparation of intermediate A) After being refluxed for 48 h, reaction mixture was cooled to RT and filtered (Yield: 76% mixture of isomers). | |
| | 6-Chloro-8-methyl-3-(trifluoromethyl)-[1,2,4]triazolo[4,3-b]pyridazine from 1-(6-chloro-4-methylpyridazin-3-yl)hydrazine (mixture) (see preparation of intermediate B) Eluent: cyclohexane/AcOEt 7/3 v/v (Yield: 21%). | (DMSO-$d_6$): 2.69 (d, 3H, J = 1.3 Hz); 7.69 (m, 1H, J = 1.3 Hz) |
| | 6-Chloro-8-methyl-3-(trifluoromethyl)-[1,2,4]triazolo[4,3-b]pyridazine and 2-(pyridin-3-yl)-5-(trifluoromethyl)-phenol (Protocol SB; K$_2$CO$_3$ (3 eq); 10 min at 120° C. on microwave) Trituration in diethyl ether (Yield: 6%). | Beige solid (DMSO-$d_6$): 2.66 (s, 3H); 7.42-7.48 (m, 2H); 7.85 (s, 2H); 7.94 (td, 1H, J = 8.0 Hz, J = 2.3 Hz); 8.07 (s, 1H); 8.58 (dd, 1H, J = 4.8 Hz, J = 1.7 Hz); 8.71 (d, 1H, J = 1.5 Hz) Mass: 439 [M + H]+ (MP: 151-153° C.) |
| 5-33 | 1-(6-Chloro-4-methylpyridazin-3-yl)hydrazine from 3,6-dichloro-4-methylpyridazine (see preparation of intermediate A) After being refluxed for 48 h, reaction mixture was cooled to RT and filtered (Yield: 76% mixture of isomers). | |
| | 6-Chloro-7-methyl-3-(trifluoromethyl)-[1,2,4]triazolo[4,3-b]pyridazine from 1-(6-chloro-5-methylpyridazin-3-yl)hydrazine (see preparation of intermediate B) Eluent: cyclohexane/AcOEt 7/3 v/v (Yield: 33%). | (DMSO-$d_6$): 2.47 (d, 3H, J = 1.3 Hz); 8.62 (m, 1H, J = 1.2 Hz) |
| | 6-Chloro-7-methyl-3-(trifluoromethyl)-[1,2,4]triazolo[4,3-b]pyridazine and 2-(pyridin-3-yl)-5-(trifluoromethyl)phenol (Protocol SB; K$_2$CO$_3$ (3 eq); 10 min at 120° C. on microwave) Trituration in diethyl ether/cyclohexane (Yield: 10%). | Beige solid (DMSO-$d_6$): 2.32 (s, 3H); 7.46 (m, 1H, J = 4.9 Hz, J = 0.8 Hz); 7.87 (s, 2H); 7.96 (td, 1H, J = 7.9 Hz, J = 2.3 Hz); 8.13 (s, 1H); 8.42 (d, 1H, J = 1.3 Hz); 8.57 (dd, 1H, J = 4.8 Hz, J = 1.6 Hz); 8.72 (d, 1H, J = 1.6 Hz) Mass: 439 [M + H]+ (MP: 173-175° C.) |
| 5-42 | 2-(Pyrimidin-5-yl)-3-(trifluoromethyl)-phenol from 2-bromo-3-(trifluoromethyl)phenol and pyrimidin-5-ylboronic acid (Protocol SA; 15 min at 120° C. on microwave). Eluent: dichlorommethane/AcOEt 7/3 to 5/5 (Yield: 14%) | |
| | 3,6-Dichloro-8-methyl-[1,2,4]triazolo[4,3-b]pyridazine and 2-(pyrimidin-5-yl)-3-(trifluoromethyl)-phenol (Protocol SB; K$_2$CO$_3$ (3 eq); 10 min at 100° C. on microwave) Trituration in ethanol (Yield: 59%). | Ocher solid (DMSO-$d_6$): 2.53 (d, 3H, J = 2.1 Hz); 7.08 (d, 1H, J = 2.1 Hz); 7.85-8.0 (m, 3H); 8.78 (s, 2H); 9.20 (s, 1H) Mass: 406/408 [M + H]+ (MP: 209.0-211.0° C.) |
| 5-43 | 6-Chloro-3-ethyl-7-methyl-[1,2,4]triazolo[4,3-b]pyridazine from 1-(6-chloro-methylpyridazin-3-yl)hydrazine (mixture of 4 and 5 | (DMSO-$d_6$): 1.37 (t, 3H, J = 7.6 Hz); 2.41 (d, 3H, J = 1.2 Hz); 3.08 (q, 2H, J = 7.6 Hz); 8.32 (d, 1H, J = 1.2 Hz) |

TABLE 3-1-continued

Ra is W, Rf-Rj are hydrogen, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | methyl isomers) (see preparation of intermediate B) (in propionyl chloride, 100° C.). Eluent: AcOEt (Yield: 13%). 6-Chloro-3-ethyl-7-methyl-[1,2,4]triazolo[4,3-b]pyridazine and 2-(pyrimidin-5-yl)-5-(trifluoromethyl)-phenol (Protocol SB; K$_2$CO$_3$ (3 eq); 15 min at 120° C. on microwave) Trituration in diethyl ether then heptanes (Yield: 43%) | Beige solid (DMSO-d$_6$): 1.15 (t, 3H, J = 7.5 Hz); 2.29 (d, 3H, J = 1.1 Hz); 2.75 (q, 2H, J = 7.5 Hz); 7.88-7.98 (m, 2H); 8.14-8.19 (m, 2H); 9.03 (s, 2H); 9.19 (s, 1H) Mass: 401 [M + H]+ (MP: 149-150° C.). |
| 5-44 | 6-Chloro-7-methyl-[1,2,4]triazolo[4,3-b]pyridazine from 1-(6-chloro-methylpyridazin-3-yl)hydrazine (mixture of 4 and 5 methyl isomers) (see preparation of intermediate B) (in formic acid, 1 hour at 100° C.). Eluent: cyclohexane/AcOEt 3/7 v/v (Yield: 15%). | (DMSO-d$_6$): 2.42 (d, 3H, J = 1.2 Hz); 8.39 (s, 1H); 9.62 (s, 1H) |
| | 7-Methyl-6-chloro-[1,2,4]triazolo[4,3-b]pyridazine and 2-(pyrimidin-5-yl)-5-(trifluoromethyl)phenol (Protocol SB; K$_2$CO$_3$ (3 eq); 10 min at 120° C. on microwave) Trituration in diethyl ether then heptanes (Yield: 48%) | Beige solid (DMSO-d$_6$): 2.32 (d, 3H, J = 1.2 Hz); 7.88-7.98 (m, 2H); 8.13 (s, 1H); 8.20 (s, 1H); 9.01 (s, 2H); 9.18 (s, 1H); 9.29 (d, 1H, J = 0.7 Hz) Mass: 373 [M + H]+ (MP: 179-181° C.). |
| 5-46 | 6-Chloro-8-methyl-[1,2,4]triazolo[4,3-b]pyridazine from 1-(6-chloro-methylpyridazin-3-yl)hydrazine (mixture or 4 and 5 methyl isomers) (see preparation of intermediate B) (in formic acid, 1 hour at 100° C.). Eluent: cyclohexane/AcOEt 3/7 v/v (Yield: 14%). | (DMSO-d$_6$): 2.64 (d, 3H, J = 1.1 Hz); 7.42 (d, 1H, J = 1.5 Hz); 9.65 (s, 1H) |
| | 8-Methyl-6-chloro-[1,2,4]triazolo[4,3-b]pyridazine and 2-(pyrimidin-5-yl)-5-(trifluoromethyl)phenol (Protocol SB; K$_2$CO$_3$ (3 eq); 15 min at 120° C. on microwave). Eluent: dichloromethane/MeOH 9/1 v/v; then Trituration in diethyl ether (Yield: 32%) | Beige solid (DMSO-d$_6$): 2.00 (d, 3H, J = 1.2 Hz); 7.20 (d, 1H, J = 1.2 Hz); 7.87-7.98 (m, 2H); 8.08 (s, 1H); 9.00 (s, 2H); 9.19 (s, 1H); 9.37 (s, 1H) Mass: 373 [M + H]+ (MP: 230-234° C.). |
| 5-48 | 6-Chloro-3-ethyl-8-methyl-[1,2,4]triazolo[4,3-b]pyridazine from 1-(6-chloro-methylpyridazin-3-yl)hydrazine (mixture or 4 and 5 methyl isomers) (see preparation of intermediate B) (in propionyl chloride, 100° C.). Eluent: AcOEt (Yield: 11%). | (DMSO-d$_6$): 1.37 (t, 3H, J = 7.6 Hz); 2.62 (d, 3H, J = 0.9 Hz); 3.08 (q, 2H, J = 7.6 Hz); 7.37 (d, 1H, J = 1.2 Hz) |
| | 6-Chloro-3-ethyl-8-methyl-[1,2,4]triazolo[4,3-b]pyridazine and 2-(pyrimidin-5-yl)-5-(trifluoromethyl)phenol (Protocol SB; K$_2$CO$_3$ (3 eq); 15 min at 120° C. on microwave). Eluent: dichloromethane/MeOH 95/5 v/v then trituration in diethyl ether (Yield: 8%) | Beige solid (DMSO-d$_6$): 1.18 (t, 3H, J = 7.6 Hz); 2.58 (d, 3H, J = 0.9 Hz); 2.80 (q, 2H, J = 7.6 Hz); 7.15 (d, 1H, J = 1.2 Hz); 7.86-7.97 (m, 2H); 8.12 (s, 1H); 9.02 (s, 2H); 9.21 (s, 1H) Mass: 401 [M + H]+ (MP: 182-184° C.). |
| 5-49 | 6-Chloro-3-ethyl-7-methyl-[1,2,4]triazolo[4,3-b]pyridazine and 2-(pyridin-3-yl)-5-(trifluoromethyl)phenol (Protocol SB; K$_2$CO$_3$ (3 eq); 15 min at 120° C. on microwave) Trituration in diethyl ether (Yield: 35%) | Beige solid (DMSO-d$_6$): 1.15 (t, 3H, J = 7.6 Hz); 2.29 (s, 3H); 2.74 (q 2H, J = 7.6 Hz); 7.43-7.47 (m, 1H); 7.86 (s, 2H); 7.96 (d, 1H, J = 7.9 Hz); 8.12 (s, 2H); 8.56 (d, 1H, J = 3.5 Hz); 8.72 (d, 1H, J = 1.5 Hz) Mass: 400 [M + H]+ (MP: 174-176° C.). |
| 5-58 | 4-Chloro-2-(pyrimidin-5-yl)phenol from 2-bromo-4-chlorophenol and pyrimidine-5-boronic acid (Protocol SA; 10 min at 110° C.) Eluent: cyclohexane/AcOEt 5/5 v/v (Yield: 23%). | (DMSO-d$_6$): 7.02 (d, 1H, J = 8.4 Hz); 7.31-7.33 (m, 1H); 7.50 (s, 1H); 9.00 (s, 2H); 9.14 (s, 1H); 10.32 (s(l), 1H) |
| | 3,6-Dichloro-8-methyl-[1,2,4]triazolo[4,3-b]pyridazine and 4- | Purple solid (DMSO-d$_6$): 2.58 (s, 3H); 7.25 (d, 1H, |

TABLE 3-1-continued

Ra is W, Rf-Rj are hydrogen, at least one of Rb-Re is other
than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
|  | chloro-2-(pyrimidin-5-yl)phenol (Protocol SB; K$_2$CO$_3$ (3 eq); 10 mn at 110° C. on microwave) Precipitation with water; washings with diethyl ether (Yield: 51%) | J = 1.1 Hz); 7.62 (d, 1H, J = 8.7 Hz); 7.70 (dd, 1H, J = 8.7 Hz , J = 2.3 Hz); 7.86 (d, 1H, J = 2.3 Hz); 8.96 (s, 2H); 9.17 (s, 1H) Mass: 373 [M + H]+ (MP: 208-210° C.). |
| 5-59 | 3,6-Dichloro-7-methyl-[1,2,4]triazolo[4,3-b]pyridazine and 4-chloro-2-(pyrimidin-5-yl)phenol (Protocol SB; K$_2$CO$_3$ (3 eq); 10 min at 110° C. on microwave) Precipitation with water; washings with diethyl ether (Yield: 59%) | White solid (DMSO-d$_6$): 2.29 (d, 3H, J = 0.9 Hz); 7.67-7.75 (m, 2H); 7.86 (d, 1H, J = 2.0 Hz); 8.25 (d, 1H, J = 1.2 Hz); 8.97 (s, 2H); 9.16 (s, 1H) Mass: 373 [M + H]+ (MP: 224-226° C.). |
| 5-60 | 3,6-Dichloro-[1,2,4]triazolo[3,4-a]phthalazine and 4-chloro-2-(pyrimidin-5-yl)phenol (Protocol SB; K$_2$CO$_3$ (3 eq); 10 min at 110° C. on microwave) Precipitation with water; washings with diethyl ether (Yield: 43%) | White solid (DMSO-d$_6$): 7.74-7.78 (m, 2H); 7.90 (d, 1H, J = 1.4 Hz); 8.00 (t, 1H, J = 7.6 Hz); 8.14 (t, 1H, J = 7.6 Hz); 8.37 (d, 1H, J = 8.2 Hz); 8.51 (d, 1H, J = 7.9 Hz); 9.07-9.10 (m, 3H) Mass: 409 [M + H]+ (MP: 252-253° C.). |
| 5-61 | 6-Chloro-7-methyl-3-(trifluoromethyl)-[1,2,4]triazolo[4,3-b]pyridazine and 2-(pyrimidin-5-yl)-5-(trifluoromethyl)phenol (Protocol SB; K$_2$CO$_3$ (3 eq); 10 mn at 120° C. on microwave) Trituration in diethyl ether (Yield: 67%) | White solid (DMSO-d$_6$): 2.34 (d, 3H, J = 0.8 Hz); 7.89-7.92 (m, 2H); 8.21 (s, 1H); 8.44 (d, 1H, J = 1.2 Hz); 9.04 (s, 2H); 9.22 (s, 1H) Mass: 441 [M + H]+ (MP: 174-179° C.). |
| 5-62 | 6-Chloro-3-(trifluoromethyl)-[1,2,4]triazolo[3,4-a]phthalazine from 1-(4-chlorophthalazin-1-yl)hydrazine see preparation of intermediate B (3 hours at 100° C.). (Yield: 87%). | (DMSO-d$_6$): 8.15 (t, 1H, J = 8.2 Hz); 8.26 (t, 1H, J = 7.6 Hz); 8.42 (d, 1H, J = 8.2 Hz); 8.71 (d, 1H, J = 7.9 Hz) |
|  | 6-Chloro-3-(trifluoromethyl)-[1,2,4]triazolo[3,4-a]phthalazine and 2-(pyrimidin-5-yl)-5-(trifluoromethyl)phenol (Protocol SB; K$_2$CO$_3$ (3 eq); 10 min at 120° C. on microwave) Precipitation with water; trituration in diethyl ether (Yield: 4%) | White solid (DMSO-d$_6$): 7.92-8.11 (m, 3H); 8.21 (t, 1H, J = 7.6 Hz); 8.28 (s, 1H); 8.40 (d, 1H, J = 7.9 Hz); 8.64 (d, 1H, J = 7.6 Hz); 9.13 (s, 2H); 9.18 (s, 1H) Mass: 477 [M + H]+ (MP: 197-200° C.). |
| 5-63 | 6-Chloro-8-methyl-3-(trifluoromethyl)-[1,2,4]triazolo[4,3-b]pyridazine and 2-(pyrimidin-5-yl)-5-(trifluoromethyl)phenol (Protocol SB; K$_2$CO$_3$ (3 eq); 20 min at 120° C. on microwave). Eluent: cyclohexane/AcOEt 3/7 v/v then trituration in diethyl ether (Yield: 9%) | White solid (DMSO-d$_6$): 2.67 (d, 3H, J = 1.2 Hz); 7.45 (d, 1H, J = 1.2 Hz); 7.87-7.98 (m, 2H); 8.14 (s, 1H); 9.01 (s, 2H); 9.22 (s, 1H) Mass: 441 [M + H]+ (MP: 167-172° C.). |
| 5-64 | 6-Chloro-[1,2,4]triazolo[3,4-a]phthalazine from 1-(4-chlorophthalazin-1-yl)hydrazine (see preparation of intermediate B (in formic acid, 3 hours at 100° C.) Precipitation with water (Yield: 89%). | (DMSO-d$_6$): 8.03 (t, 1H, J = 8.2 Hz); 8.17 (t, 1H, J = 7.6 Hz); 8.32 (d, 1H, J = 8.2 Hz); 8.59 (d, 1H, J = 8.2 Hz); 9.63 (s, 1H) |
|  | 6-Chloro-[1,2,4]triazolo[3,4-a]phthalazine and 2-(pyrimidin-5-yl)-5-(trifluoromethyl)phenol (Protocol SB; K$_2$CO$_3$ (3 eq); 10 min at 120° C. on microwave) Precipitation with water; trituration in diethyl ether (Yield: 12%) | White solid (DMSO-d$_6$): 7.92-8.02 (m, 3H); 8.12 (t, 1H, J = 7.9 Hz); 8.23 (s, 1H); 8.40 (d, 1H, J = 8.2 Hz); 8.51 (d, 1H, J = 7.9 Hz); 9.12 (s, 3H); 9.32 (s, 1H) Mass: 409 [M + H]+ (MP: 220-230° C.). |
| 5-65 | 3,6-Dichloro-7-methyl-[1,2,4]triazolo[4,3-b]pyridazine and 5-(5-methyl-1,2,4-oxadiazol-3-yl)biphenyl-2-ol (Protocol SB; K$_2$CO$_3$ (4 eq); 20 mn at 120° C. on microwave) Trituration in diethyl ether (Yield: 70%) | Beige solid (DMSO d6): 2.30 (d, 3H, J = 1.4 Hz); 2.71 (s, 3H); 7.10 (d, 1H, J = 8.4 Hz); 7.30-7.45 (m, 3H); 7.45-7.50 (m, 2H); 7.73 (d, 1H, J = 8.5 Hz); 8.09 (d, 1H, J = 2.0 Hz); 8.13 (dd, 1H, J = 8.5 Hz, J = 2.0 Hz); 10.31 (s large, 1H, J = 1.4 Hz) Mass: 418/420 [M + H]+ (MP: 156-158° C.). |

TABLE 3-2

Ra is W, at least one Rf-Rj is other than hydrogen atom, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| 5-16 | 3,6-Dichloro-8-methyl-[1,2,4]triazolo[4,3-b]pyridazine and 2-(6-methylpyridin-3-yl)-5-(trifluoromethyl)phenol (Protocol SB; K$_2$CO$_3$ (3 eq); 10 min at 120° C. on microwave) Trituration in diethyl ether and cristallisation from dichloromehane/ethanol (Yield: 75%). | Pink solid (DMSO-d$_6$): 2.47 (s, 3H); 2.58 (d, 3H, J = 1.2 Hz); 7.25 (d, 1H, J = 1.2 Hz); 7.30 (d, 1H, J = 8.2 Hz); 7.78-7.86 (m, 3H); 8.03 (s, 1H); 8.57 (d, 1H, J = 2.0 Hz) Mass: 419/421 [M + H]+ (MP: 225-227° C.) |
| 5-17 | 3,6-Dichloro-7-methyl-[1,2,4]triazolo[4,3-b]pyridazine and 2-(6-methylpyridin-3-yl)-5-(trifluoromethyl)-phenol (Protocol SB; K$_2$CO$_3$ (3 eq); 5 min at 80° C. on microwave) Trituration in AcOEt (Yield: 72%). | White solid (DMSO-d$_6$): 2.30 (d, 3H, J = 1.3 Hz); 2.46 (s, 3H); 7.30 (d, 1H, J = 8.0 Hz); 7.8-7.9 (m, 3H); 8.09 (s, 1H); 8.25 (d, 1H, J = 1.3 Hz); 8.58 (d, 1H, J = 1.9 Hz) Mass: 419/421 [M + H]+ (MP: 213-215° C.) |
| 5-18 | 3,6-Dichloro-[1,2,4]triazolo[3,4-a]phthalazine and 2-(6-methylpyridin-3-yl)-5-(trifluoromethyl)phenol (Protocol SB; K$_2$CO$_3$ (3 eq); 5 min at 120° C. on microwave) Trituration in AcOEt (Yield: 72%). | White solid (DMSO-d$_6$): 2.41 (s, 3H); 7.23 (d, 1H, J = 8.1 Hz); 7.8-7.9 (m, 2H); 7.94 (dd, 1H, J = 8.1 Hz, J = 2.3 Hz); 8.01 (t, 1H, J = 7.9 Hz); 8.12 (t, 1H, J = 7.9 Hz); 8.18 (s, 1H); 8.34 (d, 1H, J = 7.9 Hz); 8.50 (d, 1H, J = 7.9 Hz); 8.69 (d, 1H, J = 2.3 Hz) Mass: 455/457 [M + H]+ (MP: 240.0-242.0° C.) |
| 5-19 | 3,6-Dichloro-8-methyl-[1,2,4]triazolo[4,3-b]pyridazine and 2-(2-methylpyridin-3-yl)-5-(trifluoromethyl)phenol (Protocol SB; K$_2$CO$_3$ (3 eq); 10 min at 80° C. on microwave) Trituration in diethyl ether then cristallisation from dicholoromethane/ethanol (Yield: 68%). | Ocher solid (DMSO-d$_6$): 3.85 (s, 3H); 6.86 (d, 1H, J = 8.5 Hz); 7.39 (d, 1H, J = 9.9 Hz); 7.83 (s, 2H); 7.88 (dd, 1H, J = 8.5 Hz, J = 2.0 Hz); 8.05 (s, 1H); 8.34 (d, 1H, J = 2.0 Hz); 8.45 (d, 1H, J = 9.9 Hz) Mass: 419/421 [M + H]+ (MP: 216.0-218.0° C.) |
| 5-20 | 3,6-Dichloro-7-methyl-[1,2,4]triazolo[4,3-b]pyridazine and 2-(2-methylpyridin-3-yl)-5-(trifluoromethyl)phenol (Protocol SB; K$_2$CO$_3$ (3 eq); 10 min at 100° C. on microwave). Eluent: cyclohexane/AcOEt 6/4 v/v (Yield: 62%). | Ocher solid (DMSO-d$_6$): 3.85 (s, 3H); 6.86 (d, 1H, J = 8.5 Hz); 7.39 (d, 1H, J = 9.9 Hz); 7.83 (s, 2H); 7.88 (dd, 1H, J = 8.5 Hz, J = 2.0 Hz); 8.05 (s, 1H); 8.34 (d, 1H, J = 2.0 Hz); 8.45 (d, 1H, J = 9.9 Hz) Mass: 419/421 [M + H]+ (MP: 168-170° C.) |
| 5-21 | 3,6-Dichloro-[1,2,4]triazolo[3,4-a]phthalazine and 2-(2-methylpyridin-3-yl)-5-(trifluoromethyl)phenol (Protocol SB; K$_2$CO$_3$ (3 eq); 10 min at 120° C. on microwave) Trituration in diethyl ether (Yield: 73%). | White solid (DMSO-d$_6$): 3.85 (s, 3H); 6.86 (d, 1H, J = 8.5 Hz); 7.39 (d, 1H, J = 9.9 Hz); 7.83 (s, 2H); 7.88 (dd, 1H, J = 8.5 Hz, J = 2.0 Hz); 8.05 (s, 1H); 8.34 (d, 1H, J = 2.0 Hz); 8.45 (d, 1H, J = 9.9 Hz) Mass: 455/457 [M + H]+ (MP: 164-166° C.) |
| 5-23 | 2-(2-Methoxypyridin-3-yl)-5-(trifluoromethyl)phenol from 2-bromo-5-(trifluoromethyl)phenol and 2-methoxy-3-(4,4,5,5-tetramethyl-1,3,2-dioxaborolan-2-yl)pyridine (Protocol SA; 10 min at 120° C. on microwave). Eluent: cyclohexane/AcOEt 8/2 v/v (Yield: 95%). 3,6-Dichloro-8-methyl-[1,2,4]triazolo[4,3-b]pyridazine and 2-(2-methoxypyridin-3-yl)-5-(trifluoromethyl)phenol (Protocol SB; 15 min at 110° C. on microwave) Trituration in diethyl ether (Yield: 61%). | (DMSO-d$_6$): 3.83 (s, 3H); 7.06 (dd, 1H, J = 7.2 Hz, J = 5.0 Hz); 7.17-7.19 (m, 2H); 7.37 (d, 1H, J = 7.7 Hz); 7.64 (dd, 1H, J = 7.3 Hz, J = 2.0 Hz); 8.19 (dd, 1H, J = 5.0 Hz, J = 2.0 Hz); 10.16 (s, 1H)<br><br>White solid (DMSO-d$_6$): 2.57 (d, 3H, J = 1.2 Hz); 3.66 (s, 3H); 7.04 (dd, 1H, J = 7.3 Hz, J = 5.0 Hz); 7.12 (d, 1H, J = 1.3 Hz); 7.68 (dd, 1H, J = 7.3 Hz, J = 1.9 Hz); 7.72 (d, 1H, J = 8.1 Hz); 7.77 (dd, 1H, J = 8.1 Hz, J = 1.2 Hz); 8.00 (s, 1H); 8.18 (dd, 1H, J = 5.0 Hz, J = 1.9 Hz) Mass: 435.8 [M + H]+ (MP: 156-158° C.). |
| 5-24 | 3,6-Dichloro-7-methyl-[1,2,4]triazolo[4,3-b]pyridazine and 2-(2-methoxypyridin-3-yl)-5-(trifluoromethyl)phenol (Protocol SB; 15 min at 110° C. on microwave) Trituration in diethyl ether (Yield: 57%) | (DMSO-d$_6$): 2.13 (d, 3H, J = 1.2 Hz); 3.65 (s, 3H); 7.03 (dd, 1H, J = 7.3 Hz, J = 5.0 Hz); 7.69 (dd, 1H, J = 7.3 Hz, J = 1.9 Hz); 7.74 (d, 1H, J = 8.0 Hz); 7.81 (dd, 1H, J = 8.0 Hz, J = 1.3 Hz); 8.07 (d, 1H, J = 0.7 Hz); 8.18 (dd, 1H, J = 5.0 Hz, J = 1.9 Hz); 8.22 (d, 1H, J = 1.3 Hz) Mass: 435.8 [M + H]+ (MP: 176-178° C.) |

TABLE 3-2-continued

Ra is W, at least one Rf-Rj is other than hydrogen atom, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| 5-25 | 3,6-Dichloro-7,8-dimethyl-[1,2,4]triazolo[4,3-b]pyridazine and 2-(2-methoxypyridin-3-yl)-5-(trifluoromethyl)phenol (Protocol SB; K$_2$CO$_3$ (3 eq); 15 min at 110° C. on microwave). Eluent: cyclohexane/AcOEt 3/7 v/v (Yield: 61%) | White solid (DMSO-d$_6$): 2.08 (d, 3H, J = 0.7 Hz); 2.51 (d, 3H, J = 0.6 Hz); 3.65 (s, 3H); 7.01 (dd, 1H, J = 7.3 Hz, J = 5.0 Hz); 7.68 (dd, 1H, J = 4.3 Hz, J = 1.9 Hz); 7.72 (d, 1H, J = 8.0 Hz); 7.79 (dd, 1H, J = 8.0 Hz, J = 1.2 Hz); 8.03 (d, 1H, J = 0.8 Hz); 8.16 (dd, 1H, J = 5.0 Hz, J = 1.9 Hz) Mass: 450-452 [M + H]+ (MP: 182-184° C.) |
| 5-26 | 2-(2-Methoxy-5-(trifluoromethyl)pyridin-3-yl)-5-(trifluoromethyl)-phenol from 2-bromo-5-(trifluoromethyl)-phenol and 2-methoxy-5-(trifluoromethyl)pyridin-3-ylboronic acid (Protocol SA; 10 min at 120° C. on microwave). Eluent: cyclohexane/AcOEt 8/2 v/v (Yield: 83%). | (DMSO-d$_6$): 3.92 (s, 3H); 7.21-7.22 (m, 2H); 7.45 (dd, 1H, J = 8.2 Hz, J = 0.7 Hz); 8.01 (d, 1H, J = 2.2 Hz); 8.62-8.63 (m, 1H); 10.36 (s, 1H) |
|  | 3,6-Dichloro-7-methyl-[1,2,4]triazolo[4,3-b]pyridazine and 2-(2-methoxy-5-(trifluoromethyl)pyridin-3-yl)-5-(trifluoromethyl)phenol (Protocol SB; 15 min at 110° C. on microwave) Trituration in diethyl ether (Yield: 50%). | Pink solid (DMSO-d$_6$): 2.16 (s, 3H); 3.77 (s, 3H); 7.85 (s, 2H); 8.12 (s, 2H); 8.23 (s, 1H); 8.60 (s, 1H) Mass: 503.8 [M + H]+ (MP: 194-196° C.). |
| 5-27 | 3,6-Dichloro-8-methyl-[1,2,4]triazolo[4,3-b]pyridazine and 2-(2-methoxy-5-methylpyridin-3-yl)-5-(trifluoromethyl)phenol (Protocol SB; 15 min at 110° C. on microwave) Trituration in diethyl ether (Yield: 28%). | Brown solid (DMSO-d$_6$): 2.18 (s, 3H); 2.57 (d, 3H, J = 1.2 Hz); 3.60 (s, 3H); 7.11 (d, 1H, J = 1.3 Hz); 7.51 (d, 1H, J = 2.0 Hz); 7.70 (d, 1H, J = 8.0 Hz); 7.78 (d, 1H, J = 8.0 Hz); 7.97 (d, 1H, J = 1.5 Hz); 7.99 (s, 1H) Mass: 449.8 [M + H]+ (MP: 117-119° C.). |
| 5-28 | 3,6-Dichloro-7-methyl-[1,2,4]triazolo[4,3-b]pyridazine and 2-(2-methoxy-5-methylpyridin-3-yl)-5-(trifluoromethyl)phenol (Protocol SB; 15 min at 110° C. on microwave) Trituration in diethyl ether (Yield: 61%). | Beige solid (DMSO-d$_6$): 2.14 (d, 3H, J = 1.3 Hz); 2.16 (s, 3H); 3.59 (s, 3H); 7.54 (d, 1H, J = 1.9 Hz); 7.73 (d, 1H, J = 8.0 Hz); 7.80 (dd, 1H, J = 8.0 Hz, J = 1.1 Hz); 7.97 (dd, 1H, J = 2.3 Hz, J = 0.7 Hz); 8.07 (d, 1H, J = 0.8 Hz); 8.21 (d, 1H, J = 1.3 Hz) Mass: 449.8/451.8 [M + H]+ (MP: 164-166° C.) |
| 5-34 | 3,6-Dichloro-8-methyl-[1,2,4]triazolo-[4,3-b]pyridazine and 2-(2-methoxypyrimidin-5-yl)-5-(trifluoro-methyl)phenol (Protocol SB; K2CO3 (3 eq); 15 min at 110° C. on microwave) Trituration in diethyl ether (Yield: 51%). | Beige solid (DMSO-d$_6$): 2.60 (d, 3H, J = 1.0 Hz); 3.93 (s, 3H); 7.30 (d, 1H, J = 1.3 Hz); 7.83-7.92 (m, 2H); 8.07 (s, 1H); 8.81 (s, 2H) Mass: 436.8/438.8 [M + H]+ (MP: 176-178° C.) |
| 5-35 | 3,6-Dichloro-7-methyl-[1,2,4]triazolo-[4,3-b]pyridazine and 2-(2-methoxy-pyrimidin-5-yl)-5-(trifluoromethyl)-phenol (Protocol SB; K$_2$CO$_3$ (3 eq); 15 min at 110° C. on microwave) Trituration in diethyl ether (Yield: 51%). | Beige solid (DMSO-d$_6$): 2.33 (d, 3H, J = 1.3 Hz); 3.93 (s, 3H); 7.84-7.92 (m, 2H); 8.14 (s, 1H); 8.27 (d, 1H, J = 1.3 Hz); 8.82 (s, 2H) Mass: 436.8/438.8 [M + H]+ (MP: 180-181° C.) |
| 5-36 | 3,6-Dichloro-[1,2,4]triazolo[3,4-a]phthalazine and 2-(2-methoxy-pyrimidin-5-yl)-5-(trifluoromethyl)-phenol (Protocol SB; K$_2$CO$_3$ (3 eq); 15 min at 110° C. on microwave) Trituration in diethyl ether and crystallization from acetonitrile (Yield: 22%). | White solid (DMSO-d$_6$): 3.88 (s, 3H); 7.87-7.890 (m, 1H); 7.94-7.96 (m, 1H); 8.01 (td, 1H, J = 8.2 Hz, J = 1.2 Hz); 8.15 (td, 1H, J = 8.0 Hz, J = 1.2 Hz); 8.22 (s, 1H); 8.40 (d, 1H, J = 7.7 Hz); 8.52 (d, 1H, J = 7.5 Hz); 8.92 (s, 2H) Mass: 472.8/474.8 [M + H]+ (MP: 232-234° C.) |
| 5-37 | 2-(2-Methylpyrimidin-5-yl)-5-(trifluoro-methyl)phenol from 2-bromo-5-trifuormethylphenol and 2-methyl-pyrimidin-5-ylboronic acid (Protocol SA; 10 min at 120° C. on microwave). Eluent: cyclohexane/AcOEt 3/7 v/v (Yield: 12%). | (DMSO-d$_6$): 2.67 (s, 3H); 7.27-7.29 (m, 2H); 7.63 (d, 1H, J = 7.7 Hz); 8.91 (s, 2H); 10.71 (s (large), 1H) |

TABLE 3-2-continued

Ra is W, at least one Rf-Rj is other than hydrogen atom, at least one of Rb-Re is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | 3,6-Dichloro-8-methyl-[1,2,4]triazolo[4,3-b]pyridazine and 2-(2-methoxypyrimidin-5-yl)-5-(trifluoromethyl)phenol (Protocol SB; K$_2$CO$_3$ (3 eq); 15 min at 110° C. on microwave). Eluent: dichloromethane/MeOH 95/5 v/v (Yield: 37%) | White solid (DMSO-d$_6$): 2.59 (d, 3H, J = 1.3 Hz); 2.64 (s, 3H); 7.29 (d, 1H, J = 1.3 Hz); 7.86 (dd, 1H, J = 8.1 Hz, J = 1.2 Hz); 7.93 (d, 1H, J = 8.1 Hz); 8.09 (s, 1H); 8.88 (s, 2H) Mass: 421 [M + H]+ (MP: 200-202° C.) |
| 5-38 | 2-(4-Isopropylpyrimidin-5-yl)-5-(trifluoromethyl)phenol from 2-bromo-5-(trifluoromethyl)phenol and 4-isopropylpyrimidin-5-ylboronic acid (Protocol SA; 10 min at 120° C. on microwave). Eluent: cyclohexane/AcOEt 3/7 v/v (Yield: 27%). | (DMSO-d$_6$): 1.11-1.24 (m, 6H); 2.84-2.93 (m, 1H); 7.25-7.29 (m, 2H); 7.42 (d, 1H, J = 7.7 Hz); 8.51 (s, 1H); 9.15 (s, 1H); 10.53 (s (large), 1H) |
| | 3,6-Dichloro-8-methyl-[1,2,4]triazolo[4,3-b]pyridazine and 2-(4-isopropylpyrimidin-5-yl)-5-(trifluoromethyl)phenol (Protocol SB; K$_2$CO$_3$ (3 eq); 10 min at 120° C. on microwave). Eluent: AcOEt (Yield: 62%). | White solid (DMSO-d$_6$): 1.01 (d, 3H, J = 6.6 Hz); 1.11 (d, 3H, J = 6.7 Hz); 2.54 (d, 3H, J = 1.2 Hz); 2.87-8.96 (m, 1H, J = 6.9 Hz); 7.14 (d, 1H, J = 1.3 Hz); 7.79 (d, 1H, J = 7.9 Hz); 7.88 (dd, 1H, J = 8.0 Hz, J = 1.1 Hz); 8.08 (s, 1H); 8.59 (s, 1H); 9.12 (s, 1H) Mass: 448.8/450.8 [M + H]+ (MP: 194-196° C.) |
| 5-39 | 2-(2-Methoxy-4-methyl-pyridin-3-yl)-5-(trifluoromethyl)phenol from 2-methoxy-3-bromo-4-methylpyridine and 2-hydroxy-4-(trifluoromethyl)-phenylboronic acid (Protocol SA; 10 min at 120° C. on microwave). Eluent: cyclohexane/AcOEt 8/2 v/v (Yield: 51%) | (DMSO-d$_6$): 2.00 (s, 3H); 3.74 (s, 3H); 6.94 (d, 1H, J = 5.2 Hz); 7.17-7.25 (m, 3H); 8.05 (d, 1H, J = 5.1 Hz); 10.08 (s, 1H) |
| | 3,6-Dichloro-8-methyl-[1,2,4]triazolo[4,3-b]pyridazine and 2-(2-methoxy-4-methylpyridin-3-yl)-5-(trifluoromethyl)phenol (Protocol SB; K$_2$CO$_3$ (3 eq); 10 min at 120° C. on microwave). Eluent: cyclohexane/AcOEt 3/7 v/v (Yield: 69%) | White solid (DMSO-d$_6$): 2.05 (s, 3H); 2.52 (d, 3H, J = 1.0 Hz); 3.66 (s, 3H); 6.85 (d, 1H, J = 5.3 Hz); 7.03 (d, 1H, J = 1.3 Hz); 7.64 (d, 1H, J = 8.0 Hz); 7.78 (d, 1H, J = 8.0 Hz); 7.97 (s, 1H); 7.98 (d, 1H, J = 5.1 Hz) Mass: 449.9 [M + H]+ (MP: 139-141° C.) |
| 5-40 | 3,6-Dichloro-7-methyl-[1,2,4]triazolo[4,3-b]pyridazine and 2-(2-methoxy-4-methylpyridin-3-yl)-5-(trifluoromethyl)phenol (Protocol SB; K$_2$CO$_3$ (3 eq); 15 min at 110° C. on microwave). Eluent: AcOEt (Yield: 40%). | White solid (DMSO-d$_6$): 2.02 (s, 3H); 2.07 (d, 3H, J = 0.9 Hz); 3.65 (s, 3H); 6.83 (d, 1H, J = 5.2 Hz); 7.67 (d, 1H, J = 8.0 Hz); 7.82 (d, 1H, J = 8.0 Hz); 7.99 (d, 1H, J = 5.8 Hz); 8.02 (s, 1H); 8.16 (d, 1H, J = 1.2 Hz) Mass: 449.9 [M + H]+ (MP: 161-162° C.) |
| 5-41 | 2-(2-Methoxy-5-fluoropyridin-3-yl)-5-(trifluoromethyl)phenol from 2-hydroxy-4-(trifluoromethyl)phenyl-boronic acid and 3-bromo-5-fluoro-2-methoxypyridine (Protocol SA; 10 min at 120° C. on microwave) Trituration in heptane (Yield: 49%) | (DMSO-d$_6$): 3.81 (s, 3H); 7.18-7.20 (m, 2H); 7.41 (d, 1H, J = 7.4 Hz); 7.69 (dd, 1H, J = 8.6 Hz, J = 3.1 Hz); 8.18 (d, 1H, J = 3.0 Hz); 10.32 (s, 1H) |
| | 3,6-Dichloro-7-methyl-[1,2,4]triazolo[4,3-b]pyridazine and 2-(2-methoxy-5-fluoropyridin-3-yl)-5-(trifluoromethyl)phenol (Protocol SB; K$_2$CO$_3$ (3 eq); 15 min at 110° C. on microwave). Eluent: cyclohexane/AcOEt 3/7 v/v (Yield: 68%). | White solid (DMSO-d$_6$): 2.15 (d, 3H, J = 1.3 Hz); 3.63 (s, 3H); 7.63-7.84 (m, 3H); 8.12 (s, 1H); 8.20 (d, 1H, J = 3.0 Hz); 8.24 (d, 1H, J = 1.4 Hz) Mass: 453.87 [M + H]+ (MP: 163-166° C.) |
| 5-45 | 2-(4-Methylpyrimidin-5-yl)-5-(trifluoromethyl)phenol from 2-hydroxy-4-(trifluoromethyl)phenyl-boronic acid and 5-bromo-1-methyl-1H-imidazole (Protocol SA; 15 min at 120° C. on microwave) Eluent: cyclohexane/AcOEt 6/4 v/v (Yield: 66%). | (DMSO-d$_6$): 2.34 (s, 3H); 7.27-7.29 (m, 2H); 7.44 (d, 1H, J = 7.6 Hz); 8.55 (s, 1H); 9.06 (s, 1H); 10.56 (s, 1H) |

TABLE 3-2-continued

Ra is W, at least one Rf-Rj is other than hydrogen atom, at least one of Rb-Re
is other than hydrogen atom, and at least one R2 or R3 is not hydrogen

| Cpd. | Starting compounds Reaction conditions and purification | Appearance, $^1$H NMR (solvent) data, Mass (ES+ or ES−) data (MP) |
|---|---|---|
| | 3,6-Dichloro-8-methyl-[1,2,4]triazolo[4,3-b]pyridazine and 2-(4-methylpyrimidin-5-yl)-5-(trifluoromethyl)phenol (Protocol SB; 15 min at 110° C. on microwave). Eluent: dichloromethane/MeOH 95/5 v/v (Yield: 67%). | Yellow solid (DMSO-$d_6$): 2.38 (s, 3H); 2.54 (s, 3H); 7.18 (s, 1H); 7.82-7.90 (m, 2H); 8.08 (s, 1H); 8.61 (s, 1H); 9.01 (s, 1H) Mass: 421/423 [M + H]+ (MP: 186-188° C.). |
| 5-47 | 3,6-Dichloro-7-methyl-[1,2,4]triazolo[4,3-b]pyridazine and 2-(4-methylpyrimidin-5-yl)-5-(trifluoromethyl)phenol (Protocol SB; 15 min at 110° C. on microwave). Eluent: dichloromethane/MeOH 95/5 v/v then trituration in diethyl ether (Yield: 55%); | White solid (DMSO-$d_6$): 2.38 (s, 3H); 2.20 (d, 3H, J = 0.9 Hz); 2.37 (s, 3H); 7.85-7.92 (m, 2H); 8.14 (s, 1H); 8.21 (d, 1H, J = 1.2 Hz); 8.65 (s, 1H); 9.00 (s, 1H) Mass: 421/423 [M + H]+ (MP: 123-125° C.). |
| 5-50 | 2-(2,4-Dimethoxypyrimidin-5-yl)-5-(trifluoromethyl)phenol from 2,4-dimethoxypyrimidin-5-yl-boronic acid and 2-bromo-5-(trifluoromethyl)phenol (Protocol SA; 15 min at 120° C.) Eluent: cyclohexane/AcOEt 7/3 v/v (Yield: 24%). | (DMSO-$d_6$): 4.09 (s, 3H); 4.10 (s, 3H); 7.31-7.35 (m, 3H); 8.32 (s, 1H) |
| | 3,6-Dichloro-8-methyl-[1,2,4]triazolo[4,3-b]pyridazine and 2-(2,4-dimethoxypyrimidin-5-yl)-5-(trifluoromethyl)phenol (Protocol SB; $K_2CO_3$ (3 eq); 15 min at 110° C. on microwave). Eluent: dichloromethane/MeOH 95/5 v/v (Yield: 87%) | Beige solid (DMSO-$d_6$): 2.59 (d, 3H, J = 1.2 Hz); 3.74 (s, 3H); 3.91 (s, 3H); 7.19 (d, 1H, J = 1.1 Hz); 7.73-7.81 (m, 2H); 8.02 (s, 1H); 8.32 (s, 1H) Mass: 467/469 [M + H]+ (MP: 164-165° C.). |
| 5-51 | 3,6-Dichloro-7-methyl-[1,2,4]triazolo[4,3-b]pyridazine and 2-(2,4-dimethoxypyrimidin-5-yl)-5-(trifluoromethyl)phenol (Protocol SB; $K_2CO_3$ (3 eq); 15 min at 110° C. on microwave). Eluent: dichloromethane/MeOH 95/5 v/v (Yield: 84%) | White solid (DMSO-$d_6$): 2.22 (d, 3H, J = 0.9 Hz); 3.75 (s, 3H); 3.91 (s, 3H); 7.75-7.83 (m, 2H); 8.10 (s, 1H); 8.26 (d, 1H, J = 1.2 Hz); 8.35 (s, 1H) Mass: 467/469 [M + H]+ (MP: 161-163° C.). |
| 5-52 | 2-(4-Ethylpyrimidin-5-yl)-5-(trifluoromethyl)phenol from 2-hydroxy-4-(trifluoromethyl)phenyl-boronic acid and 5-bromo-1-ethyl-1H-imidazole (Protocol SA; 15 min at 120° C.) Trituration in diethyl ether (Yield: 69%). | (DMSO-$d_6$): 1.35 (t, 3H, J = 7.0 Hz); 2.60 (q, 2H, J = 7.0 Hz); 7.2-7.3 (m, 2H); 7.42 (d, 1H, J = 7.6 Hz); 8.53 (s, 1H); 9.12 (s, 1H); 10.52 (s, 1H) |
| | 3,6-Dichloro-7-methyl-[1,2,4]triazolo[4,3-b]pyridazine and 2-(4-ethylpyrimidin-5-yl)-5-(trifluoromethyl)phenol (Protocol SB; $K_2CO_3$ (3 eq); 10 min at 120° C. on microwave) Eluent: dichloromethane/AcOEt 3/7; then trituration in diethyl ether v/v (Yield: 72%) | White solid (DMSO-$d_6$): 1.05 (t, 3H, J = 7.0 Hz); 2.16 (d, 3H, J = 1.4 Hz); 2.64 (s large, 2H); 7.84 (d, 1H, J = 8.0 Hz); 7.91 (dd, 1H, J = 8.0 Hz, J = 1.1 Hz); 8.14 (d, 1H); 8.20 (d, 1H, J = 1.4 Hz); 8.63 (s, 1H); 9.08 (s, 1H) Mass: 434/436 [M + H]+ (MP: 186-188° C.). |
| 5-53 | 3,6-Dichloro-8-methyl-[1,2,4]triazolo[4,3-b]pyridazine and 2-(4-ethylpyrimidin-5-yl)-5-(trifluoromethyl)phenol (Protocol SB; $K_2CO_3$ (3 eq); 10 min at 120° C. on microwave) Eluent: dichloromethane/AcOEt 3/7; then trituration in diethyl ether v/v (Yield: 40%) | White solid (DMSO-$d_6$): 1.10 (t, 3H, J = 7.6 Hz); 2.54 (d, 3H, J = 1.4 Hz); 2.64 (q, 2H, J = 7.6 Hz); 7.15 (d, 1H, J = 1.4 Hz); 7.81 (d, 1H, J = 8.0 Hz); 7.85 (dd, 1H, J = 8.0 Hz, J = 1.1 Hz); 8.14 (d, 1H, J = 1.1 Hz); 8.60 (s, 1H); 9.08 (s, 1H) Mass: 434/436 [M + H]+ (MP: 173-175° C.). |
| 5-54 | 3,6-Dichloro-[1,2,4]triazolo[3,4-a]phthalazine and 2-(2,4-dimethoxypyrimidin-5-yl)-5-(trifluoromethyl)phenol (Protocol SB; $K_2CO_3$ (3 eq); 15 min at 110° C. on microwave) Precipitation with water; washings with EtOH then diethyl ether v/v (Yield: 45%) | White solid (DMSO-$d_6$): 3.70 (s, 3H); 3.84 (s, 3H); 7.79-7.86 (m, 2H); 8.00 (t, 1H, J = 7.0 Hz); 8.12-8.19 (m, 3H); 8.42 (s, 1H); 8.52 (d, 1H, J = 7.9 Hz) Mass: 503 [M + H]+ (MP: 240° C.). |

TABLE 3-2-continued

Ra is W, at least one Rf-Rj is other than hydrogen atom, at least one of Rb-Re is other than hydrogen atom, and at least one R2 or R3 is not hydrogen

| Cpd. | Starting compounds<br>Reaction conditions and purification | Appearance, $^1$H NMR (solvent) data,<br>Mass (ES+ or ES−) data (MP) |
|---|---|---|
| 5-55 | 4-Chloro-2-(2-methoxypyrimidin-5-yl)phenol from 2-bromo-4-chlorophenol and 2-methoxy-pyrimidin-5-yl-boronic acid (Protocol SA; 15 min at 120° C.) Eluent: cyclohexane/AcOEt 5/5 v/v (Yield: 38%). | (DMSO-$d_6$): 3.96 (s, 3H); 6.99 (d, 1H, J = 8.8 Hz); 7.27 (dd, 1H, J = 8.7 Hz, J = 2.6 Hz); 70.44 (d, 1H, J = 2.6 Hz); 8.80 (s, 2H); 10.22 (s(l), 1H) |
|  | 3,6-Dichloro-8-methyl-[1,2,4]triazolo[4,3-b]pyridazine and 4-chloro-2-(2-methoxypyrimidin-5-yl)phenol (Protocol SB; K$_2$CO$_3$ (3 eq); 15 min at 110° C. on microwave). Eluent: dichloromethane/MeOH 95/5 v/v (Yield: 49%) | White solid<br>(DMSO-$d_6$): 2.59 (s, 3H); 3.92 (s, 3H); 7.26 (s, 1H); 7.56-7.66 (m, 2H); 7.79 (s, 1H); 8.76 (s, 2H)<br>Mass: 403 [M + H]+ (MP: 170-172° C.). |
| 5-56 | 3,6-Dichloro-7-methyl-[1,2,4]triazolo[4,3-b]pyridazine and 4-chloro-2-(2-methoxypyrimidin-5-yl)phenol (Protocol SB; K$_2$CO$_3$ (3 eq); 10 min at 110° C. on microwave). Eluent: dichloromethane/MeOH 95/5 v/v (Yield: 43%) | White solid<br>(DMSO-$d_6$): 2.32 (d, 3H, J = 0.9 Hz); 3.92 (s, 3H); 7.65 (s, 2H); 7.79 (s, 1H); 8.26 (d, 1H, J = 1.2 Hz); 8.76 (s, 2H)<br>Mass: 403 [M + H]+ (MP: 189-192° C.). |
| 5-57 | 3,6-Dichloro-[1,2,4]triazolo[3,4-a]phthalazine and 4-chloro-2-(2-methoxypyrimidin-5-yl)phenol (Protocol SB; K$_2$CO$_3$ (3 eq); 10 mn at 110° C. on microwave) Precipitation with water; washings with diethyl ether (Yield: 51%) | White solid<br>(DMSO-$d_6$): 3.86 (s, 3H); 7.66-7.75 (m, 2H); 7.83 (d, 1H, J = 2.3 Hz); 8.01 (t, 1H, J = 7.3 Hz); 8.15 (t, 1H, J = 7.6 Hz); 8.40 (d, 1H, J = 8.2 Hz); 8.52 (d, 1H, J = 7.9 Hz); 8.87 (s, 2H)<br>Mass: 439 [M + H]+ (MP: 213-215° C.). |

Example 3

Cellular Activation Assay of Rev-Erb Alpha or Rev-Erb Beta by Compounds According to the Invention Materials & Methods Fusion Proteins In this system, Rev-Erb alpha or Rev-Erb beta is expressed as a fusion to the Gal4 DNA-binding domain and the cofactor NCoR is expressed as a fusion to the activation domain of the Herpes Simplex Virus tegument protein VP16. These fusion proteins were included in plasmids at a concentration of 1 μg/μL. The pBS-SK+ vector was added to the preparation to adjust the DNA quantity to a fixed value for each condition.

Transfection Mix

The transfection mix (Jet-PEI protocol, Polyplus transfection) comprised:
3 mL of Jet PEI Mix (180 μL Jet-Pei and NaCl at 150 mM) and
3 mL of the DNA Mix or of the DNA Mix control (wherein the Gal4-Rev-Erb alpha plasmid was replaced by a pGal4phi plasmid).
DNA Mix comprised 1.2 mL of DNA and 1.8 mL of NaCl at 150 mM with, in a T225 flask:
90 ng of Gal4-Rev-Erb alpha, or 90 ng of Gal4-Rev-Erb beta,
4500 ng of VP16-NCoR,
27000 ng of Gal4-RE and
13410 ng of pBS-SK+.

Cells

HEK293 cells were cultured in DMEM (Invitrogen 41965) comprising 10% FBS, P/S, 1% glutamine, 1% pyruvate (Invitrogen 11360) and 1% amino acids (Invitrogen 11140). Cells were then batch co-transfected with plasmid vectors (described in the table above) using as Jet-PEI as reagent (Polyplus) following the protocol specified below.

The 6 mL-transfection mix was transferred in a T225 flask. HEK293 cells were then added at a concentration of 12 Millions of cells for 54 mL of medium (DMEM comprising 10% FBS and 1% P/S). Cells incubated over-night at 37° C. and under 5% CO2.

The following protocol has been adapted to run on a robotic platform.

M2H Assay

This cell-based assay is performed using 384-well Greiner white plates (Reference 781080). After the incubation, cells were rinsed with PBS, trypsinized, centrifuged and resuspended in free-serum DMEM without phenol red (Invitrogen 31053). Cells were counted and adjusted to 0.5 Million per mL and plated at a concentration of 10,000 cells in 20 μL per well. They were incubated a minimum of 4 hours at 37° C. under 5% CO$_2$. Cells were treated with 20 μL of the compound to analyze (concentration of 2× diluted in DMEM without FBS containing a maximum of 1% DMSO) and incubated over-night (18 hours, 37° C. and 5% CO$_2$). Each compound has been tested at 6 different concentrations to depict a dose-effect allowing the measure of biochemical parameters such as EC50 and TOP activation (%).

Luminescence Measurement

Cells were incubated 30 minutes with 40 μL/well of Steady Glow (Promega) and luminescence was read with TECAN Genios Pro (100 ms/w). Four experiments were carried out for each compound.

Each compound has been tested at 6 different concentrations to depict a dose-effect allowing the measure of biochemical parameters such as EC$_{50}$ and TOP activation (%).

Results & Conclusions

The mammalian two-hybrid system (M2H) assay consists herein in studying the ability of compounds according to the invention to activate Rev-Erbalpha in cells and thus modulate the interaction with its corepressor. The interaction of the two proteins is assessed with the help of the Luciferase reporter gene. HEK293 cells were transfected with two gene constructions: Gal4-RE VP16-NCoR and Gal4-Rev-Erbalpha or with Gal4-RE, sVP16-NCoR and Gal4-Rev-Erb beta.

The ability of compounds according to the invention of activating Rev-Erbalpha alpha or Rev-Erb beta was assessed in the described cell-based assay. $EC_{50}$ and TOP activation (%) were measured. Compounds which displayed an $EC_{50}$ inferior to 6 µM in the M2H assay or a TOP activation of at least 130% (relative to the activation obtained with the DMSO) were considered Rev-Erbalpha agonists or Rev-Erb beta agonists.

M2H Rev-Erb Alpha:

Compounds belonging to General formula (I) such as Cpd.1-11, Cpd.1-12, Cpd.1-13, Cpd.1-14, Cpd.4-63, Cpd.4-65, Cpd.4-70, Cpd.4-86, Cpd.4-88, Cpd.4-89, Cpd.4-92, Cpd.4-96, Cpd.4-98, Cpd.4-103, Cpd.4-104, Cpd.4-107, Cpd.4-109, Cpd.4-124, Cpd.4-140, Cpd.4-147, Cpd.4-156, Cpd.4-157, Cpd.4-159, Cpd.4-163, Cpd.4-171, Cpd.4-177, Cpd.4-180, Cpd.4-194, Cpd.4-195, Cpd.4-199, Cpd.5-32, Cpd.5-44, Cpd.5-46, Cpd.5-54, and Cpd.5-59 displayed an $EC_{50}$ superior to 6 µM while having a TOP activation superior to 130% at the tested dose.

Several compounds belonging to General formula (I) displayed an $EC_{50}$ comprised between 1 and 6 µM in particular Cpd.1-1, Cpd.1-8, Cpd.2-1, Cpd.2-3, Cpd.2-4, Cpd.3-7, Cpd.3-8, Cpd.3-11, Cpd.3-12, Cpd.3-14, Cpd.4-5, Cpd.4-8, Cpd.4-9, Cpd.4-11, Cpd.4-12, Cpd.4-32, Cpd.4-36, Cpd.4-41, Cpd.4-42, Cpd.4-48, Cpd.4-49, Cpd.4-61, Cpd.4-62, Cpd.4-64, Cpd.4-66, Cpd.4-72, Cpd.4-73, Cpd.4-75, Cpd.4-77, Cpd.4-79, Cpd.4-82, Cpd.4-84, Cpd.4-87, Cpd.4-97, Cpd.4-99, Cpd.4-100, Cpd.4-105, Cpd.4-106, Cpd.4-119, Cpd.4-122, Cpd.4-125, Cpd.4-126, Cpd.4-127, Cpd.4-128, Cpd.4-129, Cpd.4-130, Cpd.4-134, Cpd.4-138, Cpd.4-141, Cpd.4-142, Cpd.4-145, Cpd.4-148, Cpd.4-149, Cpd.4-150, Cpd.4-151, Cpd.4-152, Cpd.4-153, Cpd.4-154, Cpd.4-155, Cpd.4-160, Cpd.4-161, Cpd.4-162, Cpd.4-164, Cpd.4-165, Cpd.4-166, Cpd.4-167, Cpd.4-168, Cpd.4-173, Cpd.4-174, Cpd.4-176, Cpd.4-178, Cpd.4-179, Cpd.4-182, Cpd.4-183, Cpd.4-184, Cpd.4-186, Cpd.4-187, Cpd.4-190, Cpd.4-191, Cpd.4-192, Cpd.4-196, Cpd.5-23, Cpd.5-24, Cpd.5-25, Cpd.5-26, Cpd.5-27, Cpd.5-28, Cpd.5-29, Cpd.5-30, Cpd.5-31, Cpd.5-33, Cpd.5-35, Cpd.5-37, Cpd.5-38, Cpd.5-39, Cpd.5-40, Cpd.5-42, Cpd.5-43, Cpd.5-45, Cpd.5-47, Cpd.5-48, Cpd.5-49, Cpd.5-50, Cpd.5-51, Cpd.5-52, Cpd.5-53, Cpd.5-55, Cpd.5-56, Cpd.5-58, Cpd.5-61, Cpd.5-62, Cpd.5-63, Cpd.5-64, and Cpd.5-65.

Cpd.1-2, Cpd.3-1, Cpd.3-2, Cpd.3-3, Cpd.3-4, Cpd.3-5, Cpd.3-6, Cpd.3-9, Cpd.3-10, Cpd.3-13, Cpd.4-2, Cpd.4-3, Cpd.4-4, Cpd.4-6, Cpd.4-7, Cpd.4-10, Cpd.4-13, Cpd.4-14, Cpd.4-15, Cpd.4-16, Cpd.4-17, Cpd.4-19, Cpd.4-20, Cpd.4-21, Cpd.4-22, Cpd.4-23, Cpd.4-24, Cpd.4-26, Cpd.4-28, Cpd.4-29, Cpd.4-30, Cpd.4-31, Cpd.4-34, Cpd.4-35, Cpd.4-37, Cpd.4-38, Cpd.4-39, Cpd.4-40, Cpd.4-50, Cpd.4-51, Cpd.4-52, Cpd.4-53, Cpd.4-54, Cpd.4-56, Cpd.4-57, Cpd.4-58, Cpd.4-60, Cpd.4-68, Cpd.4-69, Cpd.4-71, Cpd.4-76, Cpd.4-78, Cpd.4-80, Cpd.4-81, Cpd.4-101, Cpd.4-108, Cpd.4-110, Cpd.4-111, Cpd.4-113, Cpd.4-114, Cpd.4-115, Cpd.4-116, Cpd.4-117, Cpd.4-118, Cpd.4-120, Cpd.4-121, Cpd.4-123, Cpd.4-131, Cpd.4-132, Cpd.4-133, Cpd.4-135, Cpd.4-136, Cpd.4-137, Cpd.4-139, Cpd.4-143, Cpd.4-144, Cpd.4-146, Cpd.4-158, Cpd.4-169, Cpd.4-170, Cpd.4-172, Cpd.4-175, Cpd.4-181, Cpd.4-185, Cpd.4-188, Cpd.4-193, Cpd.4-197, Cpd.4-198, Cpd.5-2, Cpd.5-3, Cpd.5-5, Cpd.5-7, Cpd.5-9, Cpd.5-10, Cpd.5-11, Cpd.5-12, Cpd.5-13, Cpd.5-14, Cpd.5-16, Cpd.5-17, Cpd.5-18, Cpd.5-19, Cpd.5-20, Cpd.5-21, Cpd.5-22, Cpd.5-34, Cpd.5-36, Cpd.5-41, Cpd.5-57, and Cpd.5-60 displayed an $EC_{50}$ comprised between 0.1 and 1 µM.

Best compounds such as Cpd.4-1 (FIG. 10), Cpd.4-18, Cpd.4-25, Cpd.4-27, Cpd.4-33, Cpd.4-43, Cpd.4-44, Cpd.4-45, Cpd.4-46, Cpd.4-47, Cpd.4-55, Cpd.4-67, Cpd.4-112, Cpd.4-189, Cpd.5-1, Cpd.5-6, and Cpd.5-15, displayed an $EC_{50}$ inferior to 0.1 µM.

Indeed, less satisfactory results were obtained with compounds presenting specific substitutions in R1 as an oxygen atom (such as Cpd.1-5) or a phenyl or benzyl group (such as Cpd.1-6 and Cpd.1-7, respectively).

M2H Rev-Erb Beta:

The compounds of interest were tested. Some compounds belonging to General formula (I) such as Cpd.4-46, 4-45, 4-18, 4-58, 4-54 and Cpd 4-19 displayed an EC50 comprised between 0.1 and 1 µM.

Example 4

TR-FRET Assay of Rev-Erb Alpha

Materials & Methods

TR-FRET Reagents

Recombinant histidine-tagged Rev-Erb alpha ligand binding domain (LBD; SEQ ID NO: 1) and NCoR peptide ID1 (SEQ ID NO: 2) were tagged with fluorophores. Histidine-tagged Rev-Erb alpha LBD protein was set up in a one to one ratio of 20 nM of His D2 (Cis Bio International 61HSDLB). The NCoR peptide (ID1) was prepared in-house. We used a concentration of 30 nM NCoR and 10 nM Terbium-labeled streptavidin (Cis Bio International 610SATLB).

TR-FRET Assay

The buffer for this assay comprised PBS pH 7.2, $NaH_2PO_4$ at 4 g/L, $Na_2HPO_4$ at 27 g/L and NaCl at 9 g/l in deionized water. Before using the buffer in the assay, a mixture comprising 1 mM of DTT, 2 mM of CHAPS, 1 mM of EDTA and 0.1% BSA fatty acid free was added to the appropriate amount of buffer. The protein mixture comprising recombinant Rev-Erb alpha LBD His (20 nM), the NCoR ID1 (30 nM) and their respective fluorophores were added to each well of a 384-well plate in a volume 18 µl. The compounds to analyze were diluted in PBS 10% DMSO and was added in a volume of 2 µL in a well. The final mixture volume was 20 µL and the mixture was allowed equilibrate for 2 hours at room temperature. Fluorescence intensity was then counted on the TECAN Genios Pro as a ratio of the fluorescence measured at 665 nm and that measured at 620 nm obtained in the absence of the compound (buffer only) or with the compound. Four experiments were carried out for each compound.

Each compound has been tested at 6 different concentrations to depict a dose-effect enabling the measure of biochemical parameters such as EC50 and TOP activation (%).

Results & Conclusions

The Homogenous Time Resolved Fluorescence (HTRF) assay allows studying the ability of compounds according to the invention to activate Rev-Erb alpha and thus modulate the interaction with its corepressor. The molecular interactions between these bio-molecules are assessed in a cell-free assay by coupling each partner with a fluorescent label and detecting the level of energy transfer. This energy transfer occurs when the distance between the donor (SA Terbium complex) and the acceptor (D2) is small enough.

The ability of compounds according to the invention of activating Rev-Erb alpha was assessed in the described acellular assay. $EC_{50}$ and TOP activation were measured. Compounds which displayed an $EC_{50}$ inferior to 6 µM in the TR-FRET assay and a TOP activation of at least 150% (relative to the activation obtained with DMSO) were considered Rev-Erb alpha agonists.

Several compounds belonging to General Formula (I) displayed an $EC_{50}$ comprised between 1.1 and 6 µM in particular Cpds 1-3, 1-4, 1-8, 1-9, 2-2, 3-3, 4-1 (FIG. 7b), 4-11 and 4-12. Cpds 1-1, 1-2, 2-3, 2-4, 3-1, 3-4, 3-5, 4-4, 4-5, 4-8 and 4-9 displayed an $EC_{50}$ comprised between 0.1 and 1 µM. Best compounds (such as Cpds. 3-2, 4-3, 4-6, 4-7, 4-10) displayed an $EC_{50}$ inferior to 0.1 µM.

At this scope, the metabolic stability of said compounds can be established for evaluating their suitability for in vivo studies where efficacy and pharmacokinetic parameters for therapeutic administration (such as clearance) can be assessed. Compounds that present satisfactory level of metabolic stability on in mouse or human liver microsomes (for example more than 40% of parent remaining after a 1-hour incubation) can be considered suitable for in vivo studies. Similar properties have been demonstrated for a number of compounds of General Formula (I) and in particular for those presenting a halogenated group (such as Chlorine atom, a fluorine atom or a $CF_3$ group) in R1 and in Rc and/or Rd positions, and in presence or not of a W group in either Ra and/or Rb positions.

Example 5

In Vivo Evaluation of Compound Cpd-4-39

Compound 4-39 of the invention has been tested in a T2 diabetic related mouse model, the db/db mice.
Experimental Protocol Description
Animals 7-weeks-old male db/db mice were purchased from Charles River (France). Mice were 9-weeks-old at the beginning of the study. All mice were housed 2 per cage under controlled conditions of humidity, lighting and temperature. They had free access to food (R03, SAFE) and water.

Mice were randomized according to their body weight, and the non-fasting glycaemia, and assigned to 3 different groups:
Group 1: Control_Vehicle n=8
Group 2: Cpd-4-39 25 mg/kg n=8
Group 3: Cpd-4-39 100 mg/kg n=8
Treatments and Sample Analysis The treatments were administered once daily, by gavage (10 mL/kg) for 28 consecutive days (unless otherwise mentioned). For oral administrations, compound was suspended in CMC 1%+Tween 80 0.1%.

Non fasting blood glucose level was determined from tail vein blood using a glucometer (Smart Chek, Kitvia), Blood samples were withdrawn under anesthesia by retro-orbital puncture at the end of the treatment period. Tubes containing blood were rapidly centrifuged after collection (15 minutes at 4,000 rpm/4° C.) and the plasma fraction was collected. Plasma aliquots were stored at −20° C. for further analyses.
HbA1c The blood concentration of glycosylated hemoglobin A1c was determined using the Randox kit for Daytona automate (Randox, cat# HA 3830) according to the manufacturer's recommendations. Total hemoglobin and HbA1c concentrations were measured and the HbA1c result was expressed as a percentage of the total hemoglobin concentration.
Triglycerides The triglyceride content of plasma was measured using the Randox kit for Daytona automate (Randox, cat# TR 3823) according to the manufacturer's recommendations. In this protocol, the triglycerides are hydrolyzed by a lipase. The resulting glycerol concentration is then measured by an enzymatic method and spectrophotometric measurement. Results are expressed in mg/dL.
Oral Glucose Tolerance Test Oral glucose tolerance test (OGTT) was performed as followed, at day 35 of treatment, after a 16-hour fasting period, an oral glucose load was administered at T=0 (2 g/kg of glucose, 10 mL/kg) and glycemia was measured at the tail vein at T=15, 30, 60, 90, 120 & 180 minutes.

At the end of the treatment period, animals were anesthetized with isoflurane and then sacrificed by cervical dislocation. Liver, quadriceps muscle and epididymal adipose tissues were collected. The Student's t-test was used to test for statistical differences between drug and vehicle treatments when a single dose of drug was used while ANOVA followed by Dunnett's Multiple Comparison post hoc test was used for dose responses.
Results As presented on FIG. 12 (a) glycemia from db/db mice treated with compound Cpd-4-39 at 100 mpk is significantly reduced compared to control mice (CMC/vehicule). In addition to the reduction of circulating glucose, HbA1c FIG. 12 (b) is also significantly reduced in Cpd-4-39 treated animals. Circulating triglycerides were also reduced in db/db mice treated with Cpd-4-39 FIG. 12 (c). Those results indicate that an orally given Rev-Erb alpha ligand is able to modify important blood indicators of the pharmacological impact of therapeutic intervention intended to improve metabolic disorders and T2 diabetes in particular in the considered models.

Gene expression studies have been performed on mRNA isolated from different metabolic tissues such as liver, adipose tissue and skeletal muscle. Small is considered as a target gene of Rev-Erbα. Activation of Rev-Erbα activity should then translate in a reduction of Small gene expression. As depict on FIGS. 13 (a, b, c) the treatment of db/db mice with Cps-4-39 has lead to a significant inhibition of Small expression in the studied organs.

Oral glucose tolerance test is a widely used assay perform to assess the body's tolerance to an orally glucose bolus, it is considered as a good marker of insulin resistance and diabetes. Mice treated with Cpd-4-39 showed an improved evolution of their blood glucose FIG. 14(a) through the time of the experiment. Improvement of the body's insulin sensitivity is illustrated on FIG. 3(b). Determination of the area under the curve clearly demonstrates the Cpd-4-39 dependent effect on glucose tolerance in db/db mice.

Example 6

In Vivo Evaluation of Compound Cpd-4-99

Compound 4-99 of the invention has been tested in a metabolic disorder related mouse model, the Diet Induced Obesity mice (high fat diet).
Experimental Protocol Description
Animals Four week-old male C57Bl/6J mice (from Janvier, France) were fed with an high fat diet (D12492, SSNIFF) for up to 10 weeks. All mice were housed 2 per cage under controlled conditions of humidity, lighting and temperature. At the end of the 10 week of diets, mice were randomized according to their body weight gain, body weight, and their non-fasting glycaemia. The treatments with compound of interest were administered once daily, by gavage (10 mL/kg) for 28 consecutive days. For oral administrations, the drugs were suspended in CMC 1%+Tween 80 0.1%.

As previously described animals were assayed for their non fasting glycaemia and biochemical parameters such as Hb1Ac.

At the end of the treatment period, animals were anesthetized with isoflurane and then sacrificed by cervical dislocation. The Student's t-test was used to test for statistical differences between drug and vehicle treatments when a single dose of drug was used.

After 28 days of treatment, Cpd-4-99 compound is able to significantly reduce the non fasting blood glucose concentration (FIG. 15a). Hb1Ac levels are also significantly reduced (FIG. 15b). As obtained with Cpd-4-39 compound Cpd-4-99 is able to reduce and improve two important parameters such as glycemia and Hb1Ac regarding the Type 2 diabetes pathology or related pathologies.

REFERENCES

Ando H et al., 2005. Endocrinology; 146: 5631-6.
Anzulovich A et al., 2006. J Lipid Res; 47: 2690-700.
Barish G D et al., 2005. Mol Endocrinol; 19: 2466-77.
Bauer M, 2004. STP Pharma Pratiques. 14: 281-291.
Burris T P, 2008. Mol Endocrinol; 22: 1509-20.
Carey J et al., 2006. Org Biomol Chem; 4: 2337-47.
Chaturvedi P et al., 2006. Arthritis Rheum; 54: 3513-22.
Chawla A and Lazar M, 1993. J Biol Chem; 268: 16265-9.
Cho H et al., 2012. Nature; 485:123-7.
Colombo M and Peretto I, 2008. Drug Discov Today; 13: 677-84.
Di L et al., 2009. Curr Pharm Des; 15: 2184-94.
Duez H et al., 2009. J Appl Physiol; 107: 1972-80.
Erdemir D et al., 2007. Curr Opin Drug Discov Devel; 10: 746-55.
Fontaine C et al., 2003. J Biol Chem; 278: 37672-80.
Fontaine C et al., 2008. Mol Endocrinol; 22: 1797-811.
Grant D et al., 2010. ACS Chem Biol; 5: 925-32.
Green C B et al., 2008. Cell; 134: 728-42.
Guan L P et al., 2010. Eur J Med Chem; 45: 1746-52.
Harding and Lazar, 1995. Mol Cell Biol; 15: 4791-802.
Kojetin D et al., 2010. ACS Chem Biol; 6: 131-4.
Kojetin D et al., 2011. Curr Pharm Des; 17: 320-4.
Kumar N et al., 2010. Endocrinology; 151: 3015-25.
Kumar L et al., 2007. Drug Discov Today; 12: 1046-53.
Lund J et al., 2001. J Endocrinol; 171: 557-64.
Mayr L and Bojanic D, 2009. Curr Opin Pharmacol; 9: 580-8.
McKenna and O'Malley, 2002. Endocrinology; 143: 2461-5.
Meng Q J et al., 2008. J Cell Sci; 121: 3629-35.
Migita H et al., 2004. FEBS Lett; 561: 69-74.
Moore J T et al., 2006. ChemMedChem; 1: 504-23.
Morissette S et al., 2004. Adv Drug Deliv Rev; 56: 275-300.
Mutlib A E, 2008. Chem Res Toxicol; 21: 1672-89.
O'Driscoll C, 2009. Chemistry & Industry; 5: 24-6.
Preitner N et al., 2002. Cell; 110: 251-60.
Raghuram S et al., 2007. Nat Struct Mol Biol; 14: 1207-13.
Ramakrishnan S et al., 2005. J Biol Chem; 280: 8651-9.
Raspe E et al., 2001. J Biol Chem; 276: 2865-71.
Raspe E et al., 2002. J Lipid Res; 43: 2172-9.
Roughley S and Jordan A, 2011. J Med Chem; 54: 3451-79.
Sato T K et al., 2004. Neuron; 43: 527-37.
Solt L et al., 2011. Future Med Chem; 3: 623-38.
Solt L A et al.; 2012. Nature; 485: 62-8.
Suwazono Y et al., 2008. Obesity (Silver Spring); 16: 1887-93.
Villar H and Hansen M, 2009. Curr Opin Drug Discov Devel; 12: 367-75.
Wishart D, 2008. Drugs R&D; 9: 307-22.
Yin L et al., 2007. Science; 318: 1786-9.
Yin S and Grosso J, 2008. Curr Opin Drug Discov Devel; 11: 771-7.
Zhao H and Guo Z, 2009. Drug Discov Today; 14: 516-22.

The invention claimed is:
1. A compound of General Formula (I)

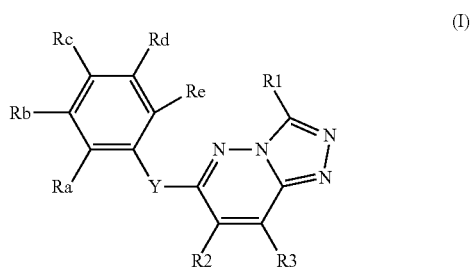

wherein

R1 represents a hydrogen atom, a halogen atom, an amino group, a hydroxyl group, a COOH group, a CO-alkyl group, a COO-alkyl group, a $CONH_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a $CONH_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, with a cycloalkylamino group, with an alkylcarbamate group, or with an heterocyclic group substituted or not with an alkyl group, or with an alkylsulfonyl group, wherein either Ra represents a W or W—Z— group, and Rb represents a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group; and W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

each of Y and Z represents independently an oxygen atom, a sulphuratom, a CH$_2$, or a carbonyl group;

with the proviso that when Rb is a W—Z group and Z is a CH$_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group;

wherein at least one group of Ra, Rb, Rc, Rd and Re is a halogen atom, a hydroxyl group, a COOH group, a CO-alkyl group, a COO-alkyl group, a CONH$_2$ group, an amino group, an alkyl group, an alkoxy group, an alkylthio group, or an alkylamino group.

2. A compound of General Formula (I)

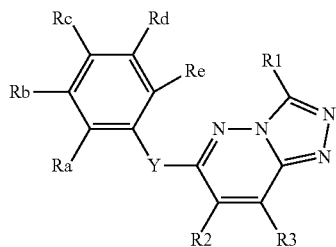

(Ia)

wherein

R1 represents a hydrogen atom, a halogen atom, an amino group, a hydroxyl group, a COOH group, a CO-alkyl group, a COO-alkyl group, a CONH$_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a CONH$_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, with a cycloalkylamino group, with an alkylcarbamate group, or with an heterocyclic group substituted or not with an alkyl group, or with an alkylsulfonyl group, wherein either Ra represents a W or W—Z— group, and Rb represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group; and W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

each of Y and Z represents independently an oxygen atom, a sulphuratom, a CH$_2$, or a carbonyl group;

with the proviso that when Rb is a W—Z group and Z is a CH$_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group;

wherein at least one of Rb, Rc, Rd and Re is a halogen atom, a hydroxyl group, a COOH group, a CO-alkyl group, a COO-alkyl group, a CONH2 group, an amino group, an alkyl group, an alkoxy group, an alkylthio group, or an alkylamino group.

3. The compound according to claim 1, wherein R1 is a halogen atom, an alkyl group, an alkoxy group, an alkylthio group, or an alkylamino group.

4. The compound according to claim 1, wherein, when any of the substituent groups is an alkyl group, an alkoxy group, an alkylthio group, or an alkylamino group, said group contains 1 to 4 carbon atoms.

5. The compound according to claim 1, wherein Y is an oxygen atom or a CH$_2$ group.

6. A compound of General Formula (I)

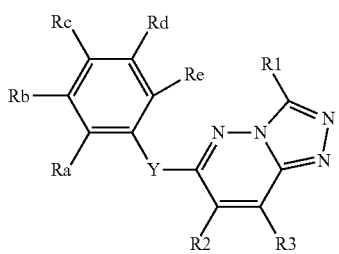

wherein
R1 represents a hydrogen atom, a halogen atom, an amino group, a hydroxyl group, a COOH group, a CO-alkyl group, a COO-alkyl group, a $CONH_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a $CONH_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, with a cycloalkylamino group, with an alkylcarbamate group, or with an heterocyclic group substituted or not with an alkyl group, or with an alkylsulfonyl group, wherein either
Ra represents a W or W—Z— group, and Rb represents a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a $CONH_2$ group, an amino group, an alkyl group, an alkoxy group, an alkylthio group, an alkylamino group; and W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a $CONH_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

each of Y and Z represents independently an oxygen atom, a sulphur atom, a $CH_2$, or a carbonyl group;

with the proviso that when Rb is a W—Z group and Z is a $CH_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group;

wherein Ra represents a W or a W—Z— group, and R1, together with at least one of Rb, Rc, and Rd represents independently an halogen atom, an alkyl group, an alkoxy group, or an alkyl group substituted with one or more halogen atoms.

7. The compound according to claim 6, wherein Ra represents a W group, and R1 and at least one group among Rc and Rd is a halogen atom or an alkyl group containing 1 to 4 carbon atoms that is substituted with one or more halogen atoms.

8. A compound of General Formula (I)

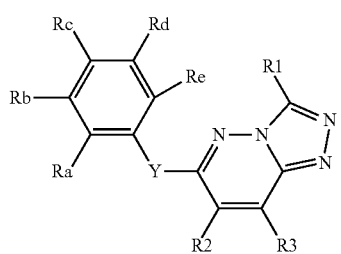

wherein
R1 represents a hydrogen atom, a halogen atom, an amino group, a hydroxyl group, a COOH group, a CO-alkyl group, a COO-alkyl group, a $CONH_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a $CONH_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, with a cycloalkylamino group, with an alkylcarbamate group, or with an heterocyclic group substituted or not with an alkyl group, or with an alkylsulfonyl group, wherein either
Ra represents a W or W—Z— group, and Rb represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group; and W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

each of Y and Z represents independently an oxygen atom, a sulphuratom, a CH$_2$, or a carbonyl group;

with the proviso that when Rb is a W—Z group and Z is a CH$_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group;

wherein R2 and R3, together with the carbon atoms to which they are attached, form a 6-membered cycle.

9. The compound according to claim 8, wherein R2 and R3, together with the carbon atoms to which they are attached, form a phenyl.

10. A compound of General Formula (I)

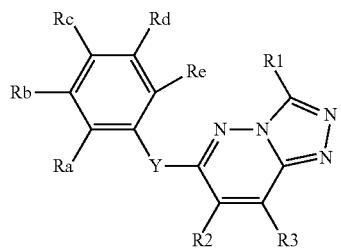

wherein

R1 represents a hydrogen atom, a halogen atom, an amino group, a hydroxyl group, a COOH group, a CO-alkyl group, a COO-alkyl group, a CONH$_2$ group, an alkyl group, an alkoxy group, an alkylthio group, or an alkylamino group;

R2 and R3, identical or different, represent a hydrogen atom, an alkyl group, a cyclic group or R2 and R3, together with the carbon atoms to which they are attached, form a substituted or unsubstituted 5- to 8-membered cycle;

Rc, Rd, and Re represent independently a hydrogen atom, a halogen atom, a hydroxyl group, a COOH group, a CO-alkyl group, a COO-alkyl group, a CONH$_2$ group, an amino group, an alkylcarbonylamino group, a nitro group, a cyano group, an alkoxy group, an alkylthio group, an alkylamino group, a heterocyclic group, an alkylsulfonamide group, or an alkyl group substituted or not with one or more halogen atoms, with an hydroxyl group, with an alkylcarbonyloxy group, with an amino group, with an alkylamino, with a cycloalkylamino group, with an alkylcarbamate group, or with an heterocyclic group substituted or not with an alkyl group, or with an alkylsulfonyl group, wherein either Ra represents a W or W—Z— group, and Rb represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group, or Rb represents a W or W—Z— group, and Ra represents a hydrogen atom, a halogen atom, a hydroxyl group, a COOH group, a CO-alkyl group, a COO-alkyl group, a CONH$_2$ group, an amino group, an alkyl group, an alkoxy group, an alkylthio group, an alkylamino group; and W represents a cyclic group selected from a cycloalkyl, aryl and heterocyclic group, W being substituted or not with one or more substituent groups chosen from a halogen atom, an hydroxyl group, a COOH group, a CO-alkyl group, a COO-alkyl group, a CONH$_2$ group, an amino group, a nitro group, an alkylsulfonamide group, an alkylcarbonylamino group, an alkoxy group, a cycloalkyloxy group, an alkylthio group, an alkylamino group, or an alkyl group substituted or not with one or more halogen atoms, with an alkylamino group, with a cycloalkylamino group, with a heterocyclic group substituted or not with an alkyl group;

wherein any of the alkyl, alkoxy, alkylamino, and alkylthio group in R1, R2, R3, Ra, Rb, Rc, Rd, Re, or within W is substituted or not with one or more halogen atoms, an aryl group, an heterocyclic group, an alkylamino group, an amino group or a hydroxy group;

each of Y and Z represents independently an oxygen atom, a sulphuratom, a CH$_2$, or a carbonyl group;

with the proviso that when Rb is a W—Z group and Z is a CH$_2$ group, W is not a morpholino or a 2-oxa-5-azabicyclo[2.2.1]heptyl group;

with the proviso that when Rb is a W group, R1 is a methyl group, Y is an oxygen atom and Ra, Rc, Rd, Re, R2 and R3 are hydrogen atoms, W is not a pyrrolidinone group; and with the proviso that when Rb is a W group, R1 is a trifluoromethyl group, Y is an oxygen atom and Ra, Rc, Rd, Re, R2 and R3 are hydrogen atoms, W is not a triazole group;

wherein R3 is a hydrogen atom and R2 is an alkyl or cyclic group or wherein R2 is a hydrogen atom and R3 is an alkyl or cyclic group.

11. The compound according to claim 10, wherein R2 or R3 is a C1-C4 alkyl.

12. A pharmaceutical composition comprising the compound as defined in claim 1 and a pharmaceutically acceptable carrier.

13. The pharmaceutical composition of claim 12, wherein said composition is formulated as an injectable suspension, a gel, an oil, a pill, a suppository, a powder, a capsule, an aerosol, or means of galenic forms for a prolonged and/or slow release.

14. The compound according to claim 2, wherein R1 is a halogen atom, an alkyl group, an alkoxy group, an alkylthio group, or an alkylamino group.

15. The compound according to claim 2, wherein, when any of the substituent groups is an alkyl group, an alkoxy group, an alkylthio group, or an alkylamino group, said group contains 1 to 4 carbon atoms.

16. The compound according to claim 2, wherein Y is an oxygen atom or a $CH_2$ group.

17. A pharmaceutical composition comprising the compound as defined in claim 2 and a pharmaceutically acceptable carrier.

18. A pharmaceutical composition comprising the compound as defined in claim 6 and a pharmaceutically acceptable carrier.

19. A pharmaceutical composition comprising the compound as defined in claim 8 and a pharmaceutically acceptable carrier.

20. A pharmaceutical composition comprising the compound as defined in claim 10 and a pharmaceutically acceptable carrier.

21. The pharmaceutical composition of claim 17, wherein said composition is formulated as an injectable suspension, a gel, an oil, a pill, a suppository, a powder, a capsule, an aerosol, or means of galenic forms for a prolonged and/or slow release.

22. The pharmaceutical composition of claim 18, wherein said composition is formulated as an injectable suspension, a gel, an oil, a pill, a suppository, a powder, a capsule, an aerosol, or means of galenic forms for a prolonged and/or slow release.

23. The pharmaceutical composition of claim 19, wherein said composition is formulated as an injectable suspension, a gel, an oil, a pill, a suppository, a powder, a capsule, an aerosol, or means of galenic forms for a prolonged and/or slow release.

24. The pharmaceutical composition of claim 20, wherein said composition is formulated as an injectable suspension, a gel, an oil, a pill, a suppository, a powder, a capsule, an aerosol, or means of galenic forms for a prolonged and/or slow release.

* * * * *